US012679832B2

(12) United States Patent
Xi et al.

(10) Patent No.: US 12,679,832 B2
(45) Date of Patent: Jul. 14, 2026

(54) COMPOUNDS AND THEIR USES AS CD38 INHIBITORS

(71) Applicant: Nanjing Immunophage Biotech Co., Ltd., Shanghai (CN)

(72) Inventors: Jianbei Xi, Nanjing (CN); Guohuang Fan, Nanjing (CN); Jianfei Wang, Nanjing (CN); Kin Chiu Fong, Nanjing (CN)

(73) Assignee: Nanjing Immunophage Biotech Co., Ltd., Nanjing (CN)

(*) Notice: Subject to any disclaimer, the term of this patent is extended or adjusted under 35 U.S.C. 154(b) by 0 days.

(21) Appl. No.: 19/224,687

(22) Filed: May 30, 2025

(65) Prior Publication Data

US 2025/0382283 A1 Dec. 18, 2025

Related U.S. Application Data

(63) Continuation of application No. 18/288,793, filed as application No. PCT/CN2022/089735 on Apr. 28, 2022.

(30) Foreign Application Priority Data

Apr. 30, 2021 (WO) ................ PCT/CN2021/091613
Aug. 31, 2021 (WO) ................ PCT/CN2021/115754

(51) Int. Cl.

| | |
|---|---|
| ***C07D 413/04*** | (2006.01) |
| ***A61K 31/416*** | (2006.01) |
| ***A61K 31/423*** | (2006.01) |
| ***A61K 31/427*** | (2006.01) |
| ***A61K 31/4439*** | (2006.01) |
| ***A61K 31/4965*** | (2006.01) |
| ***A61K 31/501*** | (2006.01) |
| ***A61K 31/506*** | (2006.01) |
| ***A61K 31/5377*** | (2006.01) |
| ***C07D 277/28*** | (2006.01) |
| ***C07D 401/04*** | (2006.01) |
| ***C07D 401/14*** | (2006.01) |
| ***C07D 405/14*** | (2006.01) |
| ***C07D 417/04*** | (2006.01) |
| ***C07D 417/14*** | (2006.01) |

(52) U.S. Cl.
CPC .......... *C07D 413/04* (2013.01); *A61K 31/416* (2013.01); *A61K 31/423* (2013.01); *A61K 31/427* (2013.01); *A61K 31/4439* (2013.01); *A61K 31/4965* (2013.01); *A61K 31/501* (2013.01); *A61K 31/506* (2013.01); *A61K 31/5377* (2013.01); *C07D 277/28* (2013.01); *C07D 401/04* (2013.01); *C07D 401/14* (2013.01); *C07D 405/14* (2013.01); *C07D 417/04* (2013.01); *C07D 417/14* (2013.01)

(58) Field of Classification Search
CPC .. A61K 31/416; A61K 31/423; A61K 31/427; A61K 31/4439; A61K 31/4965; A61K 31/501; A61K 31/506; A61K 31/5377; C07D 413/04; C07D 227/28; C07D 401/04; C07D 401/14; C07D 405/14; C07D 417/04; C07D 417/14
See application file for complete search history.

(56) References Cited

U.S. PATENT DOCUMENTS

| | | | |
|---|---|---|---|
| 2007/0149547 | A1 | 6/2007 | Bonnefous et al. |
| 2014/0249135 | A1 | 9/2014 | Burger et al. |
| 2021/0032251 | A1 | 2/2021 | Schenkel et al. |

FOREIGN PATENT DOCUMENTS

| | | | |
|---|---|---|---|
| CN | 112279837 | A | 1/2021 |
| EP | 4225310 | A1 | 8/2023 |
| WO | WO 2015/187499 | A1 | 12/2015 |
| WO | WO 2016/087975 | A1 | 6/2016 |
| WO | WO 2018/090869 | A1 | 5/2018 |
| WO | WO 2019/014460 | A1 | 1/2019 |
| WO | WO 2019/227059 | A1 | 11/2019 |
| WO | WO 2020/051207 | A2 | 3/2020 |
| WO | WO 2021/021986 | A1 | 2/2021 |
| WO | WO 2021/087087 | A1 | 5/2021 |
| WO | WO 2021/207186 | A1 | 10/2021 |
| WO | WO 2022/077034 | A1 | 4/2022 |
| WO | WO 2022/165114 | A1 | 8/2022 |
| WO | WO 2023/288195 | A1 | 1/2023 |

OTHER PUBLICATIONS

Becherer, J.D. et al. "Discovery of 4-Amino-8-quinoline Carboxamides as Novel, Submicromolar Inhibitors of NAD-Hydrolyzing Enzyme CD38", J. Med. Chem. vol. 58, Aug. 12, 2015, pp. 7021-7056.

(Continued)

*Primary Examiner* — Renee Claytor
*Assistant Examiner* — Andrew P Lee
(74) *Attorney, Agent, or Firm* — Travis Young; Bozicevic, Field & Francis LLP

(57) ABSTRACT

The present invention provides compounds of Formula I which can be used as CD38 inhibitors; methods for the production of the compounds of the invention; pharmaceutical compositions comprising the compounds of the invention; as well as uses and methods for treating a disease mediated by CD38 by administering the compounds of the invention.

Formula I

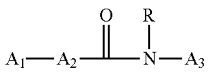

28 Claims, No Drawings

(56) References Cited

OTHER PUBLICATIONS

CAS Registry No. 1241723-70-5; STN Entry Date Sep. 16, 2010; 5-chloro-N-(2,6-dimethylphenyl)-2-(1Himidazol-1-yl)-4-pyrimidinecarboxamide.
CAS Registry No. 1241721-76-5; STN Entry Date Sep. 16, 2010; 5-chloro-N-(2,4-dimethylphenyl)-2-(1Himidazol-1-yl)-4-pyrimidinecarboxamide.
CAS Registry No. 1241717-19-0; STN Entry Date Sep. 16, 2010; 5-bromo-2-(1H-imidazol-1-yl)-N-[3-(trifluoromethyl)phenyl]-4-pyrimidinecarboxamide.
CAS Registry No. 1241717-07-6; STN Entry Date Sep. 16, 2010; 5-bromo-N-(2-fluorophenyl)-2-(1 Himidazol-1-yl)-4-pyrimidinecarboxamide.
CAS Registry No. 1241716-41-5; STN Entry Date Sep. 16, 2010; 5-chloro-N-(2-fluorophenyl)-2-(1 Himidazol-1-yl)-4-pyrimidinecarboxamide.
Li, Y. et al. "Discovery of a First-in-Class CD38 Inhibitor for the Treatment of Mitochondrial Myopathy", J. Med. Chem. vol. 66, Sep. 11, 2023, pp. 12762-12775.
PCT International Search Report and Written Opinion, PCT Application No. PCT/CN2022/089735, Jul. 27, 2022, pp. 1-11.
"RN:1241723-70-5, 1241721-76-5 et al.", STN Registry, Sep. 16, 2010.

COMPOUNDS AND THEIR USES AS CD38 INHIBITORS

TECHNICAL FIELD

The present invention relates to novel compounds; methods for the production of the compounds of the invention; pharmaceutical compositions comprising the compounds of the invention; as well as uses and methods for treating a disease mediated by CD38 by administering the compounds of the invention. In particular, the compounds of the invention may be used as CD38 inhibitors.

DESCRIPTION OF RELATED ART

CD38 is a protein of 300 amino acids encoded by homologous genes located on chromosome 4 and 5 in humans and mice, respectively. Within the cell, CD38 is often found localized on the cell surface, but it can also be detected in intracellular compartments such as the endoplasmic reticulum, nuclear membrane and mitochondria. Structurally, CD38 is a single chain glycoprotein with a single transmembrane segment and can topologically behave as a type II or type III membrane protein depending on its membrane orientation. In the most common type II orientation, CD38's short amino tail faces into the cytosol while CD38's catalytic domain faces the extracellular environment. A type III orientation, with the catalytic domain facing the cytosol, has been also reported. These two orientations have functional implications, given that CD38's enzymatic substrates and products would be consumed and produced in the extracellular or the intracellular compartments.

CD38 catalyzes the synthesis of nicotinamide (NAM) and ADPR using nicotinamide adenine dinucleotide ($NAD^+$) as a substrate. $NAD^+$, an essential cofactor that regulates energy metabolism, can be converted to cADPR with the release of NAM. Interestingly, cADPR can also be hydrolyzed to ADP-ribose by CD38. Thus, CD38 has both ADP-ribosyl cyclase and cADPR hydrolase enzymatic activities. Both ADPR and cADPR act as second messengers controlling several cell functions through calcium ($Ca^{2+}$) mobilization. In additional to its enzymatic function, CD38 can also act as a receptor to CD31. Through the latter interaction, CD38 could act as an adhesion molecule mediating selectin-like binding of hematopoietic cells to endothelial cells and facilitating their transmigration to tissue.

CD38 is a ubiquitous protein expressed in multiple tissues. Nonhematopoietic tissue expression include prostatic epithelial cells, pancreatic islet astrocytes, smooth muscle cells, retinal tubes, kidney, gut, and brain in both mice and humans. However, CD38 is most highly expressed in hematopoietic tissues such as the bone barrow and lymph nodes. Within immune cells, CD38 is highly expressed in B cells, macrophages, dendritic cells (DCs), innate lymphoid cells (ILC), natural killer (NK) cells, T cells, neutrophils, and monocytes. Nevertheless, the level of CD38 expression among these populations may differ between human and mouse, as observed in a transcriptional comparison between species.

The surface marker and multifunctional enzyme CD38 appears to provide a link between inflammation and age-and disease-related decline in tissue homeostasis and, therefore, represents a critical target for therapeutic intervention. CD38 is expressed predominately on immune cells in response to stimulation by cytokines, endotoxins, and interferon. Expression of the enzyme is regulated by a promoter region containing binding sites for NF-KB, RXR, LXR, and STAT suggesting that it plays a key role in the inflammatory response. CD38 expression causes a substantial decline in cellular $NAD^+$ levels, thus altering the availability of substrates for enzymes regulating cellular homeostasis. Thus, infiltration of CD38-expressing immune cells during infection, aging, or tumorigenesis has the potential to alter $NAD^+$ homeostasis in parenchymal tissues or the tumor microenvironment; disrupt normal metabolic processes; and undermine tissue integrity.

The important role of CD38 in multiple diseases including neurodegeneration, neuroinflammation, cancer development and autoimmune diseases suggests that targeted inhibition of CD38 is a potential therapeutic approach for the treatment of neurodegenerative diseases, cancer, autoimmune diseases, and other inflammatory diseases. One of the most important strategies targeting CD38 is to develop small molecule inhibitors against CD38, which have demonstrated promising preclinical efficacy.

SUMMARY OF THE INVENTION

The present invention provides novel compounds that function as CD38 inhibitors. The inventors of the instant invention have found that some compounds disclosed herein wherein cycloalkyl (e.g., cyclohexyl) as $A_3$ has been replaced with a phenyl group optionally having one or two carbon atoms replaced with N (e.g., phenyl, pyridinyl or pyrimidinyl) show improved inhibition activity and improved CYP inhibition, indicating reduced drug-drug interaction (DDI). Due to the replacement of C with N in the phenyl group as $A_3$ as mentioned above, the resultant compounds show better solubility and better pharmacokinetic (PK) profiles (including longer half-life, higher in vivo exposure and slower in vivo metabolism) and those compounds have been proved to have been well-tolerated in animal tests, indicating good safety windows.

In one aspect, the invention provides a compound of formula I:

Formula I

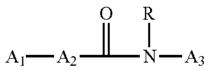

wherein

- $A_1$ is halogen; or 5 or 6 membered unsaturated monocyclic heterocycle containing 1 to 3 heteroatoms selected from the group consisting of N, O and S, and optionally substituted with one or two $C_{1-6}$ alkyl optionally substituted with 1, 2 or 3 halogen;
- $A_2$ is

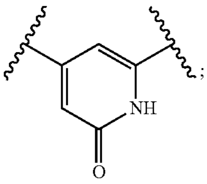;
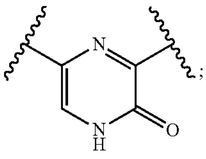; or
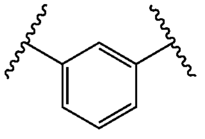

optionally having one or two carbon atoms replaced with nitrogen;

wherein $A_2$ is optionally substituted with 0 or 1 —OH; —CN; halogen; $C_{1-6}$ alkyl optionally substituted with 1, 2 or 3 halogen; $C_{2-6}$ alkynyl; $C_{1-6}$ alkoxy; $C_{3-6}$ cycloalkoxy, in which the cycloalkyl optionally has one carbon atom replaced with O or S; $—NR_1R_2$, in which each of $R_1$ and $R_2$ independently is H, $C_{1-6}$ alkyl, $—C(O)C_{1-6}$ alkyl;

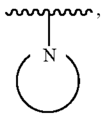 [SMILES: *N]

in which

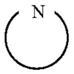

is a 5 or 6 membered saturated or unsaturated heterocycle containing 1 to 3 heteroatoms selected from the group consisting of N, O and S, and optionally substituted with 1-2 $C_{1-6}$ alkyl;

$A_3$ is selected from the group consisting of

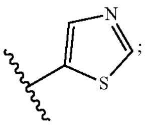 [SMILES: *c1cncs1]

$C_{1-6}$ alkyl; $—(CHR_3)_n—C_{3-8}$ cycloalkyl, in which the $C_{3-8}$ cycloalkyl optionally has one or two carbon atoms replaced with N, O or S, n is 0, 1 or 2, and $R_3$ is H or $C_{1-6}$ alkyl; or

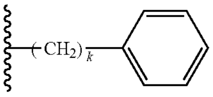

in which the phenyl optionally has one or two carbon atoms replaced with N, k is 0, 1 or 2;

wherein $A_3$ is optionally substituted with 0, 1 or 2 substituents independently selected from the group consisting of —OH; —CN; $—OCH_2CH_2OCH_3$; —CO—$C_{1-6}$ alkyl; halogen; $C_{1-6}$ alkyl optionally substituted with 1-3 halogen, methoxy or hydroxy; $C_{1-6}$ alkoxy optionally substituted with $NH_2$, dimethylamino, hydroxy or carboxy; $C_{3-6}$ cycloalkoxy; or $C_{3-8}$ cycloalkyl, in which the $C_{3-8}$ cycloalkyl optionally has one or two carbon atoms replaced with N, O or S and is optionally substituted with 1-3 halogen, $C_{1-6}$alkyl, $C_{1-6}$alkyl or hydroxy;

R is H or $C_{1-6}$ alkyl;

or a pharmaceutically acceptable salt, ester, stereoisomer, tautomer, solvate, prodrug, or combination thereof.

In some embodiments, the invention provides a compound of formula I:

Formula I

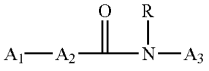

wherein $A_1$ is halogen; or 5 or 6 membered unsaturated monocyclic heterocycle containing 1 to 3 heteroatoms selected from the group consisting of N, O and S, and optionally substituted with one or two $C_{1-6}$ alkyl optionally substituted with 1, 2 or 3 halogen;

$A_2$ is

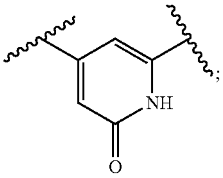
;
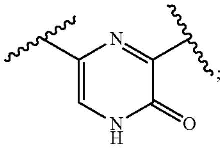
;
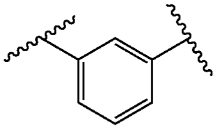

optionally having one or two carbon atoms replaced with nitrogen; or

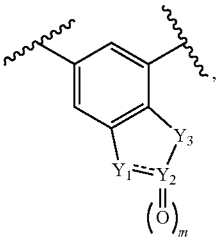

in which m is 0 or 1, when m is 1, the bond between $Y_1$ and $Y_2$ is a single bond, each of $Y_1$ and $Y_3$ independently is $CH_2$, O, S or NH, $Y_2$ is C, when m is 0 and the bond between $Y_1$ and $Y_2$ is a double bond, each of $Y_1$ and $Y_2$ independently is CH or N, $Y_3$ is $CH_2$, O, S or NH, when m is 0 and the bond between $Y_1$ and $Y_2$ is a single bond, each of $Y_1$, $Y_2$ and $Y_3$ independently is CH2, O, S or NH;

wherein $A_2$ is optionally substituted with 0 or 1 —OH; —CN; halogen; $C_{1-6}$ alkyl optionally substituted with 1, 2 or 3 halogen; $C_{2-6}$ alkynyl; $C_{1-6}$ alkoxy; $C_{3-6}$ cycloalkoxy, in which the cycloalkyl optionally has one carbon atom replaced with O or S; $—NR_1R_2$, in which each of $R_1$ and $R_2$ independently is H, $C_{1-6}$ alkyl, $—C(O)C_{1-6}$ alkyl;

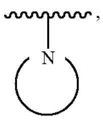 [SMILES: *N]

in which

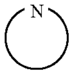

is a 5 or 6 membered saturated or unsaturated heterocycle containing 1 to 3 heteroatoms selected from the group consisting of N, O and S, and optionally substituted with 1—2 $C_{1-6}$ alkyl;

$A_3$ is selected from the group consisting of

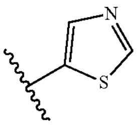

;

$C_{1-6}$ alkyl; —$(CHR_3)_n$—$C_{3-8}$ cycloalkyl, in which the $C_{3-8}$ cycloalkyl optionally has one or two carbon atoms replaced with N, O or S, n is 0, 1 or 2, and $R_3$ is H or $C_{1-6}$ alkyl; or

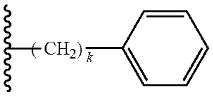

, in which the phenyl optionally has one carbon atom replaced with N, k is 0, 1 or 2;

wherein $A_3$ is optionally substituted with 0, 1 or 2 substituents independently selected from the group consisting of —OH; —CN; —$OCH_2CH_2OCH_3$; —CO—$C_{1-6}$ alkyl; halogen; $C_{1-6}$ alkyl optionally substituted with 1-3 halogen; $C_{1-6}$ alkoxy; $C_{3-6}$ cycloalkoxy;

R is H or $C_{1-6}$ alkyl;

or a pharmaceutically acceptable salt, ester, stereoisomer, tautomer, solvate, prodrug, or combination thereof.

In some embodiments, the compound is not any one of the following:

6-(1H-imidazol-1-yl)-N-((1r,4r)-4-methoxycyclohexyl) picolinamide;
N-cyclohexyl-6-(1H-imidazol-1-yl)picolinamide;
2-(1H-imidazol-1-yl)-N-((1r,4r)-4-methoxycyclohexyl) pyrimidine-4-carboxamide;
6-(1H-imidazol-1-yl)-N-phenylpicolinamide;
3-(1H-imidazol-1-yl)-N-(2-methoxycyclohexyl) benzamide;
3-(1H-imidazol-1-yl)-N-(thiazol-4-yl)benzamide;
N-cyclohexyl-3-(thiazol-2-yl)benzamide;
N-(3,5-dimethylphenyl)-2-(1H-imidazol-1-yl)-N-methylisonicotinamide;
5-chloro-N-(4-fluorophenyl)-2-(1H-imidazol-1-yl)pyrimidine-4-carboxamide;
5-chloro-N-(2-fluorophenyl)-2-(1H-imidazol-1-yl)pyrimidine-4-carboxamid;
5-bromo-N-(4-chlorophenyl)-2-(1H-imidazol-1-yl)pyrimidine-4-carboxamide;
5-chloro-N-(2-chlorophenyl)-2-(1H-imidazol-1-yl)pyrimidine-4-carboxamide;
5-chloro-2-(1H-imidazol-1-yl)-N-phenylpyrimidine-4-carboxamide;
5-chloro-2-(1H-imidazol-1-yl)-N-p-tolylpyrimidine-4-carboxamide;
5-bromo-2-(1H-imidazol-1-yl)-N-(3-(trifluoromethyl) phenyl)pyrimidine-4-carboxamide; or
6-(1H-imidazol-1-yl)-N-(4-(trifluoromethyl)phenyl)picolinamide.

In some embodiments, $A_2$ is selected from the group consisting of

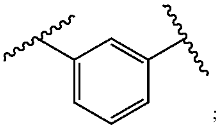
;
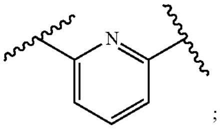
;
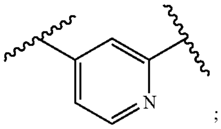
;
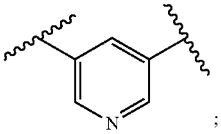
;
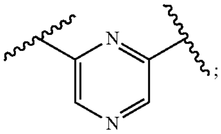
;
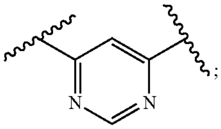
;
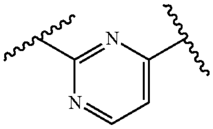
; or
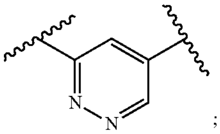
;

wherein $A_2$ is optionally substituted with 0 or 1 —OH, —CN, —F, —Cl, methyl, isopropyl, trifluoromethyl, methoxy, isopropoxy, cyclobutoxy, oxetan-3-yloxy, ethynyl, —$NH_2$, —$NHCH_3$, —$N(CH_3)_2$, —$NHC(O)CH_3$,

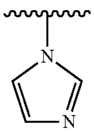
,
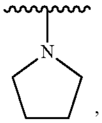
,
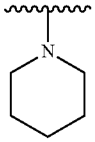
,
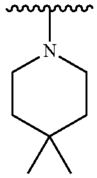
,
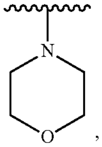
,
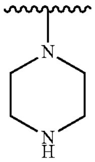
,
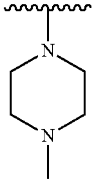
.

In some preferred embodiments, $A_1$ is Cl;

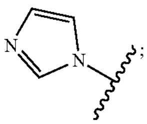
;
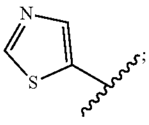
;
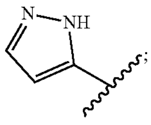
;
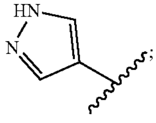
;
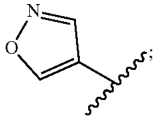
;
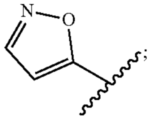
;
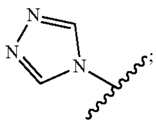
;
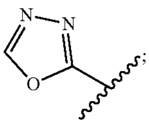
;
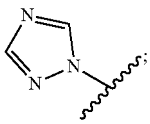
;

-continued

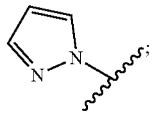 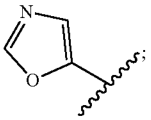 or 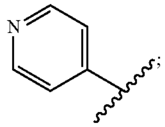

and $A_1$ is optionally substituted with one or two methyl or trifluoromethyl when it is not Cl.

In some embodiments, $A_3$ is a phenyl group which has one or two carbon atoms replaced with N. In some embodiments, $A_3$ is a phenyl group which has one carbon atom replaced with N. In some embodiments, $A_3$ is a phenyl group which has two carbon atoms replaced with N.

In some more preferred embodiments, $A_3$ is selected from the group consisting of

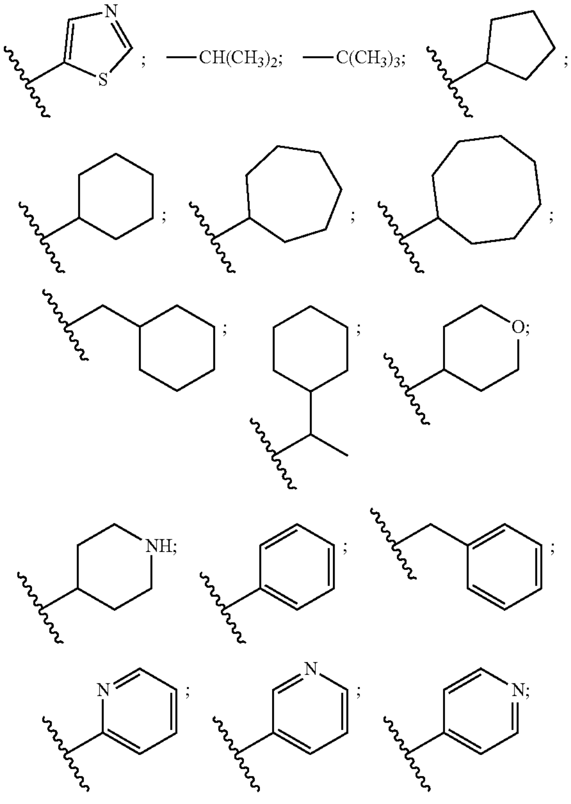

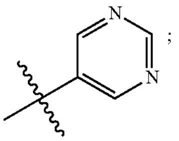 or 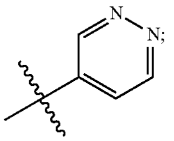

wherein $A_3$ is optionally substituted with 0, 1 or 2 substituents independently selected from the group consisting of —OH, —CN, —$OCH_2CH_2OCH_3$, 2-methoxypropan-2-yl, 2-hydroxypropan-2-yl, 2-(dimethylamino)ethoxy, —$COCH_3$, —F, —Cl, methyl, trifluoromethyl, methoxy, isopropoxy, cyclopropoxy, piperazin-1-yl, morpholino, or 3-hydroxypyrrolidin-1-yl.

In some more preferred embodiments, As is selected from the group consisting of

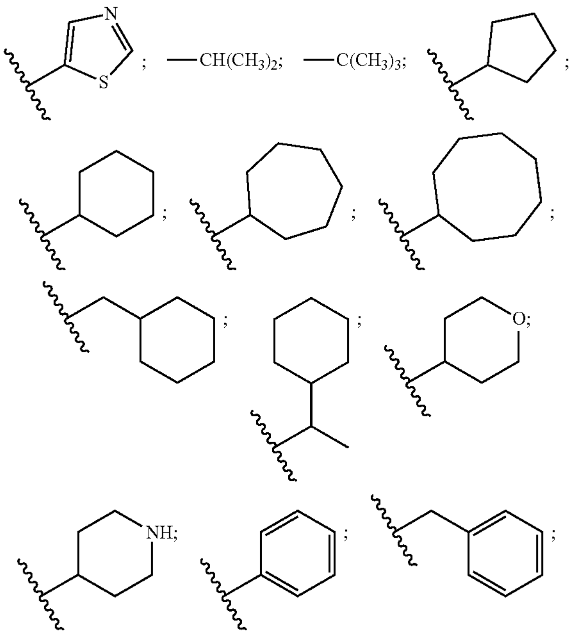

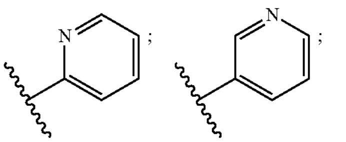 or 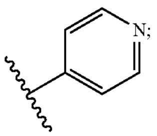

wherein $A_3$ is optionally substituted with 0, 1 or 2 substituents independently selected from the group consisting of —OH, —CN, —$OCH_2CH_2OCH_3$, —$COCH_3$, —F, —Cl, methyl, trifluoromethyl, methoxy, isopropoxy, cyclopropoxy, hydroxyethoxy, or carboxymethoxy.

In an embodiment, $A_2$ is selected from the group consisting of

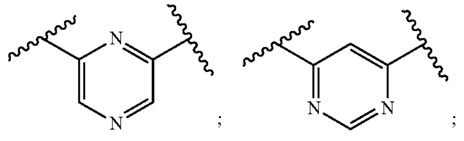

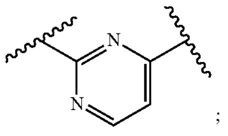 ; or 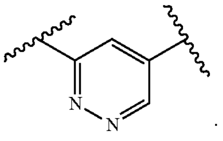 .

In a preferred embodiment, $A_2$ is optionally substituted with 0 or 1 —CN, methyl, isopropyl, trifluoromethyl, methoxy, cyclobutoxy, oxetan-3-yloxy, —$NH_2$, —$NHCH_3$, —$N(CH_3)_2$,

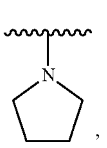 , 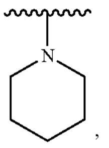 , or 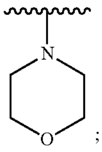

$A_1$ is

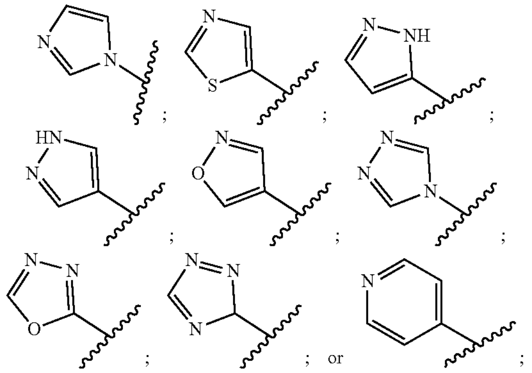

; ; ; ; ; ; ; ; or ;

and $A_1$ is optionally substituted with one or two methyl or trifluoromethyl;

$A_3$ is optionally substituted with 0, 1 or 2 substituents independently selected from the group consisting of —CN, —$OCH_2CH_2OCH_3$, —$COCH_3$, —F, —Cl, methyl, trifluoromethyl, or methoxy;

R is H or methyl.

In another embodiment, $A_2$ is selected from the group consisting of

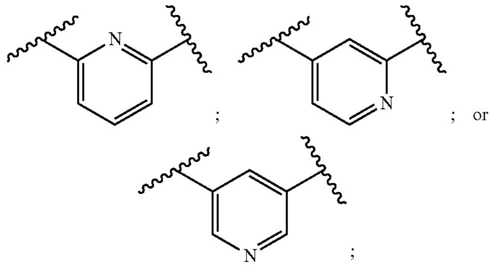

; ; or ;

and $A_2$ is optionally substituted with 0 or 1 —OH, —F, —Cl, methyl, isopropyl, trifluoromethyl, methoxy, ethynyl, —$NH_2$,

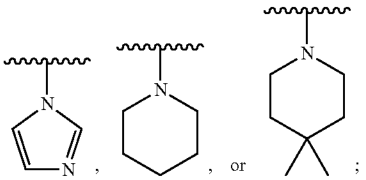

, , or ;

$A_1$ is

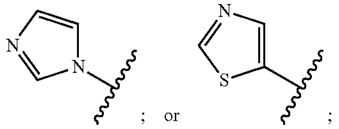 [SMILES: *n1ccnc1 ; *c1cncs1]

; or ;

and $A_1$ is optionally substituted with one or two trifluoromethyl;

$A_3$ is

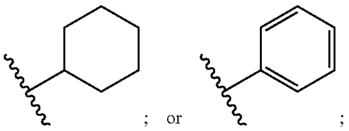 [SMILES: *C1CCCCC1 ; *c1ccccc1]

; or ;

and $A_3$ is optionally substituted with 0, 1 or 2 —F, methyl, methoxy; R is H.

In yet another embodiment, $A_2$ is

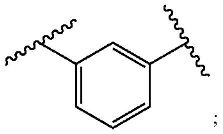 [SMILES: *c1cccc(*)c1]

;

and $A_2$ is optionally substituted with 0 or 1 —F, —$NH_2$, or —$NHC(O)CH_3$;

$A_1$ is

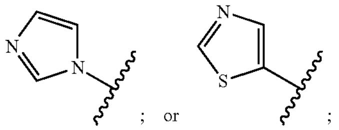 [SMILES: *n1ccnc1 ; *c1cncs1]

; or ;

and $A_1$ is unsubstituted;

$A_3$ is

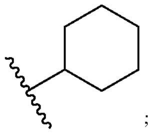 [SMILES: *C1CCCCC1]

;

and $A_3$ is optionally substituted with 0, 1 or 2 methoxy; R is H.

In alternative embodiments, $A_2$ is selected from the group consisting of

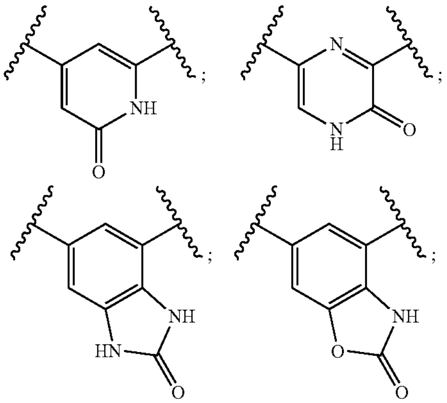

; ; ; ;

-continued

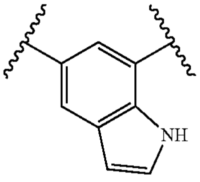;
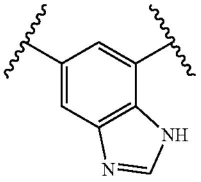;

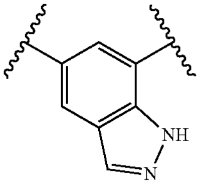; or 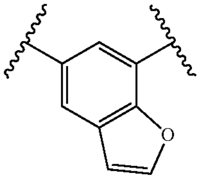;

and $A_2$ is unsubstituted.

In an embodiment, $A_2$ is

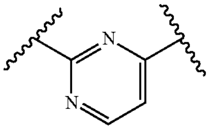, which is unsubstituted; and $A_3$ is

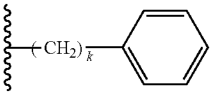, in which k is 0, 1 or 2, preferably k is 0 and said phenyl group is substituted with 0, 1 or 2 substituents independently selected from the group consisting of —OH; —CN; —$OCH_2CH_2OCH_3$; —CO—$C_{1-6}$ alkyl; halogen; $C_{1-6}$ alkyl optionally substituted with 1-3 halogen, methoxy or hydroxy; $C_{1-6}$ alkoxy optionally substituted with $NH_2$ or dimethylamino; $C_{3-6}$ cycloalkoxy; or $C_{3-8}$ cycloalkyl, in which the $C_{3-8}$ cycloalkyl optionally has one or two carbon atoms replaced with N, O or S and is optionally substituted with 1-3 halogen, $C_{1-6}$ alkyl, $C_{1-6}$alkyl or hydroxy.

In an embodiment, $A_2$ is

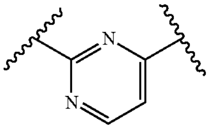, which is optionally substituted with 0 or 1 —CN, methyl, isopropyl, trifluoromethyl, methoxy, cyclobutoxy, oxetan-3-yloxy, —$NH_2$, —$NHCH_3$, —$N(CH_3)_2$; preferably substituted with trifluoromethyl; and $A_3$ is a phenyl group which has one or two carbon atoms replaced with N, preferably $A_3$ is

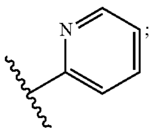; 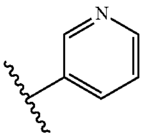; 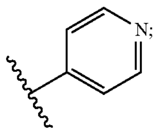;

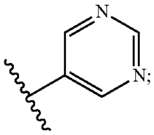; or 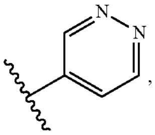, each of which is optionally substituted with 0, 1, or 2 substituents selected from —CN, —$OCH_2CH_2OCH_3$, —$COCH_3$, —F, —Cl, methyl, trifluoromethyl, hydroxyethoxy, carboxymethoxy, hydroxy or methoxy, preferably substituted with —$OCH_2CH_2OCH_3$, hydroxyethoxy, carboxymethoxy, hydroxy or methoxy.

In an embodiment, R is H.

In a preferred embodiment, $A_1$ is

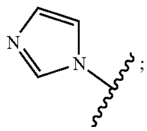; 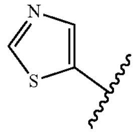; 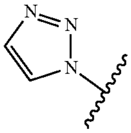; or

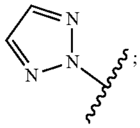;

and $A_1$ is unsubstituted.

In a more preferred embodiment, $A_3$ is

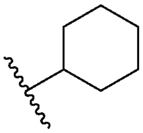;

and $A_3$ is optionally substituted with 0, 1 or 2 methoxy.

In alternative embodiments, the compound is selected from

1

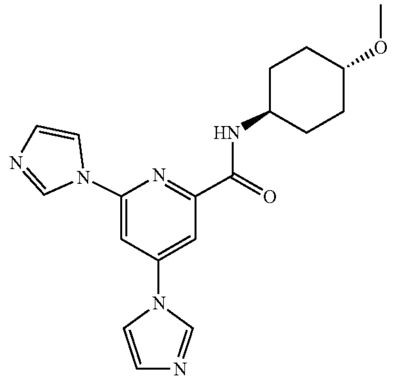

4,6-di(1H-imidazol-1-yl)-N-((1r,4r)-4-methoxycyclohexyl)picolinamide

2

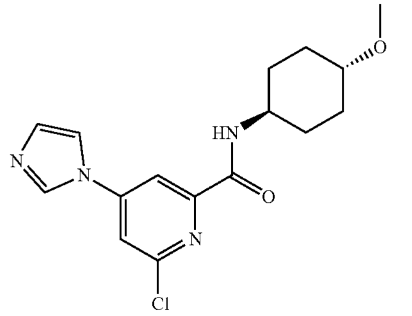

6-chloro-4-(1H-imidazol-1-yl)-N-((1r,4r)-4-methoxycyclohexyl)picolinamide

3

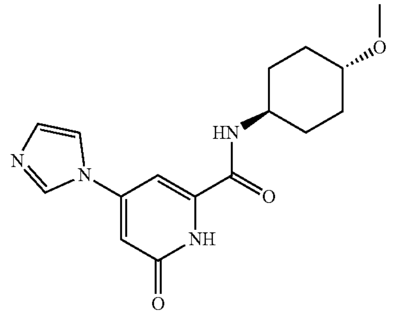

4-(1H-imidazol-1-yl)-N-((1r,4r)-4-methoxycyclohexyl)-6-oxo-1,6-dihydropyridine-2-carboxamide

4

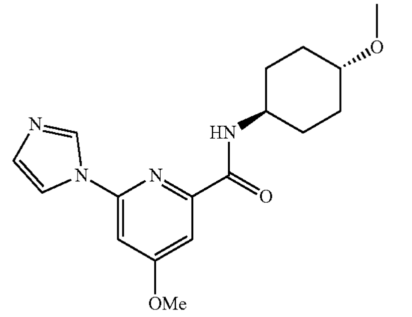

6-(1H-imidazol-1-yl)-4-methoxy-N-((1r,4r)-4-methoxycyclohexyl)picolinamide

-continued

5

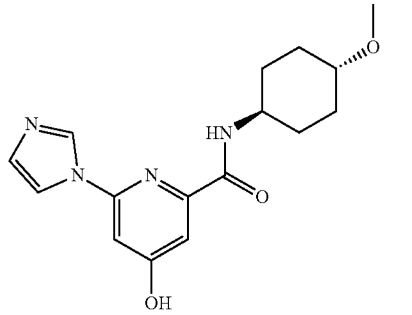

4-hydroxy-6-(1H-imidazol-1-yl)-N-((1r,4r)-4-methoxycyclohexyl)picolinamide

6

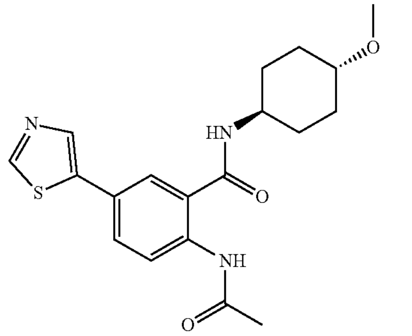

2-acetamido-N-((1r,4r)-4-methoxycyclohexyl-5-(thiazol-5-yl)benzamide

7

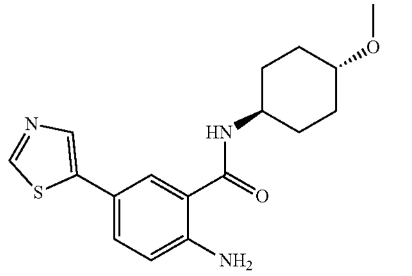

2-amino-N-((1r,4r)-4-methoxycyclohexyl-5-(thiazol-5-yl)benzamide

8

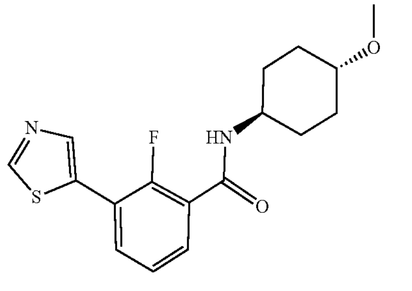

2-fluoro-N-((1r,4r)-4-methoxycyclohexyl-3-(thiazol-5-yl)benzamide

-continued

9

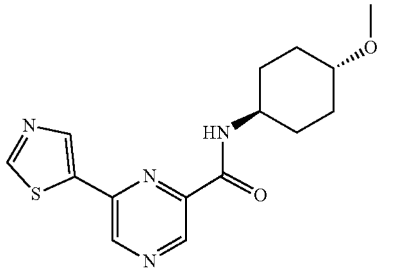

N-((1r,4r)-4-methoxycyclohexyl)-6-(thiazol-5-yl)pyrazine-2-carboxamide

10

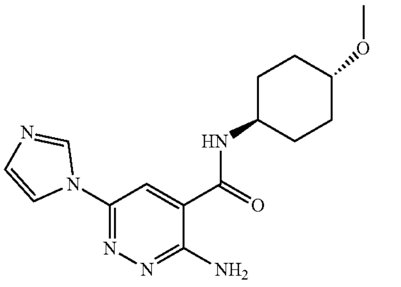

3-amino-6-(1H-imidazol-1-yl)-N-((1r,4r)-4-methoxycyclohexyl)pyridazine-4-carboxamide

11

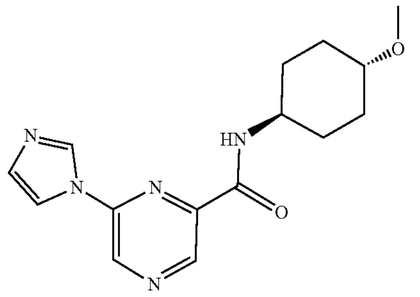

6-(1H-imidazol-1-yl)-N-((1r,4r)-4-methoxycyclohexyl)pyrazine-2-carboxamide

12

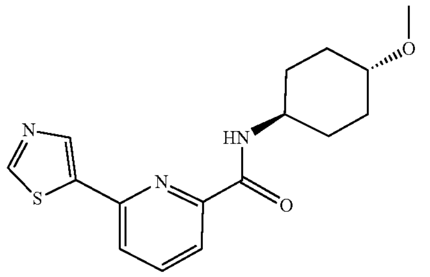

N-((1r,4r)-4-methoxycyclohexyl)-6-(thiazol-5-yl)picolinamide

-continued

13

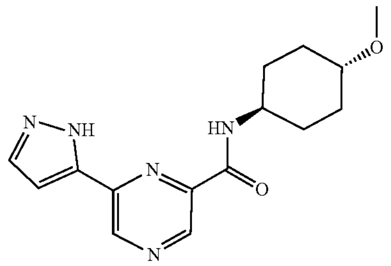

N-((1r,4r)-4-methoxycyclohexyl)-6-(1H-pyrazol-5-yl)pyrazine-2-carboxamide

14

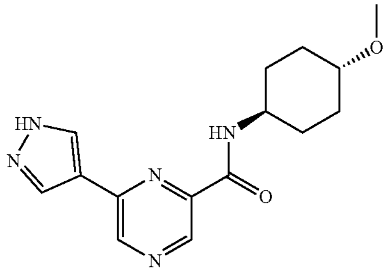

N-((1r,4r)-4-methoxycyclohexyl)-6-(1H-pyrazol-4-yl)pyrazine-2-carboxamide

15

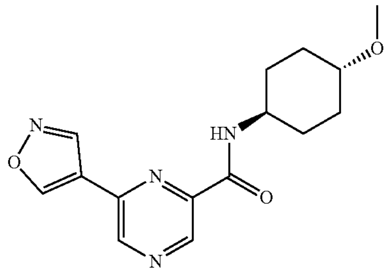

6-(isoxazol-4-yl)-N-((1r,4r)-4-methoxycyclohexyl) pyrazine-2-carboxamide

16

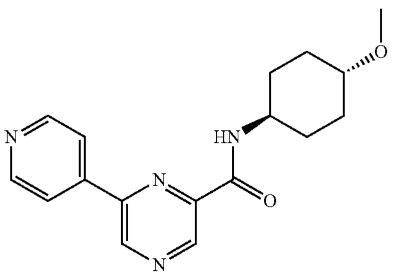

N-((1r,4r)-4-methoxycyclohexyl)-6-(pyridin-4-yl)pyrazine-2-carboxamide

-continued

17

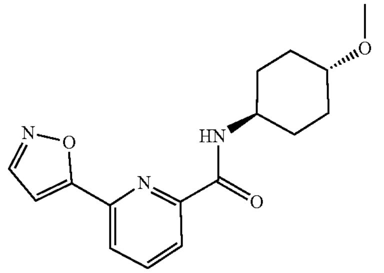

6-(isoxazol-5-yl)-N-((1r,4r)-4-methoxycyclohexyl)picolinamide

18

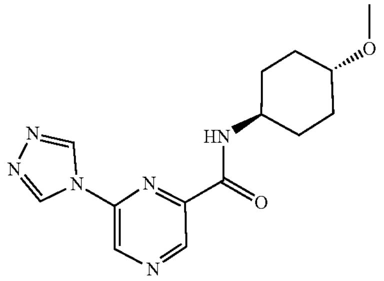

N-((1r,4r)-4-methoxycyclohexyl)-6-(4H-1,2,4-triazol-4-yl)pyrazine-2-carboxamide

19

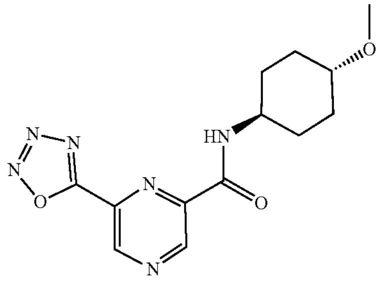

N-((1r,4r)-4-methoxycyclohexyl)-6-(1,3,4-oxadiazol-2-yl)pyrazine-2-carboxamide

20

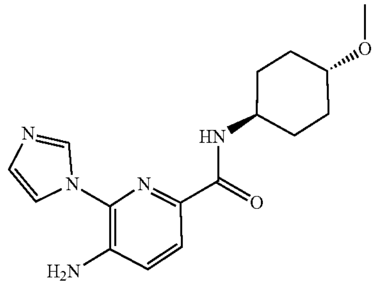

5-amino-6-(1H-imidazol-1-yl)-N-((1r,4r)-4-methoxycyclohexyl)picolinamide

-continued

21

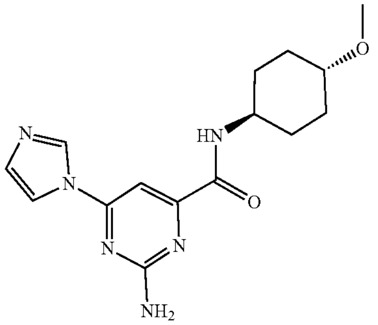

2-amino-6-(1H-imidazol-1-yl)-N-((1r,4r)-4-methoxycyclohexyl)pyrimidine-4-carboxamide

22

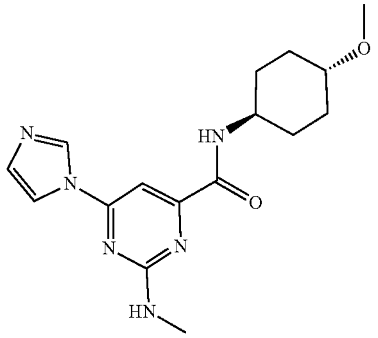

6-(1H-imidazol-1-yl)-N-((1r,4r)-4-methoxycyclohexyl)-2-(methylamino)pyrimidine-4-carboxamide

23

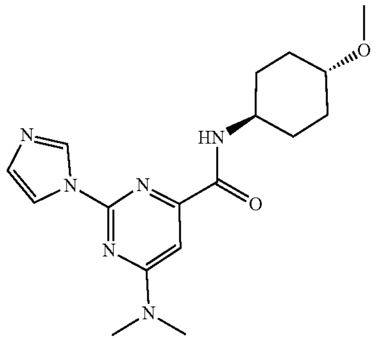

6-(dimethylamino)-2-(1H-imidazol-1-yl)-N-((1r,4r)-4-methoxycyclohexyl)pyrimidine-4-carboxamide

24

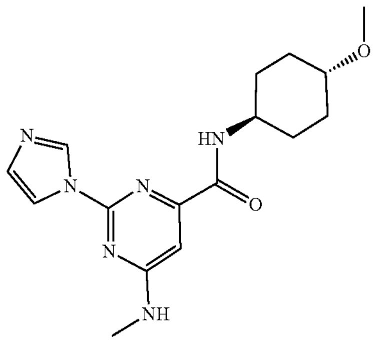

2-(1H-imidazol-1-yl)-N-((1r,4r)-4-methoxycyclohexyl)-6-(methylamino)pyrimidine-4-carboxamide -continued

25

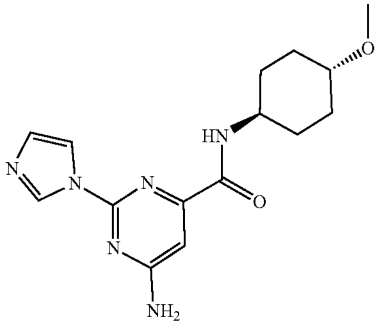

6-amino-2-(1H-imidazol-1-yl)-N-((1r,4r)-4-methoxycyclohexyl)pyrimidine-4-carboxamide

26

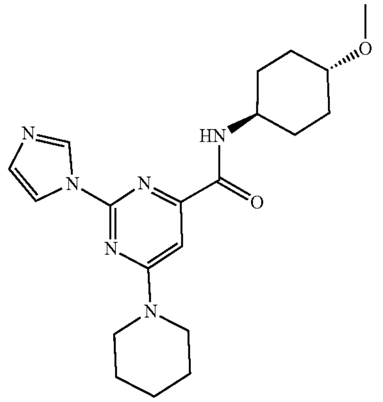

2-(1H-imidazol-1-yl)-N-((1r,4r)-4-methoxycyclohexyl)-6-(piperidin-1-yl)pyrimidine-4-carboxamide

27

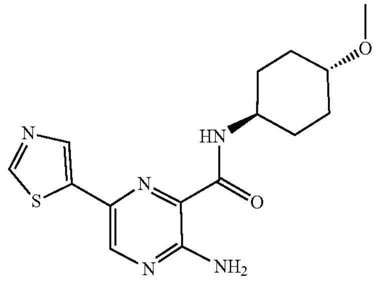

3-amino-N-((1r,4r)-4-methoxycyclohexyl)-6-(thiazol-5-yl)pyrazine-2-carboxamide

28

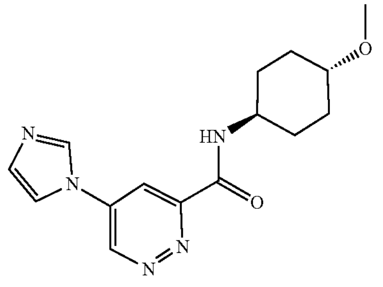

5-(1H-imidazol-1-yl)-N-((1r,4r)-4-methoxycyclohexyl)pyridazine-3-carboxamide

-continued

29

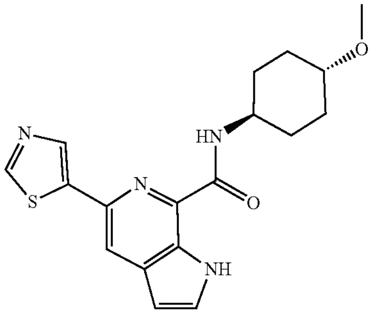

N-((1r,4r)-4-methoxycyclohexyl)-5-(thiazol-5-yl)1H--indole-7-carboxamide

30

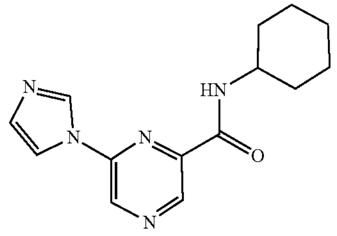

N-cyclohexyl-6-(1H-imidazol-1-yl) pyrazine-2-carboxamide

31

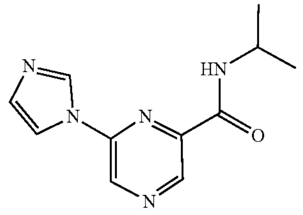

6-(1H-imidazol-1-yl)-N-isopropylpyrazine-2-carboxamide

32

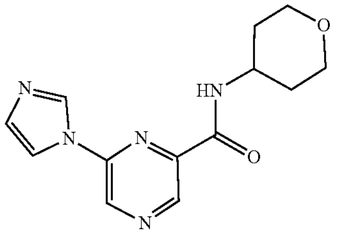

6-(1H-imidazol-1-yl)-N-(tetrahydro-2H-pyran-4-yl)pyrazine-2-carboxamide

33

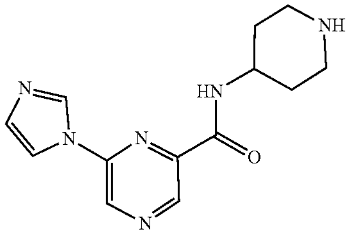

6-(1H-imidazol-1-yl)-N-(piperidin-4-yl-pyrazine-2-carboxamide

-continued

34

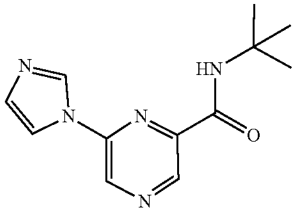

N-(tert-butyl)-6-(1H-imidazol-1-yl)pyrazine-2-carboxamide

35

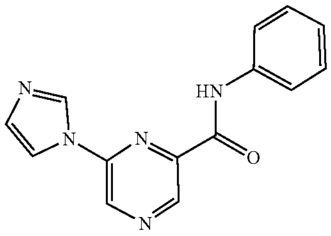

6-(1H-imidazol-1-yl)-N-phenylpyrazine-2-carboxamide

36

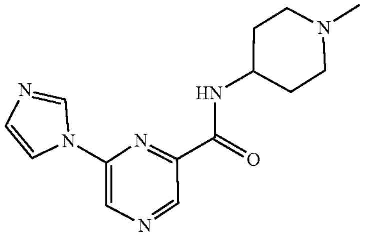

6-(1H-imidazol-1-yl)-N-methylpiperidin-4-yl)pyraine-2-carboxamide

37

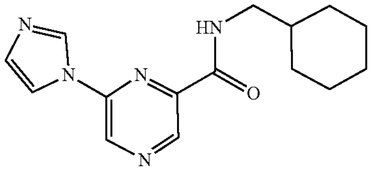

N-(cyclohexylmethyl)-6-(1H-imidazol-1-yl)pyrazine-2-carboxamide

38

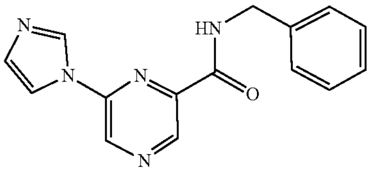

N-benzyl-6-(1H-imidazol-1-yl)pyrazine-2-carboxamide

-continued

39

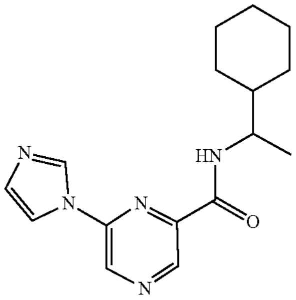

N-(1-cyclohexylethyl)-6-(1H-imidazol-1-yl)pyrazine-2-carboxamide

40

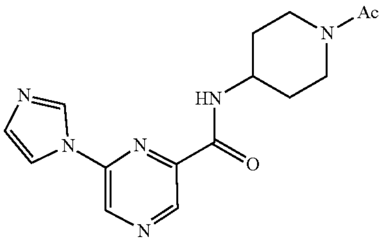

N-(1-acetylpiperidin-4-yl)-6-(1H-imidazol-1-yl)pyrazine-2-carboxamide

41

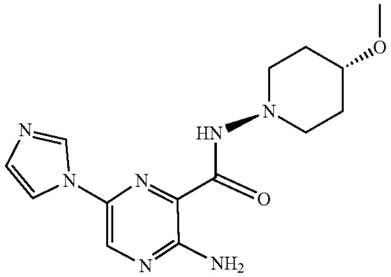

3-amino-6-(1H-imidazol-1-yl)-N-((1r,4r)-4-methoxycyclohexyl)pyrazine-2-carboxamide

42

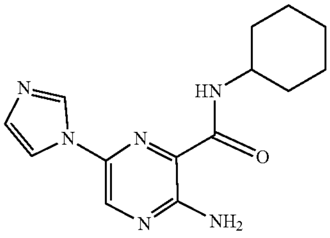

3-amino-N-cyclohexyl-6-(1H-imidazol-1-yl)pyrazine-2-carboxamide

-continued

43

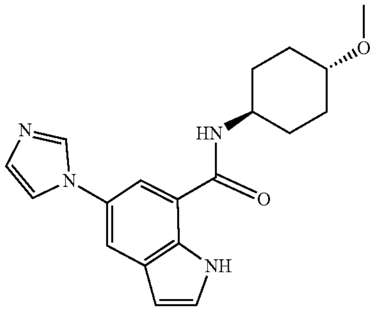

5-(1H-imidazol-1-yl)-N-((1r,4r)-4-methoxycyclohexyl)-1H-indole-7-carboxamide

44

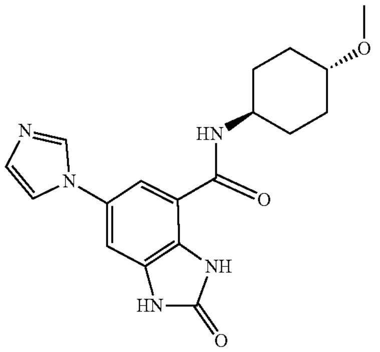

6-(1H-imidazol-1-yl)-N-((1r,4r)-4-methoxycyclohexyl)-2-oxo-2,3-dihydro-1H-benzo[d]imidazole-4-carboxamide

45

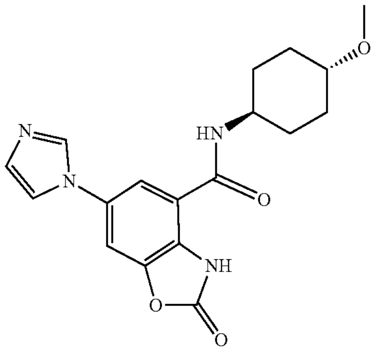

6-(1H-imidazol-1-yl)-N-((1r,4r)-4-methoxycyclohexyl)-2-oxo-2,3-dihydrobenzo[d]oxoazole-4-carboxamide

46

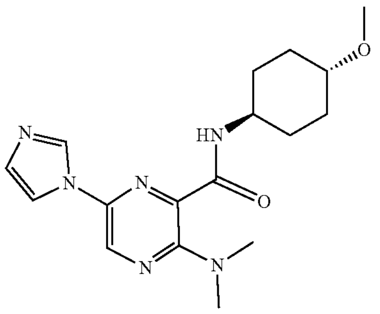

3-(dimethylamino)-6-(1H-imidazol-1-yl)-N-((1r,4r)-4-methoxycyclohexyl)pyrazine-2-carboxamide -continued

47

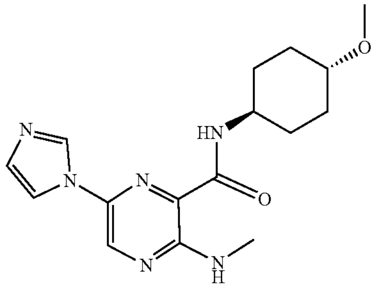

6-(1H-imidazol-1-yl)-N-((1r,4r)-4-methoxycyclohexyl)-3-(methylamino)pyrazine-2-carboxamide

48

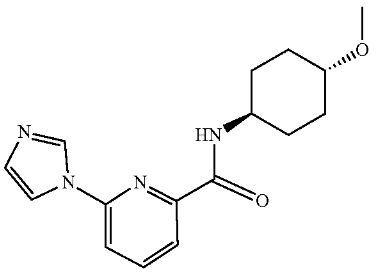

6-(1H-imidazol-1-yl)-N-((1r,4r)-4-methoxycyclohexyl)picolinamide

49

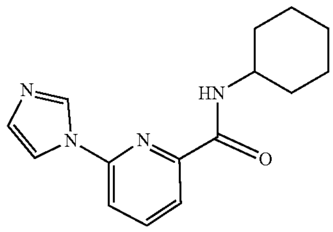

N-cyclohexyl-6-(1H-imidazol-1-yl)picolinamide

50

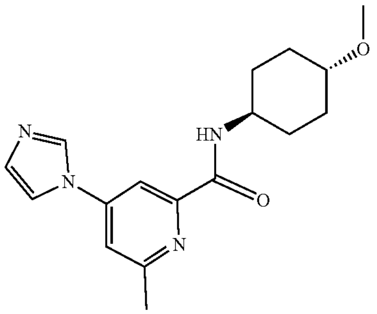

4-(1H-imidazol-1-yl)-N-((1r,4r)-4-methoxycyclohexyl)-6-methylpicolinamide

-continued

51

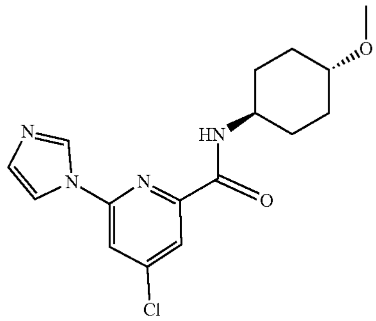

4-chloro-6-(1H-imidazol-1-yl)-N-((1r,4r)-4-methoxycyclohexyl)picolinamide

52

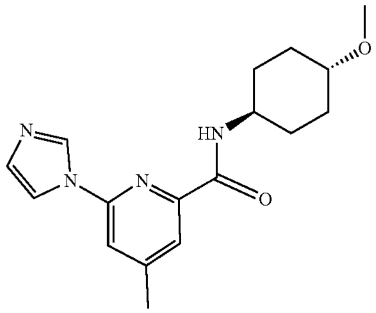

6-(1H-imidazol-1-yl)-N-((1r,4r)-4-methoxycyclohenyl)-4-methylpicolinamide

53

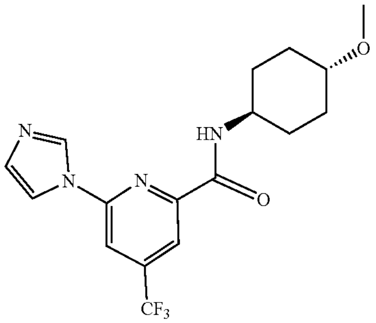

6-(1H-imidazol-1-yl)-N-((1r,4r)-4-methoxycycloheyl)-4-(trifluonomethyl)picolinamide

54

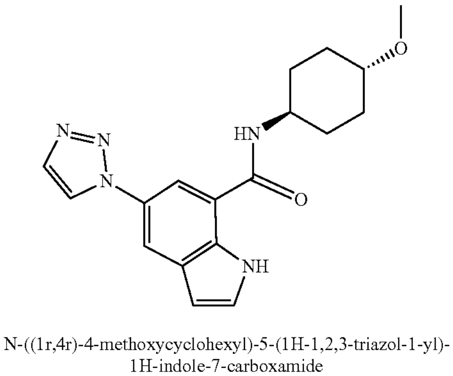

N-((1r,4r)-4-methoxycyclohexyl)-5-(1H-1,2,3-triazol-1-yl)-1H-indole-7-carboxamide -continued

55

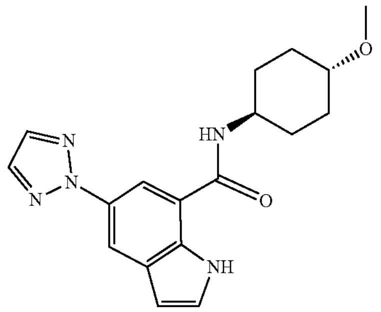

N-((1r,4r)-4-methoxycyclohexyl)-5-(2H-1,2,3-triazol-2-yl)-1H-indole-7-carboxamide

56

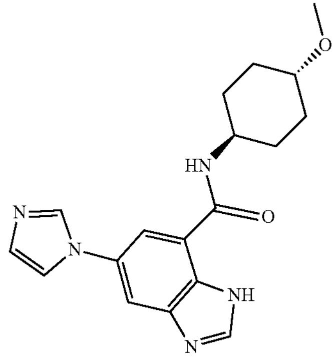

5-(1H-imidazol-1-yl)-N-((1r,4r)-4-methoxycyclohexyl)-1H-benzol[d]imidazole-7-carboxamide

57

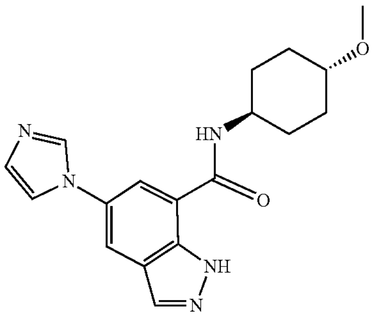

5-(1H-imidazol-1-yl)-N-((1r,4r)-4-methoxycyclohexyl)-1H-indazole-7-carboxamide

58

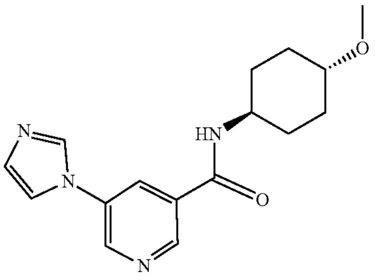

5-(1H-imidazol-1-yl)-N-((1r,4r)-4-methoxycyclohexyl)nicotinamide

-continued

59

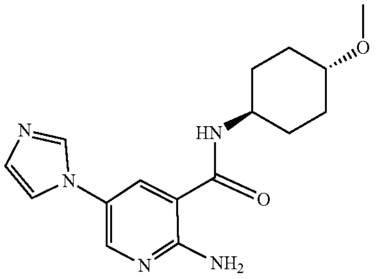

2-amino-5-(1H-imidazol-1-yl)-N-((1r,4r)-4-methoxycyclohexyl)nicotinamide

60

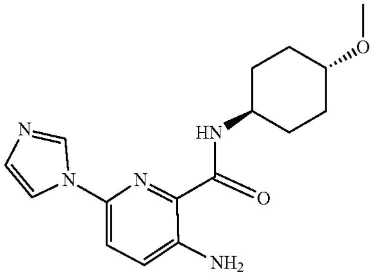

3-amino-6-(1H-imidazol-1-yl)-N-((1r,4r)-4-methoxycyclohexyl)picolinamide

61

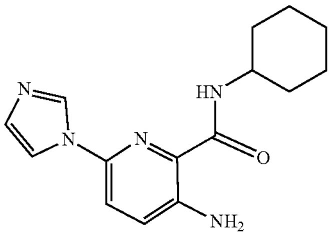

3-amino-N-cyclohexyl-6-(1H-imidazol-1-yl)picolinamide

62

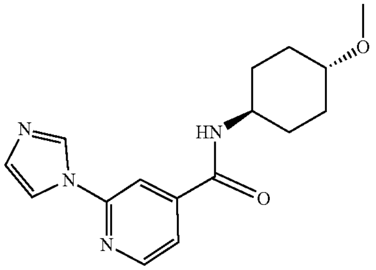

2-(1H-imidazol-1-yl)-N-((1r,4r)-4-methoxycyclohexyl)isonicotinamide

-continued

63

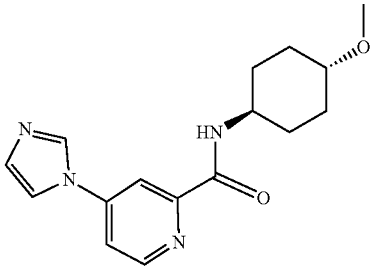

4-(1H-imidazol-1-yl)-N-((1r,4r)-4-methoxycyclohexyl)picolinamide

64

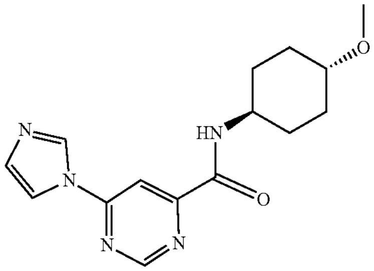

6-(1H-imidazol-1-yl)-N-((1r,4r)-4-methoxycyclohexyl)pyrimidine-4-carboxamide

65

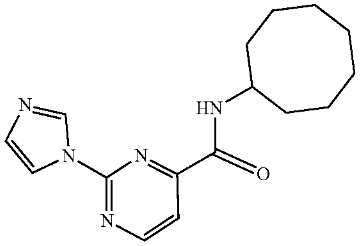

N-cyclooctyl-2-(1H-imicazol-1-yl)pyrimidine-4-carboxamide

66

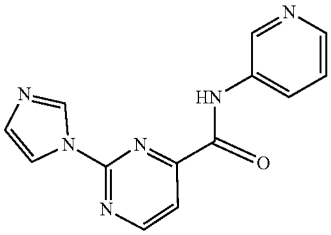

2-(1H-imidazol-1-yl)-N-(pyridin-3-yl)pyrimidine-4-carboxamide-

67

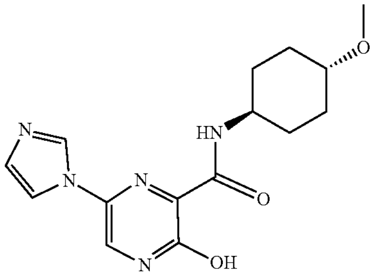

3-hydroxy-6-(1H-imidazol-1-yl)-N-((1r,4r)-4-methoxycyclohexyl)pyrazine-2-carboxamide -continued

68

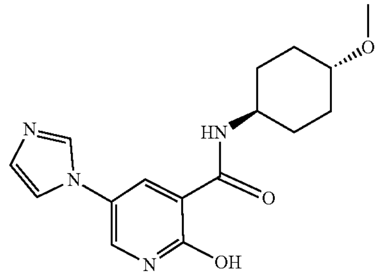

2-hydroxy-5-(1H-imidazol-1-yl)-N-((1r,4r)-4-methoxycyclohexyl)nicotinamide

69

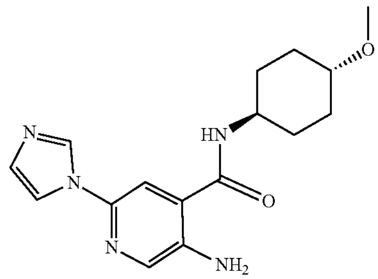

5-amino-2-(1H-imidazol-1-yl)-N-((1r,4r)-4-methoxycyclohexyl)isonicotinamide

70

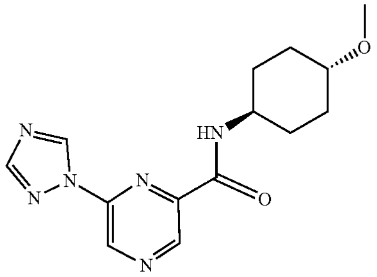

N-((1r,4r)methoxycyclohexyl)-6-(1H-1,2,4-triazol-1-yl)pyrazine-2-carboxamide

71

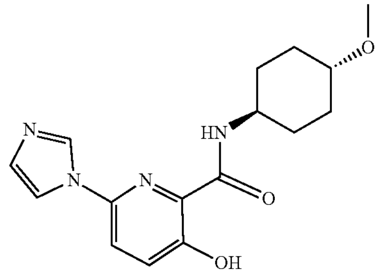

3-hydroxy-6-(1H-imidazol-1-yl)-N-((1r,4r)-4-methoxycyclohexyl)picolinamide

-continued

72

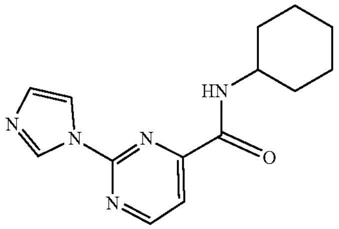

N-cyclohexyl-2-(1H-imidazol-1-yl)pyrimidine-4-carboxamide

73

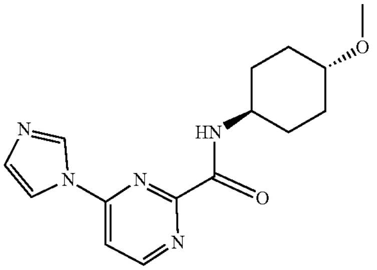

4-(1H-imidazol-1-yl)-N-((1r,4r)-4-methoxycyclohexyl)pyrimidine-2-carboxamide

74

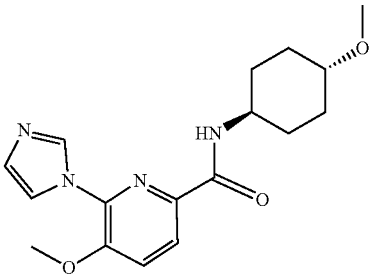

6-(1H-imidazol-1-yl)-5-methoxy-N-((1r,4r)-4-methoxycyclohexyl)picolinamide

75

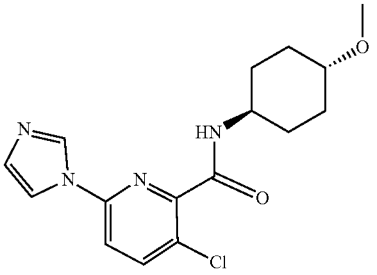

3-chloro-6-(1H-imidazol-1-yl)-N-((1r,4r)-4-methoxycyclohexyl)picolinamide

-continued

76

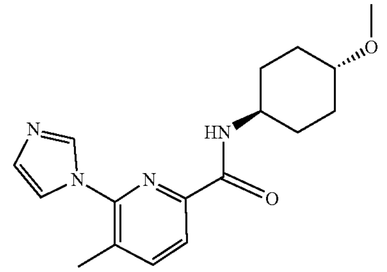

6-(1H-imidazol-1-yl)-N-((1r,4r)-4-methoxycyclohexyl)-5-methylpicolinamide

77

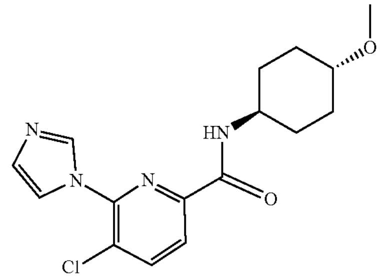

5-chloro-6-(1H-imidazol-1-yl)-N-((1r,4r)-4-methoxycyclohexyl)picolinamide

78

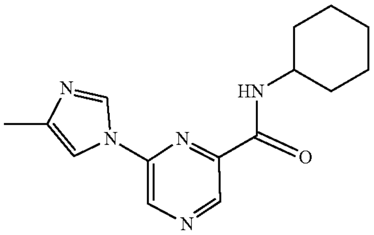

N-cyclohexyl-6-(4-methyl-1H-imidazol-1-yl)pyrazine-2-carboxamide

79

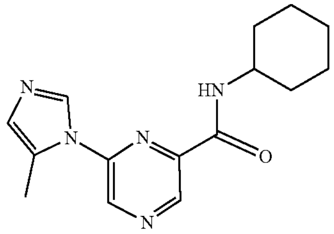

N-cyclohexyl-6-(5-methyl-1H-imidazol-1-yl)pyrazine-2-carboxamide

80

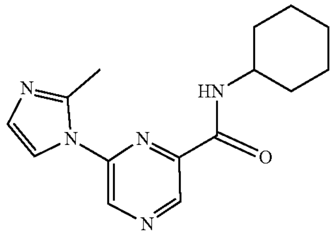

N-cyclohexyl-6-(2-methyl-1H-imidazol-1-yl)pyrazine-2-carboxamide

-continued

81

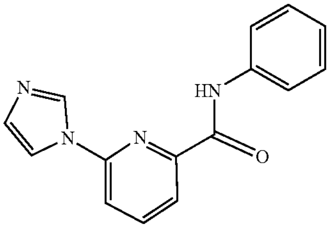

6-(1H-imidazol-1-yl)phenylpicolinamide

82

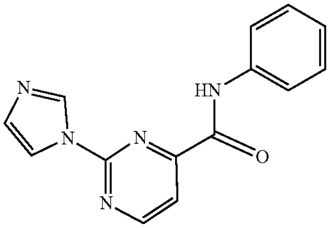

2-(1H-imidazol-1-yl)phenylpyrimidine-4-carboxamide

83

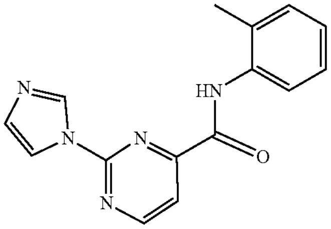

2-(1H-imidazol-1-yl)-N-(o-tolyl)pyrimidine-4-carboxamide

84

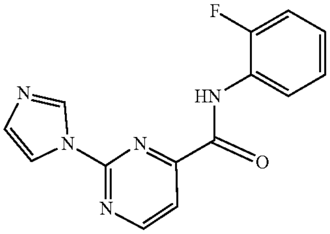

N-(2-fluorophenyl)-2-(1H-imidazol-1-yl)pyrimidine-4-carboxamide

85

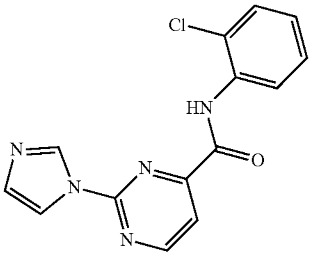

N-(2-chlorophenyl)-2-(1H-imidazol-1-yl)pyrimidine-4-carboxamide

-continued

86

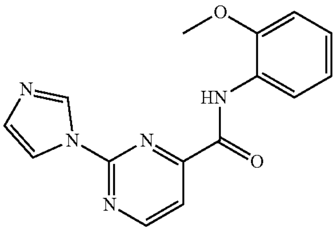

2-(1H-imidazol-1-yl)-N-(2-methoxyphenyl)pyrimidine-4-carboxamide

87

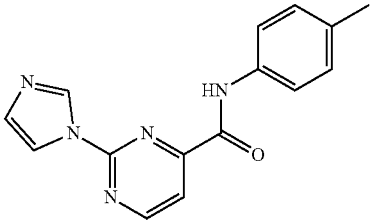

2-(1H-imidazol-1-yl)-N-(p-tolyl)pyrimidine-4-carboxamide

88

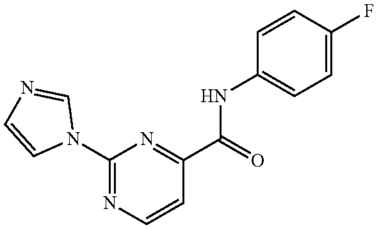

N-(4-fluorophenyl)-2-(1H-imidazol-1-yl)pyrimidine-4-carboxamide

89

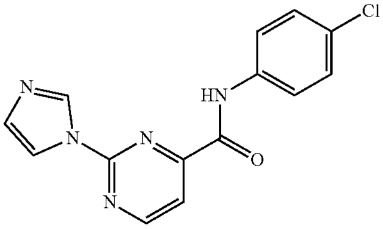

N-(4-chlorophenyl)-2-(1H-imidazol-1-yl)pyrimidine-4-carboxamide

90

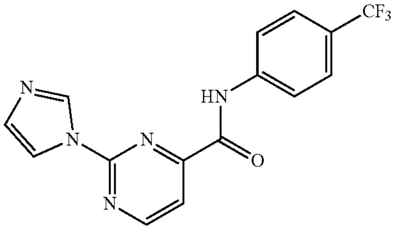

2-(1H-imidazol-1-yl)-N-(4-(trifluoromethyl)phenyl)pyrimidine-4-carboxamide

-continued

91

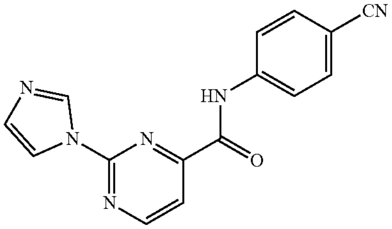

N-(4-cyanophenyl)-2-(1H-imidazol-1-yl)pyrimidine-4-carboxamide

92

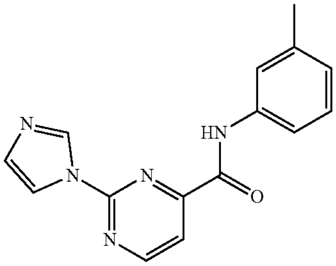

2-(1H-imidazol-1-yl)-N-(m-tolyl)pyrimidine-4-carboxamide

93

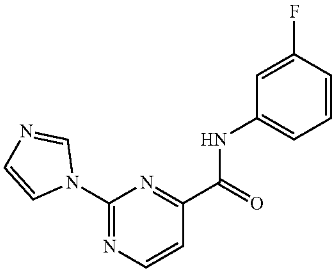

N-(3-fluorophenyl)-2-(1H-imidazol-1-yl)pyrimidine-4-carboxamide

94

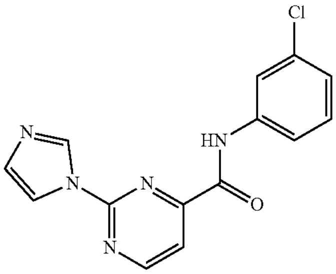

N-(3-chlorophenyl)-2-(1H-imidazol-1-yl)pyrimidine-4-carboxamide

95

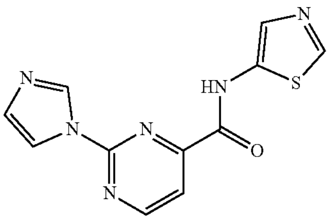

2-(1H-imidazol-1-yl)-N-(thiazol-5-yl)pyrimidine-4-carboxamide

-continued

96

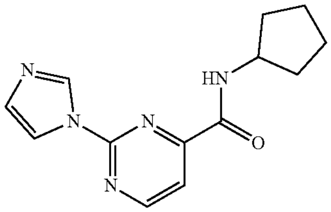

N-cyclopentyl-2-(1H-imidazol-1-yl)pyrimidine-4-carboxamide

97

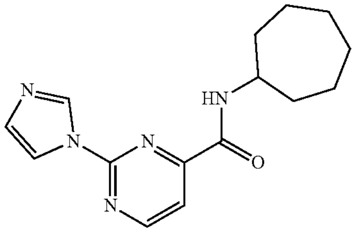

N-cycloheptyl-2-(1H-imidazol-1-yl)pyrimidine-4-carboxamide

98

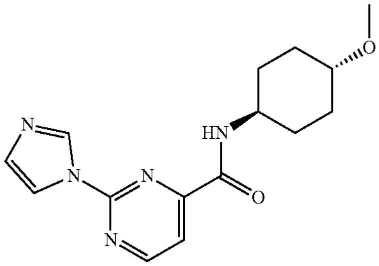

2-(1H-imidazol-1-yl)-N-((1r,4r)-4-methoxycyclohexyl)pyrimidine-4-carboxamide

99

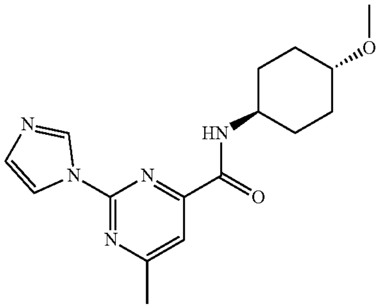

2-(1H-imidazol-1-yl)-N-((1r,4r)-4-methoxycyclohexyl)-6-methylpyrimidine-4-carboxamide -continued

100

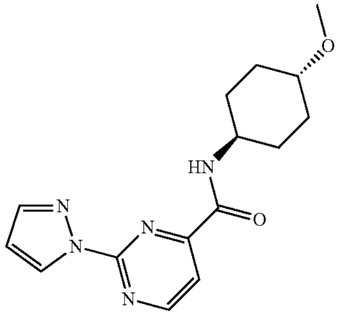

N-((1r,4r)-4-methoxycyclohexyl)-2-(1H-pyrazol-1-yl)pyrimidine-4-carboxamide

101

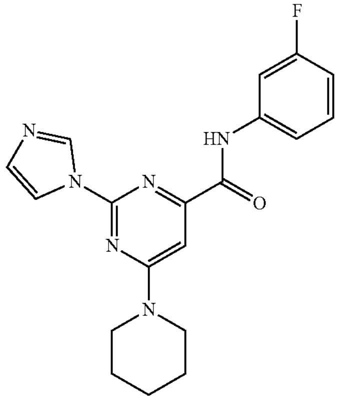

N-(3-fluorophenyl)-2-(1H-imidazol-1-yl)-6-(piperidin-1-yl)pyrimidine-4-carboxamide

102

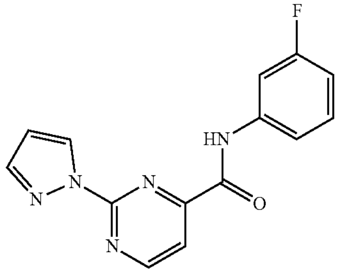

N-(3-fluorophenyl)-2-(1H-pyrazol-1-yl)pyrimidine-4-carboxamide

103

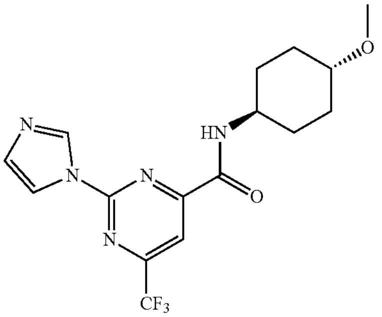

2-(1H-imidazol-1-yl)-N-((1r,4r)-4-methoxycyclohexyl)-6-(trifluoromethyl)pyrimidine-4-carboxamide -continued

104

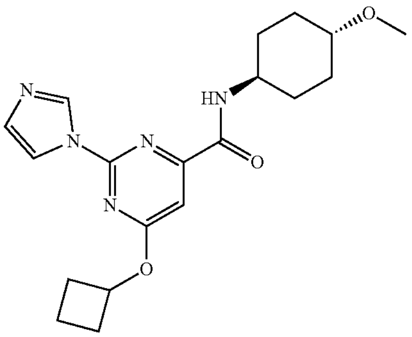

6-cyclobutoxy-2-(1H-imidazol-1-yl)-N-((1r,4r)-4-methoxycyclohexyl)pyrimidine-4-carboxamide

105

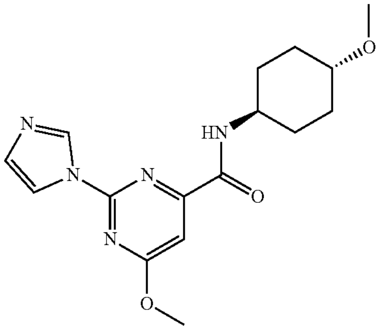

2-(1H-imidazol-1-yl)-6-methoxy-N-((1r,4r)-4-methoxycyclohexyl)pyrimidine-4-carboxamide

106

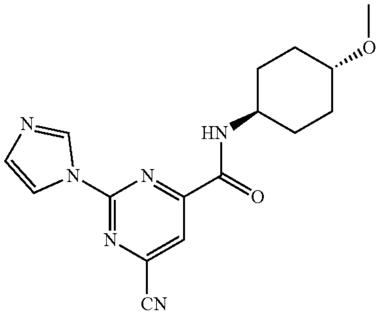

6-cyano-2-(1H-imidazol-1-yl)-N-((1r,4r)-4-methoxycyclohexyl)pyrimidine-4-carboxamide

107

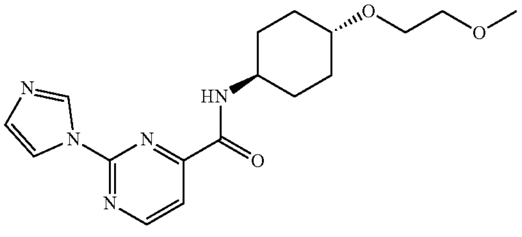

2-(1H-imidazol-1-yl)-N-((1r,4r)-4-(2-methoxyethoxy)cyclohexyl)pyrimidine-4-carboxamide -continued

108

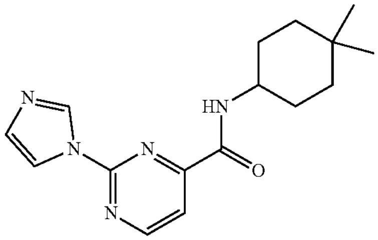

N-(4,4-dimethylcyclohexyl)-2-(1H-imidazol-1-yl)pyrimidine-4-carboxamide

109

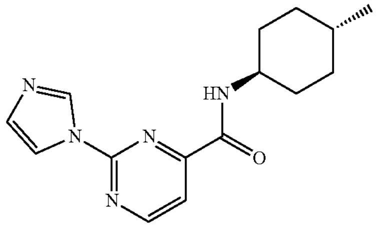

2-(1H-imidazol-1-yl)-N-((1r,4r)-4-methylcyclohexyl)pyrimidine-4-carboxamide

110

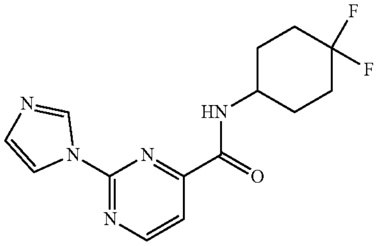

N-(4,4-difluorocyclohexyl)-2-(1H-imidazol-1-yl)pyrimidine-4-carboxamide

111

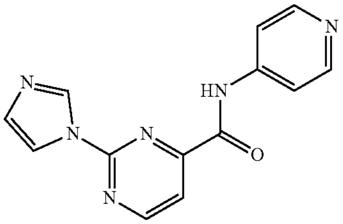

2-(1H-imidazol-1-yl)-N-(pyridin-4-yl)pyrimidine-4-carboxamide

112

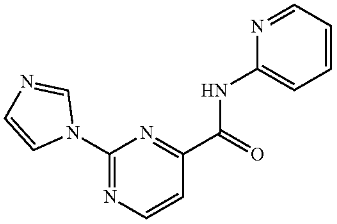

2-(1H-imidazol-1-yl)-N-(pyridin-2-yl)pyrimidine-4-carboxamide

-continued

113

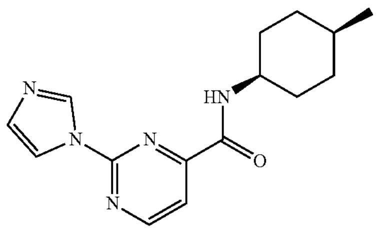

2-(1H-imidazol-1-yl)-N-((1s,4s)-4-methylcyclohexyl)pyrimidine-4-carboxamide

114

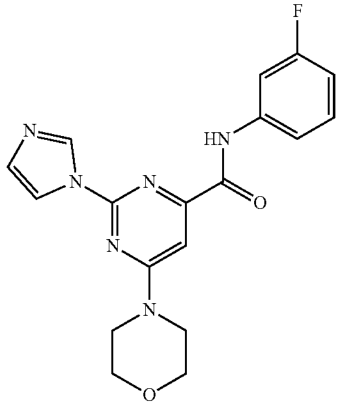

N-(3-fluorophenyl)-2-(1H-imidazol-1-yl)-6-morpholinopyrimidine-4-carboxamide

115

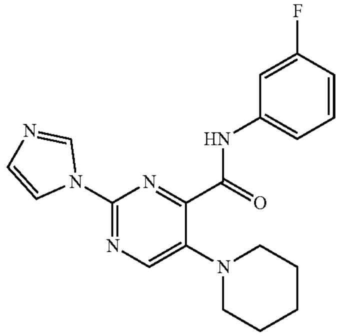

N-(3-fluorophenyl)-2-(1H-imidazol-1-yl)-5-(piperidin-1-yl)pyrimidine-4-carboxamide

116

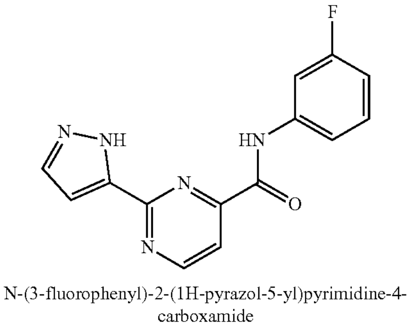

N-(3-fluorophenyl)-2-(1H-pyrazol-5-yl)pyrimidine-4-carboxamide

-continued

117

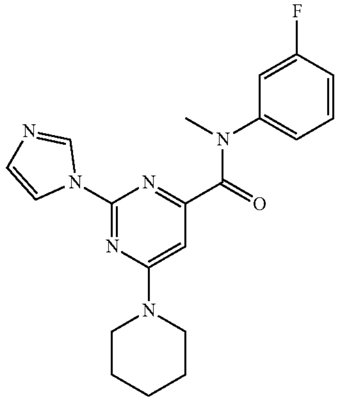

N-(3-fluorophenyl)-2-(1H-imidazol-1-yl)-N-methyl-6-(piperidin-1-yl)pyrimidine-4-carboxamide

118

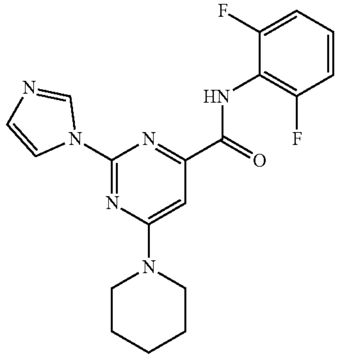

N-(2,6-difluorophenyl)-2-(1H-imidazol-1-yl)-6-(piperidin-1-yl)pyrimidine-4-carboxamide

119

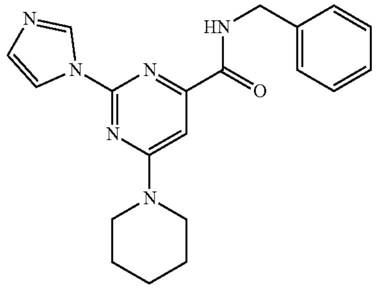

N-benzyl-2-(1H-imidazol-1-yl)-6-(piperidin-1-yl)pyrimidine-4-carboxamide

-continued

120

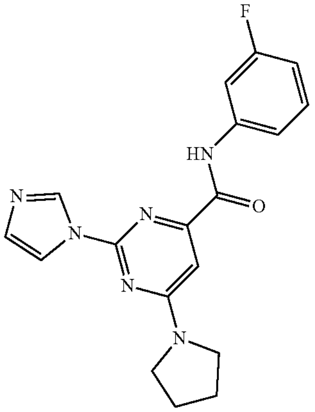

N-(3-fluorophenyl)-2-(1H-imidazol-1-yl)-6-(pyrrolidin-1-yl)pyrimidine-4-carboxamide

121

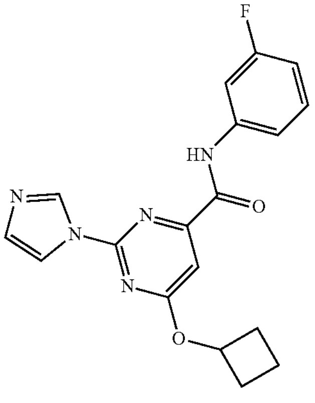

6-cyclobutoxy-N-(3-fluorophenyl)-2-(1H-imidazol-1-yl)pyrimidine-4-carboxamide

122

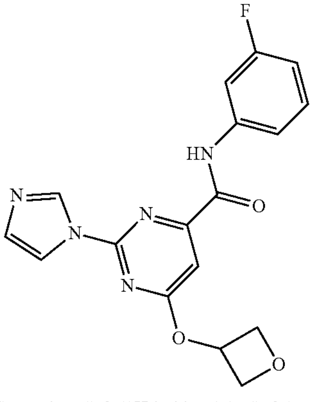

N-(3-fluorophenyl)-2-(1H-imidazol-1-yl)-6-(oxetan-3-yloxy)pyrimidine-4-carboxamide -continued

123

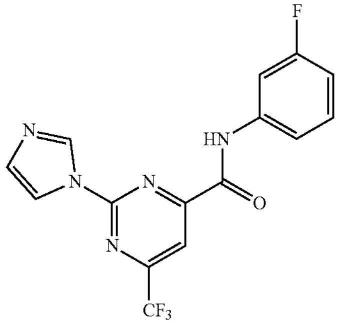

N-(3-fluorophenyl)-2-(1H-imidazol-1-yl)-6-(trifluoromethyl)pyrimidine-4-carboxamide

124

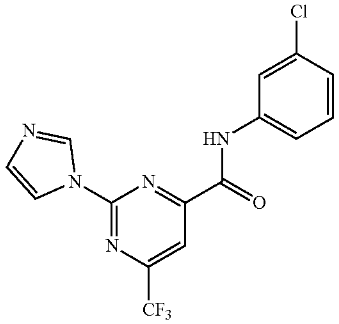

N-(3-chlorophenyl)-2-(1H-imidazol-1-yl)-6-(trifluoromethyl)pyrimidine-4-carboxamide

125

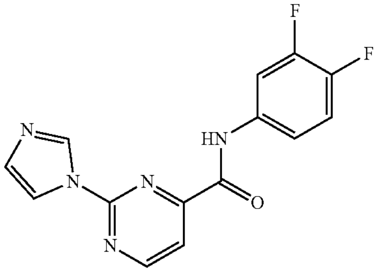

N-(3,4-difluorophenyl)-2-(1H-imidazol-1-yl)pyrimidine-4-carboxamide

126

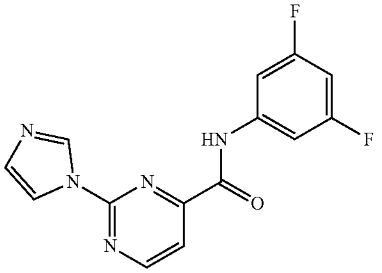

N-(3,5-difluorophenyl)-2-(1H-imidazol-1-yl)pyrimidine-4-carboxamide

127

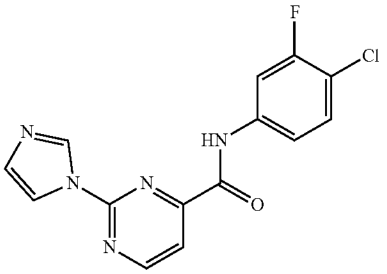

N-(4-chloro-3-fluorophenyl)-2-(1H-imidazol-1-yl)pyrimidine-4-carboxamide

128

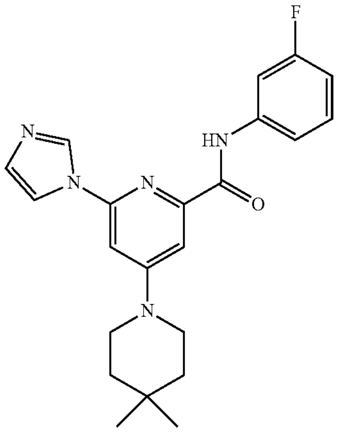

4-(4,4-dimethylpiperidin-1-yl)-N-(3-fluorophenyl)-6-(1H-imidazol-1-yl)picolinamide

129

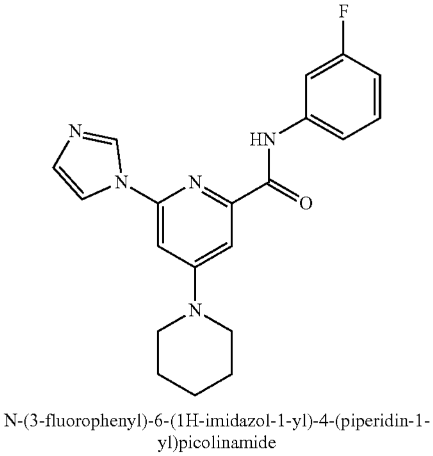

N-(3-fluorophenyl)-6-(1H-imidazol-1-yl)-4-(piperidin-1-yl)picolinamide

130

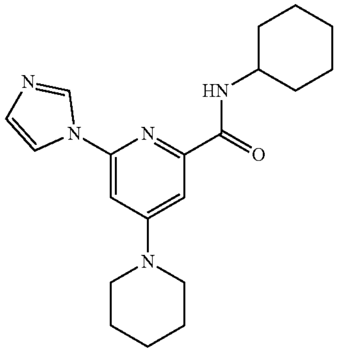

N-cyclohexyl-6-(1H-imidazol-1-yl)-4-(piperidin-1-yl)picolinamide

131

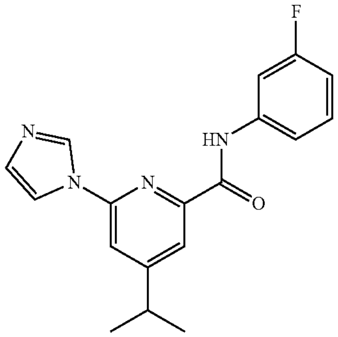

N-(3-fluorophenyl)-6-(1H-imidazol-1-yl)-4-isopropylpicolinamide

132

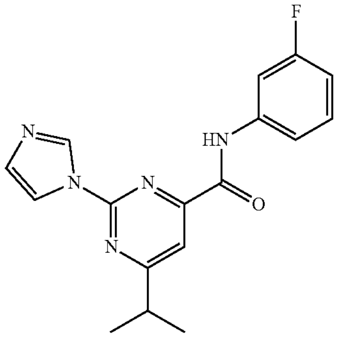

N-(3-fluorophenyl)-2-(1H-imidazol-1-yl)-6-isopropylpyrimidine-4-carboxamide

133

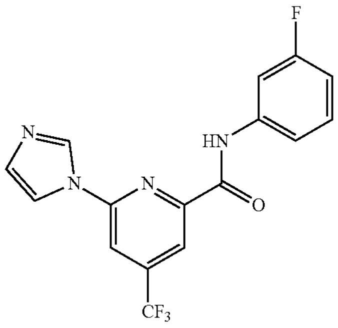

N-(3-fluorophenyl)-6-(1H-imidazol-1-yl)-4-(trifluoromethyl)picolinamide

-continued

134

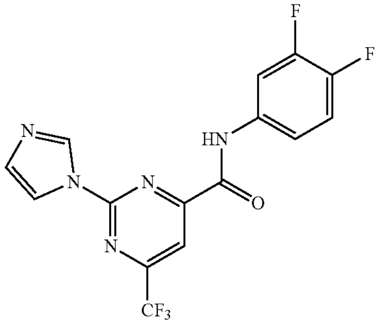

N-(3,4-difluorophenyl)-2-(1H-imidazol-1-yl)-6-(trifluoromethyl)pyrimidine-4-carboxamide

135

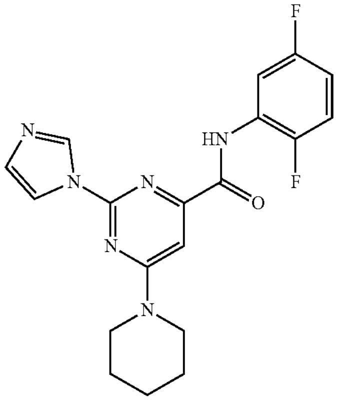

N-(2,5-difluorophenyl)-2-(1H-imidazol-1-yl)-6-(piperidin-1-yl)pyrimidine-4-carboxamide

136

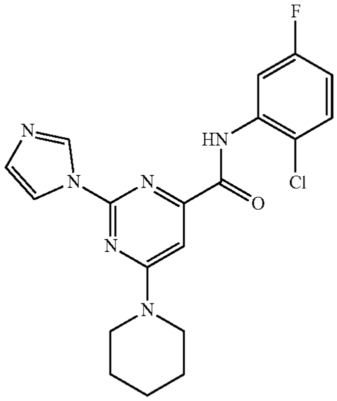

N-(2-chloro-5-fluorophenyl)-2-(1H-imidazol-1-yl)-6-(piperidin-1-yl)pyrimidine-4-carboxamide -continued

137

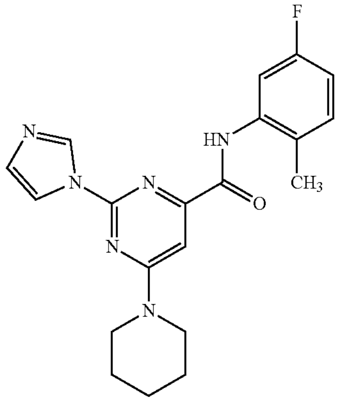

N-(5-fluoro-2-methylphenyl)-2-(1H-imidazol-1-yl)-6-(piperidin-1-yl)pyrimidine-4-carboxamide

138

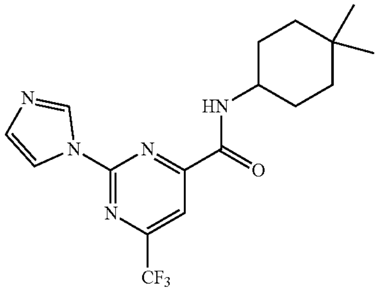

N-(4,4-dimethylcyclohexyl)-2-(1H-imidazol-1-yl)-6-(trifluoromethyl)pyrimidine-4-carboxamide

139

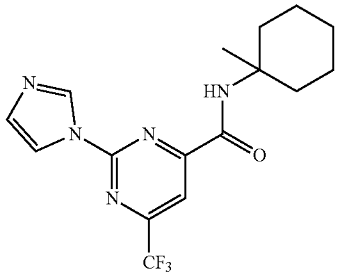

2-(1H-imidazol-1-yl)-N-(1-methylcyclohexyl)-6-(trifluoromethyl)pyrimidine-4-carboxamide

140

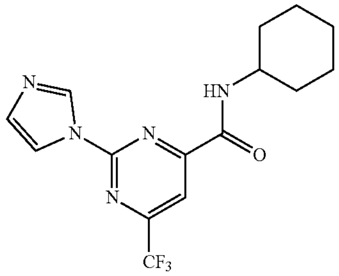

N-cyclohexyl-2-(1H-imidazol-1-yl)-6-(trifluoromethyl)pyrimidine-4-carboxamide

-continued

141

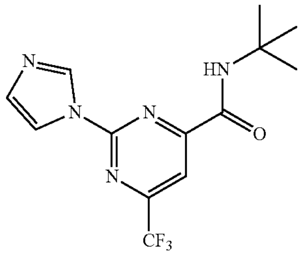

N-(tert-butyl)-2-(1H-imidazol-1-yl)-6-(trifluoromethyl)pyrimidine-4-carboxamide

142

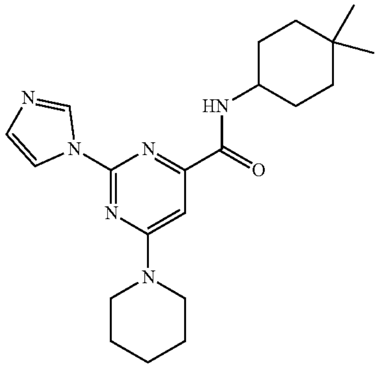

N-(4,4-dimethylcyclohexyl)-2-(1H-imidazol-1-yl)-6-(piperidin-1-yl)pyrimidine-4-carboxamide

143

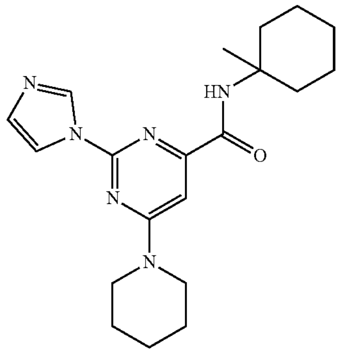

2-(1H-imidazol-1-yl)-N-(1-methylcyclohexyl)-6-(piperidin-1-yl)pyrimidine-4-carboxamide

144

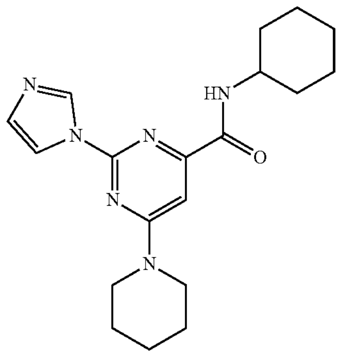

N-cyclohexyl-2-(1H-imidazol-1-yl)-6-(piperidin-1-yl)pyrimidine-4-carboxamide

-continued

145

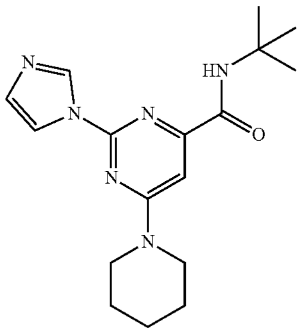

N-(tert-butyl)-2-(1H-imidazol-1-yl)-6-(piperidin-1-yl)pyrimidine-4-carboxamide

146

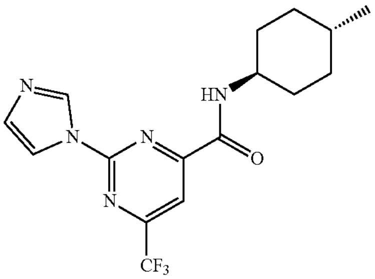

2-(1H-imidazol-1-yl)-N-((1r,4r)-4-methylcyclohexyl)-6-(trifluoromethyl)pyrimidine-4-carboxamide

147

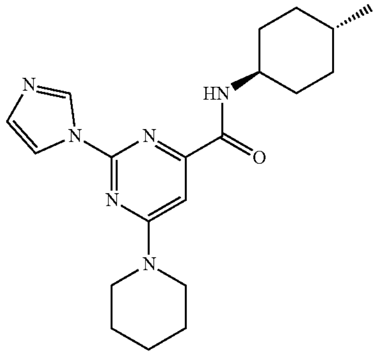

2-(1H-imidazol-1-yl)-N-((1r,4r)-4-methylcyclohexyl)-6-(piperidin-1-yl)pyrimidine-4-carboxamide

148

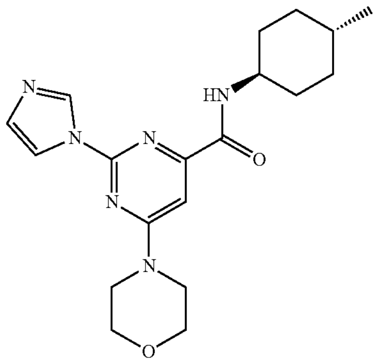

2-(1H-imidazol-1-yl)-N-((1r,4r)-4-methylcyclohexyl)-6-morpholinopyrimidine-4-carboxamide -continued

149

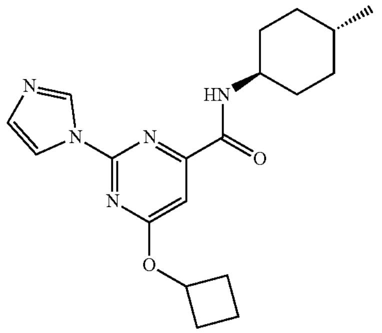

6-cyclobutoxy-2-(1H-imidazol-1-yl)-N-((1r,4r)-4-methylcyclohexyl)pyrimidine-4-carboxamide

150

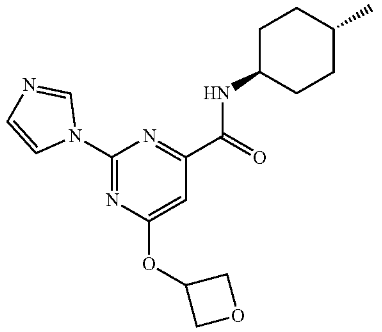

2-(1H-imidazol-1-yl)-N-((1r,4r)-4-methylcyclohexyl)-6-(oxetan-3-yloxy)pyrimidine-4-carboxamide

151

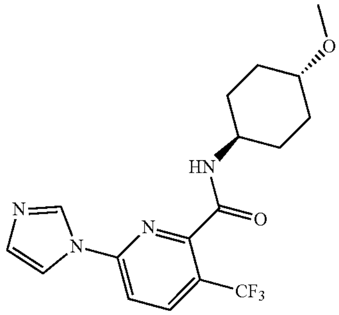

6-(1H-imidazol-1-yl)-N-((1r,4r)-4-methoxycyclohexyl)-3-(trifluoromethyl)picolinamide

152

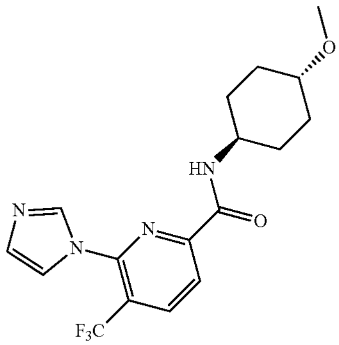

6-(1H-imidazol-1-yl)-N-((1r,4r)-4-methoxycyclohexyl)-5-(trifluoromethyl)picolinamide -continued

153

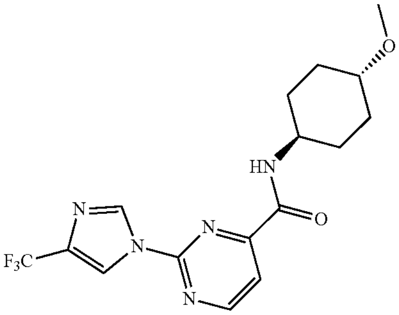

N-((1r,4r)-4-methoxycyclohexyl)-2-(4-(trifluoromethyl)-1H-imidazol-1-yl)pyrimidine-4-carboxamide

154

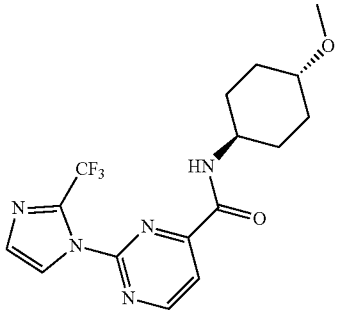

N-((1r,4r)-4-methoxycyclohexyl)-2-(2-(trifluoromethyl)-1H-imidazol-1-yl)pyrimidine-4-carboxamide

155

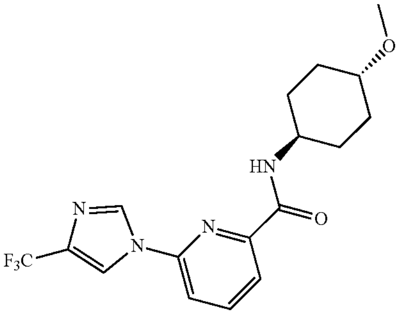

N-((1r,4r)-4-methoxycyclohexyl)-6-(4-(trifluoromethyl)-1H-imidazol-1-yl)picolinamide

156

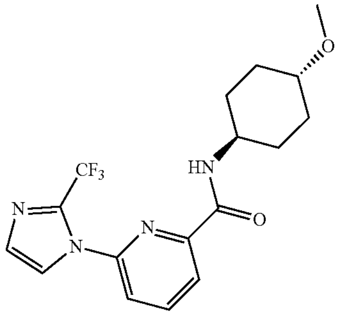

N-((1r,4r)-4-methoxycyclohexyl)-6-(2-(trifluoromethyl)-1H-imidazol-1-yl)picolinamide -continued

157

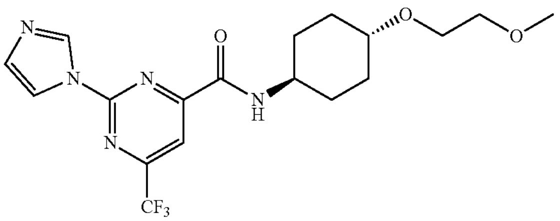

2-(1H-imidazol-1-yl)-N-((1r,4r)-4-(2-methoxyethoxy)cyclohexyl)-6-(trifluoromethyl)pyrimidine-4-carboxamide

158

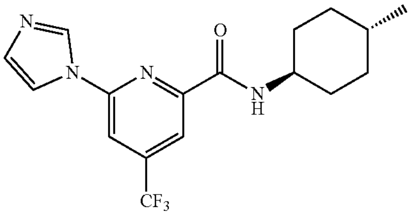

6-(1H-imidazol-1-yl)-N-((1r,4r)-4-methylcyclohexyl)-4-(trifluoromethyl)picolinamide

159

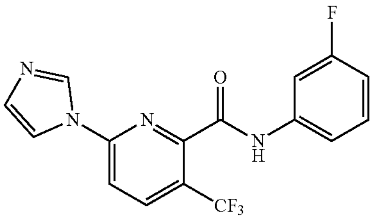

N-(3-fluorophenyl)-6-(1H-imidazol-1-yl)-3-(trifluoromethyl)picolinamide

160

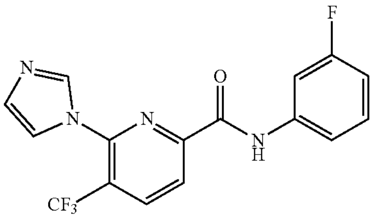

N-(3-fluorophenyl)-6-(1H-imidazol-1-yl)-5-(trifluoromethyl)picolinamide

161

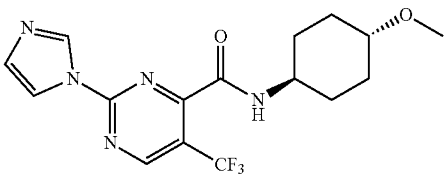

2-(1H-imidazol-1-yl)-N-((1r,4r)-4-methoxycyclohexyl)-5-(trifluoromethyl)pyrimidine-4-carboxamide -continued

162

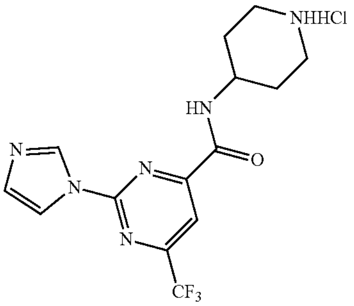

2-(1H-imidazol-1-yl)-N-(piperidin-4-yl)-6-(trifluoromethyl)pyrimidine-4-carboxamide hydrochloride

163

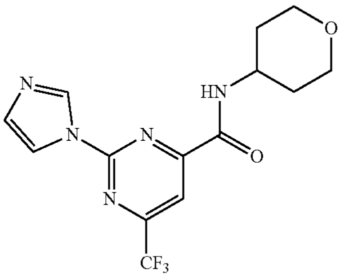

2-(1H-imidazol-1-yl)-N-(tetrahydro-2H-pyran-4-yl)-6-(trifluoromethyl)pyrimidine-4-carboxamide

164

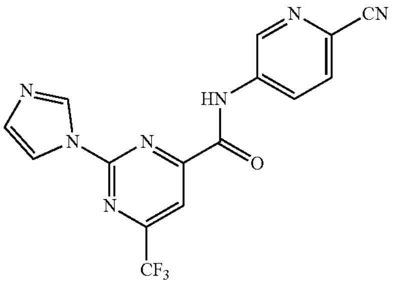

N-(6-cyanopyridin-3-yl)-2-(1H-imidazol-1-yl)-6-(trifluoromethyl)pyrimidine-4-carboxamide

165

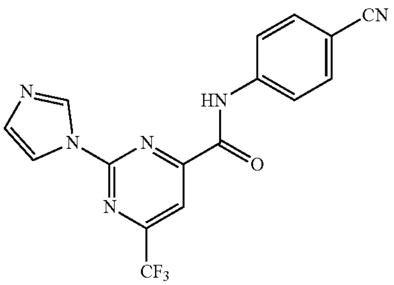

N-(4-cyanophenyl)-2-(1H-imidazol-1-yl)-6-(trifluoromethyl)pyrimidine-4-carboxamide

166

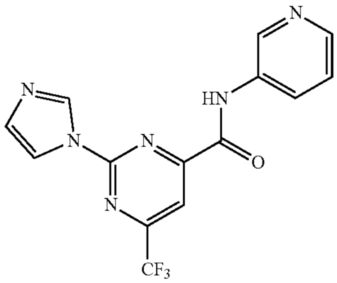

2-(1H-imidazol-1-yl)-N-(pyridin-3-yl)-6-(trifluoromethyl)pyrimidine-4-carboxamide

167

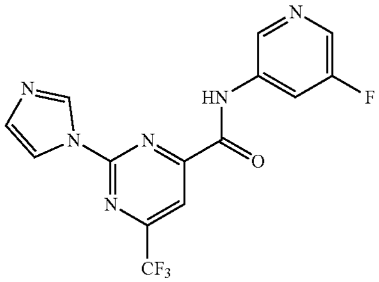

N-(5-fluoropyridin-3-yl)-2-(1H-imidazol-1-yl)-6-(trifluoromethyl)pyrimidine-4-carboxamide

168

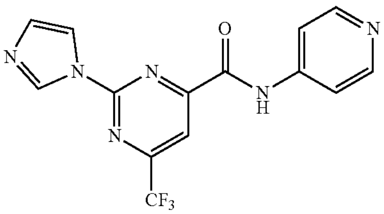

2-(1H-imidazol-1-yl)-N-(pyridin-4-yl)-6-(trifluoromethyl)pyrimidine-4-carboxamide

169

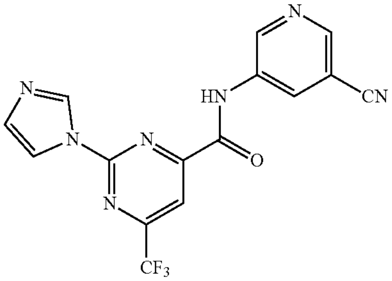

N-(5-cyanopyridin-3-yl)-2-(1H-imidazol-1-yl)-6-(trifluoromethyl)pyrimidine-4-carboxamide

176

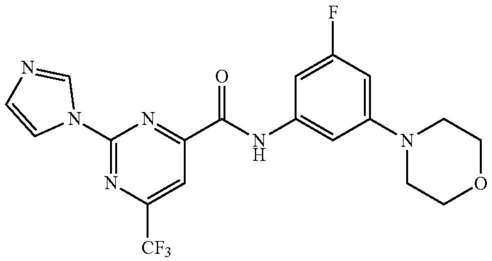

N-(3-fluoro-5-morpholinophenyl)-2-(1H-imidazol-1-yl)-6-(trifluoromethyl)pyrimidine-4-carboxamide

170

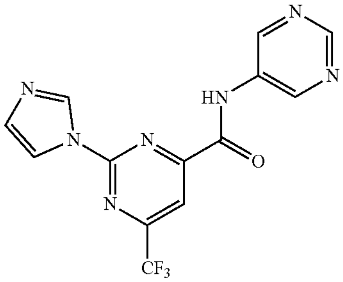

2-(1H-imidazol-1-yl)-N-(pyrimidin-5-yl)-6-(trifluoromethyl)pyrimidine-4-carboxamide

177

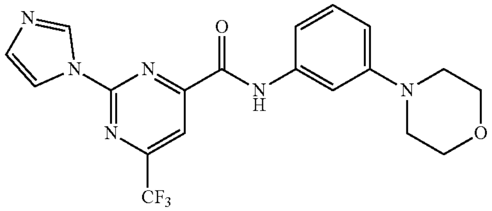

2-(1H-imidazol-1-yl)-N-(3-morpholinophenyl)-6-(trifluoromethyl)pyrimidine-4-carboxamide

171

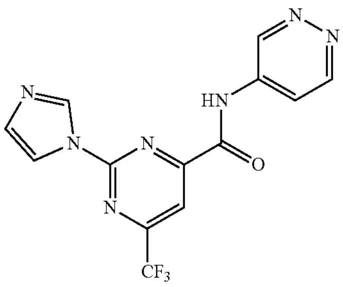

2-(1H-imidazol-1-yl)-N-(pyridazin-4-yl)-6-(trifluoromethyl)pyrimidine-4-carboxamide -continued

178

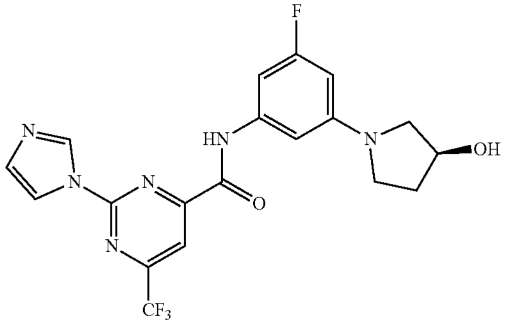

(S)-N-(3-fluoro-5-(3-hydroxypyrrolidin-1-yl)phenyl)-2-(1H-imidazol-1-yl)-6-(trifluoromethyl)pyrimidine-4-carboxamide

172

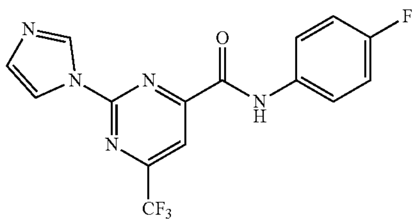

N-(4-fluorophenyl)-2-(1H-imidazol-1-yl)-6-(trifluoromethyl)pyrimidine-4-carboxamide

179

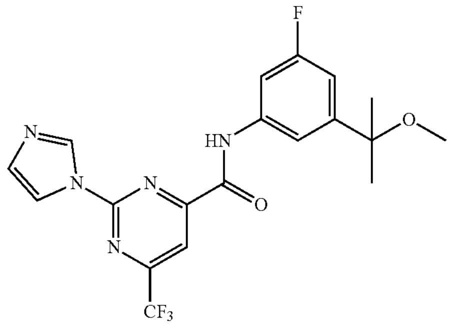

N-(3-fluoro-5-(2-methoxypropan-2-yl)phenyl)-2-(1H-imidazol-1-yl)-6-(trifluoromethyl)pyrimidine-4-carboxamide

173

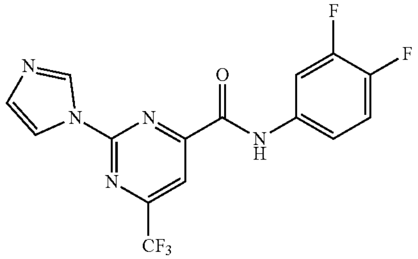

N-(3,4-difluorophenyl)-2-(1H-imidazol-1-yl)-6-(trifluoromethyl)pyrimidine-4-carboxamide -continued

180

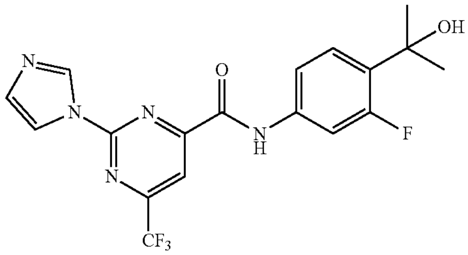

N-(3-fluoro-4-(2-hydroxypropan-2-yl)phenyl)-2-(1H-imidazol-1-yl)-6-(trifluoromethyl)pyrimidine-4-carboxamide

174

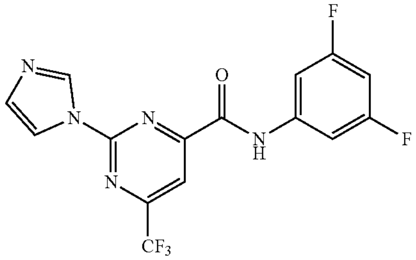

N-(3,5-difluorophenyl)-2-(1H-imidazol-1-yl)-6-(trifluoromethyl)pyrimidine-4-carboxamide

181

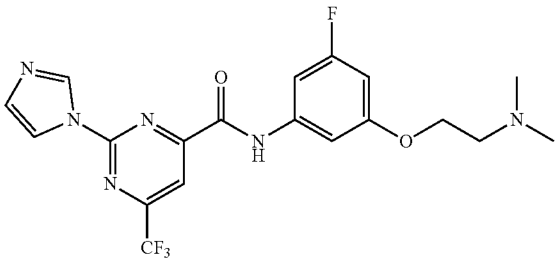

N-(3-(2-(dimethylamino)ethoxy)-5-fluorophenyl-2-(1H-imidazol-1-yl)-6-(trifluoromethyl)pyrimidine-4-carboxamide

175

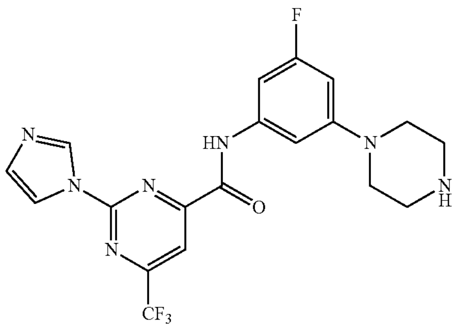

N-(3-fluoro-5-(piperazin-1-yl)phenyl)-2-(1H-imidazol-1-yl)-6-(trifluoromethyl)pyrimidine-4-carboxamide -continued

182

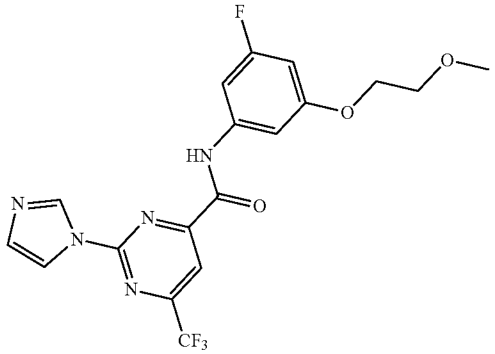

N-(3-fluoro-5-(2-methoxyethoxy)phenyl)-2-(1H-imidazol-1-yl)-6-(trifluoromethyl)pyrimidine-4-carboxamide

183

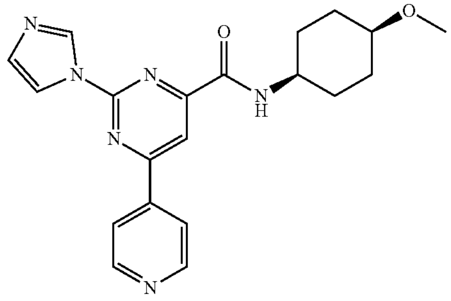

2-(1H-imidazol-1-yl)-N-((1r,4r)-4-methoxycyclohexyl)-6-(pyridin-4-yl)pyrimidine-4-carboxamide

190

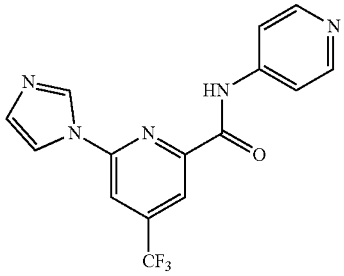

6-(1H-imidazol-1-yl)-N-(pyridin-4-yl)-4-(trifluoromethyl)picolinamide

184

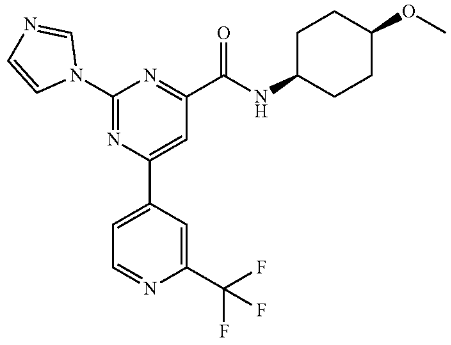

2-(1H-imidazol-1-yl)-N-((1r,4r)-4-methoxycyclohexyl)-6-(2-(trifluoromethyl)pyridin-4-yl)pyrimidine-4-carboxamide -continued

191

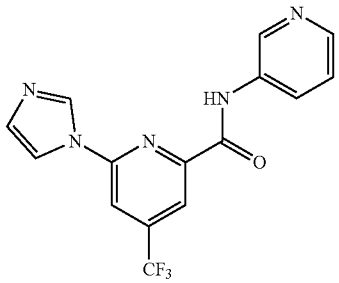

6-(1H-imidazol-1-yl)-N-(pyridin-3-yl)-4-(trifluoromethyl)picolinamide

185

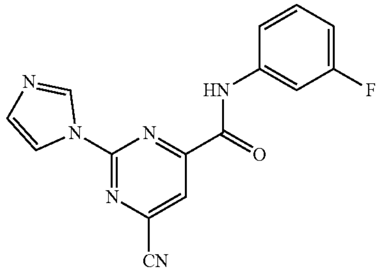

6-cyano-N-(3-fluorophenyl)-2-(1H-imidazol-1-yl)pyrimidine-4-carboxamide

192

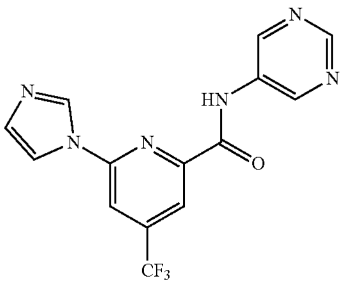

6-(1H-imidazol-1-yl)-N-(pyrimidin-5-yl)-4-(trifluoromethyl)picolinamide

186

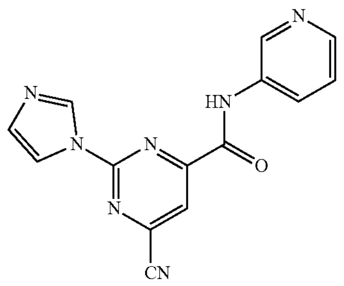

6-cyano-2-(1H-imidazol-1-yl)-N-(pyridin-3-yl)pyrimidine-4-carboxamide

-continued

193

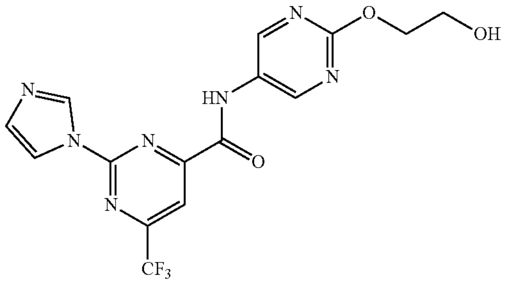

N-(2-(2-hydroxyethoxy)pyrimidin-5-yl)-2-(1H-imidazol-1-yl)-6-(trifluoromethyl)pyrimidine-4-carboxamide

187

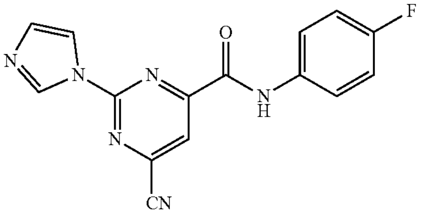

6-cyano-N-(4-fluorophenyl)-2-(1H-imidazol-1-yl)pyrimidine-4-carboxamide

194

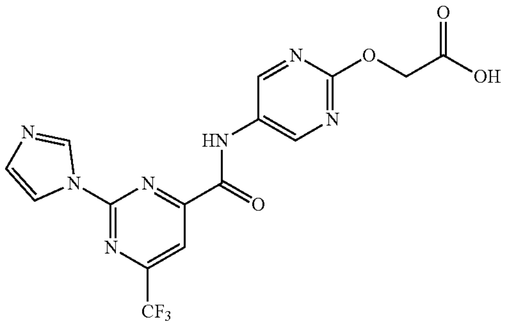

2-((5-(2-(1H-imidazol-1-yl)-6-(trifluoromethyl)pyrimidine-4-carboxamido)pyrimidin-2-yl)oxy)acetic acid

188

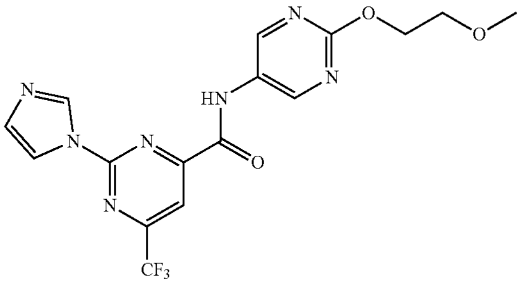

2-(1H-imidazol-1-yl)-N-(2-(2-methoxyethoxy)pyrimidin-5-yl)-6-(trifluoromethyl)pyrimidine-4-carboxamide -continued

195

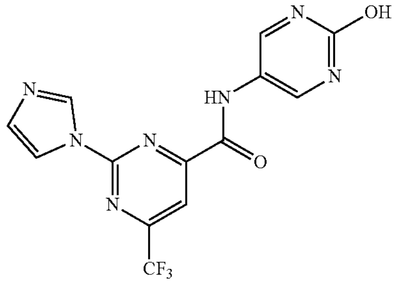

N-(2-hydroxypyrimidin-5-yl)-2-(1H-imidazol-1-yl)-6-(trifluoromethyl)pyrimidine-4-carboxamide

189

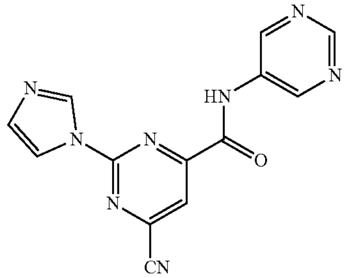

6-cyano-2-(1H-imidazol-1-yl)-N-(pyrimidin-5-yl)pyrimidine-4-carboxamide

In another aspect, the invention provides a pharmaceutical composition, comprising a compound of formula I described above, or a pharmaceutically acceptable salt thereof; and a pharmaceutically acceptable carrier or excipient.

In yet another aspect, the invention provides the use of a compound of formula I or a pharmaceutical composition described above, for the treatment of a disease mediated by CD38.

Preferably, the disease mediated by CD38 is neurodegenerative disease selected from dementia, Alzheimer's disease (AD), Parkinson's disease;

tumor selected from glioblastomas, lung cancer, colon cancer, liver cancer, breast cancer, gastric cancer, bladder cancer, melanoma;

autoimmune disease selected from diabetes, rheumatoid arthritis (RA), multiple sclerosis (MS), systemic lupus erythematosus (SLE);

inflammatory disease selected from asthma, chronic obstructive pulmonary disease (COPD), pneumonia, non-alcoholic steatohepatitis (NASH).

In yet another aspect, the invention provides the use of compound of formula I or a pharmaceutical composition described above, for the production of a medicine for the treatment of a disease mediated by CD38.

Preferably, the disease mediated by CD38 is neurodegenerative disease selected from dementia, Alzheimer's disease (AD), Parkinson's disease;

tumor selected from glioblastomas, lung cancer, colon cancer, liver cancer, breast cancer, gastric cancer, bladder cancer, melanoma;

autoimmune disease selected from diabetes, rheumatoid arthritis (RA), multiple sclerosis (MS), systemic lupus erythematosus (SLE);

inflammatory disease selected from asthma, chronic obstructive pulmonary disease (COPD), pneumonia, non-alcoholic steatohepatitis (NASH).

In yet another aspect, the invention provides a method of treating a disease mediated by CD38 in a subject in need thereof, comprising administering to the subject, a therapeutically effective amount of a compound of formula I described above, or a pharmaceutically acceptable salt thereof.

Preferably, the disease mediated by CD38 is neurodegenerative disease selected from dementia, Alzheimer's disease (AD), Parkinson's disease;

tumor selected from glioblastomas, lung cancer, colon cancer, liver cancer, breast cancer, gastric cancer, bladder cancer, melanoma;

autoimmune disease selected from diabetes, rheumatoid arthritis (RA), multiple sclerosis (MS), systemic lupus erythematosus (SLE);

inflammatory disease selected from asthma, chronic obstructive pulmonary disease (COPD), pneumonia, non-alcoholic steatohepatitis (NASH).

More preferably, the subject is human.

In yet another aspect, the invention provides a method of inhibiting CD38 function, comprising contacting a compound of formula I described above, or a pharmaceutically acceptable salt thereof, with the CD38.

In an embodiment, the CD38 is in a cell.

In another embodiment, the contacting occurs in vitro. In yet another embodiment, the contacting occurs in vivo.

DETAILED DESCRIPTION OF THE INVENTION

Definitions

In the invention, the following definitions are applicable:

The phase "CD38 inhibitor" includes any and all possible isomers, stereoisomers, enantiomers, diastereomers, tautomers, pharmaceutically acceptable salts, hydrates, solvates, and prodrugs of the CD38 inhibitors described in this invention.

The articles "a" and "an" are used in this invention to refer to one or more than one (i.e., to at least one) of the grammatical object of the article. By way of example, "an element" means one element or more than one element.

The term "and/or" is used in this invention to mean either "and" or "or" unless indicated otherwise.

The term "heterocycle" as used in this invention refers to a cyclic hydrocarbon containing 3-10 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane. In some embodiments, a heterocycle is a 5 or 6 membered unsaturated monocyclic heterocycle containing 1 to 3 heteroatoms selected from the group consisting of N, O and S. In further embodiments, a 5 or 6 membered unsaturated monocyclic heterocycle containing 1 to 3 heteroatoms selected from the group consisting of N, O and S is aromatic, and includes, but not limited to imidazolyl, pyrazolyl, isoxazolyl, oxazolyl, isothiazolyl, thiazolyl, triazolyl, oxadiazolyl, pyridinyl, pyrimidinyl, pyrazinyl or pyridazinyl.

The term "$C_{1-6}$ alkyl", alone or in combination with other groups, refers to a straight-chained or branched alkyl group having 1 to 6 carbon atoms. Examples of a $C_{1-6}$ alkyl group include, but are not limited to, methyl, ethyl, propyl, butyl, pentyl, hexyl, isopropyl, isobutyl, sec-butyl, tert-butyl, isopentyl, and neopentyl.

The term "$C_{2-6}$ alkynyl", alone or in combination with other groups, refers to alkynyl groups preferably having from 2 to 6 carbon atoms and having at least 1-2 sites of alkynyl unsaturation, preferred alkynyl groups include ethynyl ($—C≡CH$), propargyl ($—CH_2C≡CH$), and the like.

The term "$C_{3-8}$ cycloalkyl" refers to a cyclic hydrocarbon containing 3-8 carbon atoms. Examples of a cycloalkyl group include, but are not limited to, cyclopropyl, cyclobutyl, cyclopentyl, cyclohexyl, cycloheptyl and cyclooctyl. It is understood that any of the substitutable hydrogens on a cycloalkyl can be substituted with halogen, $C_1$-$C_3$ alkyl, hydroxyl, alkoxy and cyano groups. In some embodiments, "$C_{3-8}$ cycloalkyl" optionally has one or two carbon atoms replaced with N, O or S. Examples of such a cycloalkyl include, but are not limited to, oxiranyl, aziridinyl, oxetanyl, azetidinyl, tetrahydrofuranyl, pyrrolidinyl, tetrahydrothiophenyl, tetrahydrothiopyranyl, tetrahydropyranyl, piperidinyl, piperazinyl, morpholinyl or thiomorpholinyl.

The term "$C_{1-6}$ alkoxy", alone or in combination with other groups, refers to the group R'—O—, wherein R' is a $C_{1-6}$ alkyl. Examples of a $C_{1-6}$ alkoxy group include, but are not limited to, methoxy, ethoxy, propoxy, isopropoxy, butoxy, isobutoxy, sec-butoxy, tert-butoxy, pentyloxy, isopentyloxy, neopentyloxy, tert-pentyloxy, and hexyloxy.

The term "$C_{3-6}$ cycloalkoxy", alone or in combination with other groups, refers to the group R"—O—, wherein R" is a $C_{3-6}$ cycloalkyl. Examples of a $C_{3-6}$ cycloalkoxy group include, but are not limited to, cyclopropoxy, cyclobutoxy, cyclopentyloxy and cyclohexyloxy.

The term "halogen" or "halo" refers to fluoro, chloro, bromo or iodo. Preferred "halogen" groups are fluoro, chloro or bromo.

The term "phenyl" group refers to a group formed by removing one hydrogen from benzene. In some embodiments, a phenyl group optionally has one or two carbon atoms replaced with N, and include, but are limited to, pyridinyl, pyrimidinyl, pyrazinyl or pyridazinyl.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group.

Where a given group (moiety) is described in this invention as being attached to a second group and the site of attachment is not explicit, the given group may be attached at any available site of the given group to any available site of the second group. For example, a "$C_{1-6}$ alkyl-substituted phenyl", where the attachment sites are not explicit, may have any available site of the $C_{1-6}$ alkyl attached to any available site of the phenyl group. In this regard, an "available site" is a site of the group at which a hydrogen of the group may be replaced with a substituent.

"Pharmaceutically acceptable salts" refers to those salts which retain the biological effectiveness and properties of the free bases and which are obtained by reaction with inorganic acids, for example, acid, hydrobromic acid, sulfuric acid, nitric acid, and phosphoric acid or organic acids such as sulfonic acid, carboxylic acid, organic phosphoric acid, methanesulfonic acid, ethanesulfonic acid, toluenesulfonic acid, citric acid, fumaric acid, maleic acid, succinic acid, benzoic acid, salicylic acid, lactic acid, tartaric acid (e, (+) or (−)-tartaric acid or mixtures thereof), amino acids (e.g., (+) or (−)-amino acids or mixtures thereof), and the like. These salts can be prepared by methods known to those skilled in the art. "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

The term "carrier", as used in this invention, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The phase "effective amount" means an amount of a compound according to the invention which, in the context of which it is administered or used, is sufficient to achieve the desired effect or result. Depending on the context, the phase effective amount may include or be synonymous with a pharmaceutically effective amount or a therapeutically effective amount. An effective amount can be determined by methods known to those of skill in the art.

A compound of a given formula (e.g., compound of Formula I) is intended to encompass the compounds of the invention, and the pharmaceutically acceptable salts, pharmaceutically acceptable esters, isomers, tautomers, solvates, isotopes, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means.

The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(+)" is used to designate a racemic mixture where appropriate.

"Diastereoisomers" are stereoisomers that have at least two asymmetric atoms, but which are not mirror-images of each other.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of the present invention and a solvent.

The term "hydrate" refers to the complex formed by the combining of a compound of the present invention and water.

The term "prodrug" refers to compounds of the present invention that include chemical groups which, in vivo, can be converted and/or can be split off from the remainder of the molecule to provide for the active drug, a pharmaceutically acceptable salt thereof or a biologically active metabolite thereof.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably in this invention.

The term "inhibition", "inhibit" or "inhibiting" indicates a significant decrease in the baseline activity of a biological activity or process.

The term "disease" is used in this invention to mean, and is used interchangeably with, the terms disorder, condition, or illness, unless otherwise indicated.

The phrase "neurodegenerative disease" is used in this invention to define a disease characterized by progressive loss of cognitive functions, progressive loss of control of motoric functions and/or progressive loss of motoric functions. Preferably, the neurodegenerative disease is selected from the group consisting of dementia, Alzheimer's disease (AD), Multi-infarct Dementia (MID), Pick's disease, Parkinson's disease, ALS, TIA, and stroke. More preferably, the neurodegenerative disease is dementia, Alzheimer's disease (AD), or Parkinson's disease.

The term "tumor", as used in this invention, refers to an abnormal growth of tissue. A tumor may be benign or malignant. Generally, a malignant tumor is referred to as a cancer. Cancers differ from benign tumors in the ability of malignant cells to invade other tissues, either by direct growth into adjacent tissue through invasion or by implantation into distant sites by metastasis (i.e., transport through the blood or lymphatic system). Preferably, the tumor is selected from the group consisting of glioblastomas, lung cancer, colon cancer, liver cancer, breast cancer, gastric cancer, bladder cancer, melanoma.

The phase "autoimmune disease", as used in this invention, refers to a disease which arises from an inappropriate immune response of the body against substances and tissues normally present in the body (autoimmunity) of a patient. The symptoms of autoimmune diseases can range from fatigue and mild rashes to rare, serious warning signs, like seizures. Preferably, the autoimmune disease is selected from the group consisting of rheumatoid arthritis (RA), multiple sclerosis (MS), sarcoidosis, psoriasis, Crohn's disease, systemic lupus erythematosus (SLE), and diabetes mellitus type 1, and more preferably the autoimmune disease is selected from the group consisting of diabetes, rheumatoid arthritis (RA), multiple sclerosis (MS), and systemic lupus erythematosus (SLE).

The phase "inflammatory disease", as used in this invention, refers to a disease caused by, resulting from, or resulting in inflammation. The phase "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory disease preferably is asthma, chronic obstructive pulmonary disease (COPD), pneumonia, non-alcoholic steatohepatitis (NASH).

The term "treating", with regard to a subject, refers to improving at least one symptom of the subject's disease. Treating can be curing, improving, or at least partially ameliorating the disease.

The term "administer", "administering", or "administration", as used in this invention, refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

Pharmaceutical Compositions and Administration

The invention also includes pharmaceutical compositions useful for treating a disease mediated by CD38, or for inhibiting CD38 function, and the like. The compositions can be suitable for internal use and comprise an effective amount of compound of the invention as CD38 inhibitor and a pharmaceutically acceptable carrier. The CD38 inhibitors are especially useful in that they demonstrate very low systemic toxicity or no systemic toxicity.

The CD38 inhibitors can each be administered in amounts that are sufficient to treat or prevent but are not limited to cardiovascular and cerebrovascular diseases, neurodegenerative diseases, autoimmune diseases and inflammatory diseases, fibrotic diseases, metabolic disorders, and tumors or prevent the development thereof in subjects.

Administration of the CD38 inhibitors can be accomplished via any mode of administration for therapeutic agents. These modes include systemic or local administration such as oral, nasal, parenteral (intravenous), intramuscular, intrathecal, intra-vitreal, transdermal, subcutaneous, vaginal, buccal, rectal, topical administration modes or as a drug-eluting stent.

Depending on the intended mode of administration, the compositions can be in solid, semi-solid or liquid dosage form, such as injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, intra-vitreal injection, subcutaneous or intramuscular form, all using forms well known to those skilled in the pharmaceutical arts.

Illustrative pharmaceutical compositions are tablets and gelatin capsules comprising a CD38 inhibitor and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the CD38 inhibitor is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the CD38 inhibitors.

The CD38 inhibitors can be also formulated as a suppository that can be prepared from fatty emulsions or suspensions; using polyalkylene glycols such as propylene glycol, as the carrier.

In further embodiments, the pharmaceutical formulations described in this invention include, but are not limited to, aqueous liquid dispersions, self-emulsifying dispersions, solid solutions, liposomal dispersions, aerosols, solid dosage forms, powders, immediate release formulations, controlled release formulations, fast melt formulations, delayed release formulations, extended release formulations, pulsatile release formulations, multiparticulate formulations, and mixed immediate and controlled release formulations The CD38 inhibitors can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

CD38 inhibitors can also be delivered by the use of monoclonal antibodies as individual carriers to which the CD38 inhibitors are coupled. The CD38 inhibitors can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the CD38 inhibitors can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, CD38 inhibitors are not covalently bound to a polymer, e.g., a polycarboxylic acid polymer, or a polyacrylate.

Parenteral injectable administration is generally used for subcutaneous, intramuscular, or intravenous injections and infusions. Injectables can be prepared in conventional forms, either as liquid solutions or suspensions or solid forms suitable for dissolving in liquid prior to injection.

Compositions can be prepared according to conventional mixing, granulating, or coating methods, respectively, and the present pharmaceutical compositions can contain from about 0.1% to about 80%, from about 5% to about 60%, or from about 1% to about 20% of the CD38 inhibitor by weight or volume.

The dosage regimen utilizing the CD38 inhibitor is selected in accordance with a variety of factors including type, species, age, weight, sex, race, diet, and medical condition of the patient; the severity of the condition to be treated; the route of administration; the renal or hepatic function of the patient; and the particular CD38 inhibitor employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 0.1 mg to about 5000 mg of the active ingredient per unit dose which could be administered. In one embodiment, the compositions are in the form of a tablet that can be scored. Appropriate dosages of the CD38 inhibitors can be determined as set forth in Goodman, L. S.; Gilman, A. The Pharmacological Basis of Therapeutics, 5th ed.; MacMillan: New York, 1975, pp. 201-226.

CD38 inhibitors can be administered in a single daily dose, or the total daily dosage can be administered in divided doses of two, three or four times daily. Furthermore, CD38 inhibitors can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the CD38 inhibitor can range from about 0.1% to about 15%, w/w or w/v.

Uses of Compounds and Compositions Thereof

The compounds as CD38 inhibitors and compositions described above can be used to treat or prevent CD38-associated diseases. These diseases include, but are not limited to, neurodegenerative diseases, autoimmune diseases, tumors, or chronic or acute inflammatory diseases. Examples of such diseases or conditions include:

- neurodegenerative diseases, including but not limited to, dementia, Alzheimer's disease (AD), Parkinson's disease, ALS, TIA, stroke;
- rheumatic diseases (including but not limited to rheumatoid arthritis, osteoarthritis, psoriatic arthritis), spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, polymyalgia rheumatica;
- connective tissue diseases, including but not limited to, systemic lupus erythematosus, systemic sclerosis, polymyositis, dermatomyositis, Sjögren's syndrome;

vasculitides, including but not limited to, polyarteritis nodosa, Wegener's granulomatosis, Churg-Strauss syndrome;

- inflammatory diseases including asthma, chronic obstructive pulmonary disease (COPD), pneumonia, non-alcoholic steatohepatitis (NASH), consequences of trauma or ischaemia;
- sarcoidosis;
- vascular diseases including atherosclerotic vascular disease and infarction, atherosclerosis, and vascular occlusive disease (including but not limited to atherosclerosis, ischaemic heart disease, myocardial infarction, stoke, peripheral vascular disease), and vascular stent restenosis;
- autoimmune diseases, including but not limited to, diabetes mellitus, thyroiditis, myasthenia gravis, sclerosing cholangitis, primary biliary cirrhosis, rheumatoid arthritis (RA), multiple sclerosis (MS), systemic lupus erythematosus (SLE);
- pulmonary diseases, including but not limited to, diffuse interstitial lung diseases, pneumoconioses, fibrosing alveolitis, asthma, bronchitis, bronchiectasis, chronic obstructive pulmonary disease, adult respiratory distress syndrome;
- tumors whether primary or metastatic, including but not limited to, glioblastomas, prostate cancer, colon cancer, lymphoma, lung cancer, liver cancer, gastric cancer, bladder cancer, melanoma, multiple myeloma, breast cancer, stomach cancer, leukaemia, cervical cancer and metastatic cancer;
- renal diseases including glomerulonephritis, interstitial nephritis;
- disorders of the hypothalamic-pituitary-adrenal axis;
- diseases characterised by modified angiogenesis (eg diabetic retinopathy, rheumatoid arthritis, cancer), endometrial function (menstruation, implantation, endometriosis);
- complications of infective disorders including endotoxic (septic) shock, exotoxic (septic) shock, infective (true septic) shock, malarial complications, other complications of infection, pelvic inflammatory disease;
- transplant rejection, graft-versus-host disease;
- allergic diseases including allergies, atopic diseases, allergic rhinitis;
- bone diseases (eg osteoporosis, Paget's disease);
- skin diseases including psoriasis, atopic dermatitis, UV(B)-induced dermal cell activation (eg sunburn, skin cancer); pain, testicular dysfunctions and wound healing;
- gastrointestinal diseases including inflammatory bowel disease (including but not limited to ulcerative colitis, Crohn's disease), peptic ulceration, gastritis, oesophagitis, liver disease (including but not limited to cirrhosis, hepatitis).

Combination Therapy

CD38 inhibitors can be used in combination with one or more additional therapeutic agents (e.g., therapeutic compounds, compositions, treatments, therapies, and/or medical procedures). In such combination therapies, therapeutic agents of the invention may be formulated with or administered concurrently with, prior to, or subsequent to, one or more other desired therapies. The particular combination of therapies to employ in a combination regimen will take into account compatibility of the desired therapeutics and/or procedures and the desired therapeutic effect to be achieved. It will also be appreciated that the therapies employed may achieve a desired effect for the same condition, disease, or disorder, or they may achieve different effects (e.g., control of any adverse effects).

In general, for use in treatment, the compounds described herein may be used alone, as mixtures of two or more compounds, or in combination with other agents, compounds, and/or pharmaceuticals. Examples of other agents that can be combined with the compounds described herein include agents that are known to be used for the treatment of neurodegenerative diseases, inflammatory diseases, autoimmune diseases, or tumors. Another example of a potential agent to combine with the compounds described herein would include agents for the treatment of different yet associated or related symptoms or indications. Depending on the mode of administration, the agents may be formulated into suitable compositions to permit facile delivery. Each component of a combination therapy may be formulated in a variety of ways that are known in the art. For example, the first and second agents of the combination therapy may be formulated together or separately. The compound of the present invention and additional agent may be suitably administered to the patient at one time or over a series of treatments.

As described herein, in some embodiments, the combination therapy may provide "synergy" and prove to be "synergistic," i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds, agents, and/or treatments are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together. Suitable dosages for any of the above co-administered agents are those presently used and may be lowered due to the combined action (synergy) of a compound of the present invention and other co-administered agents or treatments.

Each compound of a combination therapy, as described herein, may be formulated in a variety of ways that are known in the art. For example, the first and second agents of the combination therapy may be formulated together or separately. The individually or separately formulated agents can be packaged together as a kit. Non-limiting examples include, but are not limited to, kits that contain, e.g., two pills, a pill and a powder, a suppository, and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, bl-Ver packs, bottles, tubes, and the like. Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Selection of the appropriate agents for use in combination therapy may be made by one of ordinary skill in the art, according to conventional pharmaceutical principles. One may be able to achieve therapeutic efficacy with lower dosages of each agent, thus reducing the potential for adverse side effects.

General Synthesis

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods.

Compounds of the present invention can be prepared beginning with commercially starting materials and utilizing general synthetic techniques and procedures known to those skilled in the art. Outlined below are reaction schemes suitable for preparing such compounds. Further exemplification is found in the specific Examples detailed below.

The compounds disclosed in this invention may have chiral centers, e.g., chiral carbon atoms. Such compounds thus include racemic mixtures of all stereoisomers, including enantiomers, diastereomers, and atropisomers. In addition, the compounds disclosed in this invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

Scheme 1

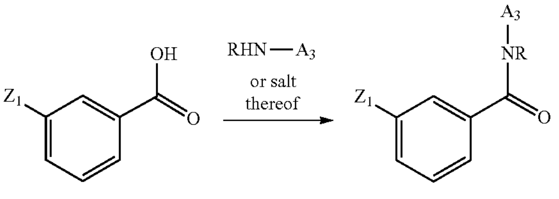

I-1 I-2

In scheme 1, the reaction between I-1 and NHR-$A_3$ or salt thereof gives I-2 under appropriate condition (e.g., using HATU, DIEA, DMF/DCM). R and $A_3$ are the same as described in this invention; $Z_1$ is a leaving group such as, but not limited to, halogen, acetyl, amino; and

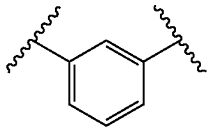 [SMILES: *c1cccc(*)c1]

optionally has one or two carbon atoms replaced with nitrogen, and is optionally substituted with 0 or 1 —OH, —CN, —F, —Cl, methyl, isopropyl, trifluoromethyl, methoxy, isopropoxy, cyclobutoxy, oxetan-3-yloxy, ethynyl, $—NH_2$, $—NHCH_3$, $—N(CH_3)_2$, $—NHC(O)CH_3$,

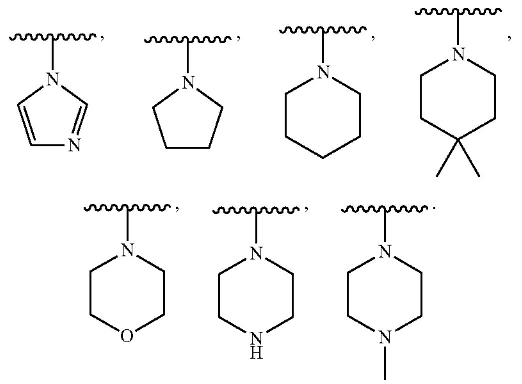

Scheme 2

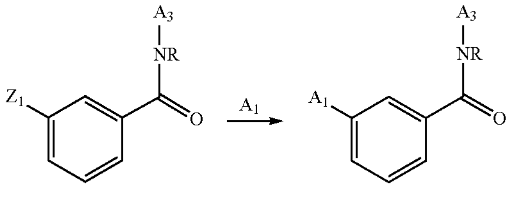

I-2 C

In scheme 2, the reaction between I-2 and $A_1$ gives C under appropriate condition (e.g., using NaH, THF, heat). $A_1$, R and $A_3$ are the same as described in this invention; Z1 is a leaving group such as, but not limited to, halogen, acetyl, amino; and

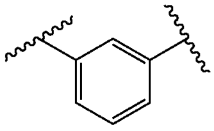 [SMILES: *c1cccc(*)c1]

optionally has one or two carbon atoms replaced with nitrogen, and is optionally substituted with 0 or 1 —OH, —CN, —F, —Cl, methyl, isopropyl, trifluoromethyl, methoxy, isopropoxy, cyclobutoxy, oxetan-3-yloxy, ethynyl, $—NH_2$, $—NHCH_3$, $—N(CH_3)_2$, $—NHC(O)CH_3$,

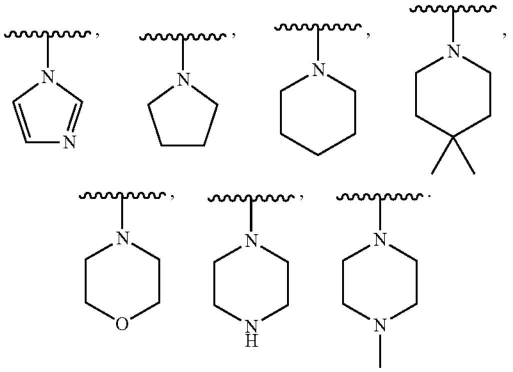

Scheme 3

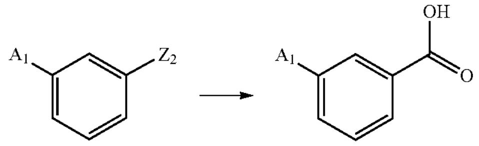

III-1 III-2

In scheme 3, III-2 may be made from III-1 by a two-step procedure. Firstly, III-1 is converted to a carboxylate under appropriate condition (e.g., using CO, $Et_3N$, $Pd(dppf)Cl_2$, MEOH, heat). Secondly, the carboxylate is converted to the carboxylic acid III-2 under appropriate condition (e.g., using NaOH, $H_2O$, MeOH, heat). $A_1$ is the same as described in this invention; $Z_2$ is a leaving group such as, but not limited to, halogen, acetyl, amino; and

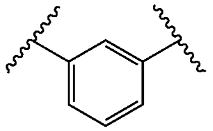

optionally has one or two carbon atoms replaced with nitrogen, and is optionally substituted with 0 or 1 —OH, —CN, —F, —Cl, methyl, isopropyl, trifluoromethyl, methoxy, isopropoxy, cyclobutoxy, oxetan-3-yloxy, ethynyl, $—NH_2$, $—NHCH_3$, $—N(CH_3)_2$, $—NHC(O)CH_3$,

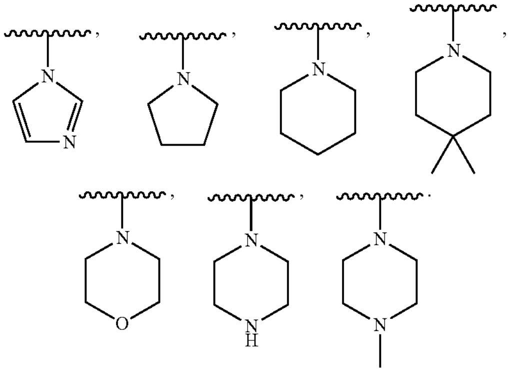

Scheme 4

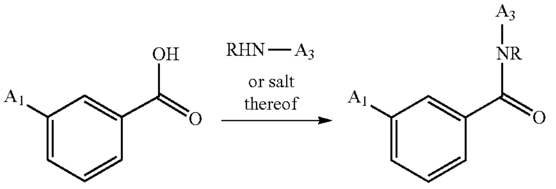

III-2 C

In scheme 4, the reaction between III-2 and NHR-$A_3$ or salt thereof gives C under appropriate condition (e.g., using CuI, $Cs_2CO_3$, DMF, heat, MW). $A_1$, R and $A_3$ are the same as described in this invention; and

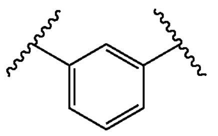 [SMILES: *c1cccc(*)c1]

optionally has one or two carbon atoms replaced with nitrogen, and is optionally substituted with 0 or 1 —OH, —CN, —F, —Cl, methyl, isopropyl, trifluoromethyl, methoxy, isopropoxy, cyclobutoxy, oxetan-3-yloxy, ethynyl, —$NH_2$, —$NHCH_3$, —$N(CH_3)_2$, —$NHC(O)CH_3$,

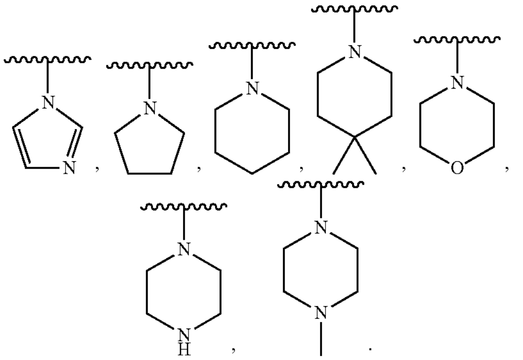

EXAMPLES

The present invention can be better understood according to the following examples. However, it would be easy for a person skilled in the art to understand that the contents described in the examples are merely intended to illustrate the present invention rather than limit the present invention described in detail in the claims.

Unless otherwise indicated, compounds of the present invention can be prepared beginning with commercially starting materials and utilizing general synthetic techniques and procedures known to those skilled in the art. Chromatography supplies and equipment may be purchased from such companies as for example AnaLogix, Inc, Burlington, WI; Analytical Sales and Services, Inc., Pompton Plains, NJ; Teledyne Isco, Lincoln, NE; VWR International, Bridgeport, NJ; and Rainin Instrument Company, Woburn, MA. Chemicals and reagents may be purchased from companies such as for example Aldrich, Argonaut Technologies, VWR and Lancaster, Invitrogen, Sigma, Promega, Solarbio, Cisbio, Signalchem, MCE. Consumables may be purchased from companies such as for example Corning, Labcyte, Greiner, Nunc. Instruments may be purchased from companies such as for example Labcyte, PerkinElmer, Eppendorf, Thermo Fisher.

Example 1

4,6-di (1H-imidazol-1-yl)-N-((1r,4r)-4-methoxycyclohexyl)picolinamide (compound 1) and 6-chloro-4-(1H-imidazol-1-yl)-N-((1r,4r)-4-methoxycyclohexyl)picolinamide (compound 2)

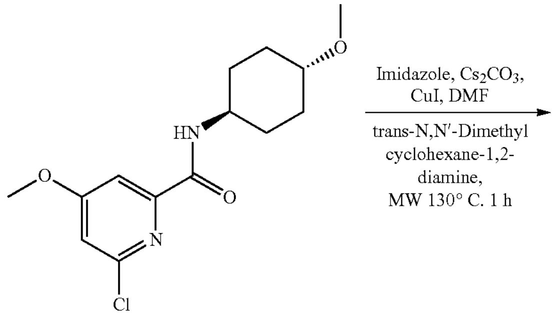

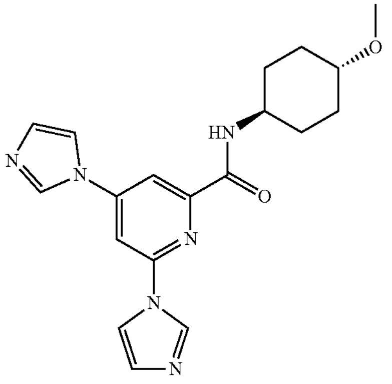

1

+

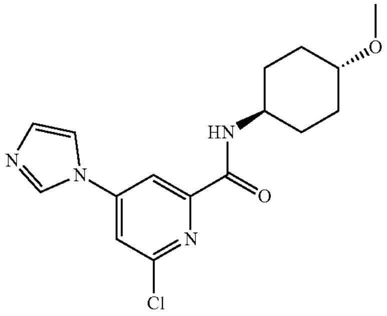

2

A mixture of 6-chloro-4-methoxy-N-((1r,4r)-4-methoxycyclohexyl)picolinamide (150 mg, 0.503 mmol), trans-N,N'-dimethylcyclohexane-1,2-diamine (14.2 mg, 0.10 mmol), imidazole (68.0 mg, 1.00 mmol), CuI (4.7 mg, 0.025 mmol), $Cs_2CO_3$ (327 mg, 1.00 mmol) in DMF (2 mL) was bubbled with $N_2$ for 3 minutes. The reaction tube was sealed and heated at 120° C. in a microwave reactor for 30 minutes. The reaction mixture was cooled and purified with prep-HPLC (Waters 2767/2545/2489/Qda, Column name: Inertsil ODS-3 10 μm 20*250 nm, Mobile Phase A: 0.1% HCOOH in water, Mobile Phase B: $CH_3CN$, Flow: 20 mL/min: Column temp: RT)) to afford compound 1 (9.74 mg, 5.3% yield) as a white solid. MS (ESI): m/z 367.1 $[M+H]^+$; $^1H$ NMR (400 MHZ, $CDCl_3$) δ 9.03 (s, 1H), 8.76 (s, 1H), 8.64 (d, J=8.6 Hz, 1H), 8.36 (s, 1H), 8.26 (s, 1H), 8.23-8.17 (m, 2H), 7.21 (d, J=9.0 Hz, 2H), 3.90-3.85 (m, 1H), 3.26 (s, 3H), 3.14 (s, 1H), 2.10-2.04 (m, 2H), 1.89-1.82 (m, 2H), 1.64-1.54 (m, 2H), 1.29-1.20 (m, 2H); and compound 2 (34.58 mg, 20.6% yield) as a white solid. MS (ESI): m/z 335.0 $[M+H]^+$; $^1H$ NMR (400 MHZ, $CDCl_3$) δ 8.71 (s, 1H), 8.47 (d, J=8.3 Hz, 1H), 8.28 (d, J=1.9 Hz, 1H), 8.20 (d, J=2.0 Hz, 1H), 8.14 (s, 1H), 7.19 (s, 1H), 3.84-3.76 (m, 1H), 3.24 (s, 3H), 3.11-3.09 (m, 1H), 2.03-2.01 (m, 2H), 1.84-1.81 (m, 2H), 1.54-1.51 (m, 2H), 1.23-1.20 (m, 2H).

Example 2

4-(1H-imidazol-1-yl)-N-((1r,4r)-4-methoxycyclohexyl)-6-oxo-1.6-dihydropyridine-2-carboxamide (compound 3)

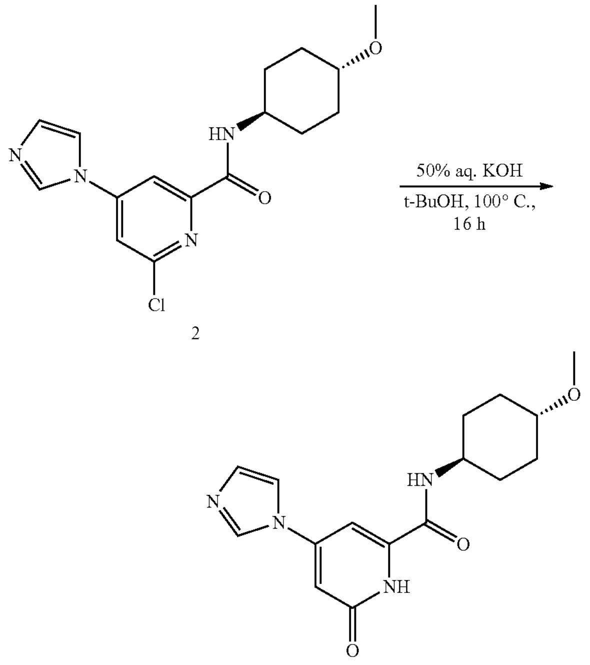

2

3

A mixture of compound 2 (180 mg, 0.53 mmol) in t-BuOH (6 mL) and 50% aqueous KOH (2 mL) was heated to reflux for 16 hours. The solution was cooled to room temperature and purified by prep-HPLC (Waters 2767/2545/2489, Waters Xbridge C18 10 μm OBD 19*250 mm, Mobile Phase A: 0.1% FA in water, Mobile Phase B: $CH_3CN$, Flow: 20 mL/min, Column temp: RT) afford the titled compound (13.49 mg, 7.9% yield) as a white solid. MS (ESI): m/z 335.0 $[M+H]^+$; $^1H$ NMR (400 MHZ, DMSO-$d_6$) δ 11.88 (s, 1H), 9.51 (s, 1H), 8.33 (s, 1H), 7.70 (s, 1H), 7.20 (s, 1H), 3.80-3.70 (m, 1H), 3.25 (s, 3H), 3.18-3.10 (m, 1H), 2.02 (dd, J=12.2, 2.6 Hz, 2H), 1.90 (dd, J=12.8, 2.2 Hz, 2H), 1.45-1.33 (m, 2H), 1.30-1.17 (m, 2H).

Example 3

6-(1H-imidazol-1-yl)-4-methoxy-N-((1r,4r)-4-methoxycyclohexyl)picolinamide (compound 4)

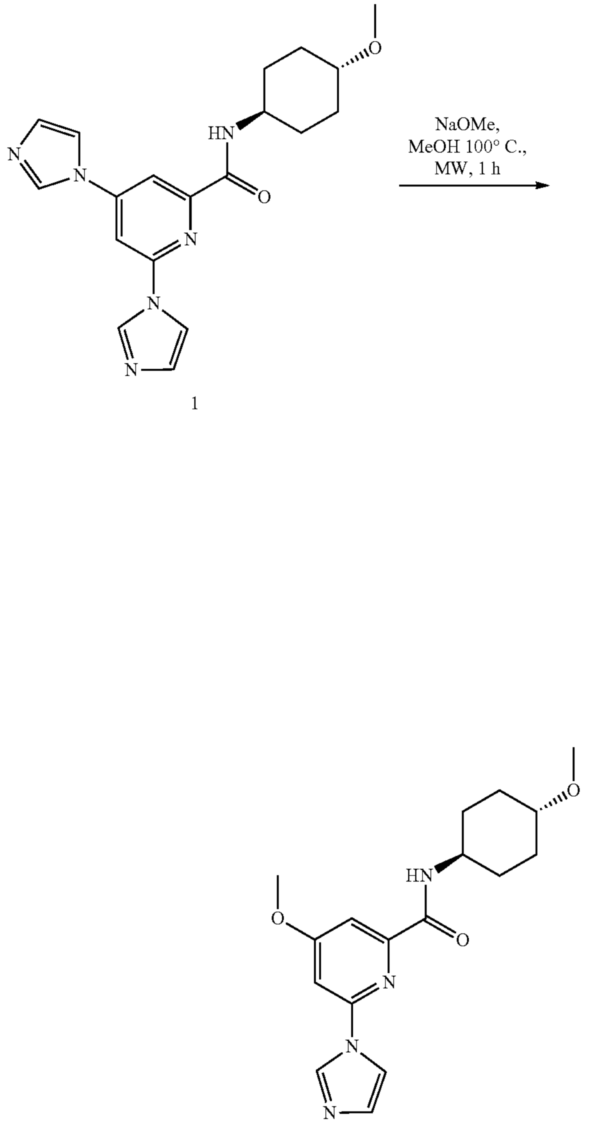

1

4

A solution of compound 1 (100 mg, 0.272 mmol) in MeOH (5 mL) was treated with MeONa (14.0 mg, 0.272 mmol). The resulting reaction mixture was heated at 100° C. in a microwave reactor for 1 hour. The solvent was removed in vacuum and the residue was purified by silica gel chromatography ($CH_2Cl_2$/MeOH=100/1-40/1) to afford the titled compound (30.29 mg, 67.2% yield) as a white solid. MS (ESI): m/z 335.5 $[M+H]^+$; $^1H$ NMR (400 MHZ, DMSO-$d_6$) δ 8.94 (s, 1H), 8.52 (d, J=8.6 Hz, 1H), 8.26 (s, 1H), 7.53 (d, J=2.1 Hz, 1H), 7.47 (d, J=2.1 Hz, 1H), 7.14 (s, 1H), 3.99 (s, 3H), 3.88-3.76 (m, 1H), 3.26 (s, 3H), 3.17-3.07 (m, 1H), 2.05 (d, J=10.5 Hz, 2H), 1.83 (d, J=10.6 Hz, 2H), 1.64-1.48 (m, 2H), 1.30-1.15 (m, 2H).

Example 4

4-hydroxy-6-(1H-imidazol-1-yl)-N-((1r,4r)-4-methoxycyclohexyl)picolinamide (compound 5)

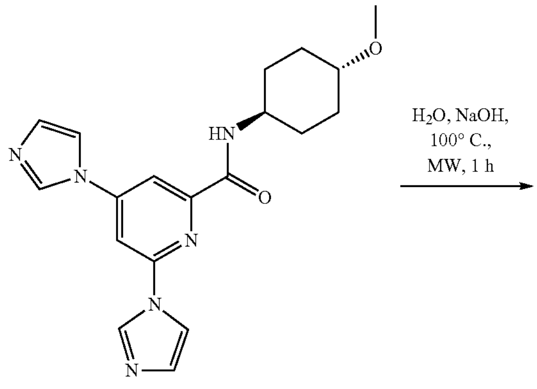

1

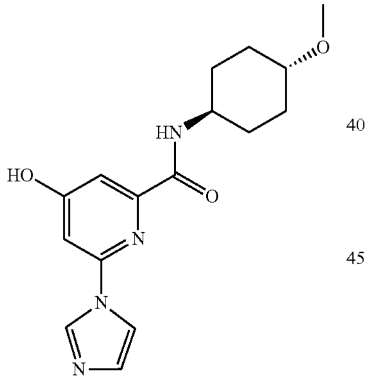

5

A solution of compound 1 (100 mg, 0.273 mmol) in $H_2O$ (5 mL) was treated with NaOH (22 mg, 0.546 mmol). The resulting reaction mixture was heated at 100° C. in a microwave reactor for 1 hour. The reaction mixture was purified by prep-HPLC (Waters 2767/2545/2489, Waters Xbridge C18 10 μm OBD 19*250 mm, Mobile Phase A: 0.1% NH4OH in water, Mobile Phase B: $CH_3CN$, Flow: 20 mL/min, Column temp: RT) to give the titled compound (3.76 mg, 4.4% yield) as a white solid. MS (ESI): m/z 317.1. $[M+H]^+$; $^1$H NMR (400 MHZ, DMSO-$d_6$) δ 8.80 (s, 1H), 8.41 (d, J=8.4 Hz, 1H), 8.34 (s, 1H), 8.10 (s, 1H), 7.31 (s, 1H), 7.16 (s, 1H), 7.09 (s, 1H), 3.84-3.72 (m, 2H), 3.25 (s, 3H), 3.16-3.06 (m, 2H), 2.04 (d, J=11.5 Hz, 2H), 1.81 (d, J=10.2 Hz, 2H), 1.60-1.48 (m, 2H), 1.27-1.15 (m, 2H).

Example 5

2-acetamido-N-((1r,4r)-4-methoxycyclohexyl)-5-(thiazol-5-yl) benzamide (compound 6)

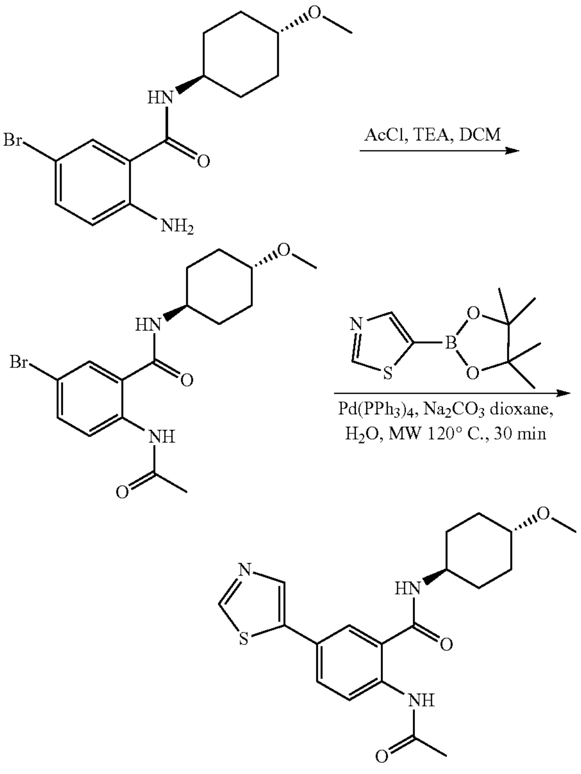

6

Step 1. 2-acetamido-5-bromo-N-((1r,4r)-4-methoxycyclohexyl)benzamide.

To a solution of 2-amino-5-bromo-N-((1r,4r)-4-methoxycyclohexyl)benzamide (400 mg, 1.22 mmol) in DCM (10 mL) were added TEA (0.51 mL, 3.67 mmol) and AcCl (0.17 mL, 2.45 mmol). The reaction mixture was stirred at room temperature for 1 hour. The resulting mixture was concentrated under reduced pressure. The residue was purified using silica gel column chromatography (PE/EA=10/1 to 1/1) to afford the titled compound (270 mg, 59.8% yield) as a yellow solid. MS (ESI): m/z 371.0 $[M+H]^+$.

Step 2. 2-acetamido-N-((1r,4r)-4-methoxycyclohexyl)-5-(thiazol-5-yl) benzamide

A mixture of 2-acetamido-5-bromo-N-((1r,4r)-4-methoxycyclohexyl)benzamide (150 mg, 0.41 mmol), thiazol-5-ylboronic acid pinacol ester (128 mg, 0.61 mmol), $Pd(PPh_3)_4$ (94 mg, 0.08 mmol), Na2CO3 (112 mg, 0.81 mmol), dioxane (2 mL) and $H_2O$ (0.5 mL) was bubbled with argon for 3 minutes. The reaction tube was sealed and was heated at 120° C. in a microwave reactor for 30 minutes. The resulting mixture was purified with prep-HPLC (Waters 2767/2545/2489, Waters Xbridge C18 10 μm OBD 19*250 mm, Mobile Phase A: 0.1% HCOOH in water, Mobile Phase B: $CH_3CN$, Flow: 20 mL/min, Column temp: RT) to afford the titled compound (27 mg, 18% yield) as a white solid. MS (ESI): m/z 374.1 $[M+H]^+$. $^1$H NMR (400 MHZ, DMSO-$d_6$) δ 11.13 (s, 1H), 9.09 (s, 1H), 8.65 (d, J=7.7 Hz, 1H), 8.40 (d, J=8.7 Hz, 1H), 8.32 (s, 1H), 7.93 (d, J=2.1 Hz, 1H), 7.78

(dd, J=8.6, 2.1 Hz, 1H), 3.86-3.76 (m, 1H), 3.25 (s, 3H), 3.17-3.09 (m, 1H), 2.10 (s, 3H), 2.06-2.03 (m, 2H), 1.92-1.90 (m, 2H), 1.44-1.35 (m, 2H), 1.25-1.27 (m, 2H).

Example 6

2-amino-N-((1r,4r)-4-methoxycyclohexyl)-5-(thiazol-5-yl) benzamide (compound 7)

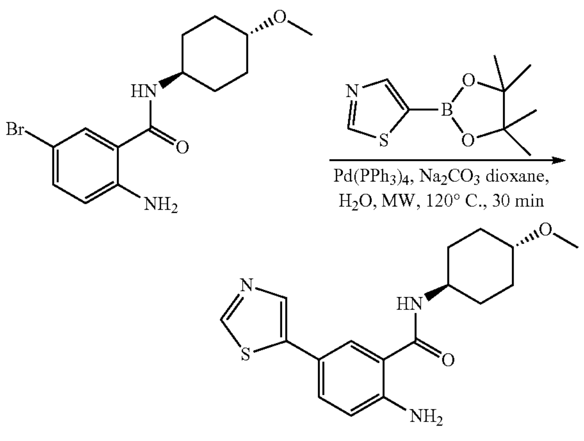

7

A mixture of 2-amino-5-bromo-N-((1r,4r)-4-methoxycyclohexyl)benzamide (150 mg, 0.459 mmol), thiazol-5-ylboronic acid pinacol ester (145 mg, 0.687 mmol), $Pd(PPh_3)_4$ (105 mg, 0.090 mmol), $Na_2CO_3$ (97.0 mg, 0.92 mmol), dioxane (2 mL) and $H_2O$ (0.5 mL) was bubbled with argon for 15 minutes.

The reaction tube was sealed and heated at 120° C. in a microwave reactor for 30 minutes. The reaction mixture was purified with prep-HPLC (Waters 2767/2545/2489, Waters Xbridge C18 10 μm OBD 19*250 mm, Mobile Phase A: 0.1% HCOOH in water, Mobile Phase B: $CH_3CN$, Flow: 20 mL/min, Column temp: RT) to afford the titled compound (9.14 mg, 6.0% yield) as a white solid. MS (ESI): m/z 332.2 $[M+H]^+$. $^1H$ NMR (400 MHZ, DMSO-$d_6$) δ 8.94 (s, 1H), 8.16 (d, J=7.8 Hz, 1H), 8.10 (s, 1H), 7.72 (d, J=1.9 Hz, 1H), 7.43 (dd, J=8.5, 2.0 Hz, 1H), 6.75 (d, J=8.5 Hz, 1H), 6.63 (s, 2H), 3.79-3.69 (m, 1H), 3.25 (s, 3H), 3.17-3.06 (m, 1H), 2.05-2.02 (m, 2H), 1.88-1.85 (m, 2H), 1.41-1.33 (m, 2H), 1.23-1.15 (m, 2H).

The compounds below were synthesized following the procedures described for compound 7.

| No. | Structure | Name | MS ESI $[M + H]^+$ | $^1H$ NMR (400 MHz, DMSO-$d_6$) δ |
|---|---|---|---|---|
| 8 | 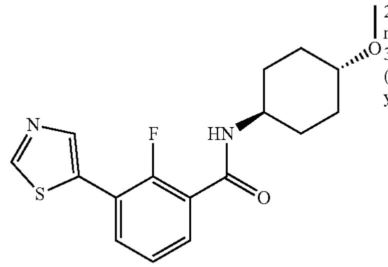 | 2-fluoro-N-((1r,4r)-4-methoxycyclohexyl)-3-(thiazol-5-yl)benzamide | 335.0 | 9.23 (s, 0.5H), 8.40 (s, 0.5H), 8.38-8.36 (m, 0.66H), 8.19-8.15 (m, 0.36H), 7.93-7.90 (m, 1H), 7.52-7.48 (m, 1.5H), 7.36-7.32 (m, 0.77H), 7.26-7.22 (m, 0.76H), 3.76-3.70 (m, 1H), 3.23 (s, 3H), 3.11-3.10 (m, 1H), 2.01-1.98 (m, 2H), 1.92-1.84 (m, 2H), 1.37-1.18 (m, 4H). |
| 12 | 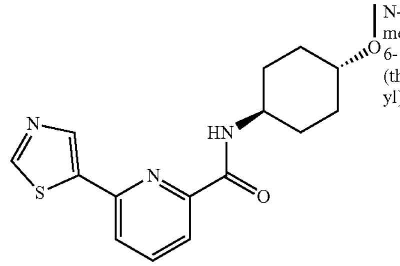 | N-((1r,4r)-4-methoxycyclohexyl)-6-(thiazol-5-yl)picolinamide | 318.5 | 9.22 (s, 1H), 8.79 (s, 1H), 8.25 (d, J = 8.4 Hz, 1H), 8.14 (dd, J = 7.9, 1.1 Hz, 1H), 8.11-8.02 (m, 1H), 7.98-7.90 (m, 1H), 3.87-3.75 (m, 1H), 3.25 (s, 3H), 3.22-3.10 (m, 1H), 2.08-1.98 (m, 2H), 1.95-1.85 (m, 2H), 1.59-1.44 (m, 2H), 1.33-1.19 (m, 2H). |

Example 7

N-((1r,4r)-4-methoxycyclohexyl)-6-(thiazol-5-yl)pyrazine-2-carboxamide (compound 9)

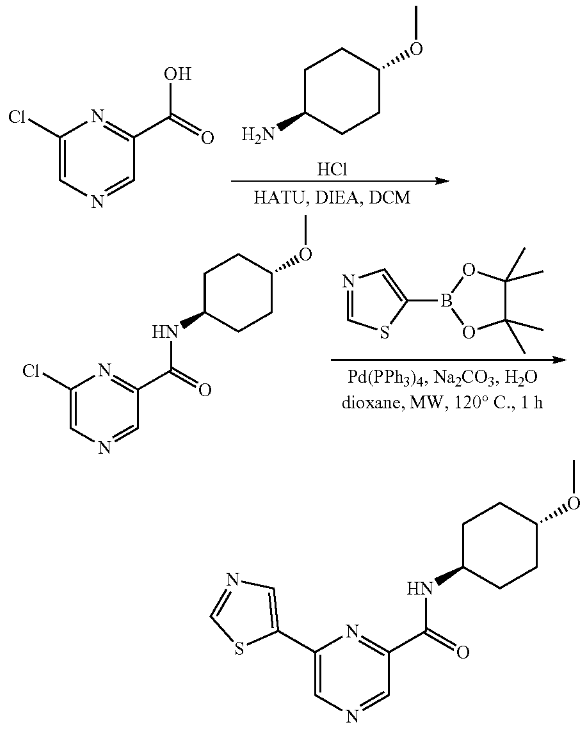

9

Step 1:6-chloro-N-((1r,4r)-4-methoxycyclohexyl)pyrazine-2-carboxamide.

To a solution of trans-4-methoxycyclohexanamine hydrochloride (1.67 g, 10.1 mmol) in DMF (10 mL) were added DIEA (1.67 mL, 10.1 mmol), HATU (3.84 g, 10.1 mmol) and 6-chloropyrazine-2-carboxylic acid (1.60 g, 10.1 mmol). The reaction mixture was stirred at room temperature for 2 hours. The mixture was diluted with ethyl acetate (50 mL). The organic layer was washed with brine (50 mL), dried over anhydrous $Na_2SO_4$, filtered and concentrated. The residue was purified by silica gel column (EA/PE=1/100 to 1/50) to afford the titled compound (1.80 g, 66.1% yield) as a white solid. MS (ESI): m/z 270.1 $[M+H]^+$.

Step 2: N-((1r,4r)-4-methoxycyclohexyl)-6-(thiazol-5-yl)pyrazine-2-carboxamide.

A mixture of 6-chloro-N-((1r,4r)-4-methoxycyclohexyl)pyrazine-2-carboxamide (100 mg, 371 mmol), thiazol-5-ylboronic acid pinacol ester (117 mg, 0.556 mmol), $Pd(PPh_3)_4$ (85.7 mg, 0.074 mmol), $Na_2CO_3$ (78.6 mg, 0.742 mmol) in dioxane (2 mL) and $H_2O$ (0.5 mL) was bubbled with argon for 3 minutes. The reaction tube was sealed and heated at 120° C. with a microwave reactor for 1 hour. The mixture was cooled to room temperature and diluted with EA (20 mL). The organic layer was washed with brine (50 mL), dried over anhydrous $Na_2SO_4$, filtered and concentrated. The residue was purified by prep-HPLC (Waters 2767/2545/2489, Waters Xbridge C18 10 μm OBD 19*250 mm, Mobile Phase A: 0.1% formic acid in water, Mobile Phase B: $CH_3CN$, Flow: 20 mL/min, Column temp: RT) to afford the titled compound (21.56 mg, 18.3% yield) as a white solid. MS (ESI): m/z 391.1 [M+H] +. NMR (400 MHZ, DMSO-$d_6$) δ 9.43 (s, 1H), 9.32 (s, 1H), 9.04 (s, 1H), 8.93 (s, 1H), 8.45 (d, J=8.7 Hz, 1H), 3.84 (s, 1H), 3.25 (s, 3H), 3.13 (d, J=10.6 Hz, 1H), 2.04 (d, J=10.2 Hz, 2H), 1.87 (d, J=10.2 Hz, 2H), 1.55-1.48 (m, 2H), 1.29-1.20 (m, 2H).

Example 8

3-amino-6-(1H-imidazol-1-yl)-N-((1r,4r)-4-methoxycyclohexyl)pyridazine-4-carboxamide (compound 10)

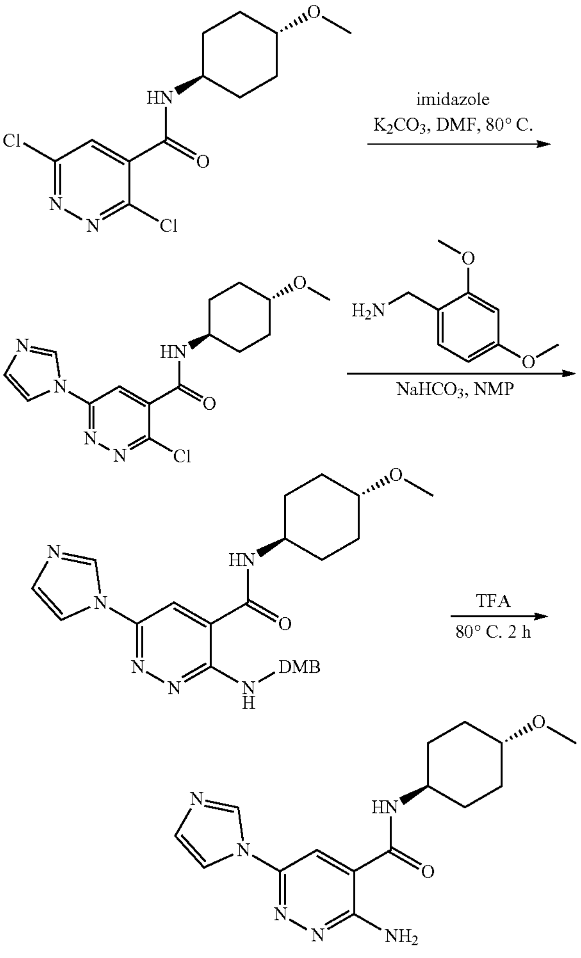

10

Step 1. 3-chloro-6-(1H-imidazol-1-yl)-N-((1r,4r)-4-methoxycyclohexyl)pyridazine-4-carboxamide A mixture of 3,6-dichloro-N-((1r,4r)-4-methoxycyclohexyl)pyridazine-4-carboxamide (380 mg, 1.25 mmol), imidazole (94.3 mg, 1.38 mmol) and $K_2CO_3$ (259 mg, 1.87 mmol) in DMF (10 mL) was heated at 80° C. for 2 hours. The reaction mixture was partitioned between $CH_2Cl_2$ (20 mL) and water (20 mL). The organic layer was separated and the aqueous layer was extracted with $CH_2Cl_2$ (20 mL×2). The combined organic layers were washed with brine (20 mL), dried over anhydrous $Na_2SO_4$, filtered and concentrated to dryness. The residue was purified by silica gel chromatography ($CH_2Cl_2$/MeOH=100/1-20/1) to afford the titled compound (90 mg, 21.4% yield) as a light yellow solid. $^1$H NMR (400 MHZ, DMSO-$d_6$) δ 8.81 (d, J=7.6 Hz, 1H), 8.70 (s, 1H), 8.43 (s, 1H), 8.11 (t, J=1.3 Hz, 1H), 7.23 (s, 1H), 3.80-3.71 (m, 1H), 3.24 (s, 3H), 3.18-3.11 (m, 1H), 2.02-1.96 (m, 4H), 1.36-1.22 (m, 4H).

Step 2 3- ((2.4-dimethoxybenzyl) amino)-6-(1H-imidazol-1-yl)-N-((1r,4r)-4-methoxycyclohexyl) pyridazine-4-carboxamide.

A mixture of 3-chloro-6-(1H-imidazol-1-yl)-N-((1r,4r)-4-methoxycyclohexyl)pyridazine-4-carboxamide (80.2 mg, 0.238 mmol), (2,4-dimethoxyphenyl) methanamine (70.2 μL, 0.476 mmol) and $NaHCO_3$ (60.1 mg, 0.715 mmol) in NMP (5 mL) was heated at 100° C. for 2 hours. The reaction mixture was partitioned between EtOAc (20 mL) and water (20 mL). The organic layer was separated and the aqueous layer was extracted with EtOAc (20 mL×2). The combined organic layers were washed with brine (20 mL), dried over anhydrous $Na_2SO_4$, filtered and concentrated to dryness. The residue was purified by silica gel chromatography ($CH_2Cl_2$/MeOH=100/1-20/1) to afford the titled compound (70.1 mg, 63.0% yield) as a colorless oil. MS (ESI): m/z 467.1 $[M+H]^+$; $^1$H NMR (400 MHZ, DMSO-$d_6$) δ 8.73 (d, J=7.6 Hz, 1H), 8.39 (s, 1H), 8.01 (s, 1H), 7.95 (t, J=5.6 Hz, 1H), 7.86 (s, 1H), 7.17 (d, J=8.4 Hz, 1H), 7.16 (s, 1H), 6.59 (d, J=2.3 Hz, 1H), 6.47 (dd, J=8.3, 2.3 Hz, 1H), 4.59 (d, J=5.5 Hz, 2H), 3.82 (s, 3H), 3.74 (s, 3H), 3.73-3.70 (m, 1H), 3.24 (s, 3H), 3.17-3.10 (m, 1H), 2.03 (d, J=12.8 Hz, 2H), 1.91 (d, J=12.5 Hz, 2H), 1.41-1.26 (m, 5H).

Step 3. 3-amino-6-(1H-imidazol-1-yl)-N-((1r,4r)-4-methoxycyclohexyl)pyridazine-4-carboxamide.

A solution of 3-((2,4-dimethoxybenzyl) amino)-6-(1H-imidazol-1-yl)-N-((1r,4r)-4-methoxycyclohexyl) pyridazine-4-carboxamide (70 mg, 0.150 mmol) in TFA (5 mL) was heated at 80° C. for 2 hours. The volatile was removed in vacuum and the residue was partitioned between EtOAc (20 mL) and saturated $Na_2CO_3$ solution (20 mL). The organic layer was separated and the aqueous layer was extracted with EtOAc (20 mL×2). The combined organic layers were washed with brine (20 mL), dried over anhydrous $Na_2SO_4$, filtered and concentrated to dryness. The residue was purified by silica gel chromatography ($CH_2Cl_2$/MeOH=100/1-10/1) to afford the titled compound (5.29 mg, 11.1% yield) as a white solid. MS (ESI): m/z 317.1 $[M+H]^+$; $^1$H NMR (400 MHZ, DMSO-$d_6$) δ 8.67 (d, J=7.7 Hz, 1H), 8.39 (s, 1H), 8.00 (s, 1H), 7.86 (s, 1H), 7.16 (d, J=6.1 Hz, 3H), 3.80-3.70 (m, 1H), 3.24 (s, 3H), 3.17-3.10 (m, 1H), 2.04 (dd, J=12.6, 2.7 Hz, 2H), 1.92 (dd, J=13.1, 2.8 Hz, 2H), 1.41-1.30 (m, 2H), 1.28-1.17 (m, 2H).

The compounds below were synthesized following the procedures described for compound 10.

| No. | Structure | Name | MS ESI $[M + H]^+$ | $^1$H NMR (400 MHz, DMSO-$d_6$) δ |
|---|---|---|---|---|
| 27 | 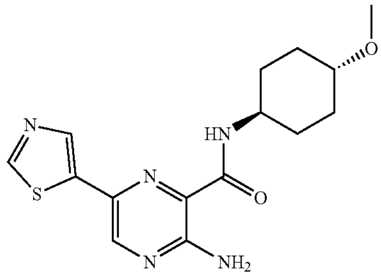 [SMILES: CO[C@H]1CC[C@H](NC(=O)c2nc(-c3cncs3)cnc2N)CC1] | 3-amino-N-((1r,4r)-4-methoxycyclohexyl)-6-(thiazol-5-yl)pyrazine-2-carboxamide | 334.1 | 9.09 (s, 1H), 8.78 (s, 1H), 8.57 (s, 1H), 8.18 (d, J = 8.4Hz, 1H), 7.76 (s, 1H), 3.78 (s, 1H), 3.25 (s, 3H), 3.18-3.12 (m, 1H), 2.01 (d, J = 10.6 Hz, 1H), 1.86 (d, J = 10.4 Hz, 2H), 1.53-1.46 (m, 2H), 1.29-1.22 (m, 2H). |
| 41 | 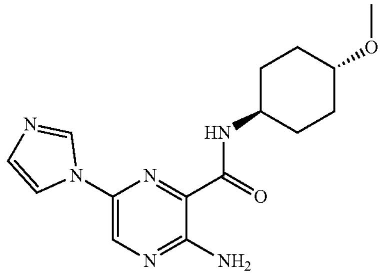 [SMILES: CO[C@H]1CC[C@H](NC(=O)c2nc(-n3ccnc3)cnc2N)CC1] | 3-amino-6-(1H-imidazol-1-yl)-N-((1r,4r)-4-methoxycyclohexyl) pyrazine-2-carboxamide | 317.1 | 8.74 (s, 1H), 8.68 (s, 1H), 8.47 (d, J = 8.6 Hz, 1H), 8.08 (s, 1H), 7.67 (s, 2H), 7.12 (s, 1H), 3.81-7.79 (m, 1H), 3.25 (s, 3H), 3.14-3.08 (m, 1H), 2.06-2.03 (m, 2H), 1.83-1.80 (m, 2H), 1.62-1.47 (m, 2H), 1.25-1.17 (m, 2H). |
| 42 | 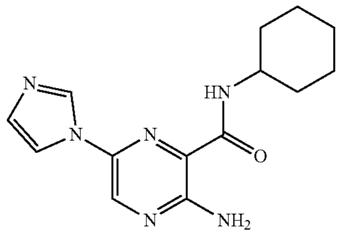 [SMILES: Nc1ncc(-n2ccnc2)nc1C(=O)NC1CCCCC1] | 3-amino-N-cyclohexyl-6-(1H-imidazol-1-yl)pyrazine-2-carboxamide | 287.1 | 8.74 (s, 1H), 8.68 (s, 1H), 8.47 (d, J = 8.7 Hz, 1H), 8.09 (t, J = 1.3 Hz, 1H), 7.67 (s, 2H), 7.12 (t, J = 1.0 Hz, 1H), 3.84-3.75 (m, 1H), 1.79 - 1.73 (m, 4H), 1.64-1.61 (m, 2H), 1.51-1.41 (m, 2H), 1.36-1.26 (m, 2H), 1.18-1.12 (m, 2H). |

-continued

| No. | Structure | Name | MS ESI $[M + H]^+$ | $^1H$ NMR (400 MHz, DMSO-$d_6$) δ |
|---|---|---|---|---|
| 46 | 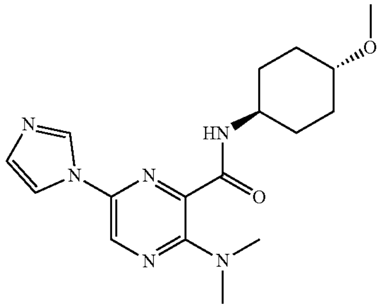 [SMILES: CO[C@H]1CC[C@H](NC(=O)c2nc(-n3ccnc3)cnc2N(C)C)CC1] | 3-(dimethylamino)-6-(1H-imidazol-1-yl)-N-((1r,4r)-4-methoxycyclohexyl) pyrazine-2-carboxamide | 345.5 | 8.61 (s, 1H), 8.56 (d, J = 7.9 Hz, 1H), 8.38 (s, 1H), 7.83 (s, 1H), 7.11 (s, 1H), 3.76-3.66 (m, 1H), 3.24 (s, 3H), 3.15-3.08 (m, 1H), 3.03 (s, 5H), 2.06-1.97 (m, 2H), 1.93-1.83 (m, 2H), 1.43-1.31 (m, 2H), 1.28-1.16 (m, 2H). |
| 47 | 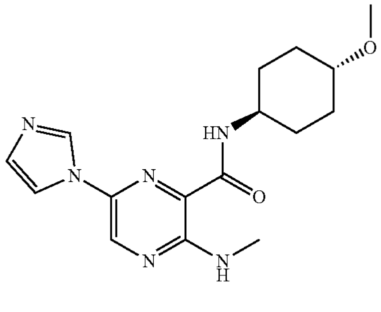 [SMILES: CNc1ncc(-n2ccnc2)nc1C(=O)N[C@H]1CC[C@H](OC)CC1] | 6-(1H-imidazol-1-yl)-N-((1r,4r)-4-methoxycyclohexyl)-3-(methylamino)pyrazine-2-carboxamide | 331.5 | 8.79 (s, 1H), 8.67-8.60 (m, 2H), 8.51 (d, J = 8.6 Hz, 1H), 8.06 (s, 1H), 7.12 (s, 1H), 3.99-3.49 (m, 1H), 3.25 (s, 3H), 3.17-2.99 (m, 1H), 2.97 (d, J = 4.9 Hz, 3H), 2.05 (d, J = 10.2 Hz, 2H), 1.82 (d, J = 10.5 Hz, 2H), 1.60-1.48 (m, 2H), 1.29-1.10 (m, 2H). |
| 59 | 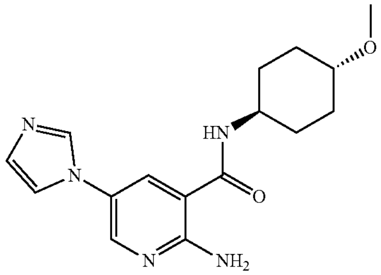 [SMILES: CO[C@H]1CC[C@H](NC(=O)c2cc(-n3ccnc3)cnc2N)CC1] | 2-amino-5-(1H-imidazol-1-yl)-N-((1r,4r)-4-methoxycyclohexyl) nicotinamide | 316.1 | 8.89 (s, 1H), 8.40 (d, J = 2.6 Hz, 1H), 8.24 (d, J = 7.5 Hz, 1H), 8.17 (d, J = 2.6 Hz, 1H), 7.91 (s, 1H), 7.56 (s, 1H), 7.42 (s, 2H), 3.78-3.70 (m, 1H), 3.24 (s, 3H), 3.14-3.08 (m, 1H), 2.03 (d, J = 10.0 Hz, 2H), 1.88 (d, J = 10.3 Hz, 2H), 1.39-1.28 (m, 2H), 1.26-1.16 (m, 2H). |
| 60 | 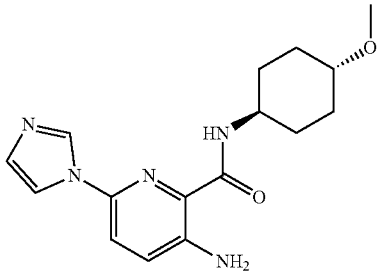 [SMILES: CO[C@H]1CC[C@H](NC(=O)c2nc(-n3ccnc3)ccc2N)CC1] | 3-amino-6-(1H-imidazol-1-yl)-N-((1r,4r)-4-methoxycyclohexyl) picolinamide | 316.1 | 8.66 (s, 1H), 8.25 (d, J = 8.7 Hz, 1H), 8.04 (s, 1H), 7.68 (d, J = 8.9 Hz, 1H), 7.35 (d, J = 8.9 Hz, 1H), 7.09 (s, 1H), 6.94 (s, 2H), 3.84-3.70 (m, 1H), 3.25 (s, 3H), 3.17-3.07 (m, 1H), 2.04 (d, J = 10.6 Hz, 2H), 1.81 (d, J = 10.1 Hz, 2H), 1.52-1.48 (m, 2H), 1.26-1.16 (m, 2H). |
| 61 | 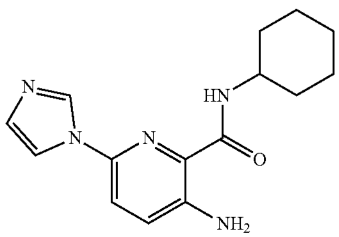 [SMILES: Nc1ccc(-n2ccnc2)nc1C(=O)NC1CCCCC1] | 3-amino-N-cyclohexyl-6-(1H-imidazol-1-yl)picolinamide | 286.2 | 8.64 (s, 1H), 8.25 (d, J = 8.7 Hz, 1H), 8.02 (s, 1H), 7.68 (d, J = 8.9 Hz, 1H), 7.36 (d, J = 8.9 Hz, 1H), 7.07 (s, 1H), 6.94 (s, 2H), 3.83-3.73 (m, 1H), 1.78-1.73(m, 4H), 1.63 (d, J = 12.6 Hz, 1H), 1.53-1.41 (m, 2H), 1.36-1.30 (m, 2H), 1.21-1.10 (m, 1H). |

-continued

| No. | Structure | Name | MS ESI $[M + H]^+$ | $^1H$ NMR (400 MHz, DMSO-$d_6$) δ |
| --- | --- | --- | --- | --- |
| 69 | 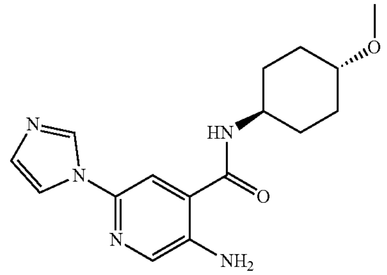 [SMILES: CO[C@H]1CC[C@H](NC(=O)c2cc(-n3ccnc3)ncc2N)CC1] | 5-amino-2-(1H-imidazol-1-yl)-N-((1r,4r)-4-methoxycyclohexyl) isonicotinamide | 316.2 | 8.56-8.39 (m, 1H), 8.34 (d, J = 7.5 Hz, 1H), 8.04 (s, 1H), 7.98-7.78 (m, 1H), 7.72 (s, 1H), 7.26-7.12 (m, 1H), 6.51 (s, 2H), 3.80-3.70 (m, 1H), 3.25 (s, 3H), 3.17-3.08 (m, 1H), 2.09-2.01 (m, 2H), 1.95-1.87 (m, 2H), 1.44 1.30 (m, 2H), 1.28-1.16 (m, 2H). |

Example 9

6-(1H-imidazol-1-yl)-N-((1r,4r)-4-methoxycyclohexyl)pyrazine-2-carboxamide (compound 11)

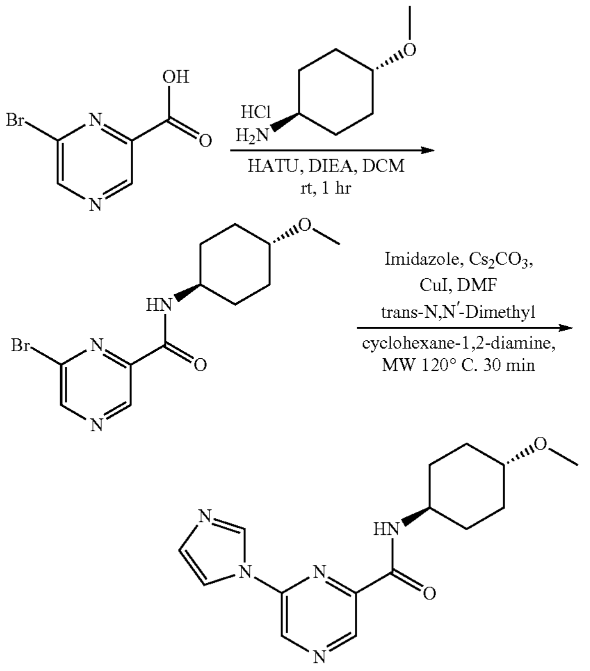

11

Step 1. 6-bromo-N-((1r,4r)-4-methoxycyclohexyl)pyrazine-2-carboxamide

To a solution of 6-bromopyrazine-2-carboxylic acid (100 mg, 0.493 mmol) in DMF (3 mL) were added HATU (225 mg, 0.591 mmol), TEA (0.20 mL, 1.48 mmol) and trans 4-methoxycyclohexanamine hydrochloride (122 mg, 0.739 mmol). The reaction mixture was stirred at room temperature for 1 hour. The resulting mixture was diluted with water (10 mL) and extracted with EA (10 mL×3). The combined organic layers were dried over anhydrous $Na_2SO_4$, filtered and the filtrate was concentrated. The residue was purified by silica gel column chromatography (PE/EA=10/1 to 1/1) to afford the titled compound (100 mg, 64.6% yield) as a yellow solid. MS (ESI): m/z 315.9 $[M+H]^+$.

Step 2. 6-(1H-imidazol-1-yl)-N-((1r,4r)-4-methoxycyclohexyl)pyrazine-2-carboxamide A mixture of 6-bromo-N-((1r,4r)-4-methoxycyclohexyl) pyrazine-2-carboxamide (100 mg, 0.32 mmol), imidazole (43 mg, 0.64 mmol), CuI (3 mg, 0.016 mmol), $Cs_2CO_3$ (207 mg, 0.64 mmol), trans-N1, N2-dimethylcyclohexane-1,2-diamine (9.0 mg, 0.064 mmol) in DMF (2 mL) was bubbled with argon for 3 minutes. The reaction tube was sealed and heated at 110° C. in a microwave reactor for 30 minutes. The reaction mixture was cooled to room temperature and purified with prep-HPLC (Waters 2767/2545/2489/Qda, Column name: Inertsil ODS-3 10 μm 20*250 nm, Mobile Phase A: 0.1% $NH_4OH$ in water, Mobile Phase B: $CH_3CN$, Flow: 20 mL/min: Column temp: RT) to afford the titled compound (43.4 mg, 45.0% yield) as a white solid. MS (ESI): m/z 302.1 $[M+H]^+$. $^1H$ NMR (400 MHZ, DMSO-$d_6$) δ 9.38 (s, 1H), 9.07 (s, 1H), 9.00 (s, 1H), 8.71 (d, J=8.5 Hz, 1H), 8.35 (s, 1H), 7.22 (s, 1H), 3.90-3.82 (m, 1H), 3.26 (s, 3H), 3.17-3.09 (m, 1H), 2.07-2.05 (m, 2H), 1.86-1.83 (m, 2H), 1.59-1.50 (m, 2H), 1.27-1.19 (m, 2H).

The compounds below were synthesized following the procedures described for compound 11.

| No. | Structure | Name | MS ESI $[M + H]^+$ | $^1H$ NMR (400 MHz, DMSO-$d_6$) δ |
| --- | --- | --- | --- | --- |
| 13 | 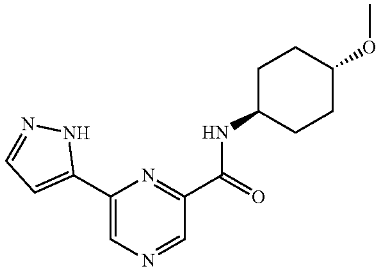 [SMILES: CO[C@H]1CC[C@H](NC(=O)c2cncc(-c3ccn[nH]3)n2)CC1] | N-((1r,4r)-4-methoxycyclohexyl)-6-(1H-pyrazol-5-yl)pyrazine-2-carboxamide | 302.1 | 9.33 (s, 1H), 9.05 (s, 1H), 8.72 (d, J = 4.4 Hz, 1H), 7.83 (d, J = 2.0 Hz, 1H), 7.26 (d, J = 2.0 Hz, 1H), 5.50-4.50 (brs, 1H), 3.90-3.82 (m, 1H), 3.26 (s, 3H), 3.19-3.11 (m, 1H), 2.07 (d, J = 10.8 Hz, 2H), 1.90 (d, J = 10.8 Hz, 2H), 1.56-1.48 (m, 2H), 1.30-1.20 (m, 2H). |

-continued

| No. | Structure | Name | MS ESI [M + H]+ | $^{1}$H NMR (400 MHz, DMSO-$d_6$) δ |
|---|---|---|---|---|
| 14 | 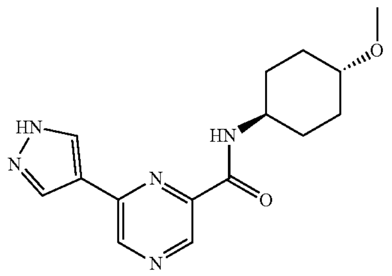 [SMILES: CO[C@H]1CC[C@H](NC(=O)c2cncc(-c3cn[nH]c3)n2)CC1] | N-((1r,4r)-4-methoxycyclohexyl)-6-(1H-pyrazol-4-yl)pyrazine-2-carboxamide | 302.2 | 13.31 (s, 1H), 9.18 (s, 1H), 8.89 (s, 1H), 8.73 (s, 1H), 8.54 (d, J = 8.6 Hz, 1H), 8.41 (s, 1H), 3.90-3.79 (m, 1H), 3.26 (s, 3H), 3.20-3.08 (m, 1H), 2.06 (d, J = 10.4 Hz, 2H), 1.87 (d, J = 10.8 Hz, 2H), 1.63-1.48 (m, 2H), 1.32-1.15 (m, 2H). |
| 15 | 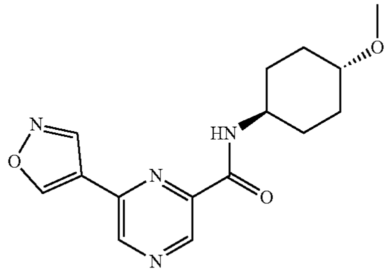 [SMILES: CO[C@H]1CC[C@H](NC(=O)c2cncc(-c3cnoc3)n2)CC1] | 6-(isoxazol-4-yl)-N-((1r,4r)-4-methoxycyclohexyl) pyrazine-2-carboxamide | 303.1 | 8.91 (s, 1H), 8.86 (s, 1H), 8.77 (s, 1H), 8.52 (d, J = 8.2 Hz, 1H), 3.81-3.77 (m, 1H), 3.24 (d, J = 1.4 Hz, 3H), 3.16-3.10 (m, 1H), 2.07-1.97 (m, 2H), 1.92-1.75 (m, 2H), 1.53-1.41 (m, 2H), 1.30-1.18 (m, 2H). |
| 16 | 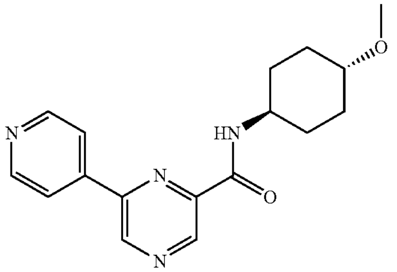 [SMILES: CO[C@H]1CC[C@H](NC(=O)c2cncc(-c3ccncc3)n2)CC1] | N-((1r,4r)-4-methoxycyclohexyl)-6-(pyridin-4-yl)pyrazine-2-carboxamide | 313.1 | 9.59 (s, 1H), 9.22 (s, 1H), 8.81 (d, J = 6.0 Hz, 2H), 8.74 (d, J = 8.5 Hz, 1H), 8.47-8.14 (m, 2H), 4.10-3.65 (m, 1H), 3.15-3.10 (m, 1H), 2.06 (d, J = 10.6 Hz, 2H), 1.88 (d, J = 10.5 Hz, 2H), 1.70-1.50 (m, 2H), 1.35-1.05 (m, 2H). |
| 30 | 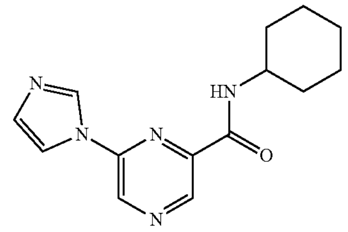 [SMILES: O=C(NC1CCCCC1)c1cncc(-n2ccnc2)n1] | N-cyclohexyl-6-(1H-imidazol-1-yl)pyrazine-2-carboxamide | 272.4 | 9.38 (s, 1H), 9.07 (s, 1H), 9.00 (s, 1H), 8.72 (d, J = 8.6 Hz, 1H), 8.36 (s, 1H), 7.22 (s, 1H), 3.91-3.79 (m, 1H), 1.80-1.74 (m, 4H), 1.70-1.60 (m, 1H), 1.52-1.43 (m, 2H), 1.38-1.25 (m, 2H), 1.20-1.08 (m, 1H). |
| 31 | 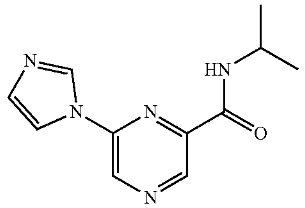 [SMILES: CC(C)NC(=O)c1cncc(-n2ccnc2)n1] | 6-(1H-imidazol-1-yl)-N-isopropylpyrazine-2-carboxamide | 232.4 | 9.39 (s, 1H), 9.08 (s, 1H), 9.00 (s, 1H), 8.74 (d, J = 8.3 Hz, 1H), 8.36 (t, J = 1.3 Hz, 1H), 7.23 (s, 1H), 4.27-4.17 (m, 1H), 1.24 (d, J = 6.6 Hz, 6H). |
| 32 | 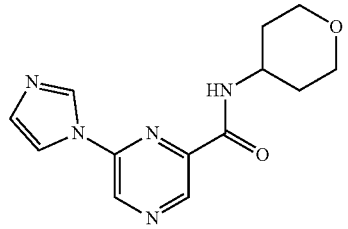 [SMILES: O=C(NC1CCOCC1)c1cncc(-n2ccnc2)n1] | 6-(1H-imidazol-1-yl)-N-(tetrahydro-2H-pyran-4-yl)pyrazine-2-carboxamide | 274.0 | 9.39 (s, 1H), 9.08 (s, 1H), 9.01 (s, 1H), 8.82 (d, J = 8.5 Hz, 1H), 8.36 (s, 1H), 7.23 (s, 1H), 4.11 (dd, J = 15.4, 7.4 Hz, 1H), 3.92 (d, J = 11.2 Hz, 2H), 3.45 (s, 2H), 1.88-1.65 (m, 4H). |

-continued

| No. | Structure | Name | MS ESI $[M + H]^+$ | $^1H$ NMR (400 MHz, DMSO-$d_6$) δ |
|---|---|---|---|---|
| 33 | 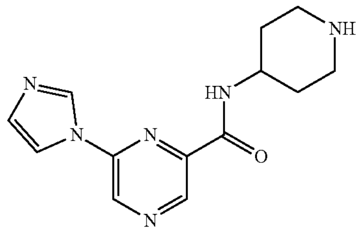 [SMILES: O=C(NC1CCNCC1)c1cncc(-n2ccnc2)n1] | 6-(1H-imidazol-1-yl)-N-(piperidin-4-yl)pyrazine-2-carboxamide | 273.2 | 9.38 (s, 1H), 9.08 (s, 1H), 9.00 (s, 1H), 8.78 (d, J = 8.5 Hz, 1H), 8.36 (s, 1H), 7.22 (s, 1H), 4.03-3.92 (m, 2H), 2.95 (m, 2H), 2.60-2.52 (m, 1H), 1.81-1.69 (m, 2H), 1.67-1.53 (m, 2H). |
| 34 | 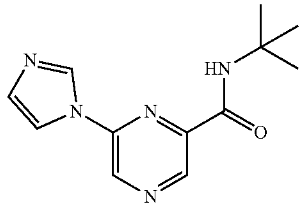 [SMILES: CC(C)(C)NC(=O)c1cncc(-n2ccnc2)n1] | N-(tert-butyl)-6-(1H-imidazol-1-yl)pyrazine-2-carboxamide | 246.1 | 9.38 (s, 1H), 9.08 (s, 1H), 8.93 (s, 1H), 8.29 (s, 1H), 8.12 (s, 1H), 7.23 (s, 1H), 1.45 (s, 9H). |
| 35 | 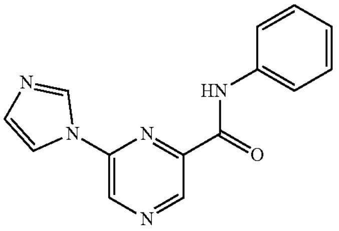 [SMILES: O=C(Nc1ccccc1)c1cncc(-n2ccnc2)n1] | 6-(1H-imidazol-1-yl)-N-phenylpyrazine-2-carboxamide | 266.1 | 10.58 (s, 1H), 9.46 (s, 1H), 9.21 (s, 1H), 9.07 (s, 1H), 8.43 (s, 1H), 7.86 (q, J = 1.1 Hz, 2H), 7.45-7.41 (m, 2H), 7.25 (s, 1H), 7.23-7.17 (m, 1H). |
| 36 | 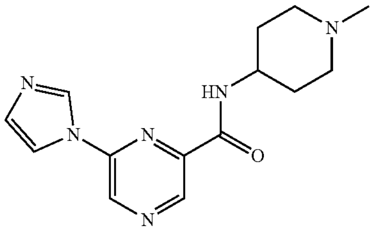 [SMILES: CN1CCC(NC(=O)c2cncc(-n3ccnc3)n2)CC1] | 6-(1H-imidazol-1-yl)-N-(1-methylpiperidin-4-yl)pyrazine-2-carboxamide | 287.2 | 9.35 (s, 1H), 8.96 (s, 1H), 8.40 (s, 1H), 7.69 (s, 1H), 7.45 (d, J = 7.1 Hz, 1H), 7.33 (s, 1H), 4.08-3.99 (m, 1H), 2.84 (d, J = 11.0 Hz, 2H), 2.33 (s, 3H), 2.21 (t, J = 10.8 Hz, 2H), 2.06 (d, J = 10.2 Hz, 2H), 1.73-1.63 (m, 2H). |
| 37 | 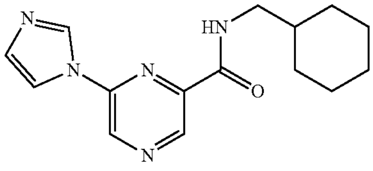 [SMILES: O=C(NCC1CCCCC1)c1cncc(-n2ccnc2)n1] | N-(cyclohexylmethyl)-6-(1H-imidazol-1-yl)pyrazine-2-carboxamide | 286.1 | 9.37 (s, 1H), 8.96 (s, 1H), 8.46 (s, 1H), 7.69 (s, 2H), 7.32 (s, 1H), 3.38 (t, J = 6.5 Hz, 2H), 1.81-1.75 (m, 4H), 1.72-1.61 (m, 2H), 1.31-1.17 (m, 3H), 1.08-0.99 (m, 2H). |
| 38 | 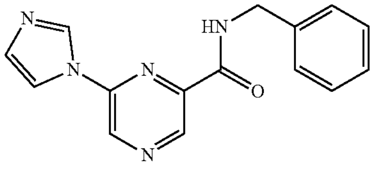 [SMILES: O=C(NCc1ccccc1)c1cncc(-n2ccnc2)n1] | N-benzyl-6-(1H-imidazol-1-yl)pyrazine-2-carboxamide | 280.0 | 9.70 (t, J = 6.3 Hz, 1H), 9.42 (s, 1H), 9.11 (s, 1H), 8.98 (s, 1H), 8.36 (s, 1H), 7.38-7.31 (m, 4H), 7.28-7.23 (m, 1H), 7.22 (s, 1H), 4.57 (d, J = 6.4 Hz, 2H). |
| 39 | 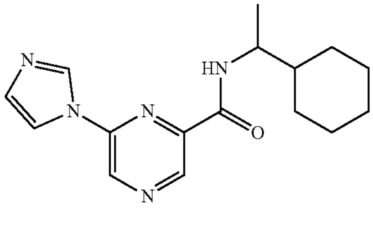 [SMILES: CC(NC(=O)c1cncc(-n2ccnc2)n1)C1CCCCC1] | N-(1-cyclohexylethyl)-6-(1H-imidazol-1-yl)pyrazine-2-carboxamide | 300.1 | 9.38 (s, 1H), 9.05 (s, 1H), 9.01 (s, 1H), 8.76 (d, J = 8.8 Hz, 1H), 8.34 (s, 1H), 7.22 (s, 1H), 4.43 (d, J = 12.8 Hz, 1H), 4.15-4.08 (m, 1H), 3.88 (d, J = 12.8 Hz, 1H), 3.16 (t, J = 12.4 Hz, 1H), 2.62 (t, J = 12.8 Hz, 1H), 2.03 (s, 3H), 1.85-1.75 (m, 2H), 1.67-1.50 (m, 2H). |

-continued

| No. | Structure | Name | MS ESI [M + H]+ | $^1$H NMR (400 MHz, DMSO-$d_6$) δ |
| --- | --- | --- | --- | --- |
| 40 | 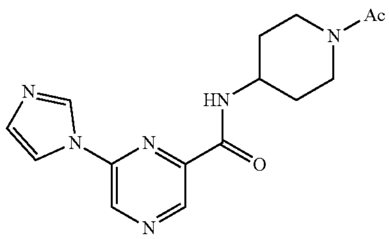 [SMILES: CC(=O)N1CCC(NC(=O)c2cncc(-n3ccnc3)n2)CC1] | N-(1-acetylpiperidin-4-yl)-6-(1H-imidazol-1-yl)pyrazine-2-carboxamide | 315.1 | 9.39 (s, 1H), 9.09 (s, 1H), 8.98 (s, 1H), 7.69 (s, 1H), 7.45 (d, J = 7.1 Hz, 1H), 7.33 (s, 1H), 4.08-3.99 (m, 1H), 2.84 (d, J = 11.0 Hz, 2H), 2.33 (s, 3H), 2.21 (t, J = 10.8 Hz, 2H), 2.06 (d, J = 10.2 Hz, 2H), 1.73-1.63 (m, 2H). |
| 48 | 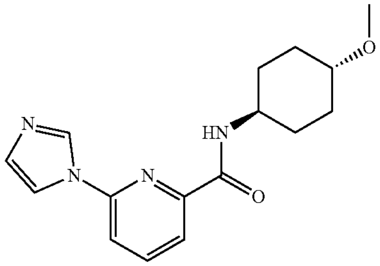 [SMILES: CO[C@H]1CC[C@H](NC(=O)c2cccc(-n3ccnc3)n2)CC1] | 6-(1H-imidazol-1-yl)-N-((1r,4r)-4-methoxycyclohexyl) picolinamide | 301.1 | 9.04 (s, 1H), 8.58 (d, J = 8.7 Hz, 1H), 8.31 (s, 1H), 8.16 (dd, J = 14.3, 6.4 Hz, 1H), 8.01 (d, J = 8.1 Hz, 1H), 7.96 (d, J = 7.5 Hz, 1H), 7.23 (s, 1H), 3.91-3.77 (m, 1H), 3.26 (s, 3H), 3.17-3.08 (m, 1H), 2.06 (d, J = 10.8 Hz, 2H), 1.84 (d, J = 10.6 Hz, 2H), 1.63-1.51 (m, 2H), 1.28-1.17 (m, 2H). |
| 49 | 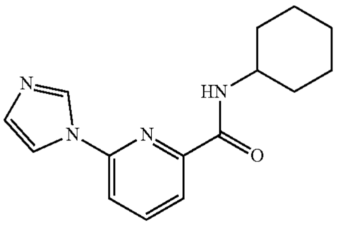 [SMILES: O=C(NC1CCCCC1)c1cccc(-n2ccnc2)n1] | N-cyclohexyl-6-(1H-imidazol-1-yl)picolinamide | 271.1 | 8.95 (s, 1H), 8.57 (d, J = 8.7 Hz, 1H), 8.34-8.23 (m, 1H), 8.16 (t, J = 7.9 Hz, 1H), 7.97 (dd, J = 16.1, 7.9 Hz, 2H), 7.16 (s, 1H), 3.93-3.76 (m, 1H), 1.87-1.70 (m, 4H), 1.69-1.60 (m, 1H), 1.57-1.43 (m, 2H), 1.39-1.25 (m, 2H), 1.21-1.08 (m, 1H). |
| 50 | 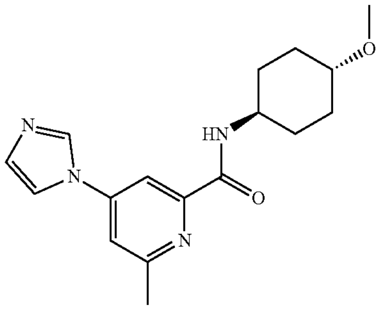 [SMILES: CO[C@H]1CC[C@H](NC(=O)c2cc(-n3ccnc3)cc(C)n2)CC1] | 4-(1H-imidazol-1-yl)-N-((1r,4r)-4-methoxycyclohexyl)-6-methylpicolinamide | 315.2 | 8.60 (s, 1H), 8.38 (d, J = 8.5 Hz, 1H), 8.08 (d, J = 2.0 Hz, 1H), 8.04 (d, J = 1.3 Hz, 1H), 7.87 (d, J = 2.0 Hz, 1H), 7.17 (s, 1H), 3.85-3.75 (m, 1H), 3.25 (s, 3H), 3.16-3.08 (m, 1H), 2.61 (s, 3H), 2.02 (d, J = 10.5 Hz, 2H), 1.86 (d, J = 10.2 Hz, 2H), 1.50 (td, J = 13.0, 3.0 Hz, 2H), 1.23 (td, J = 13.1, 3.3 Hz, 2H). |
| 51 | 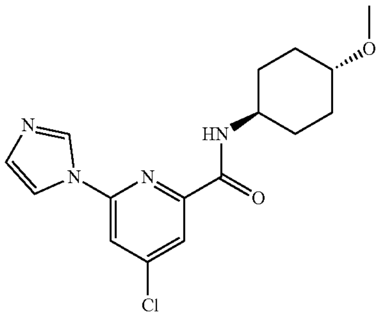 [SMILES: CO[C@H]1CC[C@H](NC(=O)c2cc(Cl)cc(-n3ccnc3)n2)CC1] | 4-chloro-6-(1H-imidazol-1-yl)-N-((1r,4r)-4-methoxycyclohexyl) picolinamide | 335.1 | 8.99 (s, 1H), 8.65 (d, J = 8.6 Hz, 1H), 8.31 (s, 1H), 8.27 (d, J = 1.6 Hz, 1H), 7.92 (d, J = 1.6 Hz, 1H), 7.17 (s, 1H), 3.83 (dd, J = 8.0, 3.7 Hz, 1H), 3.26 (s, 3H), 3.16-3.09 (m, 1H), 2.06 (d, J = 11.1 Hz, 2H), 1.83 (d, J = 10.6 Hz, 2H), 1.57 (q, J = 10.5 Hz, 2H), 1.22 (q, J = 10.4 Hz, 2H). |

-continued

| No. | Structure | Name | MS ESI $[M + H]^+$ | $^1H$ NMR (400 MHz, DMSO-$d_6$) δ |
|---|---|---|---|---|
| 52 | 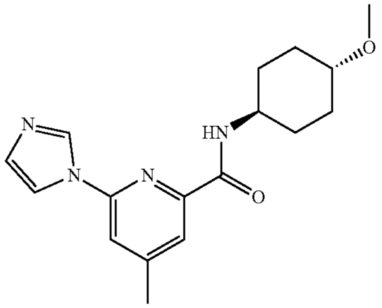 | 6-(1H-imidazol-1-yl)-N-((1r,4r)-4-methoxycyclohexyl)-4-methylpicolinamide | 315.2 | 9.49-9.40 (m, 1H), 8.58 (s, 1H), 8.43 (s, 1H), 7.97 (s, 1H), 7.89 (s, 1H), 7.47 (s, 1H), 3.82 (s, 1H), 3.26 (s, 3H), 3.13 (s, 1H), 2.50-2.48 (m, 3H), 2.04 (s, 2H), 1.82 (s, 2H), 1.55 (d, J = 15.2 Hz, 2H), 1.23 (d, J = 12.4 Hz, 2H). |
| 53 | 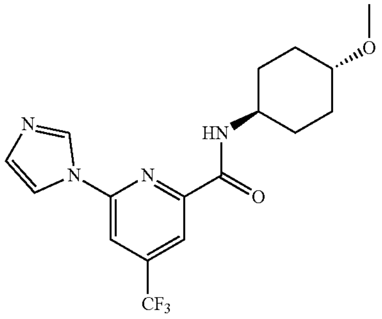 [SMILES: CO[C@H]1CC[C@H](NC(=O)c2cc(C(F)(F)F)cc(-n3ccnc3)n2)CC1] | 6-(1H-imidazol-1-yl)-N-((1r,4r)-4-methoxycyclohexyl)-4-(trifluoromethyl) picolinamide | 368.9 | 9.09 (s, 1H), 8.73 (d, J = 8.4 Hz, 1H), 8.43 (d, J = 8.4 Hz, 1H), 8.11 (s, 1H), 7.20 (s, 1H), 3.95-3.80 (m, 1H), 3.26 (s, 3H), 3.15-3.08 (m, 1H), 2.07 (d, J = 11.2 Hz, 2H), 1.85 (d, J = 10.8 Hz, 2H), 1.54 (q, J = 10.4 Hz, 2H), 1.23 (q, J = 10.4 Hz, 2H). |
| 58 | 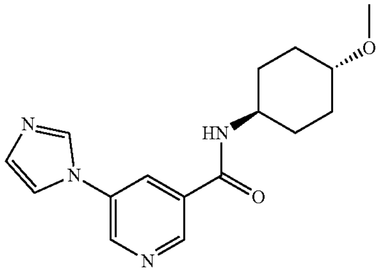 [SMILES: CO[C@H]1CC[C@H](NC(=O)c2cncc(-n3ccnc3)c2)CC1] | 5-(1H-imidazol-1-yl)-N-((1r,4r)-4-methoxycyclohexyl) nicotinamide | 301.1 | 9.07 (d, J = 2.5 Hz, 1H), 8.93 (d, J = 1.8 Hz, 1H), 8.51 (d, J = 7.5 Hz, 1H), 8.43-8.39 (m, 2H), 7.90 (s, 1H), 7.18 (s, 1H), 3.85-3.73 (m, 1H), 3.27-3.20 (m, 3H), 3.17-3.10 (m, 1H), 2.04 (d, J = 12.9 Hz, 2H), 1.92 (d, J = 9.9 Hz, 2H), 1.44-1.32 (m, 2H), 1.29-1.17 (m, 2H). |
| 62 | 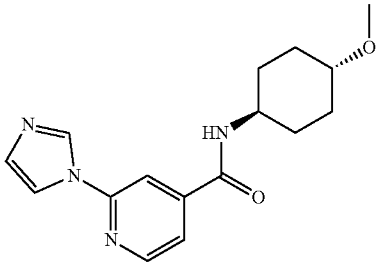 | 2-(1H-imidazol-1-yl)-N-((1r,4r)-4-methoxycyclohexyl) isonicotinamide | 301.1 | 9.03-8.93 (br, 1H), 8.64 (d, J = 5.1 Hz, 1H), 8.59 (d, J = 7.5 Hz, 1H), 8.40-8.15 (m, 1H), 8.13 (s, 1H), 7.74 (d, J = 5.0 Hz, 1H), 7.53-7.42 (m, 1H), 3.80-3.60 (m, 1H), 3.25 (s, 2H), 3.17-3.10 (m, 1H), 2.04 (d, J = 13.1 Hz, 1H), 1.91 (d, J = 10.3 Hz, 1H), 1.43-1.34 (m, 1H), 1.27-1.19 (m, 1H). |
| 70 | 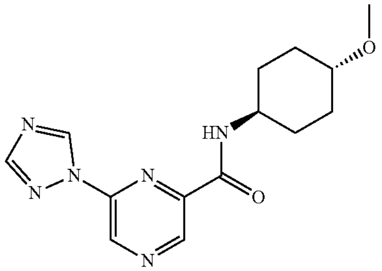 [SMILES: CO[C@H]1CC[C@H](NC(=O)c2cncc(-n3cncn3)n2)CC1] | N-((1r,4r)-4-methoxycyclohexyl)-6-(1H-1,2,4-triazol-1-yl)pyrazine-2-carboxamide | 303.2 | 9.99 (s, 1H), 9.31 (s, 1H), 9.19 (s, 1H), 8.74 (d, J = 8.5 Hz, 1H), 8.44 (s, 1H), 4.00-3.66 (m, 1H), 3.26 (s, 2H), 3.18-3.11 (m, 1H), 2.11-2.03 (m, 2H), 1.88 (d, J = 11.1 Hz, 2H), 1.59-1.48 (m, 2H), 1.30-1.19 (m, 2H). |

-continued

| No. | Structure | Name | MS ESI $[M + H]^+$ | $^1H$ NMR (400 MHz, DMSO-$d_6$) δ |
|---|---|---|---|---|
| 75 | 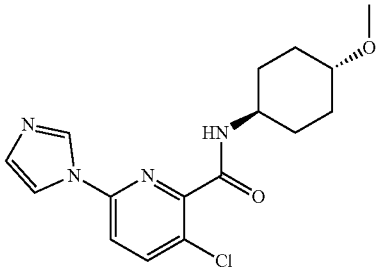 | 3-chloro-6-(1H-imidazol-1-yl)-N-((1r,4r)-4-methoxycyclohexyl) picolinamide | 335.1 | 8.63-8.55 (m, 2H), 8.23 (d, J = 8.7 Hz, 1H), 8.00 (s, 1H), 7.94 (d, J = 8.7 Hz, 1H), 7.15 (s, 1H), 3.81-3.69 (m, 1H), 3.24 (s, 3H), 3.18-3.04 (m, 1H), 2.02 (d, J = 10.4 Hz, 2H), 1.90 (d, J = 10.5 Hz, 2H), 1.43-1.32 (m, 2H), 1.29-1.17 (m, 2H). |
| 76 | 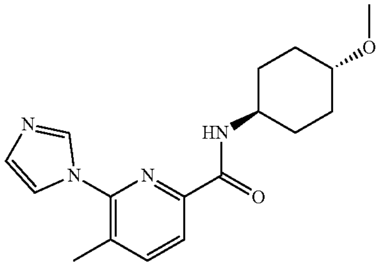 [SMILES: CO[C@H]1CC[C@H](NC(=O)c2ccc(C)c(-n3ccnc3)n2)CC1] | 6-(1H-imidazol-1-yl)-N-((1r,4r)-4-methoxycyclohexyl)-5-methylpicolinamide | 315.2 | 8.34-8.29 (m, 2H), 8.07 (d, J = 7.8 Hz, 1H), 7.98 (d, J = 7.8 Hz, 1H), 7.79 (s, 1H), 7.13 (s, 1H), 3.83-3.75 (m, 1H), 3.24 (s, 3H), 3.13-3.06 (m, 1H), 2.40 (s, 3H), 2.02 (d, J = 10.3 Hz, 2H), 1.82 (d, J = 10.5 Hz, 2H), 1.55-1.45 (m, 2H), 1.26-1.16 (m, 2H). |
| 77 | 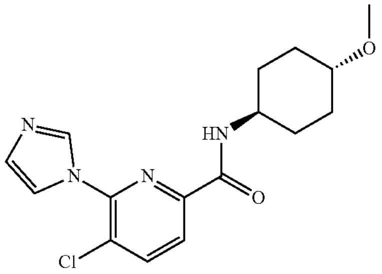 | 5-chloro-6-(1H-imidazol-1-yl)-N-((1r,4r)-4-methoxycyclohexyl) picolinamide | 335.1 | 8.45 (d, J = 8.4 Hz, 2H), 8.37 (d, J = 8.8 Hz, 1H), 8.04 (d, J = 8.0 Hz, 1H), 7.92 (br s, 1H), 7.17 (br s, 1H), 3.85-3.75 (m, 1H), 3.24 (s, 3H), 3.13-3.06 (m, 1H), 2.40 (s, 3H), 2.03 (d, J = 10.0 Hz, 2H), 1.82 (d, J = 10.4 Hz, 2H), 1.55-1.45 (m, 2H), 1.26-1.16 (m, 2H). |
| 78 | 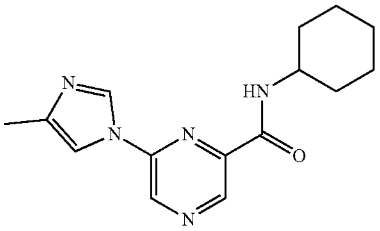 [SMILES: Cc1cn(-c2cncc(C(=O)NC3CCCCC3)n2)cn1] | N-cyclohexyl-6-(4-methyl-1H-imidazol-1-yl)pyrazine-2-carboxamide | 286.2 | 9.30 (s, 1H), 9.03 (s, 1H), 8.89 (s, 1H), 8.69 (d, J = 8.4 Hz, 2H), 8.02 (s, 1H), 3.88-3.83 (m, 1H), 2.22 (s, 3H), 1.79 (t, J = 12.8 Hz, 4H), 1.65 (d, J = 13.6 Hz, 1H), 1.53-1.44 (m, 2H), 1.35-1.28 (m, 2H), 1.16 (t, J = 12.8 Hz, 1H). |
| 79 | 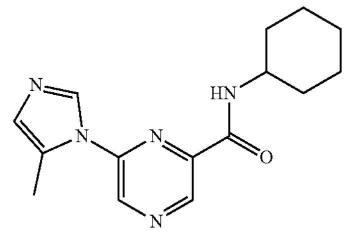 [SMILES: Cc1cncn1-c1cncc(C(=O)NC2CCCCC2)n1] | N-cyclohexyl-6-(5-methyl-1H-imidazol-1-yl)pyrazine-2-carboxamide | 285.8 | 9.18 (s, 1H), 9.15 (s, 1H), 8.50 (d, J = 8.4 Hz, 1H), 8.41 (s, 1H), 6.91 (s, 1H), 3.83 (d, J = 8.4 Hz, 1H), 2.44 (s, 3H), 1.85-1.72 (m, 4H), 1.61 (d, J = 12.4 Hz, 1H), 1.50-1.30 (m, 4H), 1.20-1.10 (m, 1H). |
| 80 | 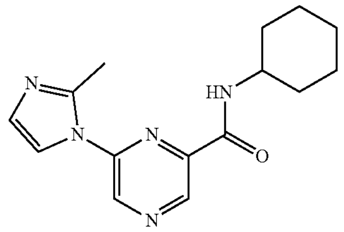 [SMILES: Cc1nccn1-c1cncc(C(=O)NC2CCCCC2)n1] | N-cyclohexyl-6-(2-methyl-1H-imidazol-1-yl)pyrazine-2-carboxamide | 286.2 | 9.12 (d, J = 5.0 Hz, 1H), 8.68 (d, J = 8.6 Hz, 1H), 8.40 (d, J = 1.7 Hz, 1H), 7.95 (d, J = 5.0 Hz, 1H), 7.19 (d, J = 1.6 Hz, 1H), 3.88-3.79 (m, 1H), 2.81 (s, 3H), 1.85-1.71 (m, 4H), 1.67-1.59 (m, 1H), 1.52-1.42 (m, 2H), 1.40-1.27 (m, 2H), 1.22-1.11 (m, 1H). |

-continued

| No. | Structure | Name | MS ESI [M + H]+ | $^1$H NMR (400 MHz, DMSO-$d_6$) δ |
|---|---|---|---|---|
| 81 | 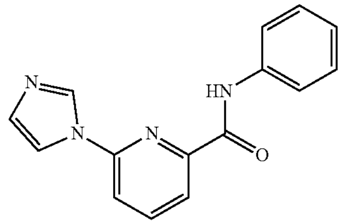 [SMILES: O=C(Nc1ccccc1)c1cccc(-n2ccnc2)n1] | 6-(1H-imidazol-1-yl)-N-phenylpicolinamide | 265.1 | 10.48 (s, 1H), 9.02 (s, 1H), 8.30 (s, 1H), 8.25 (t, J = 8.0 Hz, 1H), 8.09 (d, J = 8.0 Hz, 2H), 7.80 (d, J = 8.0 Hz, 2H), 7.42 (d, J = 8.0 Hz, 2H), 7.20-7.15 (m, 2H). |

Example 10

6-(isoxazol-5-yl)-N-((1r,4r)-4-methoxycyclohexyl) picolinamide (compound 17)

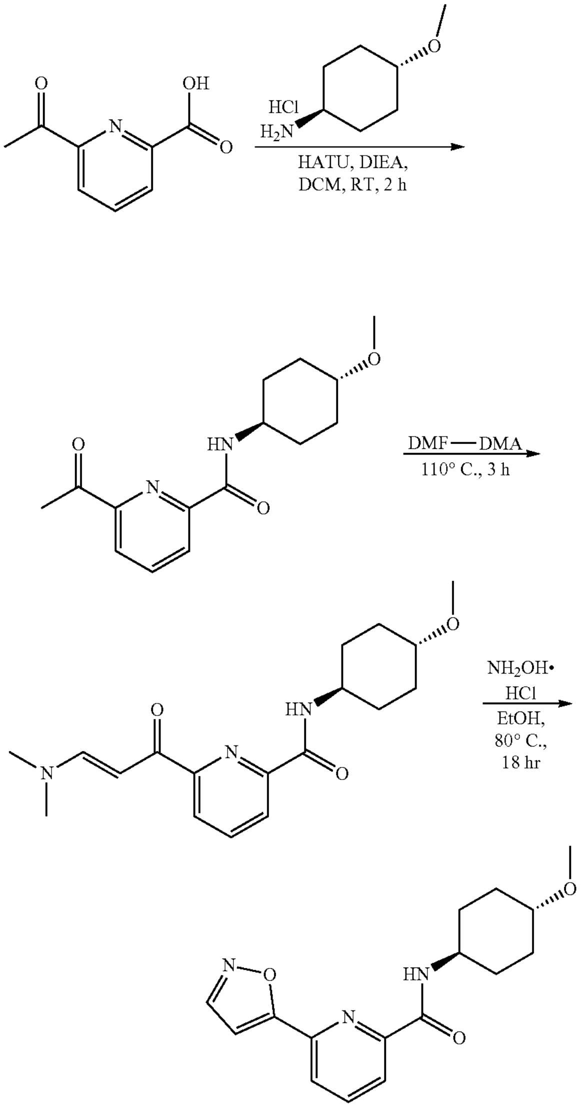

17

Step 1: 6-acetyl-N-((1r,4r)-4-methoxycyclohexyl)picolinamide

To a solution of 6-acetylpicolinic acid (800 mg, 1.93 mmol) in DCM (15 mL) were added HATU (882 mg, 2.31 mmol) and DIEA (0.96 mL, 5.80 mmol), was added trans-4-methoxycyclo hexanamine hydrochloride (384 mg, 2.32 mmol). The reaction mixture was stirred at room temperature for 1 hour. The reaction mixture was diluted with DCM (300 mL) and washed with water (100 mL). The organic layer was separated, washed with brine (100 mL), dried over anhydrous $Na_2SO_4$ and filtered in vacuum. The residue was purified by silica gel column chromatography (EA/PE=1/100-3/1) to afford the titled compound (400 mg, 67.4% yield) as a yellow solid. MS (ESI): m/z 277.1 $[M+H]^+$.

Step 2: 6-((E)-3-(dimethylamino) acryloyl)-N-((1r,4r)-4-methoxycyclohexyl)picolinamide.

A mixture of 6-acetyl-N-((1r,4r)-4-methoxycyclohexyl) picolinamide (400 mg, 1.30 mmol) and DMF-DMA (10 mL) was stirred at 110° C. for 3 hours. The mixture was cooled to room temperature and diluted with EA (100 mL), washed with brine (100 mL). The organic layer was dried over anhydrous $Na_2SO_4$, filtered and concentrated. The residue was purified by silica gel column chromatography (EA/PE=1/100~2/1) to afford the titled compound (330 mg, 61.1% yield) as a yellow solid. LC-MS (ESI): m/z 332.2 $[M+H]^+$.

Step 3: 6-(isoxazol-5-yl)-N-((1r,4r)-4-methoxycyclohexyl) picolinamide.

To a solution of 6-((E)-3-(dimethylamino) acryloyl)-N-((1r,4r)-4-methoxycyclohexyl) picolinamide (100 mg, 0.302 mmol) in EtOH (5 mL) was added $NH_2OH.HCl$ (41.9 mg, 0.603 mmol), and the reaction mixture was stirred at 85° C. for 12 hours. The resulting mixture was cooled and purified by prep-HPLC (system: Waters 2767/2545/2489/Qda, Inertsil ODS-3 10 μm 20*250 nm, Mobile Phase A: 0.1% FA in water, Mobile Phase B: $CH_3CN$, Flow: 20 mL/min: Column temp: RT) to afford the titled compound (29.80 mg, 32.8% yield) as a white solid. MS (ESI): m/z 302.2 $[M+H]^+$. $^1$H NMR (400 MHZ, DMSO-$d_6$) δ 8.82 (d, J=1.9 Hz, 1H), 8.49 (d, J=8.6 Hz, 1H), 8.20-8.08 (m, 3H), 7.53 (d, J=1.9 Hz, 1H), 3.89-3.79 (m, 1H), 3.26 (s, 3H), 3.17-3.10 (m, 1H), 2.12-1.97 (m, 2H), 1.89-1.85 m, 2H), 1.59-1.50 (m, 2H), 1.29-1.22 (m, 2H).

Example 11

N-((1r,4r)-4-methoxycyclohexyl)-6-(4H-1.2,4-triazol-4-yl) pyrazine-2-carboxamide (compound 18)

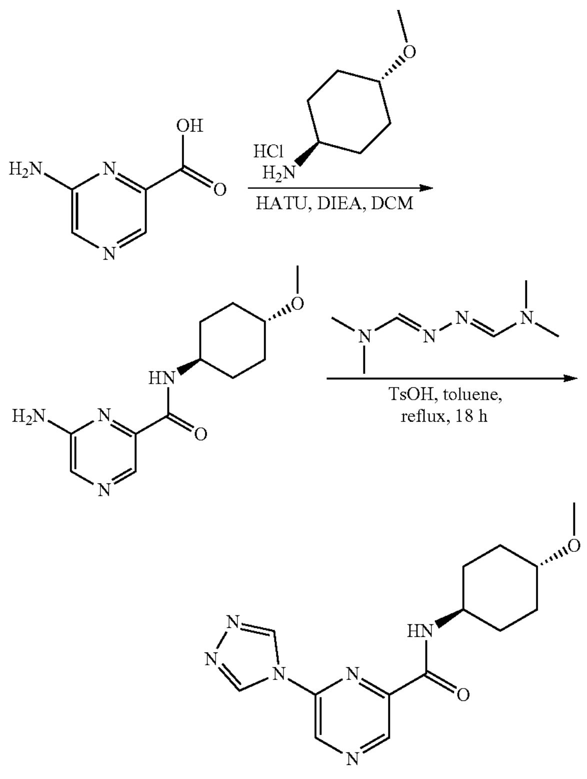

18

Step 1: 6-amino-N-((1r,4r)-4-methoxycyclohexyl)pyrazine-2-carboxamide

To a solution of 6-aminopyrazine-2-carboxylic acid (300 mg, 2.16 mmol) in DCM (15 mL), was added HATU (983 mg, 2.59 mmol), DIEA (1.07 mL, 6.47 mmol) and trans-4-methoxycyclohexanamine hydrochloride (456 mg, 2.75 mmol). The reaction mixture was stirred at room temperature for 2 hours. The resulting mixture was concentrated under reduced pressure. The residue was diluted with EA (100 mL) and brine (100 mL). The organic layer was separated, dried over anhydrous $Na_2SO_4$ and filtered. The filtrate was concentrated under reduced pressure to afford the titled compound (200 mg, 37.1% yield) as a yellow solid.

Step 2: N-((1r,4r)-4-methoxycyclohexyl)-6-(4H-1,2,4-triazol-4-yl) pyrazine-2-carboxamide.

A mixture of 6-amino-N-((1r,4r)-4-methoxycyclohexyl) pyrazine-2-carboxamide (120 mg, 0.479 mmol), N,N'-bis (dimethylaminomethylene) hydrazine (81.8 mg, 0.575 mmol), TsOH (44.9 mg, 0.623 mmol) in toluene (10 mL) was degassed with argon for 3 times. The reaction mixture was stirred at 120° C. for 18 hours. The mixture was cooled to room temperature and concentrated. The residue was purified by prep-HPLC (system: Waters 2767/2545/2489/Qda, Inertsil ODS-3 10 μm 20*250 nm, Mobile Phase A: 0.1% FA in water, Mobile Phase B: $CH_3CN$, Flow: 20 mL/min: Column temp: RT) to afford the titled compound (66.1 mg, 45.6% yield) as an off-white solid. MS (ESI): m/z 303.1 $[M+H]^+$. $^1H$ NMR (400 MHZ, DMSO-$d_6$) δ 9.73 (s, 1H), 9.43 (s, 0.5H), 9.16 (s, 0.5H), 8.72 (d, J=8.6 Hz, 0.5H), 8.22 (s, 0.5H), 8.05 (s, 0.5H), 7.96 (d, J=8.3 Hz, 0.5H), 7.48 (d, J=8.0 Hz, 0.5H), 7.12 (d, J=7.8 Hz, 0.5H), 3.94-3.65 (m, 1H), 3.25 (d, J=10.1 Hz, 3H), 3.17-3.08 (m, 1H), 2.12-1.94 (m, 2H), 1.90-1.82 (m, 2H), 1.61-1.44 (m, 1H), 1.43-1.32 (m, 1H), 1.30-1.16 (m, 2H).

Example 12

N-((1r,4r)-4-methoxycyclohexyl)-6-(1,3,4-oxadiazol-2-yl) picolinamide (compound 19)

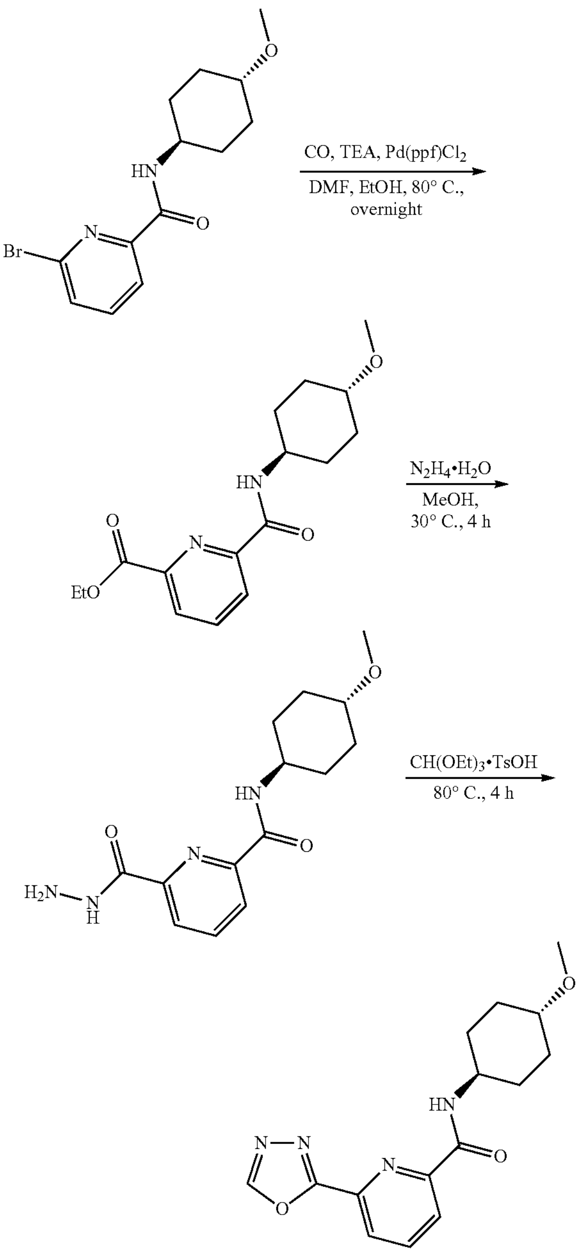

19

Step 1. ethyl 6-(((1r,4r)-4-methoxycyclohexyl)carbamoyl) picolinate

A mixture of 6-bromo-N-((1r,4r)-4-methoxycyclohexyl) picolinamide (1.00 g, 3.19 mmol), triethylamine (0.90 mL, 6.38 mmol), Pd(dppf)$Cl_2$ (230 mg, 0.31 mmol), DMF (10 mL) and EtOH (10 mL) was heated at 80° C. under CO atmosphere (1 atm) for 18 hours. The mixture was diluted with EA (50 mL), washed with brine (50 mL), dried over anhydrous $Na_2SO_4$, filtered and concentrated. The residue was purified by silica gel column (EA/PE=1/100 to 1/3) to afford the titled compound (667 mg, 68.2% yield) as a white solid. MS (ESI): 307.1 $[M+H]^+$.

Step 2. 6-(hydrazinecarbonyl)-N-((1r,4r)-4-methoxycyclohexyl)picolinamide.

A solution of ethyl 6-(((1r,4r)-4-methoxycyclohexyl)carbamoyl) picolinate (800 mg, 2.61 mmol), MeOH (15 mL) and hydrazine hydrate (0.215 mL, 4.44 mmol) was stirred at 30° C. overnight. The reaction mixture was purified by reversed phase column (ACN/$H_2O$=1/0 to 30/1) to afford the titled compound (120 mg, 15.7% yield) as a white solid, MS (ESI): m/z 293.1 $[M+H]^+$, which was used in the next step without purification.

Step 3. N-((1r,4r)-4-methoxycyclohexyl)-6-(1.3.4-oxadiazol-2-yl) picolinamide.

To a mixture of 6-(hydrazinecarbonyl)-N-((1r,4r)-4-methoxycyclohexyl)picolinamide (110 mg, 0.37 mmol), TsOH (64.8 mg, 0.37 mmol) and $CH(OEt)_3$ (2.00 mL, 12.0 mmol) was stirred at 80° C. for 4 hours. The mixture was diluted with EA (50 mL), washed with brine (50 mL), dried over anhydrous $Na_2SO_4$, filtered and concentrated. The residue was purified by prep-HPLC (Waters 2767/2545/2489, Waters Xbridge C18 10 μm OBD 19*250 mm, Mobile Phase A: 0.1% HCOOH in water, Mobile Phase B: $CH_3CN$, Flow: 20 mL/min, Column temp: RT) to afford the titled compound (5.23 mg, 4.6% yield) as a white solid. MS (ESI): m/z 303.4 $[M+H]^+$. $^1$H NMR (400 MHZ, DMSO-$d_6$) δ 9.51 (s, 1H), 8.38-8.32 (m, 1H), 8.31 (d, J=8.4 Hz, 1H), 8.27-8.21 (m, 2H), 3.87-3.78 (m, 1H), 3.25 (s, 3H), 3.18-3.10 (m, 1H), 2.03 (d, J=10.1 Hz, 2H), 1.89 (d, J=9.9 Hz, 2H), 1.60-1.40 (m, 2H), 1.30-1.20 (m, 2H).

Example 13

5-amino-6-(1H-imidazol-1-yl)-N-((1r,4r)-4-methoxycyclohexyl)picolinamide (compound 20)

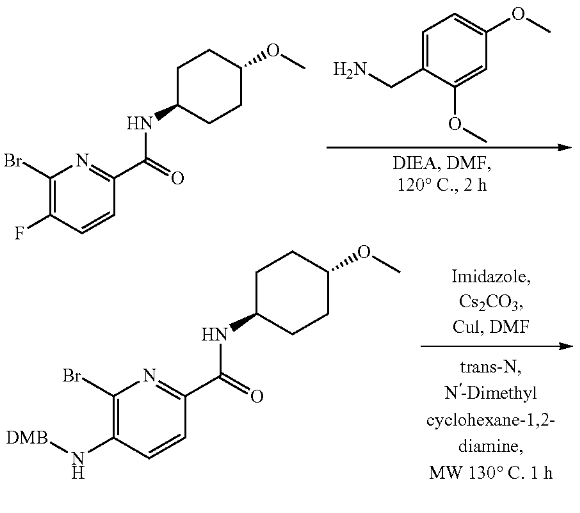

-continued

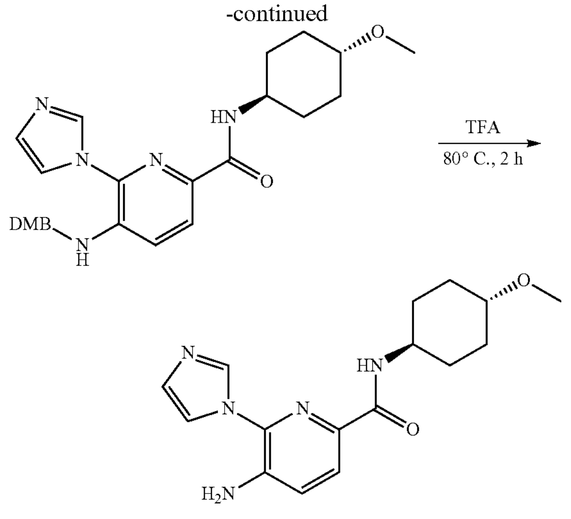

20

Step 1. 6-bromo-5- ((2.4-dimethoxybenzyl) amino)-N-((1r, 4r)-4-methoxycyclohexyl)picolinamide A mixture of 6-bromo-5-fluoro-N-((1r,4r)-4-methoxycyclohexyl)picolinamide (120 mg, 0.362 mmol), (2,4-dimethoxyphenyl)methanamine (0.11 mL, 0.725 mmol) and DIEA (0.18 mL, 1.08 mmol) in DMF (2 mL) stirred at 100° C. for 2 hours. The reaction mixture was diluted with $H_2O$ (20 mL) and extracted with EA (50 mL×2). The combined organic layer was washed with brine (20 mL), dried over anhydrous $Na_2SO_4$, filtered and concentrated. The residue was purified by silica gel column chromatography (PE/EA=20/1-2/1) to afford the titled compound (70.2 mg, 40.4% yield) as a light-yellow oil. LC-MS (ESI): m/z 480.0 $[M+H]^+$.

Step 2. 5- ((2.4-dimethoxybenzyl) amino)-6-(1H-imidazol-1-yl)-N-((1r,4r)-4-methoxycyclohexyl) picolinamide.

A mixture of 6-bromo-5- ((2,4-dimethoxybenzyl) amino)-N-((1r,4r)-4-methoxy cyclohexyl) picolinamide (70.2 mg, 0.146 mmol), imidazole (11.9 mg, 0.176 mmol), CuI (2.79 mg, 0.015 mmol), $Cs_2CO_3$ (95.3 mg, 0.293 mmol), trans-N,N'-dimethylcyclohexane-1,2-diamine (0.003 mL, 0.015 mmol) in DMF (3 mL) was bubbled with $N_2$ for 1 minute. The reaction tube was sealed and heated at 120° C. in a microwave reactor for 0.5 hour. The reaction mixture was diluted with $H_2O$ (20 mL) and extracted with EA (20 mL×2). The combined organic layer was washed with brine (20 mL), dried over anhydrous $Na_2SO_4$, filtered and concentrated. The residue was purified by silica gel column chromatography (DCM/MeOH=200/1-40/1) to afford the titled compound (45.0 mg, 66.2% yield) as a light-yellow oil. LC-MS (ESI): m/z 466.1 $[M+H]^+$.

Step 3. 5-amino-6-(1H-imidazol-1-yl)-N-((1r,4r)-4-methoxycyclohexyl)picolinamide.

A mixture of 5- ((2,4-dimethoxybenzyl) amino)-6-(1H-imidazol-1-yl)-N-((1r,4r)-4-methoxycyclohexyl) picolinamide (45.0 mg, 0.097 mmol) and TFA (5 mL) was stirred at 80° C. for 2 hours. The reaction mixture was diluted with water (20 mL), then extracted with EA (30 mL×2). The combined organic layer was washed with brine (20 mL), dried over anhydrous $Na_2SO_4$, filtered and concentrated. The residue was purified by prep-HPLC (Waters 2767/2545/2489, Waters Xbridge C18 10 μm OBD 19*250 mm, Mobile Phase A: 0.1% $NH_4OH$ in $H_2O$ Mobile Phase B: $CH_3CN$, Flow: 20 mL/min, Column temp: RT) to afford the titled compound (2.34 mg, 0.01 mmol, 7.7% yield) as a white solid. MS (ESI): m/z 316.5 $[M+H]^+$; $^1$H NMR (400 MHZ, DMSO-$d_6$) δ 8.17 (s, 1H), 7.88 (d, J=8.5 Hz, 1H), 7.80 (d, J=8.3 Hz, 1H), 7.65 (s, 1H), 7.34 (d, J=8.3 Hz, 1H), 7.13 (s, 1H), 5.87 (s, 2H), 3.78-3.69 (m, 1H), 3.23 (s, 3H), 3.13-3.04 (m, 1H), 2.00 (d, J=10.4 Hz, 2H), 1.79 (d, J=10.7 Hz, 2H), 1.46-1.38 (m, 2H), 1.24-1.14 (m, 2H).

Example 14

2-amino-6-(1H-imidazol-1-yl)-N-((1r,4r)-4-methoxycyclohexyl)pyrimidine-4-carboxamide (compound 21)

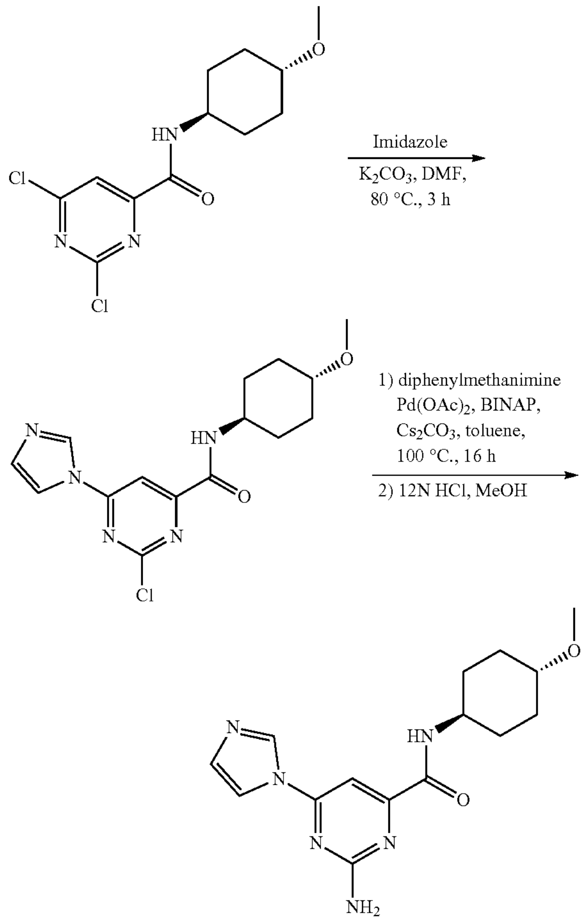

21

Step 1:2-chloro-6-(1H-imidazol-1-yl)-N-((1r,4r)-4-methoxycyclohexyl)pyrimidine-4-carboxamide A mixture of 2,6-dichloro-N-((1r,4r)-4-methoxycyclohexyl)pyrimidine-4-carboxamide (1.00 g, 3.29 mmol), imidazole (220 mg, 3.29 mmol) and $K_2CO_3$ (910 mg, 6.58 mmol) in DMF (10 mL) was heated at 80° C. for 3 hours. The reaction mixture was cooled to room temperature and partitioned between EtOAc (20 mL) and water (40 mL). The organic layer was separated and the aqueous layer was extracted with EtOAc (20 mL×2). The combined organic layers were washed with brine (20 mL), dried over anhydrous $Na_2SO_4$, filtered and concentrated. The residue was purified by silica gel chromatography ($CH_2Cl_2$/MeOH=100/1-30/1) to afford the titled compound (591 mg, 53.5% yield) as a light-green solid. MS (ESI): m/z 336.0 $[M+H]^+$. $^1H$ NMR (400 MHZ, DMSO-$d_6$) δ 8.82 (s, 1H), 8.74 (d, J=8.4 Hz, 1H), 8.38 (s, 1H), 8.16 (t, J=1.4 Hz, 1H), 7.21 (d, J=0.7 Hz, 1H), 3.87-3.75 (m, 1H), 3.25 (s, 3H), 3.14-3.05 (m, 1H), 2.03 (d, J=10.7 Hz, 2H), 1.82 (d, J=10.6 Hz, 2H), 1.61-1.48 (m, 2H), 1.28-1.16 (m, 2H).

Step 2:2-amino-6-(1H-imidazol-1-yl)-N-((1r,4r)-4-methoxycyclohexyl)pyrimidine-4-carboxamide.

A mixture of 2-chloro-6-(1H-imidazol-1-yl)-N-((1r,4r)-4-methoxycyclohexyl) pyrimidine-4-carboxamide (250 mg, 0.744 mmol), diphenylmethanimine (150 μL, 0.893 mmol), $Pd(OAc)_2$ (16.7 mg, 0.0741 mmol), BINAP (46.4 mg, 0.0741 mmol) and $Cs_2CO_3$ (485 mg, 1.49 mmol) in toluene (1.0 mL) was heated at 100° C. under $N_2$ atmosphere for 16 hours. The mixture was cooled and the resulting mixture was partitioned between EtOAc (20 mL) and water (20 mL). The organic layer was separated and the aqueous layer was extracted with EtOAc (20 mL×2). The combined organic layers were washed with brine (50 mL), dried over anhydrous $Na_2SO_4$, filtered and concentrated. The residue was dissolved into MeOH (5 mL), then concentrated HCl (384 μL) was added. The resulting mixture was stirred at room temperature for 2 hours. Saturated aqueous $Na_2CO_3$ solution (10 mL) was added. The resulting mixture was extracted with $CH_2Cl2$ (20 mL×2). The combined organic layers were washed with brine (50 mL), dried over anhydrous $Na_2SO_4$, filtered and concentrated. The residue was purified by silica gel chromatography ($CH_2Cl2$/MeOH=100/1-10/1) to afford a crude product (60 mg), which was further purified by prep-HPLC (Waters 2767/2545/2489, Waters Xbridge C18 10 μm OBD 19*250 mm, Mobile Phase A: 0.1% NH4OH in water, Mobile Phase B: $CH_3CN$, Flow: 20 mL/min, Column temp: RT) to afford HCl salt of titled compound (13.29 mg, 5.1% yield) as a white solid MS (ESI): m/z 317.1 $[M+H]^+$; $^1H$ NMR (400 MHZ, DMSO-$d_6$) δ 8.62 (s, 1H), 8.15 (d, J=8.2 Hz, 1H), 8.00 (s, 1H), 7.42 (s, 1H), 7.23 (s, 2H), 7.14 (s, 1H), 6.07 (s, 1H), 3.82-3.67 (m, 1H), 3.24 (s, 3H), 3.17-3.09 (m, 1H), 2.05-1.98 (m, 2H), 1.91-1.83 (m, 2H), 1.45-1.34 (m, 2H), 1.29-1.18 (m, 2H) and titled compound (2.98 mg, 1.3% yield) as a white solid MS (ESI): m/z 317.1 $[M+H]^+$. $^1H$ NMR (400 MHZ, DMSO-$d_6$) δ 8.76 (s, 1H), 8.50 (d, J=8.8 Hz, 1H), 8.03 (s, 1H), 7.66 (s, 2H), 7.09 (s, 1H), 6.96 (s, 1H), 3.83-3.74 (m, 1H), 3.26 (s, 3H), 3.16-3.07 (m, 1H), 2.07-2.03 (m, 2H), 1.82-1.76 (m, 2H), 1.58-1.48 (m, 2H), 1.25-1.16 (m, 2H).

The compounds below were synthesized following the procedures described for compound 21.

| No. | Structure | Name | MS ESI $[M + H]^+$ | $^1H$ NMR (400 MHz, DMSO-$d_6$) δ |
|---|---|---|---|---|
| 22 | 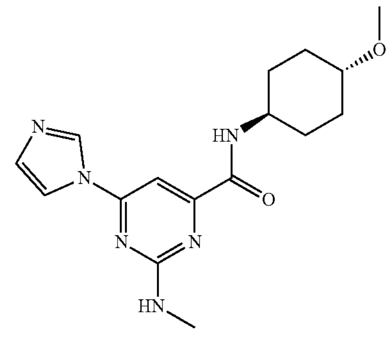 [SMILES: CNc1nc(C(=O)N[C@H]2CC[C@H](OC)CC2)cc(-n2ccnc2)n1] | 6-(1H-imidazol-1-yl)-N-((1r,4r)-4-methoxycyclohexyl)-2-(methylamino)pyrimidine-4-carboxamide | 331.1 | 8.72-8.62 (m, 1H), 8.30-7.93 (m, 2H), 7.63 (s, 1H), 7.39 (s, 1H), 7.13 (s, 1H), 3.75 (s, 1H), 3.24 (s, 3H), 3.18-3.09 (m, 1H), 2.92 (s, 3H), 2.01 (d, J = 10.0 Hz, 2H), 1.87 (d, J = 10.4 Hz, 2H), 1.54-1.33 (m, 2H), 1.28-1.19 (m, 2H). |

-continued

| No. | Structure | Name | MS ESI $[M + H]^+$ | $^1H$ NMR (400 MHz, DMSO-$d_6$) δ |
|---|---|---|---|---|
| 63 | 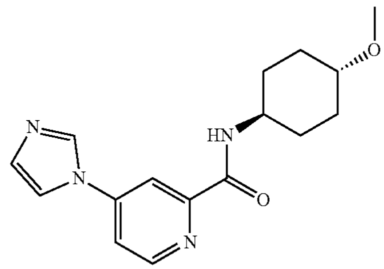 [SMILES: CO[C@H]1CC[C@H](NC(=O)c2cc(-n3ccnc3)ccn2)CC1] | 4-(1H-imidazol-1-yl)-N-((1r,4r)-4-methoxycyclohexyl) picolinamide | 301.4 | 8.71 (d, J = 5.5 Hz, 1H), 8.66 (s, 1H), 8.59 (d, J = 8.5 Hz, 1H), 8.28 (d, J = 2.1 Hz, 1H), 8.09 (s, 1H), 7.97 (dd, J = 5.5, 2.3 Hz, 1H), 7.19 (s, 1H), 3.86-3.75 (m, 1H), 3.25 (s, 3H), 3.16-3.06 (m, 1H), 2.02 (d, J = 10.6 Hz, 2H), 1.85 (d, J = 10.4 Hz, 2H), 1.56-1.44 (m, 2H), 1.29-1.17 (m, 2H). |
| 64 | 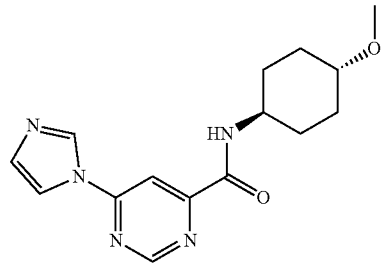 [SMILES: CO[C@H]1CC[C@H](NC(=O)c2cc(-n3ccnc3)ncn2)CC1] | 6-(1H-imidazol-1-yl)-N-((1r,4r)-4-methoxycyclohexyl) pyrimidine-4-carboxamide | 302.1 | 9.19 (d, J = 1.0 Hz, 1H), 8.85-8.77 (m, 2H), 8.37 (d, J = 1.0 Hz, 1H), 8.20 (s, 1H), 7.20 (s, 1H), 3.86-3.78 (m, 1H), 3.24 (s, 3H), 3.15-3.06 (m, 1H), 2.03 (d, J = 10.5 Hz, 2H), 1.83 (d, J = 10.0 Hz, 2H), 1.55-1.48 (m, 2H), 1.28-1.18 (m, 2H). |

Example 15

6-(dimethylamino)-2-(1H-imidazol-1-yl)-N-((1r,4r)-4-methoxycyclohexyl)pyrimidine-4-carboxamide (compound 23)

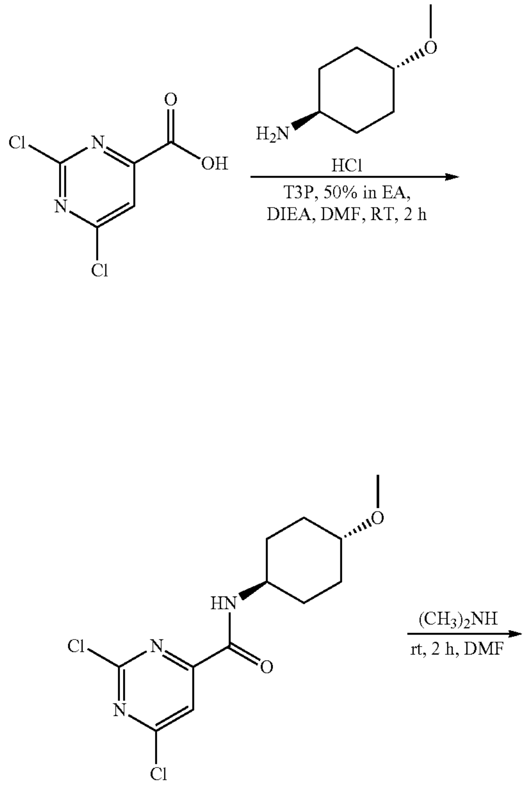

-continued

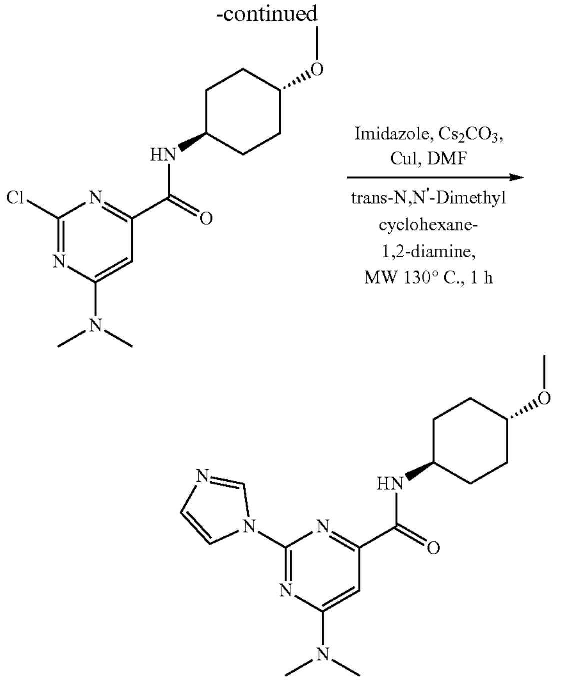

23

Step 1: 2,6-dichloro-N-((1r,4r)-4-methoxycyclohexyl)pyrimidine-4-carboxamide.

To a solution of 2,6-dichloropyrimidine-4-carboxylic acid (1.00 g, 5.18 mmol) in DMF (15 mL) were added DIEA (5.15 mL, 31.1 mmol) and T3P (4.95 mL, 15.5 mmol, 50% in EA). The reaction was stirred at room temperature for 30 min and trans-4-methoxycyclohexanamine hydrochloride (1.03 g, 6.22 mmol) was added. The reaction mixture was stirred at room temperature for 1.5 hours. The resulting mixture was diluted with water (150 mL), then extracted with DCM (100 mL×2). The combined organic layers were washed with brine (150 mL), dried over anhydrous $Na_2SO_4$, filtered and concentrated. The residue was purified by silica gel column chromatography (PE/EA=10/1 to 2/1) to afford the titled compound (479 mg, 30.3% yield) as a yellow solid. MS (ESI): m/z 304.1 $[M+H]^+$.

Step 2:2-chloro-6-(dimethylamino)-N-((1r,4r)-4-methoxycyclohexyl)pyrimidine-4-carboxamide.

To a solution of 2,6-dichloro-N-((1r,4r)-4-methoxycyclohexyl)pyrimidine-4-carboxamide (150 mg, 0.49 mmol) in DMF (6 mL) was added dimethylamine (0.74 mL, 1.48 mmol, 2.0 mol/L in THF) and the reaction was stirred at room temperature for 2 hours. The mixture was diluted with water (60 mL) and extracted with EA (50 mL×2). The combined organic layers were washed with brine (50 mL), dried over anhydrous $Na_2SO_4$, filtered and concentrated. The residue was purified by silica gel column chromatography (PE/EA=50/1 to 2/1) to afford the titled compound (110.7 mg, 71.8% yield) as a yellow oil. MS (ESI): m/z 313.1 $[M+H]^+$. $^1$H NMR (400 MHZ, DMSO-$d_6$) δ 8.26 (d, J=8.4 Hz, 1H), 7.10 (s, 1H), 3.79-3.64 (m, 1H), 3.24 (s, 3H), 3.12 (s, 6H), 3.09-3.04 (m, 1H), 2.03-1.97 (m, 2H), 1.82-1.75 (m, 2H), 1.54-1.44 (m, 2H), 1.25-1.16 (m, 2H).

Step 3: 6-(dimethylamino)-2-(1H-imidazol-1-yl)-N-((1r,4r)-4-methoxycyclohexyl)pyrimidine-4-carboxamide.

A mixture of 2-chloro-6-(dimethylamino)-N-((1r,4r)-4-methoxycyclohexyl)pyrimidine-4-carboxamide (110.7 mg, 0.35 mmol), imidazole (28.9 mg, 0.43 mmol), CuI (6.74 mg, 0.035 mmol), $Cs_2CO_3$ (231 mg, 0.708 mmol), trans-N,N'-dimethylcyclohexane-1,2-diamine (0.01 mL, 0.035 mmol) and DMF (3 mL) was bubbled with argon for 3 minutes. The reaction tube was sealed and heated in a microwave reactor at 130° C. for 1 hour. The mixture was diluted with water (60 mL) and extracted with EA (50 mL×2). The combined organic layers were washed with brine (50 mL), dried over anhydrous $Na_2SO_4$, filtered and concentrated. The residue was purified by prep-HPLC (Waters 2767/2545/2489, Waters Xbridge C18 10 μm OBD 19*250 mm, Mobile Phase A: 0.1% $NH_4OH$ in water, Mobile Phase B: $CH_3CN$, Flow: 20 mL/min, Column temp: RT) to afford the titled compound (62.8 mg, 51.5% yield) as a white solid. MS (ESI): m/z 345.2 $[M+H]^+$. $^1$H NMR (400 MHZ, DMSO-$d_6$) δ 8.92 (s, 1H), 8.61 (d, J=8.6 Hz, 1H), 8.20 (s, 1H), 7.15 (s, 1H), 7.13 (s, 1H), 3.91-3.84 (m, 1H), 3.40 (s, 3H), 3.32 (s, 3H), 3.24-3.15 (m, 4H), 2.11 (d, J=11.0 Hz, 2H), 1.89 (d, J=10.7 Hz, 2H), 1.65-1.55 (m, 2H), 1.33-1.23 (m, 2H).

The compounds below were synthesized following the procedures described for compound 23.

| No | Structure | Name | MS ESI $[M + H]^+$ | $^1$H NMR (400 MHz, DMSO-$d_6$) δ |
|---|---|---|---|---|
| 24 | 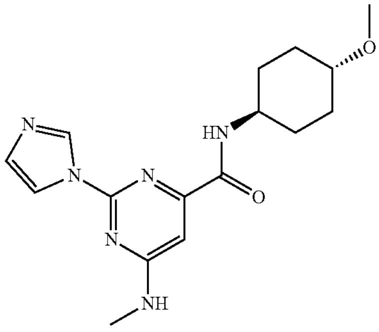 [SMILES: CNc1cc(C(=O)N[C@H]2CC[C@H](OC)CC2)nc(-n2ccnc2)n1] | 2-(1H-imidazol-1-yl)-N-((1r,4r)-4-methoxycyclohexyl)-6-(methylamino)pyrimidine-4-carboxamide | 331.1 | 8.87 (s, 1H), 8.49 (d, J = 8.6 Hz, 1H), 8.18-8.06 (m, 2H), 7.11 (s, 1H), 7.23-6.81 (m, 2H), 6.99 (s, 1H), 3.80-3.70 (m, 1H), 3.23 (s, 3H), 3.12 (t, J = 10.6 Hz, 1H), 2.95 (d, J = 4.4 Hz, 3H), 2.05 (d, J = 10.5 Hz, 2H), 1.80 (d, J = 10.4 Hz, 2H), 1.60-1.50 (m, 2H), 1.26-1.16 (m, 2H). |
| 26 | 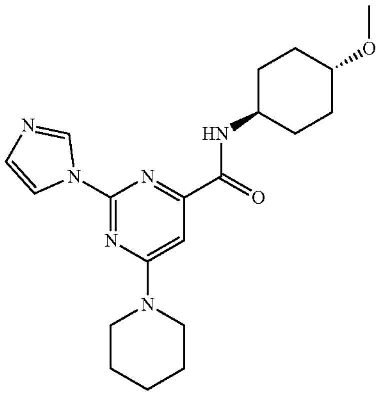 [SMILES: CO[C@H]1CC[C@H](NC(=O)c2cc(N3CCCCC3)nc(-n3ccnc3)n2)CC1] | 2-(1H-imidazol-1-yl)-N-((1r,4r)-4-methoxycyclohexyl)-6-(piperidin-1-yl)pyrimidine-4-carboxamide | 385.2 | 8.85 (s, 1H), 8.53 (d, J = 8.6 Hz, 1H), 8.13 (s, 1H), 7.18 (s, 1H), 7.09 (s, 1H), 3.88-3.57 (m, 5H), 3.26 (s, 3H), 3.16-3.09 (m, 1H), 2.05 (d, J = 10.1 Hz, 2H), 1.82 (d, J = 10.1 Hz, 2H), 1.69-1.49 (m, 8H), 1.26-1.17 (m, 2H). |

-continued

| No | Structure | Name | MS ESI $[M + H]^+$ | $^1H$ NMR (400 MHz, DMSO-$d_6$) δ |
| --- | --- | --- | --- | --- |
| 101 | 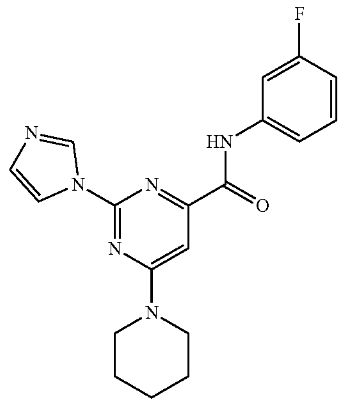 [SMILES: O=C(Nc1cccc(F)c1)c1cc(N2CCCCC2)nc(-n2ccnc2)n1] | N-(3-fluorophenyl)-2-(1H-imidazol-1-yl)-6-(piperidin-1-yl)pyrimidine-4-carboxamide | 367.3 | 10.51 (s, 1H), 8.93 (s, 1H), 8.21 (s, 1H), 7.84 (dt, J = 11.6, 2.2 Hz, 1H), 7.75 (d, J = 8.2 Hz, 1H), 7.45 (dd, J = 15.1, 8.2 Hz, 1H), 7.32 (s, 1H), 7.11 (s, 1H), 7.01 (td, J = 8.4, 2.1 Hz, 1H), 3.80 (s, 4H), 1.73-1.55 (m, 6H). |
| 114 | 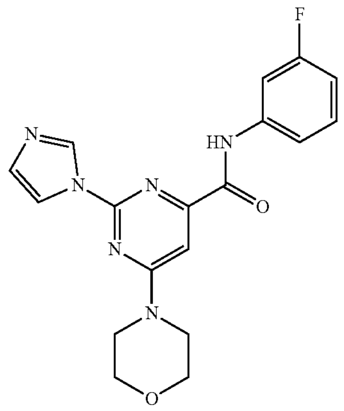 [SMILES: O=C(Nc1cccc(F)c1)c1cc(N2CCOCC2)nc(-n2ccnc2)n1] | N-(3-fluorophenyl)-2-(1H-imidazol-1-yl)-6-morpholinopyrimidine-4-carboxamide | 369.2 | 10.53 (s, 1H), 8.96 (s, 1H), 8.24 (s, 1H), 7.84 (dt, J = 11.6, 2.1 Hz, 1H), 7.75 (d, J = 8.2 Hz, 1H), 7.45 (dd, J = 15.1, 8.2 Hz, 1H), 7.35 (s, 1H), 7.12 (s, 1H), 7.02 (td, J = 8.4, 2.2 Hz, 1H), 3.91-3.62 (m, 8H). |
| 117 | 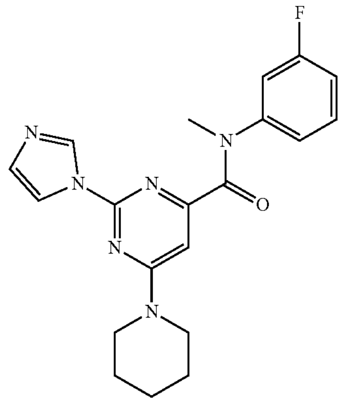 [SMILES: CN(C(=O)c1cc(N2CCCCC2)nc(-n2ccnc2)n1)c1cccc(F)c1] | N-(3-fluorophenyl)-2-(1H-imidazol-1-yl)-N-methyl-6-(piperidin-1-yl)pyrimidine-4-carboxamide | 381.1 | 8.17 (s, 1H), 7.56 (s, 1H), 7.33-7.27 (m, 2H), 7.15-7.01 (m, 3H), 6.99 (s, 1H), 6.93 (s, 1H), 3.67 (s, 4H), 3.37 (s, 3H), 1.64-1.63 (m, 2H), 1.53 (s, 4H). |
| 119 | 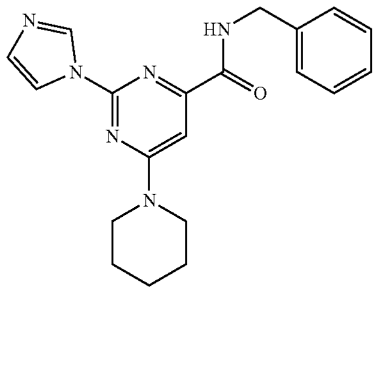 [SMILES: O=C(NCc1ccccc1)c1cc(N2CCCCC2)nc(-n2ccnc2)n1] | N-benzyl-2-(1H-imidazol-1-yl)-6-(piperidin-1-yl)pyrimidine-4-carboxamide | 363.1 | 9.55 (t, J = 6.4 Hz, 1H), 8.84 (s, 1H), 8.14 (t, J = 1.3 Hz, 1H), 7.32 (dd, J = 10.2, 2.9 Hz, 4H), 7.28-7.23 (m, 1H), 7.22 (s, 1H), 7.10-7.08 (m, 1H), 4.53 (d, J = 6.5 Hz, 2H), 1.66 (d, J = 4.6 Hz, 2H), 1.58 (d, J = 3.7 Hz, 4H). |

-continued

| No | Structure | Name | MS ESI [M + H]$^+$ | $^1$H NMR (400 MHz, DMSO-$d_6$) δ |
| --- | --- | --- | --- | --- |
| 128 | 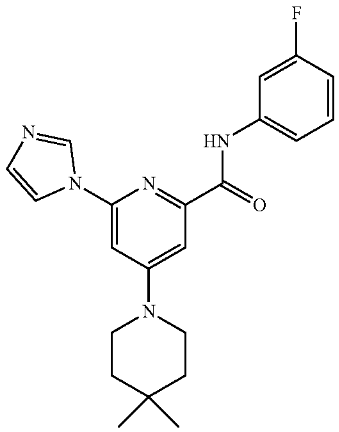 [SMILES: CC1(C)CCN(c2cc(C(=O)Nc3cccc(F)c3)nc(-n3ccnc3)c2)CC1] | 4-(4,4-dimethylpiperidin-1-yl)-N-(3-fluorophenyl)-6-(1H-imidazol-1-yl)picolinamide | 394.2 | 10.45 (s, 1H), 8.95 (s, 1H), 8.30 (s, 1H), 7.89-7.83 (m, 1H), 7.77-7.71 (m, 1H), 7.49 (d, J = 2.1 Hz, 1H), 7.47-7.39 (m, 1H), 7.26 (d, J = 2.1 Hz, 1H), 7.12 (s, 1H), 7.03-6.94 (m, 1H), 3.60-3.53 (m, 4H), 1.48-1.40 (m, 4H), 1.00 (s, 6H). |
| 129 | 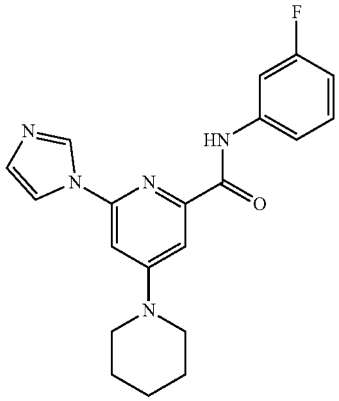 [SMILES: O=C(Nc1cccc(F)c1)c1cc(N2CCCCC2)cc(-n2ccnc2)n1] | N-(3-fluorophenyl)-6-(1H-imidazol-1-yl)-4-(piperidin-1-yl)picolinamide | 366.1 | 10.45 (s, 1H), 8.95 (s, 1H), 8.30 (s, 1H), 7.90-7.81 (m, 1H), 7.78-7.70 (m, 1H), 7.47 (d, J = 1.8 Hz, 1H), 7.46-7.37 (m, 1H), 7.25 (d, J = 1.6 Hz, 1H), 7.12 (s, 1H), 7.02-6.94 (m, 1H), 3.65-3.52 (m, 4H), 1.72-1.54 (m, 6H). |
| 130 | 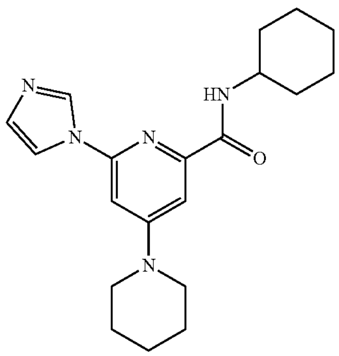 [SMILES: O=C(NC1CCCCC1)c1cc(N2CCCCC2)cc(-n2ccnc2)n1] | N-cyclohexyl-6-(1H-imidazol-1-yl)-4-(piperidin-1-yl)picolinamide | 354.2 | 8.89 (s, 1H), 8.40 (d, J = 8.8 Hz, 1H), 8.24 (s, 1H), 7.36 (d, J = 2.2 Hz, 1H), 7.18 (d, J = 2.2 Hz, 1H), 7.12 (s, 1H), 3.88-3.73 (m, 1H), 3.60-3.48 (m, 4H), 1.86-1.70 (m, 4H), 1.70-1.53 (m, 7H), 1.53-1.40 (m, 2H), 1.40-1.25 (m, 2H), 1.23-1.06 (m, 1H). |

-continued

| No | Structure | Name | MS ESI [M + H]+ | $^1$H NMR (400 MHz, DMSO-$d_6$) δ |
|---|---|---|---|---|
| 135 | 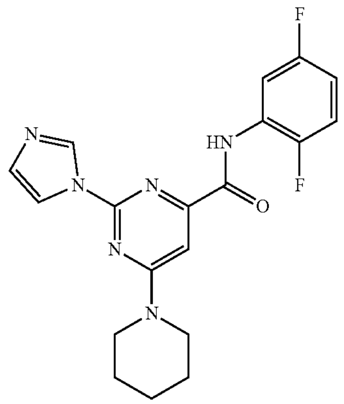 [SMILES: O=C(Nc1cc(F)ccc1F)c1cc(N2CCCCC2)nc(-n2ccnc2)n1] | N-(2,5-difluorophenyl)-2-(1H-imidazol-1-yl)-6-(piperidin-1-yl)pyrimidine-4-carboxamide | 385.1 | 10.46 (s, 1H), 8.81 (s, 1H), 8.12 (t, J = 1.2 Hz, 1H), 7.76-7.67 (m, 1H), 7.48-7.38 (m, 1H), 7.31 (s, 1H), 7.22-7.13 (m, 1H), 7.13-7.09 (m, 1H), 3.81 (s, 4H), 1.74-1.65 (m, 2H), 1.65-1.54 (m, 4H). |
| 137 | 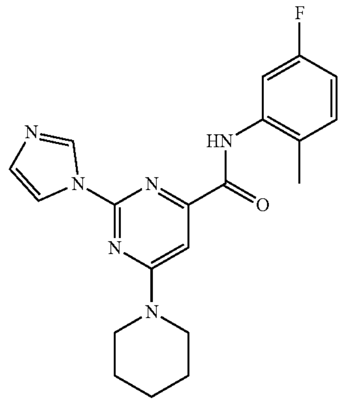 [SMILES: Cc1ccc(F)cc1NC(=O)c1cc(N2CCCCC2)nc(-n2ccnc2)n1] | N-(5-fluoro-2-methylphenyl)-2-(1H-imidazol-1-yl)-6-(piperidin-1-yl)pyrimidine-4-carboxamide | 381.2 | 10.31 (s, 1H), 8.81 (s, 1H), 8.13 (s, 1H), 7.67-7.53 (m, 1H), 7.41-7.26 (m, 2H), 7.18-6.97 (m, 2H), 3.98-3.64 (m, 4H), 2.39-2.24 (m, 3H), 1.77-1.52 (m, 6H). |
| 144 | 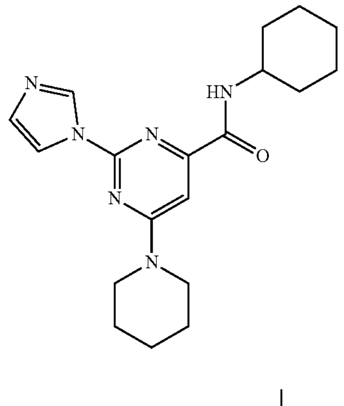 | N-cyclohexyl-2-(1H-imidazol-1-yl)-6-(piperidin-1-yl)pyrimidine-4-carboxamide | 355.2 | 8.86 (s, 1H), 8.53 (d, J = 8.6 Hz, 1H), 8.14 (s, 1H), 7.19 (s, 1H), 7.09 (s, 1H), 3.91-3.66 (m, 5H), 1.84-1.73 (m, 4H), 1.72-1.55 (m, 7H), 1.54-1.42 (m, 2H), 1.40-1.25 (m, 2H), 1.22-1.07 (m, 1H). |
| 145 | 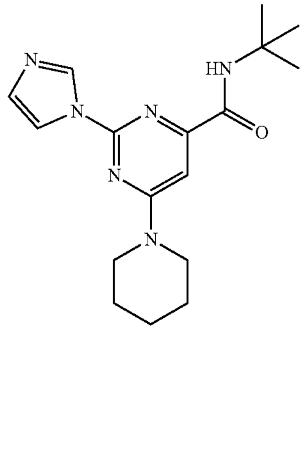 [SMILES: CC(C)(C)NC(=O)c1cc(N2CCCCC2)nc(-n2ccnc2)n1] | N-(tert-butyl)-2-(1H-imidazol-1-yl)-6-(piperidin-1-yl)pyrimidine-4-carboxamide | 329.1 | 8.75 (s, 1H), 8.05 (t, J = 1.2 Hz, 1H), 8.00 (s, 1H), 7.20 (s, 1H), 7.08 (s, 1H), 3.75 (s, 4H), 1.74-1.64 (m, 2H), 1.63-1.52 (m, 4H), 1.42 (s, 9H). |

-continued

| No | Structure | Name | MS ESI $[M + H]^+$ | $^1H$ NMR (400 MHz, DMSO-$d_6$) δ |
|---|---|---|---|---|
| 147 | 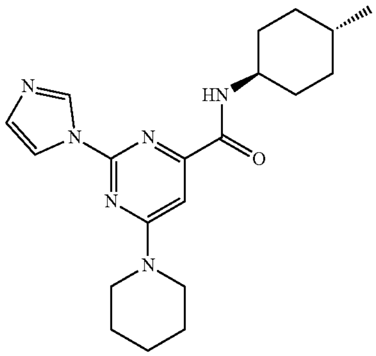 [SMILES: C[C@H]1CC[C@H](NC(=O)c2cc(N3CCCCC3)nc(-n3ccnc3)n2)CC1] | 2-(1H-imidazol-1-yl)-N-((1r,4r)-4-methylcyclohexyl)-6-(piperidin-1-yl)pyrimidine-4-carboxamide | 369.2 | 8.85 (t, J = 1.0 Hz, 1H), 8.51 (d, J = 8.8 Hz, 1H), 8.13 (t, J = 1.3 Hz, 1H), 7.17 (s, 1H), 7.09-7.06 (m, 1H), 3.89-3.61 (m, 4H), 3.58-3.20 (m, 1H), 1.84-1.63 (m, 6H), 1.62-1.44 (m, 6H), 1.43-1.27 (m, 1H), 1.12-0.96 (m, 2H), 0.90 (d, J = 6.5 Hz, 3H). |
| 148 | 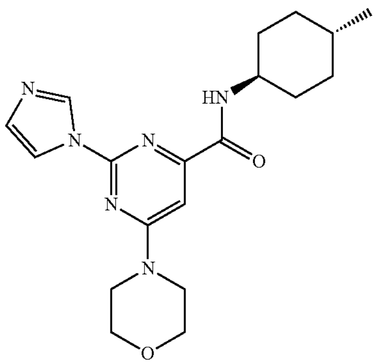 [SMILES: C[C@H]1CC[C@H](NC(=O)c2cc(N3CCOCC3)nc(-n3ccnc3)n2)CC1] | 2-(1H-imidazol-1-yl)-N-((1r,4r)-4-methylcyclohexyl)-6-morpholinopyrimidine-4-carboxamide | 371.2 | 8.88 (s, 1H), 8.54 (d, J = 8.7 Hz, 1H), 8.16 (s, 1H), 7.20 (s, 1H), 7.09 (s, 1H), 3.88-3.60 (m, 9H), 1.79-1.68 (m, 4H), 1.59-1.45 (m, 2H), 1.42-1.26 (m, 1H), 1.14-0.96 (m, 2H), 0.94-0.87 (m, 3H). |

Example 16

5-(1H-imidazol-1-yl)-N-((1r,4r)-4-methoxycyclohexyl)pyridazine-3-carboxamide (compound 28)

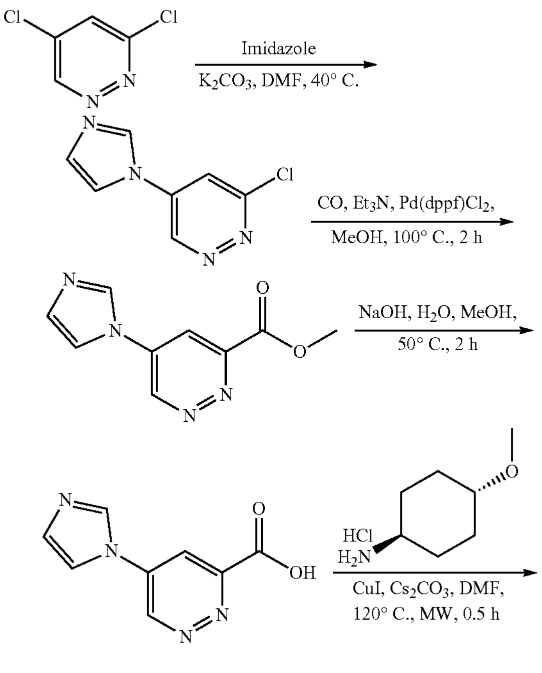

-continued

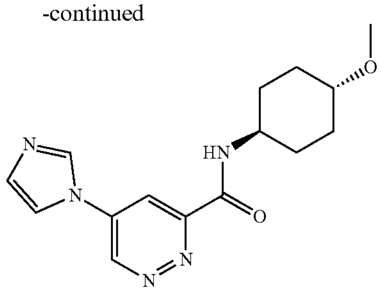

28

Step 1:3-chloro-5-(1H-imidazol-1-yl) pyridazine.

A mixture of 3,5-dichloropyridazine (2.10 g, 14.1 mmol), 1H-imidazole (0.96 g, 14.1 mmol), $K_2CO_3$ (3.90 g, 28.2 mmol) in DMF (20 mL) was stirred at 40° C. for overnight. The reaction mixture was diluted with $H_2O$ (20 mL), then extracted with EA (50 mL×2). The combined organic layers were washed with brine (20 mL), dried over anhydrous $Na_2SO_4$, filtered and concentrated. The residue was purified by silica gel column chromatography (DCM/MeOH=200/1 to 60/1) to afford the titled compound (2.40 g, 94.3% yield) as a white solid. MS (ESI): m/z 181.1 $[M+H]^+$.

Step 2: methyl 5-(1H-imidazol-1-yl) pyridazine-3-carboxylate.

A mixture of 3-chloro-5-(1H-imidazol-1-yl) pyridazine (1.02 g, 5.53 mmol), triethylamine (1.54 mL, 11.1 mmol), Pd(dppf)$Cl_2$ (0.41 g, 0.554 mmol) and MeOH (15 mL) was heated at 100° C. under the atmosphere of CO (16 atm) in an autoclave for 5 hours. The resulting mixture was cooled and filtered. The filtrate was concentrated under reduced pressure. The residue was purified by silica gel column chromatography (DCM/MeOH=200/1-40/1) to afford the titled compound (340 mg, 30.1% yield) as a red solid. MS (ESI): m/z 205.0 $[M+H]^+$.

Step 3:5-(1H-imidazol-1-yl) pyridazine-3-carboxylic acid.

A mixture of methyl 5-(1H-imidazol-1-yl) pyridazine-3-carboxylate (340 mg, 1.66 mmol), NaOH (133 mg, 3.33 mmol), MeOH (8 mL) and $H_2O$ (2 mL) was heated at 50° C. for 2 hours. The reaction mixture was cooled to room temperature. The pH of the mixture was adjusted to 2~3 with diluted HCl (1.0 M). The resulting mixture was concentrated under reduced pressure to afford the titled compound (560 mg, 100% yield), MS (ESI): m/z 191.1 [M+H] +, as an orange solid and used in the next step without purification.

Step 4:5-(1H-imidazol-1-yl)-N-((1r,4r)-4-methoxycyclohexyl)pyridazine-3-carboxamide To a mixture of 5-(1H-imidazol-1-yl) pyridazine-3-carboxylic acid (100 mg, 0.526 mmol), HATU (239 mg, 0.631 mmol), DIEA (0.26 mL, 1.578 mmol) in DMF (5 mL) was added trans-4-methoxycyclohexanamine hydrochloride (105 mg, 0.631 mmol). The mixture was stirred at room temperature for 2 hours. The reaction mixture was diluted with $H_2O$ (20 mL) and extracted with DCM (50 mL×2). The combined organic layers were washed with brine (20 mL), dried over anhydrous $Na_2SO_4$, filtered and concentrated. The residue was purified by silica gel column chromatography (DCM/MeOH=200/1-30/1) to afford the titled compound (11.5 mg, 7.3% yield) as a white solid. MS (ESI): m/z 302.1 $[M+H]^+$; $^1H$ NMR (400 MHZ, $CDCl_3$) δ 9.56 (s, 1H), 8.63-8.30 (m, 2H), 8.08 (s, 1H), 7.65-7.40 (m, 2H), 4.04 (s, 1H), 3.38 (s, 3H), 3.22 (s, 1H), 2.22-2.09 (m, 4H), 1.50-1.35 (m, 4H).

Example 17

N-cyclooctyl-2-(1H-imidazol-1-yl) pyrimidine-4-carboxamide (compound 65)

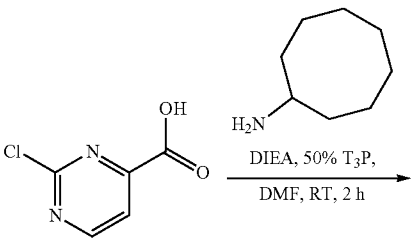

-continued

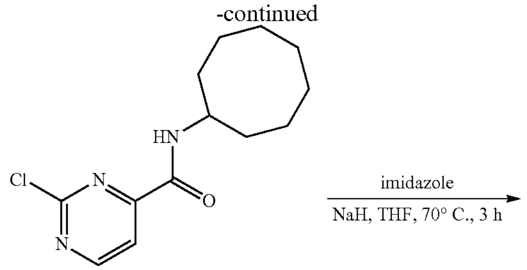

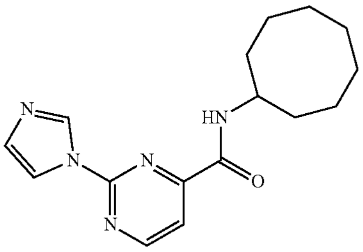

65

Step 1. 2-chloro-N-cyclooctylpyrimidine-4-carboxamide

A mixture of 2-chloropyrimidine-4-carboxylic acid (200 mg, 1.26 mmol), DIEA (0.63 mL, 3.78 mmol), T3P (0.63 mL, 3.78 mmol, 50% in EA), cyclooctylamine (0.17 mL, 1.26 mmol) in DCM (10 mL) was stirred at room temperature for 2 hours. The reaction mixture was diluted with $H_2O$ (30 mL) and the resulting mixture was extracted with EA (30 mL×2). The combined organic layers were washed with brine (30 mL), dried over anhydrous $Na_2SO_4$, filtered and concentrated. The residue was purified by silica gel column chromatography (PE/EA=20/1-7/1) to afford the titled compound (300 mg, 88.8% yield) as a yellow solid. MS (ESI): m/z 268.1 $[M+H]^+$.

Step 2. N-cyclooctyl-2-(1H-imidazol-1-yl) pyrimidine-4-carboxamide

To a solution of 2-chloro-N-cyclooctylpyrimidine-4-carboxamide (228 mg, 3.36 mmol) in THF (5 mL) was added NaH (59.2 mg, 2.46 mmol 60% in oil) at 0° C., the reaction was warmed to room temperature and stirred at this temperature for 0.5 hour. Imidazole (300 mg, 1.12 mmol) was added into the solution and the mixture was heated at 70° C. for 3 hours under $N_2$ atmosphere. The solution was quenched with $H_2O$ at 0° C., and the mixture was extracted with EA (30 mL×2). The combined organic layers were washed with brine (30 mL), dried over anhydrous $Na_2SO_4$, filtered and concentrated. The residue was purified by silica gel column chromatography (DCM/MeOH=200/1-80/1) to afford the titled compound (178 mg, 53.2% yield) as a white solid. MS (ESI): m/z 300.0 $[M+H]^+$; $^1H$ NMR (400 MHZ, DMSO-$d_6$) δ 9.06 (d, J=5.0 Hz, 1H), 8.96 (s, 1H), 8.88 (d, J=8.4 Hz, 1H), 8.22 (t, J=1.3 Hz, 1H), 7.90 (d, J=5.0 Hz, 1H), 7.18 (s, 1H), 4.17-4.03 (m, 1H), 1.87-1.71 (m, 6H), 1.64-1.47 (m, 8H).

The compounds below were synthesized following the procedures described for compound 65.

| No. | Structure | Name | MS ESI $[M + H]^+$ | $^1H$ NMR (400 MHz, DMSO-$d_6$) δ |
|---|---|---|---|---|
| 66 | 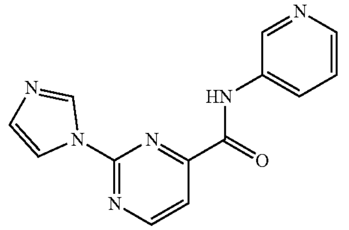 [SMILES: O=C(Nc1cccnc1)c1ccnc(-n2ccnc2)n1] | 2-(1H-imidazol-1-yl)-N-(pyridin-3-yl)pyrimidine-4-carboxamide | 267.2 | 10.89 (s, 1H), 9.16 (d, J = 5.0 Hz, 1H), 9.05-9.02 (m, 2H), 8.43 (dd, J = 4.7, 1.3 Hz, 1H), 8.32 (s, 1H), 8.29-8.24 (m, 1H), 8.06 (d, J = 5.0 Hz, 1H), 7.50 (dd, J = 8.3, 4.7 Hz, 1H), 7.22 (s, 1H). |
| 72 | 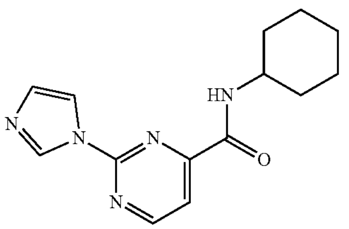 [SMILES: O=C(NC1CCCCC1)c1ccnc(-n2ccnc2)n1] | N-cyclohexyl-2-(1H-imidazol-1-yl)pyrimidine-4-carboxamide | 272.2 | 9.06 (d, J = 5.0 Hz, 1H), 8.98 (s, 1H), 8.86 (d, J = 8.6 Hz, 1H), 8.24 (s, 1H), 7.91 (d, J = 5.0 Hz, 1H), 7.18 (s, 1H), 3.91-3.79 (m, 2H), 2.55-2.46 (m, 8H), 1.88-1.72 (m, 4H), 1.65 (d, J = 12.4 Hz, 1H), 1.57-1.38 (m, 2H), 1.40-1.27 (m, 2H), 1.21-1.10 (m, 1H). |
| 73 | 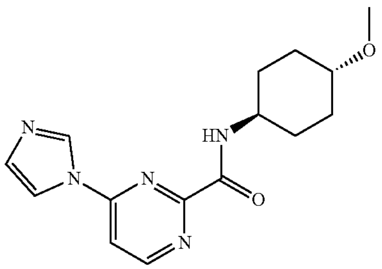 | 4-(1H-imidazol-1-yl)-N-((1r,4r)-4-methoxycyclohexyl) pyrimidine-2-carboxamide | 302.1 | 9.04 (d, J = 5.6 Hz, 1H), 8.92 (s, 1H), 8.72 (d, J = 8.4 Hz, 1H), 8.23 (t, J = 1.4 Hz, 1H), 8.06 (d, J = 5.6 Hz, 1H), 7.22 (s, 1H), 3.85-3.75 (m, 1H), 3.25 (s, 3H), 3.19-3.07 (m, 1H), 2.05 (d, J = 10.5 Hz, 2H), 1.85 (d, J = 10.4 Hz, 2H), 1.59-1.45 (m, 2H), 1.30-1.18 (m, 2H). |
| 82 | 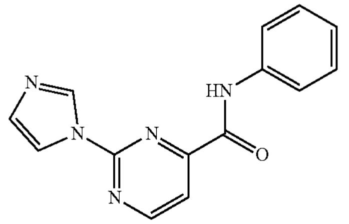 | 2-(1H-imidazol-1-yl)-N-phenylpyrimidine-4-carboxamide | 266.1 | 10.70 (s, 1H), 9.14 (s, 1H), 9.04 (s, 1H), 8.31 (s, 1H), 8.05 (s, 1H), 7.87 (d, J = 7.6 Hz, 2H), 7.45-7.40 (m, 2H), 7.25-7.19 (m, 2H). |
| 83 | 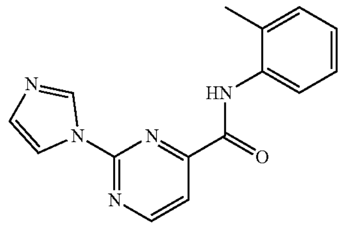 [SMILES: Cc1ccccc1NC(=O)c1ccnc(-n2ccnc2)n1] | 2-(1H-imidazol-1-yl)-N-(o-tolyl)pyrimidine-4-carboxamide | 280.1 | 10.62 (s, 1H), 9.14 (s, 1H), 8.98 (s, 1H), 8.29 (s, 1H), 8.02 (s, 1H), 7.50 (d, J = 7.6 Hz, 1H), 7.38-7.18 (m, 4H), 2.30 (s, 3H). |
| 84 | 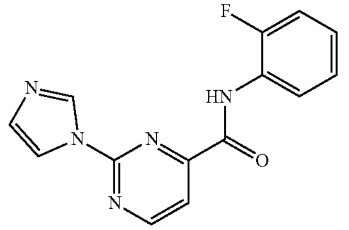 [SMILES: O=C(Nc1ccccc1F)c1ccnc(-n2ccnc2)n1] | N-(2-fluorophenyl)-2-(1H-imidazol-1-yl)pyrimidine-4-carboxamide | 284.1 | 10.77 (s, 1H), 9.15 (s, 1H), 8.98 (s, 1H), 8.28 (s, 1H), 8.02 (s, 1H), 7.68 (d, J = 7.6 Hz, 1H), 7.40-7.36 (m, 2H), 7.34-7.28 (m, 1H), 7.21 (s, 1H). |

-continued

| No. | Structure | Name | MS ESI $[M + H]^+$ | $^1H$ NMR (400 MHz, DMSO-$d_6$) δ |
|---|---|---|---|---|
| 85 | 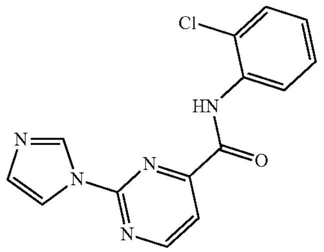 [SMILES: O=C(Nc1ccccc1Cl)c1ccnc(-n2ccnc2)n1] | N-(2-chlorophenyl)-2-(1H-imidazol-1-yl)pyrimidine-4-carboxamide | 300.0 | 10.77 (s, 1H), 9.17 (s, 1H), 8.90 (s, 1H), 8.22 (s, 1H), 8.04 (s, 1H), 7.89 (d, J = 8.0 Hz, 1H), 7.64 (d, J = 8.0 Hz, 1H), 7.50-7.33 (m, 2H), 7.21 (s, 1H). |
| 86 | 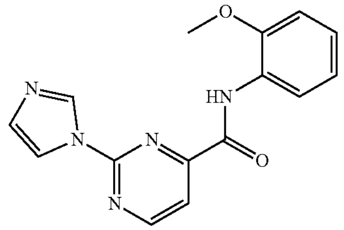 [SMILES: COc1ccccc1NC(=O)c1ccnc(-n2ccnc2)n1] | 2-(1H-imidazol-1-yl)-N-(2-methoxyphenyl) pyrimidine-4-carboxamide | 296.2 | 10.45 (s, 1H), 9.15 (s, 1H), 8.78 (s, 1H), 8.11 (s, 1H), 8.05 (d, J = 7.2 Hz, 1H), 8.03 (s, 1H), 7.26-7.16 (m, 3H), 7.03 (t, J = 7.2 Hz, 1H), 3.94 (s, 3H). |
| 87 | 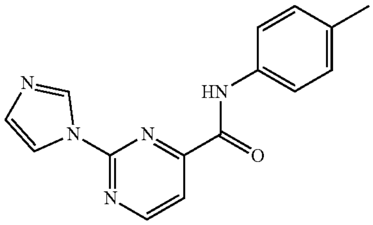 [SMILES: Cc1ccc(NC(=O)c2ccnc(-n3ccnc3)n2)cc1] | 2-(1H-imidazol-1-yl)-N-(p-tolyl)pyrimidine-4-carboxamide | 280.1 | 10.63 (s, 1H), 9.14 (s, 1H), 9.07 (s, 1H), 8.32 (s, 1H), 8.03 (s, 1H), 7.75 (s, 2H), 7.25-7.22 (m, 3H), 2.32 (s, 3H). |
| 88 | 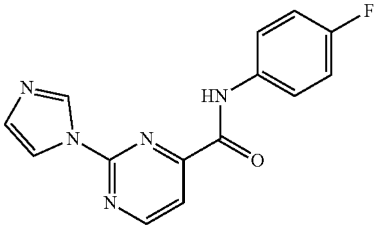 [SMILES: O=C(Nc1ccc(F)cc1)c1ccnc(-n2ccnc2)n1] | N-(4-fluorophenyl)-2-(1H-imidazol-1-yl)pyrimidine-4-carboxamide | 284.0 | 10.75 (s, 1H), 9.14 (s, 1H), 9.03 (s, 1H), 8.30 (s, 1H), 8.03 (s, 1H), 7.87 (d, J = 8.4 Hz, 2H), 7.30 (d, J = 8.8 Hz, 2H), 7.21 (s, 1H). |
| 89 | 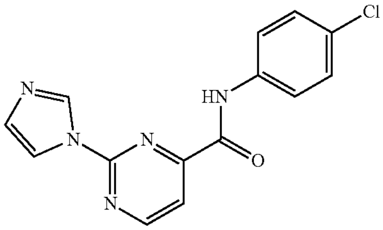 [SMILES: O=C(Nc1ccc(Cl)cc1)c1ccnc(-n2ccnc2)n1] | N-(4-chlorophenyl)-2-(1H-imidazol-1-yl)pyrimidine-4-carboxamide | 300.1 | 10.78 (s, 1H), 9.14 (s, 1H), 9.03 (s, 1H), 8.30 (s, 1H), 7.92 (s, 2H), 7.51 (d, J = 8.8 Hz, 2H), 7.21 (s, 1H). |
| 90 | 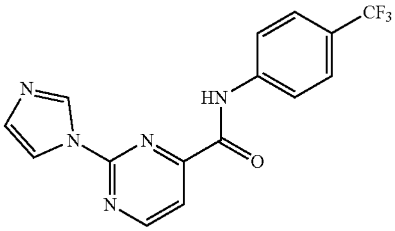 [SMILES: O=C(Nc1ccc(C(F)(F)F)cc1)c1ccnc(-n2ccnc2)n1] | 2-(1H-imidazol-1-yl)-N-(4-(trifluoromethyl) phenyl)pyrimidine-4-carboxamide | 334.0 | 10.93 (s, 1H), 9.17 (s, 1H), 9.04 (s, 1H), 8.31 (s, 1H), 8.14 (d, J = 8.8 Hz, 2H), 8.07 (s, 2H), 7.83 (d, J = 8.8 Hz, 2H), 7.22 (s, 1H). |

-continued

| No. | Structure | Name | MS ESI $[M + H]^+$ | $^1H$ NMR (400 MHz, DMSO-$d_6$) δ |
|---|---|---|---|---|
| 91 | 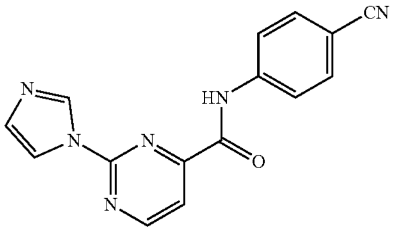 [SMILES: N#Cc1ccc(NC(=O)c2ccnc(-n3ccnc3)n2)cc1] | N-(4-cyanophenyl)-2-(1H-imidazol-1-yl)pyrimidine-4-carboxamide | 291.2 | 10.95 (s, 1H), 9.17 (s, 1H), 9.05 (s, 1H), 8.31 (s, 1H), 8.13 (d, J = 8.8 Hz, 2H), 8.06 (s, 2H), 7.92 (d, J = 8.8 Hz, 2H), 7.23 (s, 1H). |
| 92 | 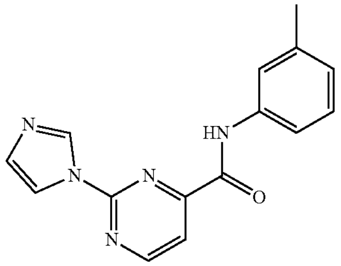 [SMILES: Cc1cccc(NC(=O)c2ccnc(-n3ccnc3)n2)c1] | 2-(1H-imidazol-1-yl)-N-(m-tolyl) pyrimidine-4-carboxamide | 280.1 | 10.62 (s, 1H), 9.14 (s, 1H), 9.04 (s, 1H), 8.31 (s, 1H), 8.03 (s, 1H), 7.69 (s, 2H), 7.32 (t, J = 7.2 Hz, 1H), 7.21 (s, 1H), 7.04 (d, J = 7.6 Hz, 1H), 2.36 (s, 3H). |
| 93 | 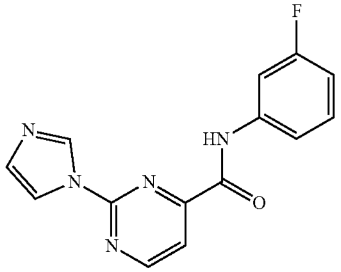 [SMILES: O=C(Nc1cccc(F)c1)c1ccnc(-n2ccnc2)n1] | N-(3-fluorophenyl)-2-(1H-imidazol-1-yl)pyrimidine-4-carboxamide | 284.2 | 10.79 (s, 1H), 9.16 (s, 1H), 9.03 (s, 1H), 8.30 (s, 1H), 8.04 (s, 1H), 7.79 (d, J = 8.0 Hz, 1H), 7.74 (d, J = 8.0 Hz, 1H), 7.50-7.45 (m, 1H), 7.21 (s, 1H), 7.08-7.03 (m, 1H). |
| 94 | 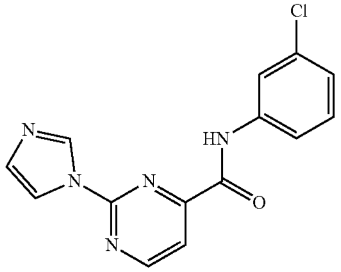 [SMILES: O=C(Nc1cccc(Cl)c1)c1ccnc(-n2ccnc2)n1] | N-(3-chlorophenyl)-2-(1H-imidazol-1-yl)pyrimidine-4-carboxamide | 300.0 | 10.78 (s, 1H), 9.15 (s, 1H), 9.04 (s, 1H), 8.31 (s, 1H), 8.03 (s, 2H), 7.89 (d, J = 8.0 Hz, 1H), 7.47 (d, J = 8.0 Hz, 1H), 7.28 (d, J = 8.0 Hz, 1H), 7.21 (s, 1H). |
| 95 | 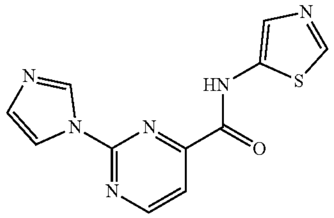 [SMILES: O=C(Nc1cncs1)c1ccnc(-n2ccnc2)n1] | 2-(1H-imidazol-1-yl)-N-(thiazol-5-yl)pyrimidine-4-carboxamide | 273.1 | 12.06 (s, 1H), 9.16 (s, 1H), 9.02 (s, 1H), 8.78 (s, 1H), 8.30 (s, 1H), 8.08 (s, 1H), 8.04 (s, 1H), 7.23 (s, 1H). |
| 96 | 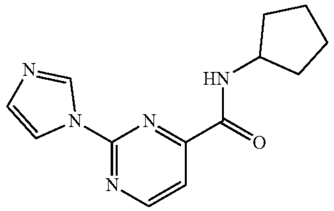 [SMILES: O=C(NC1CCCC1)c1ccnc(-n2ccnc2)n1] | N-cyclopentyl-2-(1H-imidazol-1-yl)pyrimidine-4-carboxamide | 258.1 | 9.06 (d, J = 4.8 Hz, 1H), 8.97 (s, 1H), 8.90 (d, J = 8.0 Hz, 1H), 8.23 (s, 1H), 7.90 (d, J = 4.8 Hz, 1H), 7.18 (s, 1H), 4.35-4.25 (m, 1H), 2.00-1.90 (m, 2H), 1.80-1.53 (m, 6H). |

-continued

| No. | Structure | Name | MS ESI [M + H]$^+$ | $^1$H NMR (400 MHz, DMSO-$d_6$) δ |
| --- | --- | --- | --- | --- |
| 97 | 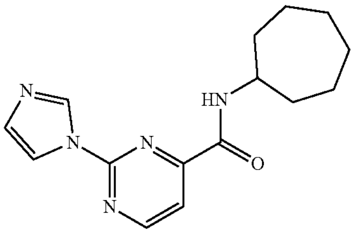 [SMILES: O=C(NC1CCCCCC1)c1ccnc(-n2ccnc2)n1] | N-cycloheptyl-2-(1H-imidazol-1-yl)pyrimidine-4-carboxamide | 286.2 | 9.06 (s, 1H), 8.98 (s, 1H), 8.90 (d, J = 8.4 Hz, 1H), 8.24 (s, 1H), 7.90 (s, 1H), 7.18 (s, 1H), 4.05-3.95 (m, 1H), 2.55-2.46 (m, 8H), 1.88-1.82 (m, 2H), 1.80-1.45 (m, 10H). |
| 98 | 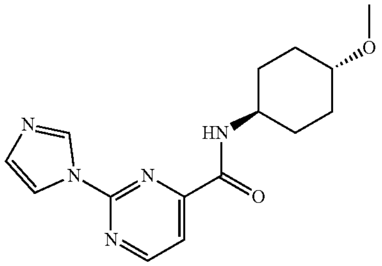 [SMILES: CO[C@H]1CC[C@H](NC(=O)c2ccnc(-n3ccnc3)n2)CC1] | 2-(1H-imidazol-1-yl)-N-((1r,4r)-4-methoxycyclohexyl) pyrimidine-4-carboxamide | 302.1 | 10.11 (s, 1H), 9.18 (d, J = 5.0 Hz, 1H), 9.03 (d, J = 8.6 Hz, 1H), 8.62 (s, 1H), 8.09 (d, J = 5.0 Hz, 1H), 7.78 (s, 1H), 3.95-3.80 (m, 1H), 3.26 (s, 3H), 3.19-3.08 (m, 1H), 2.08 (d, J = 11.0 Hz, 2H), 1.86 (d, J = 10.7 Hz, 2H), 1.65-1.53 (m, 2H), 1.30-1.17 (m, 2H). |
| 99 | 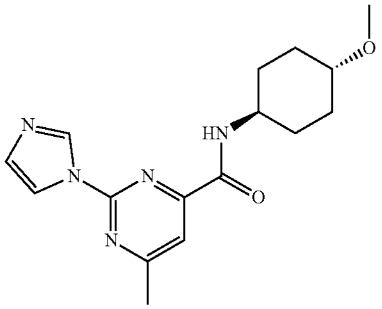 [SMILES: CO[C@H]1CC[C@H](NC(=O)c2cc(C)nc(-n3ccnc3)n2)CC1] | 2-(1H-imidazol-1-yl)-N-((1r,4r)-4-methoxycyclohexyl)-6-methylpyrimidine-4-carboxamide | 316.2 | 8.94 (s, 1H), 8.89 (d, J = 8.4 Hz, 2H), 8.20 (s, 1H), 7.83 (s, 1H), 7.16 (s, 1H), 3.88-3.83 (m, 1H), 3.26 (s, 3H), 3.18-3.10 (m, 1H), 2.63 (s, 3H), 2.07 (d, J = 10.8 Hz, 2H), 1.84 (d, J = 10.8 Hz, 2H), 1.51 (q, J = 13.2 Hz, 2H), 1.23 (q, J = 13.2 Hz, 2H). |
| 100 | 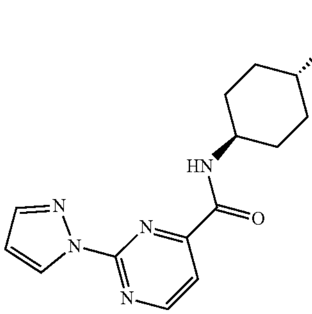 | N-((1r,4r)-4-methoxycyclohexyl)-2-(1H-pyrazol-1-yl)pyrimidine-4-carboxamide | 302.1 | 9.13 (s, 1H), 9.07 (s, 1H), 8.74 (d, J = 8.4 Hz, 1H), 7.90 (t, J = 4.8 Hz, 2H), 6.67 (s, 1H), 3.88-3.80 (m, 1H), 3.25 (s, 3H), 3.16-3.10 (m, 1H), 2.06 (d, J = 12.4 Hz, 2H), 1.86 (d, J = 12.0 Hz, 2H), 1.55-1.48 (m, 2H), 1.28-1.20 (m, 2H). |
| 102 | 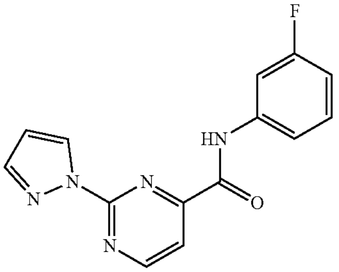 [SMILES: O=C(Nc1cccc(F)c1)c1ccnc(-n2cccn2)n1] | N-(3-fluorophenyl)-2-(1H-pyrazol-1-yl)pyrimidine-4-carboxamide | 284.1 | 10.82 (s, 1H), 9.23 (d, J = 2.4 Hz, 1H), 9.16 (d, J = 4.9 Hz, 1H), 8.02 (d, J = 4.9 Hz, 1H), 7.94 (s, 1H), 7.84 (t, J = 9.0 Hz, 1H), 7.72 (d, J = 8.1 Hz, 1H), 7.47 (dd, J = 15.1, 8.1 Hz, IH), 7.05 (td, J = 8.4, 2.1 Hz, 1H), 6.70 (d, J = 1.6 Hz, 1H). |

-continued

| No. | Structure | Name | MS ESI $[M + H]^+$ | $^1H$ NMR (400 MHz, DMSO-$d_6$) δ |
| --- | --- | --- | --- | --- |
| 107 | 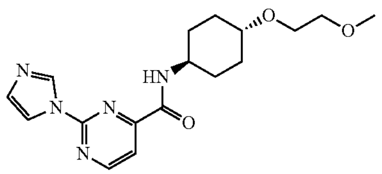 [SMILES: COCCO[C@H]1CC[C@H](NC(=O)c2ccnc(-n3ccnc3)n2)CC1] | 2-(1H-imidazol-1-yl)-N-((1r,4r)-4-(2-methoxyethoxy) cyclohexyl) pyrimidine-4-carboxamide | 346.1 | 9.06 (d, J = 5.0 Hz, 1H), 8.97 (s, 1H), 8.85 (d, J = 8.6 Hz, 1H), 8.23 (t, J = 1.3 Hz, 1H), 7.91 (d, J = 5.0 Hz, 1H), 7.18 (s, 1H), 3.91-3.78 (m, 1H), 3.55 (dd, J = 5.8, 3.9 Hz, 2H), 3.43 (dd, J = 5.8, 3.9 Hz, 2H), 3.31-3.21 (m, 4H), 2.05 (d, J = 10.6 Hz, 2H), 1.84 (d, J = 10.6 Hz, 2H), 1.65-1.50 (m, 2H), 1.34-1.18 (m, 2H). |
| 108 | 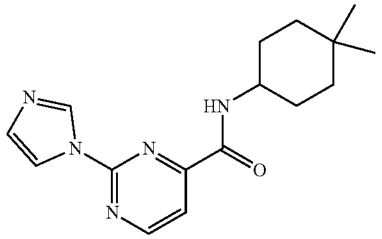 [SMILES: CC1(C)CCC(NC(=O)c2ccnc(-n3ccnc3)n2)CC1] | N-(4,4-dimethylcyclohexyl)-2-(1H-imidazol-1-yl)pyrimidine-4-carboxamide | 300.4 | 9.06 (d, J = 5.0 Hz, 1H), 8.98 (s, 1H), 8.84 (d, J = 8.7 Hz, 1H), 8.23 (t, J = 1.3 Hz, 1H), 7.91 (d, J = 5.0 Hz, 1H), 7.20-7.18 (m, 1H), 3.86-3.71 (m, 1H), 1.80-1.58 (m, 4H), 1.43 (d, J = 12.9 Hz, 2H), 1.36-1.21 (m, 2H), 0.99 (s, 3H), 0.94 (s, 3H). |
| 109 | 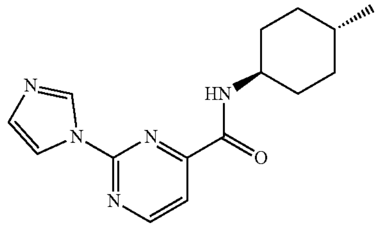 [SMILES: C[C@H]1CC[C@H](NC(=O)c2ccnc(-n3ccnc3)n2)CC1] | 2-(1H-imidazol-1-yl)-N-((1r,4r)-4-methylcyclohexyl) pyrimidine-4-carboxamide | 286.2 | 9.06 (d, J = 5.0 Hz, 1H), 8.98 (s, 1H), 8.85 (d, J = 8.7 Hz, 1H), 8.24 (s, 1H), 7.91 (d, J = 5.0 Hz, 1H), 7.18 (s, 1H), 3.88-3.74 (m, 1H), 1.84-1.69 (m, 4H), 1.62-1.47 (m, 2H), 1.42-1.30 (m, 1H), 0.91 (d, J = 6.5 Hz, 3H). |
| 110 | 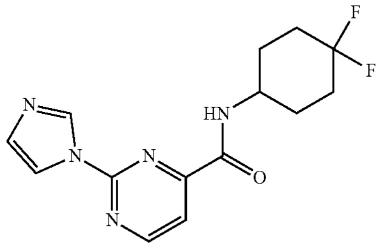 [SMILES: O=C(NC1CCC(F)(F)CC1)c1ccnc(-n2ccnc2)n1] | N-(4,4-difluorocyclohexyl)-2-(1H-imidazol-1-yl)pyrimidine-4-carboxamide | 308.3 | $^1H$ NMR (400 MHz, DMSO-$d_6$) δ 9.07 (d, J = 5.0 Hz, 1H), 8.99-8.92 (m, 2H), 8.24 (s, 1H), 7.92 (d, J = 5.0 Hz, 1H), 7.18 (s, 1H), 4.16-4.02 (m, 1H), 2.16-1.92 (m, 4H), 1.91-1.75 (m, 4H). |
| 111 | 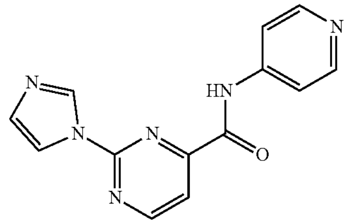 [SMILES: O=C(Nc1ccncc1)c1ccnc(-n2ccnc2)n1] | 2-(1H-imidazol-1-yl)-N-(pyridin-4-yl)pyrimidine-4-carboxamide | 267.1 | 12.29 (s, 1H), 10.76 (s, 1H), 9.35 (d, J = 5.0 Hz, 1H), 8.90 (d, J = 6.8 Hz, 2H), 8.82 (d, J = 7.2 Hz, 3H), 8.31 (d, J = 5.0 Hz, 1H), 7.86 (s, 1H). |
| 112 | 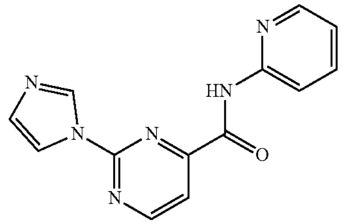 [SMILES: O=C(Nc1ccccn1)c1ccnc(-n2ccnc2)n1] | 2-(1H-imidazol-1-yl)-N-(pyridin-2-yl)pyrimidine-4-carboxamide | 267.0 | $^1H$ NMR (400 MHz, DMSO-$d_6$) δ 11.08 (s, 1H), 9.16 (d, J = 5.0 Hz, 1H), 9.00 (s, 1H), 8.51-8.46 (m, 1H), 8.30 (t, J = 1.3 Hz, 1H), 8.21 (d, J = 8.3 Hz, 1H), 8.07 (d, J = 5.0 Hz, 1H), 7.97-7.91 (m, 1H), 7.30-7.25 (m, 1H), 7.20-7.18 (m, 1H). |

-continued

| No. | Structure | Name | MS ESI $[M + H]^+$ | $^1H$ NMR (400 MHz, DMSO-$d_6$) δ |
|---|---|---|---|---|
| 113 | 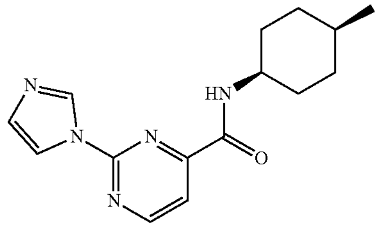 [SMILES: C[C@H]1CC[C@@H](NC(=O)c2ccnc(-n3ccnc3)n2)CC1] | 2-(1H-imidazol-1-yl)-N-((1s,4s)-4-methylcyclohexyl) pyrimidine-4-carboxamide | 286.2 | 9.07 (d, J = 5.0 Hz, 1H), 8.93 (s, 1H), 8.70 (d, J = 8.1 Hz, 1H), 8.19 (t, J = 1.3 Hz, 1H), 7.91 (d, J = 5.0 Hz, 1H), 7.19 (s, 1H), 3.95-3.85 (m, 1H), 1.83-1.76 (m, 3H), 1.63-1.53 (m, 4H), 1.47-1.43 (m, 2H), 1.00 (d, J = 7.0 Hz, 3H). |
| 116 | 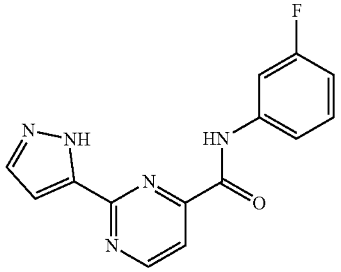 [SMILES: O=C(Nc1cccc(F)c1)c1ccnc(-c2ccn[nH]2)n1] | N-(3-fluorophenyl)-2-(1H-pyrazol-5-yl)pyrimidine-4-carboxamide | 284.0 | 10.81 (s, 1H), 9.24 (d, J = 2.4 Hz, 1H), 9.16 (d, J = 4.9 Hz, 1H), 8.02 (d, J = 4.9 Hz, 1H), 7.94 (dd, J = 3.0, 2.1 Hz, 1H), 7.85-7.80 (m, 1H), 7.73-7.70 (m, 1H), 7.51-7.44 (m, 1H), 7.08-7.01 (m, 1H), 6.70 (dd, J = 2.7, 1.6 Hz, 1H). |
| 125 | 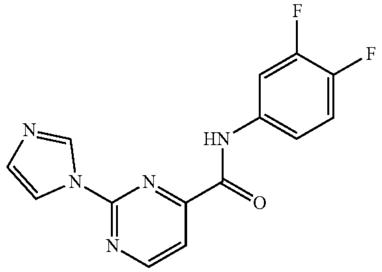 [SMILES: O=C(Nc1ccc(F)c(F)c1)c1ccnc(-n2ccnc2)n1] | N-(3,4-difluorophenyl)-2-(1H-imidazol-1-yl)pyrimidine-4-carboxamide | 302.0 | 10.80 (s, 1H), 9.15 (d, J = 5.0 Hz, 1H), 9.02 (s, 1H), 8.29 (t, J = 1.3 Hz, 1H), 8.08-7.97 (m, 2H), 7.75-7.71 (m, 1H), 7.57-7.49 (m, 1H), 7.21 (s, 1H). |
| 126 | 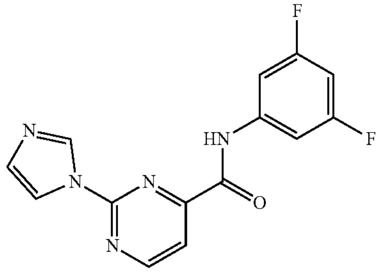 [SMILES: O=C(Nc1cc(F)cc(F)c1)c1ccnc(-n2ccnc2)n1] | N-(3,5-difluorophenyl)-2-(1H-imidazol-1-yl)pyrimidine-4-carboxamide | 302.1 | 10.86 (s, 1H), 9.16 (d, J = 5.0 Hz, 1H), 9.02 (s, 1H), 8.29 (t, J = 1.3 Hz, 1H), 8.05 (d, J = 5.0 Hz, 1H), 7.73 (dd, J = 9.6, 2.2 Hz, 2H), 7.22 (s, 1H), 7.12-7.06 (m, 1H). |
| 127 | 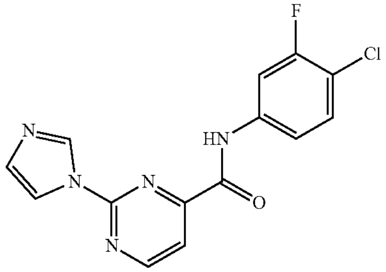 [SMILES: O=C(Nc1ccc(Cl)c(F)c1)c1ccnc(-n2ccnc2)n1] | N-(4-chloro-3-fluorophenyl)-2-(1H-imidazol-1-yl)pyrimidine-4-carboxamide | 318.0 | 10.87 (s, 1H), 9.17 (d, J = 5.0 Hz, 1H), 9.07 (s, 1H), 8.31 (s, 1H), 8.05 (dd, J = 8.4, 3.6 Hz, 2H), 7.81 (dd, J = 8.8, 1.6 Hz, 1H), 7.68 (t, J = 8.6 Hz, 1H), 7.25 (s, 1H). |

Example 18

3-hydroxy-6-(1H-imidazol-1-yl)-N-((1r,4r)-4-methoxycyclohexyl)pyrazine-2-carboxamide (compound 67)

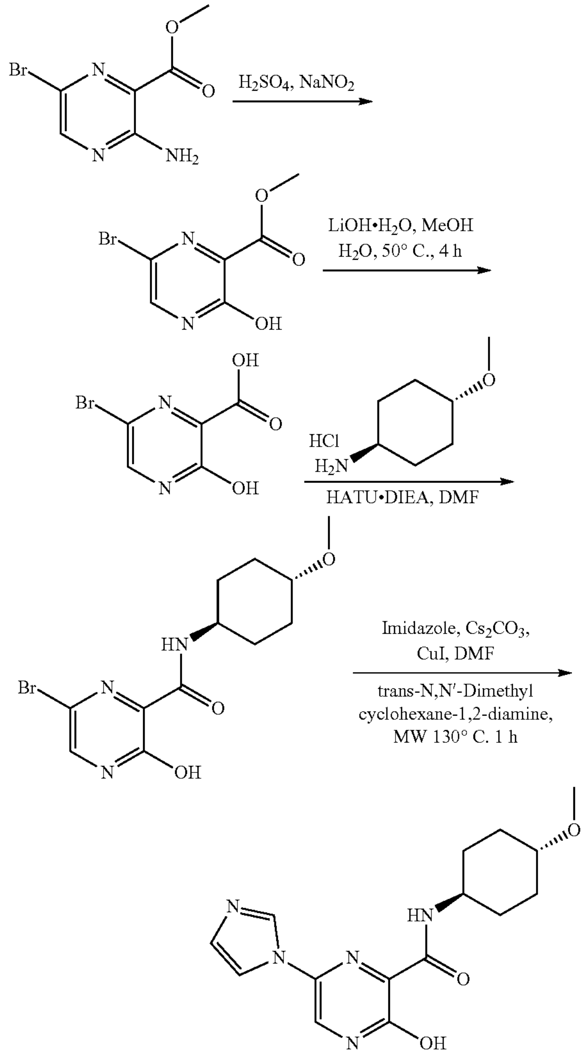

67

Step 1. methyl 6-bromo-3-hydroxypyrazine-2-carboxylate:

To a solution of methyl 3-amino-6-bromopyrazine-2-carboxylate (2.00 g, 8.62 mmol) in concentrated $H_2SO_4$ (8.0 mL) at 0° C. was added NaNO2 (1.19 g, 17.2 mmol), and the mixture was warmed up to room temperature for 2 hours. The mixture was diluted with ice/water (50 mL) to obtain a suspension. The mixture was filtered, the filter cake was collected and dried in vacuum to afford the titled compound (1.70 g, 84.6% yield) as a white solid. MS (ESI): m/z 235.0 $[M+H]^+$.

Step 2. 6-bromo-3-hydroxypyrazine-2-carboxylic acid:

To a solution of methyl 3-hydroxy-6-bromopyrazine-2-carboxylate (500 mg, 2.14 mmol) in MeOH (20 mL) and water (5 mL) was added $LiOH.H_2O$ (270 mg, 6.43 mmol). The mixture was heated to 50° C. for 4 hours. The reaction mixture was cooled to room temperature. The pH of the mixture was adjusted to 2~3 with concentrated HCl. The resulting mixture was concentrated under reduced pressure to obtain a solid. The solid was filtered and the filter cake was collected, dried in vacuum to afford the titled compound (450 mg, 95.8% yield) as a white solid. MS (ESI): 218.9 $[M+H]^+$, which was used in the next step without purification.

Step 3. 6-bromo-3-hydroxy-N-((1r,4r)-4-methoxycyclohexyl)pyrazine-2-carboxamide:

To a solution of 6-bromo-3-hydroxypyrazine-2-carboxylic acid (450 mg, 2.05 mmol) in DMF (10 mL) were added DIEA (1.02 mL, 6.16 mmol), trans-4-methoxycyclohexanamine hydrochloride (340 mg, 2.05 mmol), and HATU (860 mg, 2.26 mmol), and the reaction mixture was stirred at room temperature for 2 hours. The mixture was diluted with EA (50 mL), washed with brine (50 mL), dried over anhydrous $Na_2SO_4$, filtered and concentrated. The residue was purified by silica gel column (EA/PE=1/50 to 1/1) to afford the titled compound (500 mg, 73.7% yield) as a white solid. MS (ESI): m/z 332.0 $[M+H]^+$.

Step 4. 3-hydroxy-6-(1H-imidazol-1-yl)-N-((1r,4r)-4-methoxycyclohexyl)pyrazine-2-carboxamide.

A mixture of 6-bromo-3-hydroxy-N-((1r,4r)-4-methoxycyclohexyl)pyrazine-2-carboxamide (150 mg, 0.45 mmol), imidazole (62 mg, 0.90 mmol), CuI (8.7 mg, 0.045 mmol), $Cs_2CO_3$ (296.04 mg, 0.90 mmol), trans-N,N'-dimethylcyclohexane-1,2-diamine, (6.5 mg, 0.045 mmol) and DMF (4 mL) was bubbled with argon for 3 minutes. The reaction tube was capped and heated at 130° C. for in a microwave reactor for 1 hour. The reaction mixture was diluted with EA (20 mL), washed with brine (30 mL×2). The organic phase was concentrated under reduced pressure. The residue was purified with prep-HPLC (Waters 2767/2545/2489/Qda, Inertsil ODS-3 10 μm 20*250 nm, Mobile Phase A: 0.1% formic acid in water, Mobile Phase B: $CH_3CN$, Flow: 20 mL/min: Column temp: RT) to afford the titled compound (18.08 mg, 12.3% yield) as a white solid. MS (ESI): m/z 318.5 $[M+H]^+$. $^1H$ NMR (400 MHZ, DMSO-$d_6$) δ 13.29 (s, 1H), 9.12 (s, 1H), 8.89 (s, 1H), 8.74 (s, 1H), 8.14 (s, 1H), 7.16 (s, 1H), 3.86 (d, J=8.7 Hz, 1H), 3.26 (s, 3H), 3.13 (m, 1H), 2.06 (d, J=10.0 Hz, 2H), 1.87 (d, J=10.7 Hz, 2H), 1.60-1.48 (m, 2H), 1.30-1.18 (m, 2H).

The compounds below were synthesized following the procedures described for compound 67.

| No. | Structure | Name | MS ESI [M + H]+ | $^1$H NMR (400 MHz, DMSO-$d_6$) δ |
|---|---|---|---|---|
| 68 | 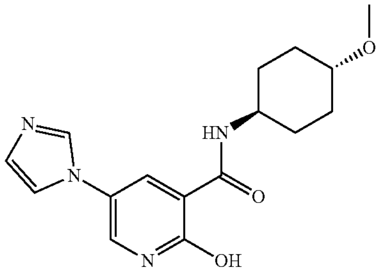 [SMILES: CO[C@H]1CC[C@H](NC(=O)c2cc(-n3ccnc3)cnc2O)CC1] | 2-hydroxy-5-(1H-imidazol-1-yl)-N-((1r,4r)-4-methoxycyclohexyl) nicotinamide | 317.2 | 12.98 (s, 1H), 9.76 (d, J = 7.5 Hz, 1H), 8.43 (s, 1H), 8.13 (s, 1H), 8.01-7.04 (m, 2H), 3.77 (s, 1H), 3.24 (s, 2H), 3.20-3.13 (m, 1H), 2.02-1.83 (m, 2H), 1.36-1.18 (m, 2H). |
| 71 | 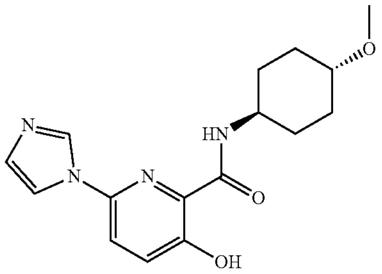 [SMILES: CO[C@H]1CC[C@H](NC(=O)c2nc(-n3ccnc3)ccc2O)CC1] | 3-hydroxy-6-(1H-imidazol-1-yl)-N-((1r,4r)-4-methoxycyclohexyl) picolinamide | 317.2 | 12.68 (s, 1H), 8.83 (d, J = 8.7 Hz, 2H), 8.18 (s, 1H), 7.95 (d, J = 8.9 Hz, 1H), 7.63 (d, J = 8.9 Hz, 1H), 7.12 (s, 1H), 3.85 (dd, J = 12.3, 7.8 Hz, 1H), 3.26 (s, 3H), 3.16-3.09 (m, 1H), 2.07 (d, J = 10.6 Hz, 2H), 1.85 (d, J = 10.4 Hz, 2H), 1.65-1.55 (m, 2H), 1.30-1.20 (m, 2H). |
| 74 | 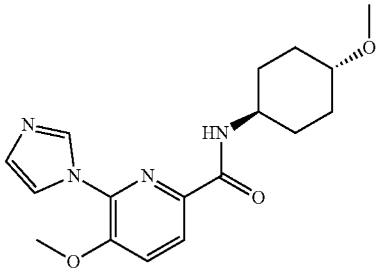 [SMILES: COc1ccc(C(=O)N[C@H]2CC[C@H](OC)CC2)nc1-n1ccnc1] | 6-(1H-imidazol-1-yl)-5-methoxy-N-((1r,4r)-4-methoxycyclohexyl) picolinamide | 331.1 | 8.64 (s, 1H), 8.28 (d, J = 8.5 Hz, 1H), 8.12 (s, 1H), 8.00 (d, J = 8.5 Hz, 1H), 7.84 (d, J = 8.6 Hz, 1H), 7.10 (s, 1H), 4.01 (s, 3H), 3.86-3.74 (m, 1H), 3.25 (s, 3H), 3.15-3.08 (m, 1H), 2.04 (d, J = 10.3 Hz, 2H), 1.82 (d, J = 11.1 Hz, 2H), 1.59-1.47 (m, 2H), 1.28-1.16 (m, 2H). |

Example 19

2-(1H-imidazol-1-yl)-N-((1r,4r)-4-methoxycyclohexyl)-6-(trifluoromethyl) pyrimidine-4-carboxamide

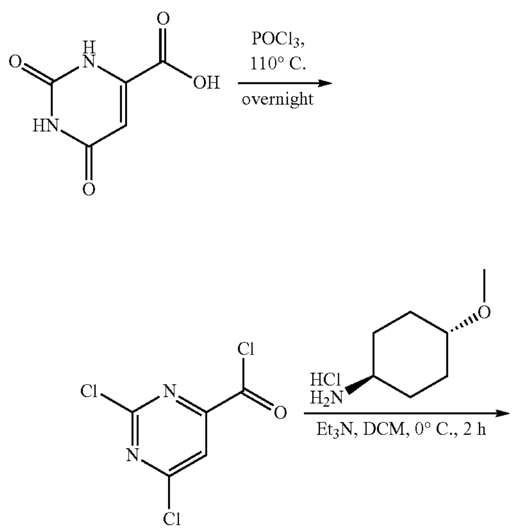

-continued

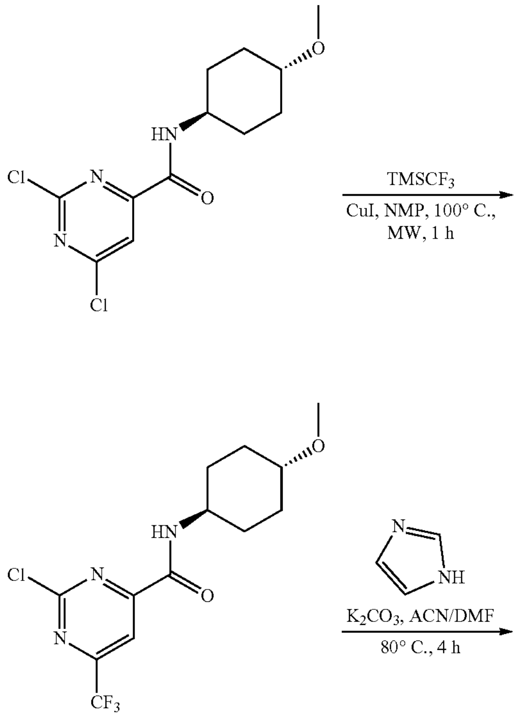

-continued

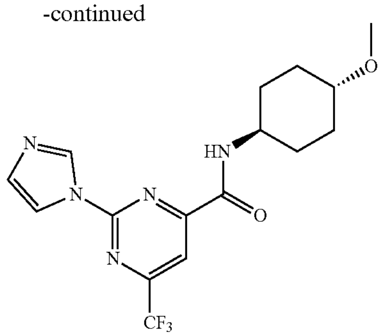

103

Step 1: 2,6-dichloropyrimidine-4-carbonyl chloride

A solution of 2,6-dioxo-1,2,3,6-tetrahydropyrimidine-4-carboxylic acid (10 g, 64.06 mmol) in $POCl_3$ (50 mL) in the presence of catalytic amount of DMF (0.25 mL, 3.20 mmol) was heated at 110° C. under $N_2$ atmosphere overnight. The volatile was removed in vacuum and the residue was extracted with Et2O (100 mL×3). The combined organic layers were dried over anhydrous $Na_2SO_4$, filtered and concentrated to dryness to afford the titled compound which was used directly in the next step without further purification.

Step 2: 2.6-dichloro-N-((1r,4r)-4-methoxycyclohexyl)pyrimidine-4-carboxamide

A mixture of (1r,4r)-4-methoxycyclohexan-1-amine hydrochloride (0.94 g, 5.68 mmol), $Et_3N$ (4.78 g, 47.29 mmol) in DCM (10 mL) was added 2,6-dichloropyrimidine-4-carbonyl chloride in $Et_2O$ (1 g, 4.73 mmol) at 0° C., then the mixture was stirred at room temperature for 1 hour under $N_2$. The reaction mixture was diluted with $H_2O$ (60 mL) and the resulting mixture was extracted with $CH_2Cl_2$ (60 mL×2). The combined organic layers were washed with brine (60 mL), dried over anhydrous $Na_2SO_4$, filtered and concentrated. The residue was purified by silica gel column chromatography (PE/EA=20/1-4/1) to afford the titled compound (689 mg, 47.9% yield) as a white solid. MS (ESI): m/z 304.0 $[M+H]^+$.

Step 3: 2-chloro-N-((1r,4r)-4-methoxycyclohexyl)-6-(trifluoromethyl) pyrimidine-4-carboxamide A mixture of 2,6-dichloro-N-((1r,4r)-4-methoxycyclohexyl)pyrimidine-4-carboxamide (300 mg, 0.99 mmol), methyl 2,2-difluoro-2-(fluorosulfonyl) acetate (0.31 mL, 2.47 mmol) and CuI (374.78 mg, 1.97 mmol) in NMP (2 mL) was heated in a microwave reactor at 100° C. for 1.5 hours. The resulting mixture was cooled and partitioned between EtOAc (20 mL) and water (20 mL). The organic layer was separated and aqueous layer was extracted with EtOAc (20 mL×2). The combined organic layers were washed with brine, dried over anhydrous $Na_2SO_4$, filtered and concentrated to dryness. The residue was purified on silica gel chromatography (PE/EA=20/1-1/1) to afford the titled compound (120 mg, 36.0% yield) as an off-white solid. MS (ESI): m/z 338.1 $[M+H]^+$. $^1$H NMR (400 MHZ, $CD_3OD$) δ 8.34 (s, 1H), 3.94-3.84 (m, 1H), 3.31 (dt, J=3.2, 1.6 Hz, 1H), 2.16-2.10 (m, 2H), 2.03-1.93 (m, 3H), 1.60-1.47 (m, 3H), 1.32 (qd, J=13.0, 3.4 Hz, 3H).

Step 4: 2-(1H-imidazol-1-yl)-N-((1r,4r)-4-methoxycyclohexyl)-6-(trifluoromethyl) pyrimidine-4-carboxamide A mixture of 2-chloro-N-((1r,4r)-4-methoxycyclohexyl)-6-(trifluoromethyl) pyrimidine-4-carboxamide (55 mg, 0.16 mmol), 1H-imidazole (33 mg, 0.49 mmol) and $K_2CO_3$ (66 mg, 0.49 mmol) in ACN (2 mL) and DMF (2 mL) was heated at 80° C. for 4 hours. The resulting mixture was partitioned between EtOAc (20 mL) and water (20 mL). The organic layer was separated and the aqueous layer was extracted with EtOAc (20 mL×2). The combined organic layers were washed with brine (20 mL), dried over anhydrous $Na_2SO_4$, filtered and concentrated to dryness. The residue was purified by prep-HPLC (Waters 2767/2545/2489/Qda, Waters sunfire C18 10 μm OBD 19*250 mm, Mobile Phase A: 0.1% HCl in water, Mobile Phase B: $CH_3CN$, Flow: 20 mL/min, Column temp: RT) to afford the titled compound (30 mg, 49.9% yield) as a yellow solid. MS (ESI): m/z 370.1 $[M+H]^+$. $^1$H NMR (400 MHZ, DMSO-$d_6$) δ 10.24 (s, 1H), 9.27 (d, J=8.5 Hz, 1H), 8.60 (s, 1H), 8.37 (s, 1H), 8.37 (s, 1H), 7.78 (s, 1H), 7.78 (s, 1H), 3.96-3.84 (m, 1H), 3.26 (s, 3H), 3.20-3.09 (m, 1H), 2.08 (d, J=11.8 Hz, 2H), 1.86 (d, J=11.0 Hz, 2H), 1.68-1.59 (m, 2H), 1.29-1.20 (m, 2H).

The compounds below were synthesized following the procedures described for compound 103.

| No. | Structure | Name | MS ESI $[M + H]^+$ | $^1$H NMR (400 MHz, DMSO-$d_6$) δ |
|---|---|---|---|---|
| 123 | 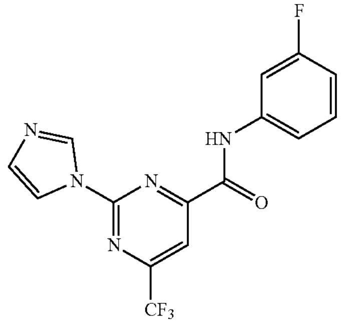 [SMILES: O=C(Nc1cccc(F)c1)c1cc(C(F)(F)F)nc(-n2ccnc2)n1] | N-(3-fluorophenyl)-2-(1H-imidazol-1-yl)-6-(trifluoromethyl) pyrimidine-4-carboxamide | 352.0 | 10.92 (s, 1H), 9.09 (s, 1H), 8.33 (s, 1H), 8.29 (s, 1H), 7.86-7.79 (m, 1H), 7.75 (d, J = 8.2 Hz, 1H), 7.50 (dd, J = 15.1, 8.1 Hz, 1H), 7.25 (s, 1H), 7.08 (td, J = 8.5, 2.4 Hz, 1H). |

-continued

| No. | Structure | Name | MS ESI [M + H]⁺ | $^1$H NMR (400 MHz, DMSO-$d_6$) δ |
|---|---|---|---|---|
| 124 | 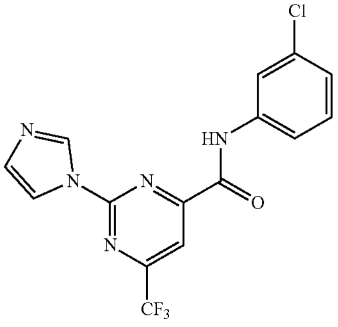 [SMILES: O=C(Nc1cccc(Cl)c1)c1cc(C(F)(F)F)nc(-n2ccnc2)n1] | N-(3-chlorophenyl)-2-(1H-imidazol-1-yl)-6-(trifluoromethyl) pyrimidine-4-carboxamide | 368.0 | 10.90 (s, 1H), 9.09 (s, 1H), 8.33 (s, 1H), 8.29 (t, J = 1.3 Hz, 1H), 8.03 (t, J = 2.0 Hz, 1H), 7.93-7.87 (m, 1H), 7.50 (t, J = 8.1 Hz, 1H), 7.31 (dd, J = 8.0, 1.2 Hz, 1H), 7.25 (s, 1H). |
| 133 | 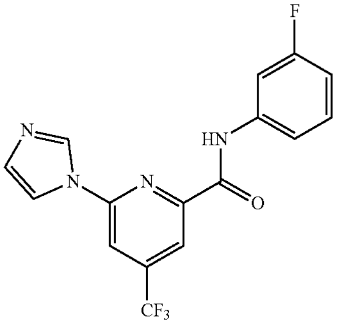 [SMILES: O=C(Nc1cccc(F)c1)c1cc(C(F)(F)F)cc(-n2ccnc2)n1] | N-(3-fluorophenyl)-6-(1H-imidazol-1-yl)-4-(trifluoromethyl) picolinamide | 351.0 | 10.70 (s, 1H), 9.14 (s, 1H), 8.54 (s, 1H), 8.49 (t, J = 1.4 Hz, 1H), 8.25 (s, 1H), 7.87-7.80 (m, 1H), 7.78-7.70 (m, 1H), 7.52-7.43 (m, 1H), 7.25-7.20 (m, 1H), 7.09-6.99 (m, 1H). |
| 138 | 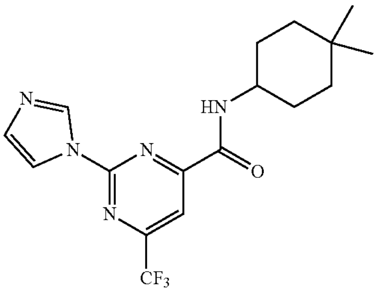 [SMILES: CC1(C)CCC(NC(=O)c2cc(C(F)(F)F)nc(-n3ccnc3)n2)CC1] | N-(4,4-dimethylcyclohexyl)-2-(1H-imidazol-1-yl)-6-(trifluoromethyl) pyrimidine-4-carboxamide | 368.2 | 9.04 (s, 1H), 8.98 (d, J = 8.6 Hz, 1H), 8.22 (s, 1H), 8.18 (s, 1H), 7.23 (s, 1H), 3.93-3.75 (m, 1H), 1.80-1.58 (m, 4H), 1.49-1.38 (m, 2H), 1.37-1.23 (m, 2H), 1.03-0.89 (m, 6H). |
| 140 | 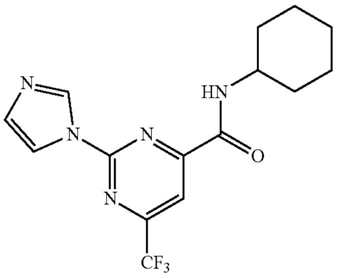 [SMILES: O=C(NC1CCCCC1)c1cc(C(F)(F)F)nc(-n2ccnc2)n1] | N-cyclohexyl-2-(1H-imidazol-1-yl)-6-(trifluoromethyl) pyrimidine-4-carboxamide | 340.0 | 9.03 (s, 1H), 9.00 (d, J = 8.6 Hz, 1H), 8.22 (t, J = 1.3 Hz, 1H), 8.18 (s, 1H), 7.24-7.20 (m, 1H), 3.94-3.78 (m, 1H), 1.91-1.73 (m, 4H), 1.72-1.60 (m, 1H), 1.58-1.44 (m, 2H), 1.43-1.27 (m, 2H), 1.26-1.11 (m, 1H). |
| 141 | 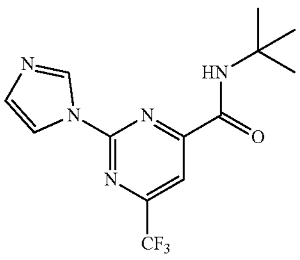 [SMILES: CC(C)(C)NC(=O)c1cc(C(F)(F)F)nc(-n2ccnc2)n1] | N-(tert-butyl)-2-(1H-imidazol-1-yl)-6-(trifluoromethyl) pyrimidine-4-carboxamide | 314.0 | 9.25-9.10 (m, 1H), 8.44-8.39 (m, 1H), 8.29-8.26 (m, 1H), 8.26-8.23 (m, 1H), 7.36-7.32 (m, 1H), 1.50-1.44 (m, 9H). |

-continued

| No. | Structure | Name | MS ESI $[M + H]^+$ | $^1H$ NMR (400 MHz, DMSO-$d_6$) δ |
|---|---|---|---|---|
| 146 | 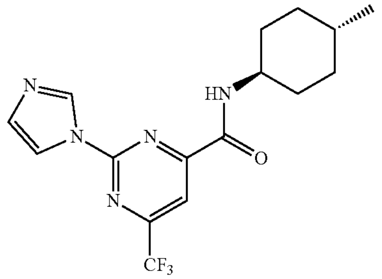 [SMILES: C[C@H]1CC[C@H](NC(=O)c2cc(C(F)(F)F)nc(-n3ccnc3)n2)CC1] | 2-(1H-imidazol-1-yl)-N-((1r,4r)-4-methylcyclohexyl)-6-(trifluoromethyl) pyrimidine-4-carboxamide | 354.0 | 9.04 (s, 1H), 9.00 (d, J = 8.6 Hz, 1H), 8.23 (t, J = 1.3 Hz, 1H), 8.18 (s, 1H), 7.22 (s, 1H), 3.93-3.76 (m, 1H), 1.87-1.71 (m, 4H), 1.63-1.49 (m, 2H), 1.44-1.31 (m, 1H), 1.13-0.98 (m, 2H), 0.91 (d, J = 6.5 Hz, 3H). |
| 151 | 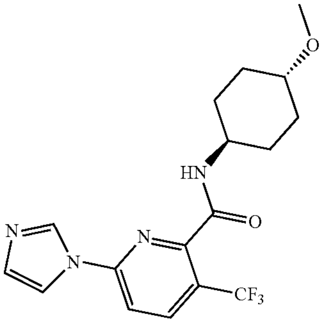 [SMILES: CO[C@H]1CC[C@H](NC(=O)c2nc(-n3ccnc3)ccc2C(F)(F)F)CC1] | 6-(1H-imidazol-1-yl)-N-((1r,4r)-4-methoxycyclohexyl)-3-(trifluoromethyl) picolinamide | 369.2 | 8.70 (s, 1H), 8.61 (d, J = 7.9 Hz, 1H), 8.49 (d, J = 8.7 Hz, 1H), 8.09 (dd, J = 5.0, 3.6 Hz, 2H), 7.19 (s, 1H), 3.79-3.69 (m, 1H), 3.24 (s, 3H), 3.17-3.08 (m, 1H), 2.02 (dd, J = 12.7, 2.4 Hz, 2H), 1.89 (dd, J = 12.8, 2.9 Hz, 2H), 1.40-1.19 (m, 4H). |
| 152 | 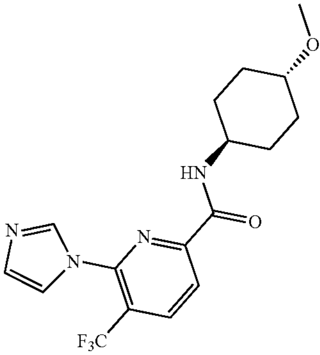 [SMILES: CO[C@H]1CC[C@H](NC(=O)c2ccc(C(F)(F)F)c(-n3ccnc3)n2)CC1] | 6-(1H-imidazol-1-yl)-N-((1r,4r)-4-methoxycyclohexyl)-5-(trifluoromethyl) picolinamide | 369.1 | 8.64 (d, J = 8.2 Hz, 1H), 8.57 (d, J = 8.4 Hz, 1H), 8.28 (d, J = 7.7 Hz, 1H), 8.18 (s, 1H), 7.65 (s, 1H), 7.15 (s, 1H), 3.87-3.76 (m, 1H), 3.24 (s, 3H), 3.13-3.04 (m, 1H), 2.02 (d, J = 10.4 Hz, 2H), 1.81 (d, J = 10.5 Hz, 2H), 1.56-1.45 (m, 2H), 1.27-1.14 (m, 2H). |
| 153 | 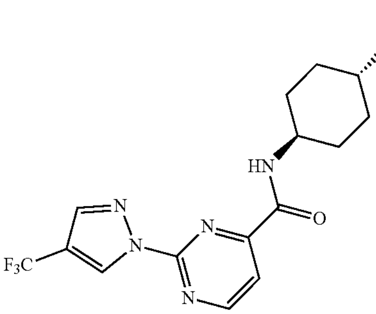 | N-((1r,4r)-4-methoxycyclohexyl)-2-(4-(trifluoromethyl)-1H-imidazol-1-yl) pyrimidine-4-carboxamide | 370.1 | 9.12 (d, J = 5.0 Hz, 1H), 9.09 (s, 1H), 8.90 (d, J = 8.6 Hz, 1H), 8.88 (d, J = 1.3 Hz, 1H), 8.01 (d, J = 5.0 Hz, 1H), 3.90-3.80 (m, 1H), 3.26 (s, 3H), 3.18-3.10 (m, 1H), 2.08 (d, J = 10.0 Hz, 2H), 1.87 (d, J = 11.2 Hz, 2H), 1.62-1.52 (m, 2H), 1.30-1.17 (m, 2H). |

-continued

| No. | Structure | Name | MS ESI [M + H]$^+$ | $^1$H NMR (400 MHz, DMSO-$d_6$) δ |
|---|---|---|---|---|
| 154 | 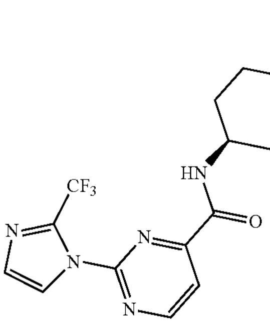 | N-((1r,4r)-4-methoxycyclohexyl)-2-(2-(trifluoromethyl)-1H-imidazol-1-yl) pyrimidine-4-carboxamide | 370.1 | 9.18 (d, J = 5.0 Hz, 1H), 8.58 (s, 1H), 8.49 (d, J = 6.6 Hz, 1H), 8.05 (d, J = 5.0 Hz, 1H), 7.38 (s, 1H), 3.89-3.76 (m, 1H), 3.25 (s, 3H), 3.18-3.12 (m, 1H), 2.05 (d, J = 11.0 Hz, 2H), 1.95-1.84 (m, 2H), 1.51-1.42 (m, 2H), 1.30-1.20 (m, 2H). |
| 157 | 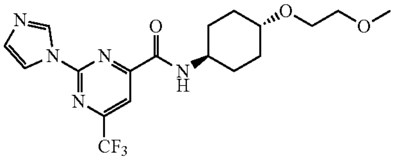 [SMILES: COCCO[C@H]1CC[C@H](NC(=O)c2cc(C(F)(F)F)nc(-n3ccnc3)n2)CC1] | 2-(1H-imidazol-1-yl)-N-((1r,4r)-4-(2-methoxyethoxy) cyclohexyl)-6-(trifluoromethyl) pyrimidine-4-carboxamide | 414.2 | 9.02 (s, 1H), 8.99 (d, J = 8.5 Hz, 1H), 8.21 (t, J = 1.4 Hz, 1H), 8.18 (s, 1H), 7.22 (dd, J = 1.4, 0.9 Hz, 1H), 3.91-3.83 (m, 1H), 3.55 (dd, J = 5.8, 3.9 Hz, 2H), 3.43 (dd, J = 5.7, 3.9 Hz, 2H), 3.30-3.24 (m, 4H), 2.06 (d, J = 11.0 Hz, 2H), 1.86 (d, J = 10.6 Hz, 2H), 1.62-1.53 (m, 2H), 1.31-1.22 (m, 2H). |
| 158 | 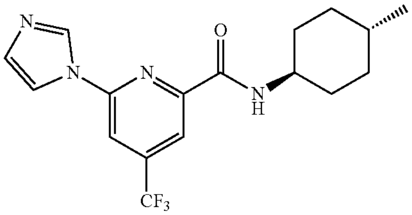 [SMILES: C[C@H]1CC[C@H](NC(=O)c2cc(C(F)(F)F)cc(-n3ccnc3)n2)CC1] | 6-(1H-imidazol-1-yl)-N-((1r,4r)-4-methylcyclohexyl)-4-(trifluoromethyl) picolinamide | 353.1 | 9.09 (s, 1H), 8.72 (d, J = 8.5 Hz, 1H), 8.43 (s, 2H), 8.11 (s, 1H), 7.19 (s, 1H), 3.88-3.78 (m, 1H), 1.82-1.72 (m, 4H), 1.61-1.52 (m, 2H), 1.42-1.32 (m, 1H), 1.12-0.99 (m, 2H), 0.91 (d, J = 6.5 Hz, 3H). |
| 159 | 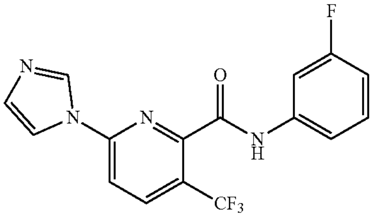 [SMILES: O=C(Nc1cccc(F)c1)c1nc(-n2ccnc2)ccc1C(F)(F)F] | N-(3-fluorophenyl)-6-(1H-imidazol-1-yl)-3-(trifluoromethyl) picolinamide | 351.1 | 10.98 (s, 1H), 8.77 (s, 1H), 8.61 (d, J = 8.7 Hz, 1H), 8.21 (d, J = 8.6 Hz, 1H), 8.15 (s, 1H), 7.69 (dt, J = 11.5, 2.1 Hz, 1H), 7.51 (d, J = 8.3 Hz, 1H), 7.46-7.41 (m, 1H), 7.21 (s, 1H), 7.05-6.98 (m, 1H). |
| 160 | 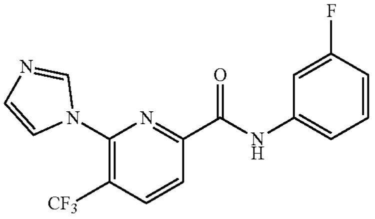 [SMILES: O=C(Nc1cccc(F)c1)c1ccc(C(F)(F)F)c(-n2ccnc2)n1] | N-(3-fluorophenyl)-6-(1H-imidazol-1-yl)-5-(trifluoromethyl) picolinamide | 351.1 | 10.74 (s, 1H), 8.73 (d, J = 8.2 Hz, 1H), 8.40 (d, J = 8.0 Hz, 1H), 8.23 (s, 1H), 7.81 (dt, J = 11.6, 2.3 Hz, 1H), 7.71 (s, 1H), 7.70-7.67 (m, 1H), 7.43 (td, J = 8.2, 7.0 Hz, 1H), 7.19-7.16 (m, 1H), 7.01 (td, J = 8.5, 2.5 Hz, 1H). |
| 161 | 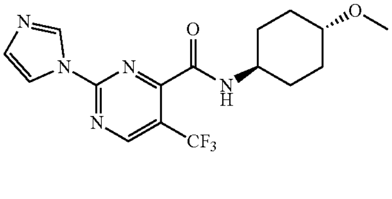 [SMILES: CO[C@H]1CC[C@H](NC(=O)c2nc(-n3ccnc3)ncc2C(F)(F)F)CC1] | 2-(1H-imidazol-1-yl)-N-((1r,4r)-4-methoxycyclohexyl)-5-(trifluoromethyl) pyrimidine-4-carboxamide | 370.1 | 9.38 (s, 1H), 8.82 (d, J = 7.7 Hz, 1H), 8.73 (s, 1H), 8.05 (s, 1H), 7.22 (s, 1H), 3.83-3.70 (m, 1H), 3.24 (s, 3H), 3.19-3.08 (m, 1H), 2.01 (d, J = 10.3 Hz, 2H), 1.90 (d, J = 10.1 Hz, 2H), 1.43-1.20 (m, 4H). |

-continued

| No. | Structure | Name | MS ESI $[M + H]^+$ | $^1H$ NMR (400 MHz, DMSO-$d_6$) δ |
|---|---|---|---|---|
| 162 | 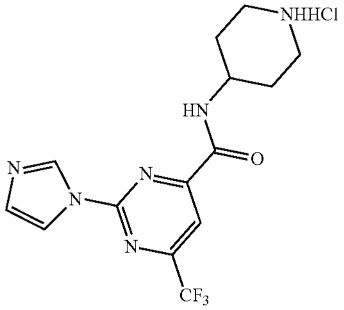 MP-8233 | 2-(1H-imidazol-1-yl)-N-(piperidin-4-yl)-6-(trifluoromethyl) pyrimidine-4-carboxamide hydrochloride | 341.1 (M − HCl + $H^+$) | 10.14 (s, 1H), 9.56 (d, J = 8.0 Hz, 1H), 9.13-9.04 (m, 2H), 8.57 (s, 1H), 8.37 (s, 1H), 7.70 (s, 1H), 4.23-4.14 (m, 1H), 3.35 (d, J = 12.6 Hz, 2H), 3.10-2.98 (m, 2H), 2.101-1.950 (m, 4H). |
| 163 | 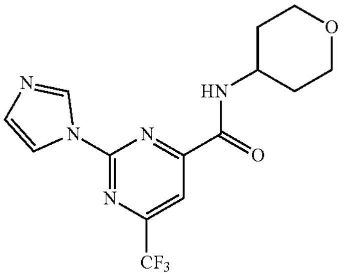 [SMILES: O=C(NC1CCOCC1)c1cc(C(F)(F)F)nc(-n2ccnc2)n1] MP-8234 | 2-(1H-imidazol-1-yl)-N-(tetrahydro-2H-pyran-4-yl)-6-(trifluoromethyl) pyrimidine-4-carboxamide | 342.1 | 9.09 (d, J = 8.3 Hz, 1H), 9.03 (s, 1H), 8.23 (s, 1H), 8.19 (s, 1H), 7.23 (s, 1H), 4.19-4.06 (m, 1H), 3.93 (d, J = 10.9 Hz, 2H), 3.42 (td, J = 11.3, 3.5 Hz, 2H), 1.85-1.72 (m, 4H). |
| 164 | 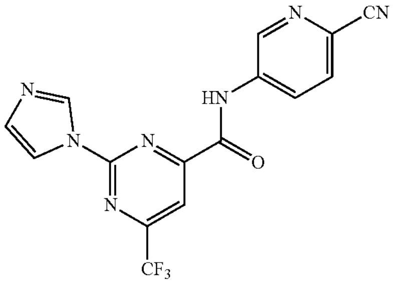 [SMILES: N#Cc1ccc(NC(=O)c2cc(C(F)(F)F)nc(-n3ccnc3)n2)cn1] IMP-8240 | N-(6-cyanopyridin-3-yl)-2-(1H-imidazol-1-yl)-6-(trifluoromethyl) pyrimidine-4-carboxamide | 360.1 | 11.28 (s, 1H), 9.24 (d, J = 2.0 Hz, 1H), 9.07 (s, 1H), 8.56 (dd, J = 8.6, 2.5 Hz, 1H), 8.37 (s, 1H), 8.28 (t, J = 1.3 Hz, 1H), 8.15 (d, J = 8.6 Hz, 1H), 7.27-7.26 (m, 1H). |
| 165 | 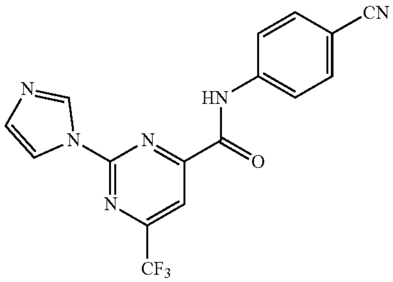 | N-(4-cyanophenyl)-2-(1H-imidazol-1-yl)-6-(trifluoromethyl) pyrimidine-4-carboxamide | 359.0 | 11.08 (s, 1H), 9.08 (s, 1H), 8.35 (s, 1H), 8.28 (s, 1H), 8.13 (d, J = 8.7 Hz, 2H), 7.94 (d, J = 8.7 Hz, 2H), 7.26 (s, 1H). |
| 166 | 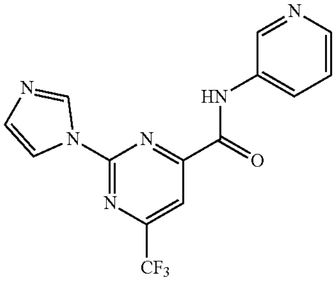 [SMILES: O=C(Nc1cccnc1)c1cc(C(F)(F)F)nc(-n2ccnc2)n1] | 2-(1H-imidazol-1-yl)-N-(pyridin-3-yl)-6-(trifluoromethyl) pyrimidine-4-carboxamide | 334.9 | 11.00 (s, 1H), 9.09 (s, 1H), 9.04 (d, J = 2.3 Hz, 1H), 8.45 (dd, J = 4.7, 1.3 Hz, 1H), 8.34 (s, 1H), 8.29 (s, 1H), 8.28-8.25 (m, 1H), 7.51 (dd, J = 8.2, 4.7 Hz, 1H), 7.26 (s, 1H). |

-continued

| No. | Structure | Name | MS ESI [M + H]+ | $^1$H NMR (400 MHz, DMSO-$d_6$) δ |
|---|---|---|---|---|
| 167 | 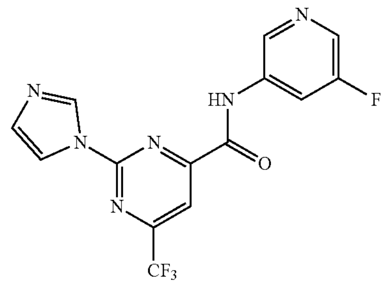 [SMILES: O=C(Nc1cncc(F)c1)c1cc(C(F)(F)F)nc(-n2ccnc2)n1] | N-(5-fluoropyridin-3-yl)-2-(1H-imidazol-1-yl)-6-(trifluoromethyl) pyrimidine-4-carboxamide | 352.9 | 11.15 (s, 1H), 9.08 (s, 1H), 8.96 (t, J = 1.5 Hz, 1H), 8.48 (d, J = 2.6 Hz, 1H), 8.35 (s, 1H), 8.29-8.24 (m, 2H), 7.26 (dd, J = 1.4, 0.9 Hz, 1H). |
| 168 | 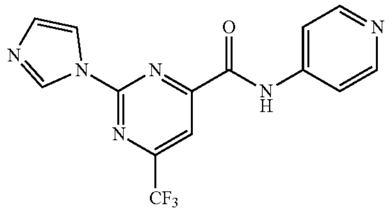 [SMILES: O=C(Nc1ccncc1)c1cc(C(F)(F)F)nc(-n2ccnc2)n1] | 2-(1H-imidazol-1-yl)-N-(pyridin-4-yl)-6-(trifluoromethyl) pyrimidine-4-carboxamide | 334.9 | 11.04 (s, 1H), 9.08 (s, 1H), 8.61 (dd, J = 4.8, 1.5 Hz, 2H), 8.35 (s, 1H), 8.29 (t, J = 1.4 Hz, 1H), 7.94 (dd, J = 4.8, 1.5 Hz, 2H), 7.26 (s, 1H). |
| 169 | 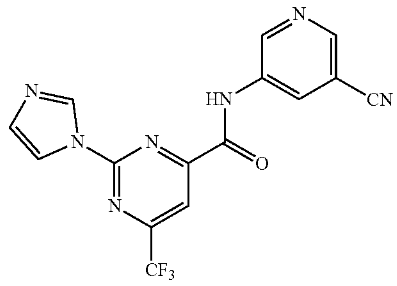 [SMILES: N#Cc1cncc(NC(=O)c2cc(C(F)(F)F)nc(-n3ccnc3)n2)c1] | N-(5-cyanopyridin-3-yl)-2-(1H-imidazol-1-yl)-6-(trifluoromethyl) pyrimidine-4-carboxamide | 360.0 | 11.21 (s, 1H), 9.32 (d, J = 2.4 Hz, 1H), 9.07 (s, 1H), 8.90 (d, J = 1.8 Hz, 1H), 8.72 (t, J = 2.1 Hz, 1H), 8.36 (s, 1H), 8.28 (s, 1H), 7.27 (s, 1H). |
| 170 | 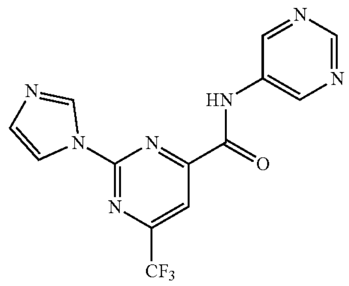 [SMILES: O=C(Nc1cncnc1)c1cc(C(F)(F)F)nc(-n2ccnc2)n1] | 2-(1H-imidazol-1-yl)-N-(pyrimidin-5-yl)-6-(trifluoromethyl) pyrimidine-4-carboxamide | 336.0 | 11.17 (s, 1H), 9.27 (s, 2H), 9.07 (s, 2H), 8.36 (s, 1H), 8.28 (s, 1H), 7.27 (s, 1H). |
| 171 | 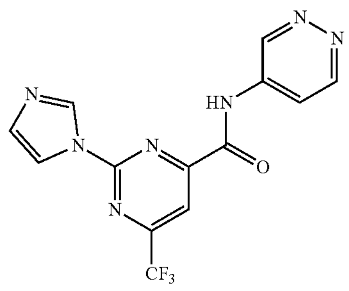 [SMILES: O=C(Nc1ccnnc1)c1cc(C(F)(F)F)nc(-n2ccnc2)n1] | 2-(1H-imidazol-1-yl)-N-(pyridazin-4-yl)-6-(trifluoromethyl) pyrimidine-4-carboxamide | 336.0 | 11.24 (s, 1H), 9.72 (dd, J = 2.6, 0.9 Hz, 1H), 9.23 (d, J = 5.9 Hz, 1H), 9.07 (s, 1H), 8.37 (s, 1H), 8.30-8.27 (t, J = 1.2 Hz, 1H), 8.24 (dd, J = 5.9, 2.7 Hz, 1H), 7.28 (s, 1H). |

-continued

| No. | Structure | Name | MS ESI $[M + H]^+$ | $^1H$ NMR (400 MHz, DMSO-$d_6$) δ |
|---|---|---|---|---|
| 172 | 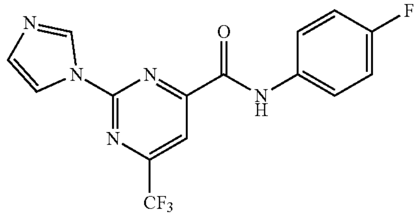 [SMILES: O=C(Nc1ccc(F)cc1)c1cc(C(F)(F)F)nc(-n2ccnc2)n1] | N-(4-fluorophenyl)-2-(1H-imidazol-1-yl)-6-(trifluoromethyl) pyrimidine-4-carboxamide | 352.0 | 10.88 (s, 1H), 9.09 (s, 1H), 8.32 (s, 1H), 8.29 (t, J = 1.4 Hz, 1H), 7.92-7.87 (m, 2H), 7.34-7.28 (m, 2H), 7.25 (d, J = 0.9 Hz, 1H). |
| 173 | 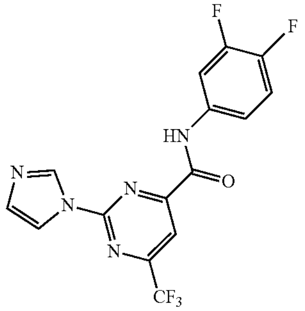 [SMILES: O=C(Nc1ccc(F)c(F)c1)c1cc(C(F)(F)F)nc(-n2ccnc2)n1] | N-(3,4-difluorophenyl)-2-(1H-imidazol-1-yl)-6-(trifluoromethyl) pyrimidine-4-carboxamide | 370.0 | 10.98 (s, 1H), 9.38 (s, 1H), 8.40 (d, J = 8.1 Hz, 2H), 8.04-7.08 (m, 1H), 7.73-7.71 (m, 1H), 7.59-7.52 (m, 1H), 7.43 (s, 1H). |
| 174 | 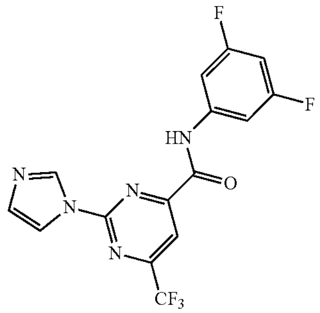 [SMILES: O=C(Nc1cc(F)cc(F)c1)c1cc(C(F)(F)F)nc(-n2ccnc2)n1] | N-(3,5-difluorophenyl)-2-(1H-imidazol-1-yl)-6-(trifluoromethyl) pyrimidine-4-carboxamide | 370.0 | 11.00 (s, 1H), 9.08 (s, 1H), 8.34 (s, 1H), 8.28 (s, 1H), 7.72 (d, J = 7.6 Hz, 2H), 7.26 (s, 1H), 7.13 (t, J = 9.1 Hz, 1H). |

Example 20

6-cyclobutoxy-2-(1H-imidazol-1-yl)-N-((1r,4r)-4-methoxycyclohexyl)pyrimidine-4-carboxamide (compound 104)

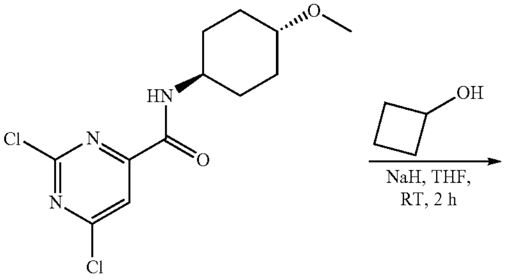

-continued

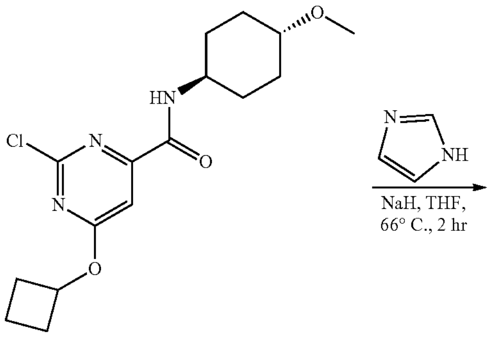

-continued

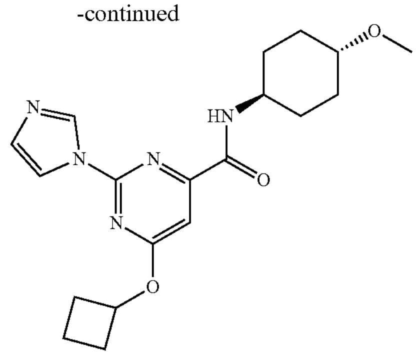

104

Step 1: 2-chloro-6-cyclobutoxy-N-((1r,4r)-4-methoxycyclohexyl)pyrimidine-4-carboxamide A mixture of cyclobutanol (0.04 mL, 0.57 mmol) in THF (5 mL) was added NaH (25.2 mg, 1.05 mmol, 60% in oil) at 0° C., the reaction was warmed to room temperature and stirred at this temperature for 0.5 hour. Then 2,6-dichloro-N-[(1r,4r)-4-methoxycyclohexyl] pyrimidine-4-carboxamide (160 mg, 0.57 mmol) was added and the mixture was stirred at room temperature for 3 hours under $N_2$ atmosphere. The mixture was quenched with $H_2O$ at 0° C., and the mixture was extracted with EA (50 mL×2). The combined organic layers were washed with brine (40 mL), dried over anhydrous $Na_2SO_4$, filtered and concentrated. The residue was purified by silica gel column chromatography (PE/EA=20/1-4/1) to afford the titled compound (200 mg, 100% yield) as a white solid. MS (ESI): m/z 340.1 $[M+H]^+$.

Step 2: 6-cyclobutoxy-2-(1H-imidazol-1-yl)-N-((1r,4r)-4-methoxycyclohexyl)pyrimidine-4-carboxamide A mixture of 1H-imidazole (80.1 mg, 1.18 mmol) in THF (5 mL) was added NaH (42.4 mg, 1.77 mmol, 60% in oil) at 0° C., the reaction was warmed to room temperature and stirred at this temperature for 0.5 hour. Then, 2-chloro-6-cyclobutoxy-N-((1r,4r)-4-methoxycyclohexyl) pyrimidine-4-carboxamide (200 mg, 0.59 mmol) was added and the mixture was stirred at 66° C. for 3 hours under $N_2$ atmosphere. The solution was quenched with $H_2O$ at 0° C., and the mixture was extracted with EA (50 mL×2). The combined organic layers were washed with brine (40 mL), dried over anhydrous $Na_2SO_4$, filtered and concentrated. The residue was purified by silica gel column chromatography (DCM/MeOH =200/1-40/1) to afford the titled compound (10.7 mg, 4.9% yield) as a white solid. MS (ESI): m/z 372.2 $[M+H]^+$. $^1H$ NMR (400 MHZ, DMSO-$d_6$) δ 8.91 (s, 1H), 8.70 (d, J=8.6 Hz, 1H), 8.19 (t, J=1.3 Hz, 1H), 7.17 (s, 1H), 7.16-7.15 (m, 1H), 5.38-5.27 (m, 1H), 3.86-3.75 (m, 1H), 3.25 (s, 3H), 3.16-3.07 (m, 1H), 2.22-2.10 (m, 2H), 2.06 (d, J=10.8 Hz, 2H), 1.83 (d, J=10.6 Hz, 3H), 1.75-1.66 (m, 1H), 1.61-1.48 (m, 2H), 1.23 (t, J=11.6 Hz, 2H).

The compounds below were synthesized following the procedures described for compound 104.

| No. | Structure | Name | MS ESI $[M + H]^+$ | $^1H$ NMR (400 MHz, DMSO-$d_6$) δ |
|---|---|---|---|---|
| 105 | 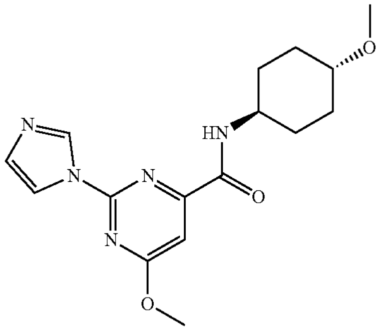 [SMILES: COc1cc(C(=O)N[C@H]2CC[C@H](OC)CC2)nc(-n2ccnc2)n1] | 2-(1H-imidazol-1-yl)-6-methoxy-N-((1r,4r)-4-methoxycyclohexyl) pyrimidine-4-carboxamide | 332.2 | 8.95 (s, 1H), 8.72 (d, J = 8.8 Hz, 1H), 8.22 (s, 1H), 7.23 (s, 1H), 7.16 (s, 1H), 4.08 (s, 3H), 3.82-3.79 (m, 1H), 3.15 (s, 3H), 3.14-3.09 (m, 1H), 2.05 (d, J = 10.4 Hz, 2H), 1.86 (d, J = 10.4 Hz, 2H), 1.65-1.53 (m, 2H), 1.26-1.17 (m, 2H). |
| 121 | 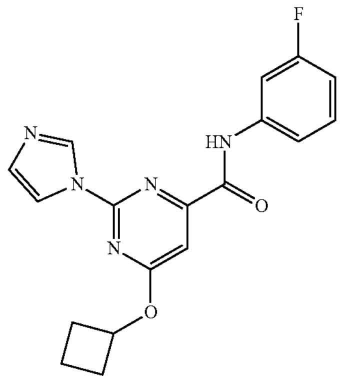 [SMILES: O=C(Nc1cccc(F)c1)c1cc(OC2CCC2)nc(-n2ccnc2)n1] | 6-cyclobutoxy-N-(3-fluorophenyl)-2-(1H-imidazol-1-yl)pyrimidine-4-carboxamide | 354.1 | 10.63 (s, 1H), 8.99 (s, 1H), 8.26 (s, 1H), 7.87-7.79 (m, 1H), 7.76-7.71 (m, 1H), 7.49-7.43 (m, 1H), 7.31 (s, 1H), 7.19 (s, 1H), 7.04 (td, J = 8.4, 2.2 Hz, 1H), 5.43-5.32 (m, 1H), 2.58-2.51 (m, 2H), 2.26-2.12 (m, 2H), 1.86-1.84 (m, 1H), 1.76-1.71 (m, 1H). |

-continued

| No. | Structure | Name | MS ESI $[M + H]^+$ | $^1H$ NMR (400 MHz, DMSO-$d_6$) δ |
|---|---|---|---|---|
| 149 | 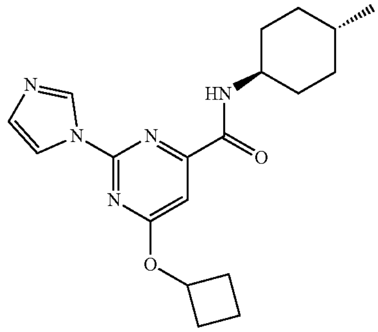 [SMILES: C[C@H]1CC[C@H](NC(=O)c2cc(OC3CCC3)nc(-n3ccnc3)n2)CC1] | 6-cyclobutoxy-2-(1H-imidazol-1-yl)-N-((1r,4r)-4-methylcyclohexyl) pyrimidine-4-carboxamide | 356.3 | 8.91 (s, 1H), 8.68 (d, J = 8.7 Hz, 1H), 8.19 (t, J = 1.3 Hz, 1H), 7.16 (s, 1H), 7.16-7.14 (m, 1H), 5.37-5.28 (m, 1H), 3.84-3.72 (m, 1H), 2.57-2.53 (m, 1H), 2.24-2.10 (m, 2H), 1.82-1.69 (m, 6H), 1.59-1.46 (m, 2H), 1.43-1.29 (m, 1H), 1.11-0.96 (m, 2H), 0.90 (d, J = 6.5 Hz, 3H). |

Example 21

6-cyano-2-(1H-imidazol-1-yl)-N-((1r,4r)-4-methoxy-cyclohexyl)pyrimidine-4-carboxamide (compound 106)

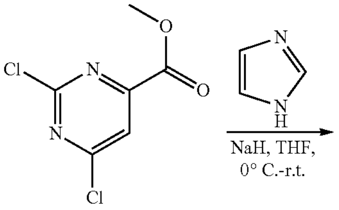

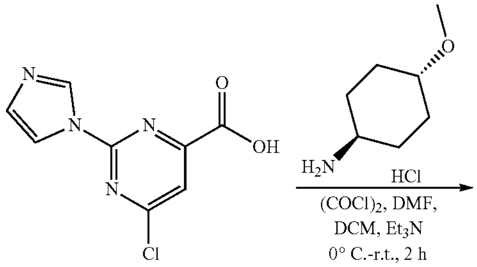

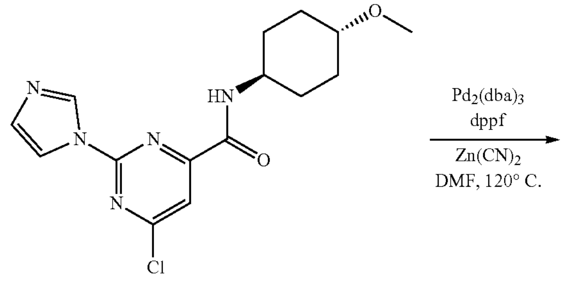

-continued

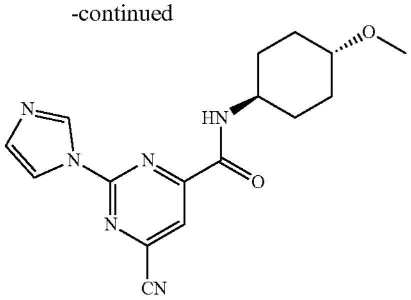

106

Step 1: 6-chloro-2-(1H-imidazol-1-yl) pyrimidine-4-carboxylic acid

To a solution of 1H-imidazole (990 mg, 14.49 mmol) in dry THF (50 mL) was added NaH (380 mg, 9.56 mmol, 60% in oil) at 0° C. under $N_2$ atmosphere. The resulting solution was added dropwise to a solution of methyl 2,6-dichloro-pyrimidine-4-carboxylate (3.00 g, 14.49 mmol) in dry THF (50 mL) at 0° C. under $N_2$ atmosphere. The resulting mixture was stirred at 0° C. for 1 hour. The solution was quenched with $H_2O$ (1 mL) at that temperature and the mixture was extracted with EtOAc (20 mL×3). The combined organic layers were washed with brine (50 mL), dried over anhydrous $Na_2SO_4$, filtered and concentrated to dryness. The residue was purified on silica gel chromatography (PE/EA=1/1-DCM/MeOH=100/1-30/1) to afford the titled compound (0.13 g, 3.8% yield) as a yellow solid. The aqueous layer was acidified to pH =4 using concentrated HCl (12 N). The resulting mixture was concentrated to dryness. The residue was dissolved in a mixture of $CH_2Cl_2$ (100 mL) and MeOH (10 mL) to obtain a suspension. The filtrate was concentrated to afford the titled compound (820 mg, 90% yield) which was used directly in the next step without further purification. MS (ESI): m/z 225.1 $[M+H]^+$.

Step 2: 6-chloro-2-(1H-imidazol-1-yl)-N-((1r,4r)-4-methoxycyclohexyl)pyrimidine-4-carboxamide To a solution of 6-chloro-2-(1H-imidazol-1-yl) pyrimidine-4-carboxylic acid (820 mg, 3.67 mmol) in dry $CH_2Cl_2$ (5 mL) were added catalytic amount of DMF (0.03 mL, 0.37 mmol) and $(COCl)_2$ (679.04 mg, 5.48 mmol) drop wise at 0° C. under $N_2$ atmosphere. The resulting mixture was stirred at room temperature for 0.5 hour. The solvent was removed in vacuum and the residue was dissolved in dry $CH_2Cl_2$ (5 mL). The resulting solution was added into a solution of (1r,4r)-4-methoxycyclohexan-1-amine hydrochloride (95.65 mg, 0.63 mmol) and $Et_3N$ (739 mg, 7.30 mmol) in dry $CH_2Cl_2$ (5 mL) at 0° C. under $N_2$ atmosphere. The resulting reaction mixture was stirred at room temperature for 1 hour. The mixture was partitioned between $CH_2Cl_2$ (20 mL) and water (20 mL). The organic layer was separated and aqueous layer was extracted with $CH_2Cl_2$ (20 mL). The combined organic layers were washed with brine (20 mL), dried over anhydrous $Na_2SO_4$, filtered and concentrated to dryness. The residue was purified on silica gel chromatography ($CH_2Cl_2$/MeOH=100/1-50/1) to afford the crude product which was further purified by prep-HPLC (Waters 2767/2545/2489/Qda, Waters sunfire C18 10 μm OBD 19*250 mm, Mobile Phase A: 0.1% HCl in water, Mobile Phase B: $CH_3CN$, Flow: 20 mL/min, Column temp: RT) to afford the titled compound (58 mg, 4.7% yield) as a white solid. MS (ESI): m/z 336.2 $[M+H]^+$.

Step 3: 6-cyano-2-(1H-imidazol-1-yl)-N-((1r,4r)-4-methoxycyclohexyl)pyrimidine-4-carboxamide A mixture of 6-chloro-2-(1H-imidazol-1-yl)-N-((1r,4r)-4-methoxycyclohexyl) pyrimidine-4-carboxamide (58 mg, 0.17 mmol), $Zn(CN)_2$ (20.28 mg, 0.17 mmol), dppf (9.75 mg, 0.02 mmol), $Pd_2(dba)_3$ (15.82 mg, 0.02 mmol) in DMF (2 mL) was heated at 120° C. for 2 hours under $N_2$ atmosphere. The mixture was partitioned between EtOAc (20 mL) and water (20 mL). The organic layer was separated and aqueous layer was extracted with EtOAc (20 mL×2). The combined organic layers were washed with brine (20 mL), dried over anhydrous $Na_2SO_4$, filtered and concentrated to dryness. The residue was purified on silica gel chromatography ($CH_2Cl_2$/MeOH=100/1-40/1) to afford the crude product which was further purified by Prep-HPLC (Waters 2767/2545/2489/Qda, Waters sunfire C18 10 μm OBD 19*250 mm, Mobile Phase A: 0.1% HCl in water, Mobile Phase B: $CH_3CN$, Flow: 20 mL/min, Column temp: RT) to afford the titled compound (10 mg, 16.7% yield) as a yellow solid. MS (ESI): m/z 327.1 $[M+H]^+$. $^1H$ NMR (400 MHZ, DMSO-$d_6$) δ 9.98 (s, 1H), 9.16 (d, J=8.5 Hz, 1H), 8.60 (s, 1H), 8.57 (s, 1H), 7.68 (s, 1H), 3.95-3.81 (m, 1H), 3.26 (s, 4H), 3.19-3.08 (m, 1H), 2.08 (d, J=10.7 Hz, 2H), 1.85 (d, J=10.5 Hz, 2H), 1.66-1.54 (m, 2H), 1.30-1.19 (m, 2H).

Example 22

N-(3-fluorophenyl)-2-(1H-imidazol-1-yl)-5-(piperidin-1-yl) pyrimidine-4-carboxamide (compound 115)

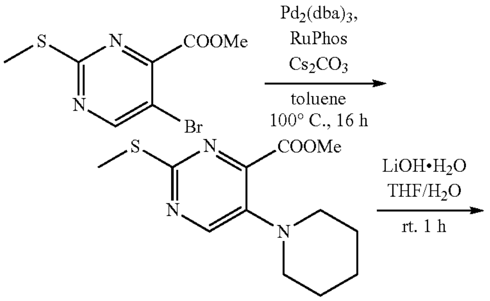

-continued

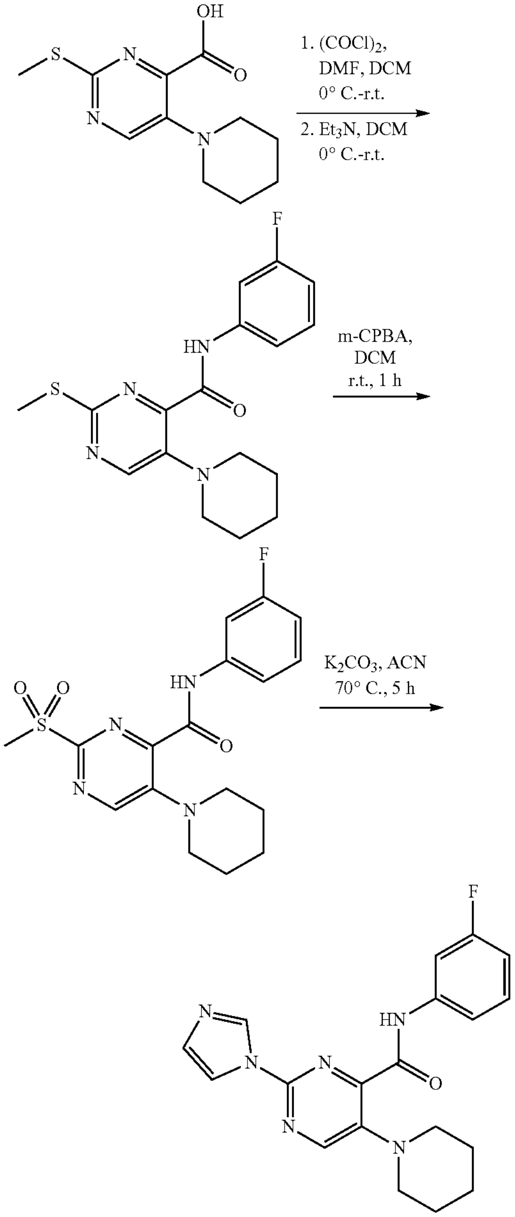

115

Step 1: methyl 2-(methylthio)-5-(piperidin-1-yl) pyrimidine-4-carboxylate

A mixture of methyl 5-bromo-2-(methylsulfanyl) pyrimidine-4-carboxylate (3 g, 11.41 mmol), piperidine (1.35 mL, 13.71 mmol), $Pd_2(dba)_3$ (1.04 mg, 1.14 mmol), RuPhos (0.53 mg, 1.14 mmol) and $Cs_2CO_3$ (7.43 mg, 22.80 mmol) in toluene (30 mL) was heated at 100° C. for 12 hours. The solvent was removed in vacuum and the residue was partitioned between EtOAc (50 mL) and water (50 mL). The organic layer was separated and aqueous layer was extracted with EtOAc (50 mL×2). The combined organic layers were washed with brine, dried over anhydrous $Na_2SO_4$, filtered and concentrated to dryness. The residue was purified on silica gel chromatography (PE/EA=10/1-5/1) to afford the titled compound (470 mg, 15.4% yield) as a yellow solid. MS (ESI): m/z 268.2 $[M+H]^+$.

Step 2: 2-(methylthio)-5-(piperidin-1-yl) pyrimidine-4-carboxylic acid

To a solution of methyl 2-(methylthio)-5-(piperidin-1-yl) pyrimidine-4-carboxylate (470 mg, 1.76 mmol) in THF (5 mL) and $H_2O$ (2 mL) was added $LiOH.H_2O$ (148 mg, 3.52 mmol). The resulting mixture was stirred at RT overnight. The solution was partitioned between EtOAc (20 mL) and water (20 mL). The organic layer was separated and 1N HCl solution was added into the aqueous layer to adjust the pH to 4. The resulting mixture was extracted with EtOAc (20 mL×2). The combined organic layers were washed with brine, dried over anhydrous $Na_2SO_4$, filtered and concentrated to afford the titled compound (70 mg, 15.7% yield) as a yellow solid. MS (ESI): m/z 254.2 $[M+H]^+$.

Step 3: N-(3-fluorophenyl)-2-(methylthio)-5-(piperidin-1-yl) pyrimidine-4-carboxamide To a solution of 2-(methylthio)-5-(piperidin-1-yl) pyrimidine-4-carboxylic acid (70 mg, 0.28 mmol) in dry DCM (5 mL) were added catalytic amount of DMF (1 μL, 0.03 mmol) and $(COCl)_2$ (51.40 mg, 0.41 mmol) drop wise at 0° C. under $N_2$ atmosphere. The resulting mixture was stirred at room temperature for 0.5 hour. The solvent was removed in vacuum and the residue was dissolved in dry DCM (5 mL). The resulting solution was added into a solution of 3-fluoroaniline (0.03 mL, 0.27 mmol) and $Et_3N$ (55.92 mg, 0.55 mmol) in dry DCM (5 mL) at 0° C. under $N_2$ atmosphere. The resulting reaction mixture was stirred at room temperature for 1 hour. The solution was partitioned between $CH_2Cl_2$ (20 mL) and water (20 mL). The organic layer was separated and aqueous layer was extracted with $CH_2Cl_2$ (20 mL×2). The combined organic layers were washed with brine, dried over anhydrous $Na_2SO_4$, filtered and concentrated to dryness. The residue was purified on silica gel chromatography (PE/EA=20/1-2/1) to afford the titled compound (55 mg, 57.5% yield) as a yellow solid. MS (ESI): m/z 347.0 $[M+H]^+$.

Step 4: N-(3-fluorophenyl)-2-(methylsulfonyl)-5-(piperidin-1-yl) pyrimidine-4-carboxamide To a solution of N-(3-fluorophenyl)-2-(methylthio)-5-(piperidin-1-yl) pyrimidine-4-carboxamide (45 mg, 0.13 mmol) in DCM (1 mL) was added m-CPBA (56.04 mg, 0.33 mmol). The resulting mixture was stirred at room temperature for 12 hours. The solution was partitioned between $CH_2Cl_2$ (20 mL) and saturated $NaHCO_3$ solution (20 mL). The organic layer was separated and aqueous layer was extracted with $CH_2Cl_2$ (20 mL×2). The combined organic layers were washed with brine, dried over anhydrous $Na_2SO_4$, filtered and concentrated to dryness. The residue was purified on silica gel chromatography (PE/EA=10/1-1/1) to afford the titled compound (35 mg, 71.2% yield) as a yellow solid. MS (ESI): m/z 379.2 $[M+H]^+$.

Step 5: N-(3-fluorophenyl)-2-(1H-imidazol-1-yl)-5-(piperidin-1-yl) pyrimidine-4-carboxamide A mixture of N-(3-fluorophenyl)-2-(methylsulfonyl)-5-(piperidin-1-yl) pyrimidine-4-carboxamide (35 mg, 0.10 mmol), 1H-imidazole (10 mg, 0.14 mmol) and $K_2CO_3$ (25.36 mg, 0.18 mmol) in ACN (4 mL) was heated at 70° C. for 2 hours. The volatile was removed in vacuum and the residue was purified on silica gel chromatography (DCM/MeOH=100/1-60/1) to afford the titled compound (16 mg, 47.2% yield) as a yellow solid. MS (ESI): m/z 367.0 $[M+H]^+$. $^1H$ NMR (400 MHZ, DMSO-$d_6$) δ 10.89 (s, 1H), 8.77 (s, 1H), 8.55 (s, 1H), 7.94 (s, 1H), 7.75-7.67 (m, 1H), 7.52-7.41 (m, 2H), 7.14 (s, 1H), 7.03-6.97 (m, 1H), 3.16-3.09 (m, 4H), 1.63-1.55 (m, 4H), 1.54-1.47 (m, 2H).

Alternative Compounds

The compounds below were also synthesized in the present invention.

| No. | Structure | Name | MS ESI $[M + H]^+$ | $^1H$ NMR (400 MHz, DMSO-$d_6$) δ |
|---|---|---|---|---|
| 29 | 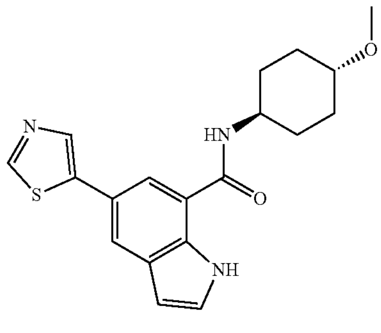 [SMILES: CO[C@H]1CC[C@H](NC(=O)c2cc(-c3cncs3)cc3cc[nH]c23)CC1] | N-((1r,4r)-4-methoxycyclohexyl)-5-(thiazol-5-yl)-1H-indole-7-carboxamide | 356.1 | 11.26 (s, 1H), 9.04 (s, 1H), 8.46 (d, J = 7.9 Hz, 1H), 8.28 (s, 1H), 8.00 (s, 1H), 7.96 (d, J = 1.4 Hz, 1H), 7.39 (t, J = 2.7 Hz, 1H), 6.54 (dd, J = 2.9, 2.0 Hz, 1H), 3.95-3.81 (m, 1H), 3.26 (s, 3H), 3.15 (ddd, J = 14.3, 10.5, 3.9 Hz, 1H), 2.08 (d, J = 10.4 Hz, 2H), 1.95 (d, J = 10.9 Hz, 2H), 1.50-1.39 (m, 2H), 1.30-1.18 (m, 2H). |
| 43 | 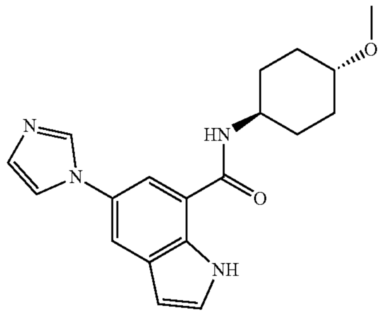 [SMILES: CO[C@H]1CC[C@H](NC(=O)c2cc(-n3ccnc3)cc3cc[nH]c23)CC1] | 5-(1H-imidazol-1-yl)-N-((1r,4r)-4-methoxycyclohexyl)-1H-indole-7-carboxamide | 339.2 | 11.30 (s, 1H), 8.49-8.37 (m, 2H), 8.18 (s, 1H), 7.93 (d, J = 1.7 Hz, 1H), 7.86 (d, J = 1.9 Hz, 1H), 7.71 (s, 1H), 7.45 (t, J = 2.8 Hz, 1H), 7.12 (s, 1H), 6.61-6.50 (m, 1H), 3.92-3.81 (m, 1H), 3.26 (s, 3H), 3.18-3.11 (m, 1H), 2.11-2.03 (m, 2H), 1.98-1.91 (m, 2H), 1.47-1.36 (m, 2H), 1.29-1.18 (m, 2H). |

-continued

| No. | Structure | Name | MS ESI $[M + H]^+$ | $^1H$ NMR (400 MHz, DMSO-$d_6$) δ |
|---|---|---|---|---|
| 44 | 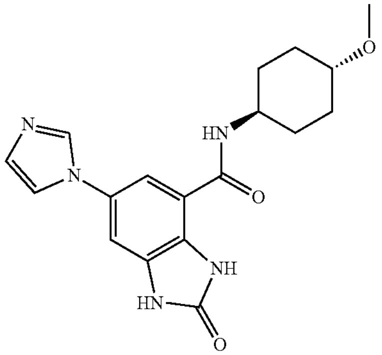 [SMILES: CO[C@H]1CC[C@H](NC(=O)c2cc(-n3ccnc3)cc3[nH]c(=O)[nH]c23)CC1] | 6-(1H-imidazol-1-yl)-N-((1r,4r)-4-methoxycyclohexyl)-2-oxo-2,3-dihydro-1H-benzo[d]imidazole-4-carboxamide | 356.2 | 11.14 (s, 1H), 10.52 (s, 1H), 8.30 (d, J = 7.1 Hz, 1H), 7.67 (s, 1H), 7.30 (s, 1H), 3.80 (s, 1H), 3.25 (s, 3H), 3.13 (t, J = 10.4 Hz, 1H), 2.05 (d, J = 11.3 Hz, 2H), 1.91 (d, J = 11.8 Hz, 2H), 1.38 (d, J = 12.6 Hz, 2H), 1.21 (d, J = 12.6 Hz, 2H). |
| 45 | 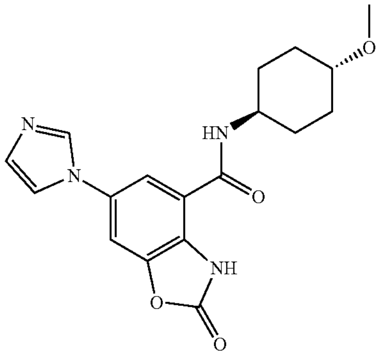 [SMILES: CO[C@H]1CC[C@H](NC(=O)c2cc(-n3ccnc3)cc3oc(=O)[nH]c23)CC1] | 6-(1H-imidazol-1-yl)-N-((1r,4r)-4-methoxycyclohexyl)-2-oxo-2,3-dihydrobenzo[d]oxazole-4-carboxamide | 357.2 | 8.62 (s, 1H), 8.21 (s, 1H), 7.89-7.68 (m, 3H), 7.12 (s, 1H), 3.79 (dd, J = 7.0, 2.8 Hz, 1H), 3.25 (s, 3H), 3.18-3.10 (m, 1H), 2.05 (d, J = 10.5 Hz, 2H), 1.93 (d, J = 10.7 Hz, 2H), 1.38 (dd, J = 24.1, 11.6 Hz, 2H), 1.29-1.18 (m, 2H). |
| 54 | 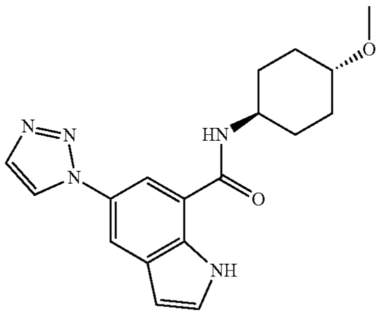 [SMILES: CO[C@H]1CC[C@H](NC(=O)c2cc(-n3ccnn3)cc3cc[nH]c23)CC1] | N-((1r,4r)-4-methoxycyclohexyl)-5-(1H-1,2,3-triazol-1-yl)-1H-indole-7-carboxamide | 340.1 | 11.40 (s, 1H), 8.75 (d, J = 0.9 Hz, 1H), 8.53 (d, J = 7.8 Hz, 1H), 8.17 (d, J = 1.8 Hz, 1H), 8.14 (d, J = 1.9 Hz, 1H), 7.98 (d, J = 1.0 Hz, 1H), 7.49 (t, J = 2.8 Hz, 1H), 6.65-6.60 (m, 1H), 3.93-3.83 (m, 1H), 3.26 (s, 3H), 3.17-3.10 (m, 1H), 2.07 (d, J = 10.6 Hz, 2H), 1.94 (d, J = 11.3 Hz, 2H), 1.49-1.38 (m, 2H), 1.29-1.18 (m, 2H). |
| 55 | 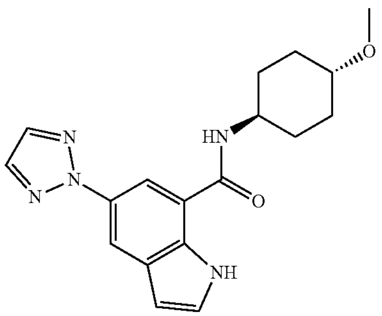 [SMILES: CO[C@H]1CC[C@H](NC(=O)c2cc(-n3nccn3)cc3cc[nH]c23)CC1] | N-((1r,4r)-4-methoxycyclohexyl)-5-(2H-1,2,3-triazol-2-yl)-1H-indole-7-carboxamide | 340.1 | 11.32 (s, 1H), 8.66 (d, J = 7.6 Hz, 1H), 8.32 (s, 2H), 8.11 (s, 2H), 7.45 (t, J = 2.8 Hz, 1H), 6.68-6.56 (m, 1H), 3.93-3.83 (m, 1H), 3.26 (s, 3H), 3.17-3.09 (m, 1H), 2.07 (d, J = 10.5 Hz, 2H), 1.97-1.88 (m, 2H), 1.52-1.41 (m, 2H), 1.29-1.17 (m, 2H). |

-continued

| No. | Structure | Name | MS ESI $[M + H]^+$ | $^1H$ NMR (400 MHz, DMSO-$d_6$) δ |
|---|---|---|---|---|
| 56 | 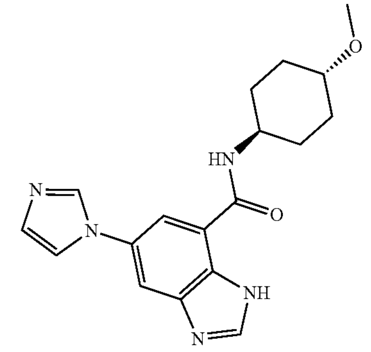 [SMILES: CO[C@H]1CC[C@H](NC(=O)c2cc(-n3ccnc3)cc3nc[nH]c23)CC1] | 5-(1H-imidazol-1-yl)-N-((1r,4r)-4-methoxycyclohexyl)-1H-benzo[d]imidazole-7-carboxamide | 340.6 | 13.28-12.67 (m, 1H), 9.86 (s, 1H), 8.58 (s, 1H), 8.32 (s, 1H), 7.98 (s, 2H), 7.86 (s, 1H), 7.21 (s, 1H), 3.90 (s, 1H), 3.26 (s, 4H), 2.02 (m, 4H), 1.46-1.28 (m, 4H). |
| 57 | 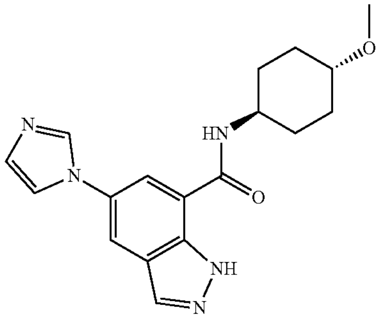 [SMILES: CO[C@H]1CC[C@H](NC(=O)c2cc(-n3ccnc3)cc3cn[nH]c23)CC1] | 5-(1H-imidazol-1-yl)-N-((1r,4r)-4-methoxycyclohexyl)-1H-indazole-7-carboxamide | 340.4 | 9.80 (s, 1H), 8.14 (s, 2H), 7.99 (s, 1H), 7.89 (s, 1H), 7.68 (s, 1H), 7.10 (s, 1H), 3.93-3.83 (m, 1H), 3.26 (s, 3H), 3.23-3.15 (m, 1H), 2.11-1.95 (m, 4H), 1.48-1.35 (m, 2H), 1.34-1.23 (m, 2H). |

Example 23

N-(3-fluoro-5-(piperazin-1-yl) phenyl)-2-(1H-imidazol-1-yl)-6-(trifluoromethyl) pyrimidine-4-carboxamide

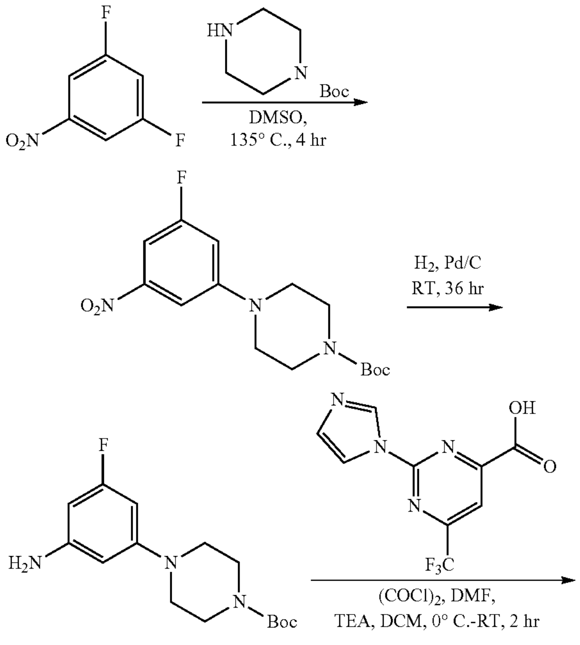

-continued

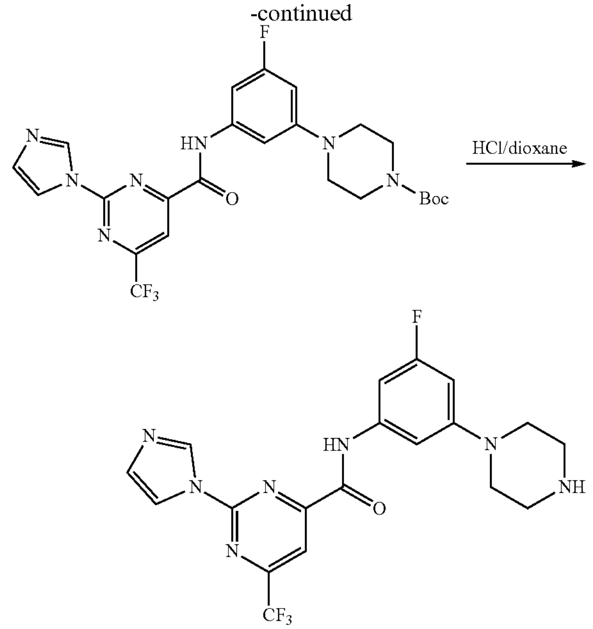

175

Step 1. tert-butyl 4-(3-fluoro-5-nitrophenyl) piperazine-1-carboxylate

To a solution of 1,3-difluoro-5-nitrobenzene (2.13 mL, 18.9 mmol) in DMSO (20 mL) was added tert-butyl piperazine-1-carboxylate (3.51 g, 18.9 mmol), and the reaction was stirred at 135° C. for 4 hours. The mixture was diluted with water (300 mL) and the resulting mixture was extracted with EA (150 mL×3). The organic layers were combined, washed with brine (100 mL), dried over anhydrous $Na_2SO_4$, filtered and concentrated in vacuum. The residue was purified by silica gel column chromatography (PE/EA=100/1 to 20/1) to afford the titled compound (4.50 g, 73.3% yield) as a yellow solid. LC-MS (ESI): m/z 270.1 $[M-55]^+$ $^1H$ NMR (400 MHZ, DMSO-$d_6$) δ 7.54 (s, 1H), 7.38 (dt, J=8.4, 2.0 Hz, 1H), 7.26 (dt, J=12.2, 2.2 Hz, 1H), 3.52-3.39 (m, 6H), 1.43 (s, 9H).

Step 2. tert-butyl 4-(3-amino-5-fluorophenyl) piperazine-1-carboxylate

To a solution of tert-butyl 4-(3-fluoro-5-nitrophenyl) piperazine-1-carboxylate (2.00 g, 6.15 mmol) in MeOH (20 mL) was added 10% Pd/C (400 mg) under $N_2$. The suspension was degassed under vacuum and purged with $H_2$ for several times. The resulting mixture was stirred under $H_2$ (1 atm) at room temperature for 36 hours. The reaction mixture was filtered with celite and the filtrate was concentrated in vacuum. The residue was mixed with water (100 mL) and the resulting mixture was extracted with EA (100 mL×2). The organic layers were combined, washed with brine (100 mL), dried over anhydrous $Na_2SO_4$, filtered and concentrated in vacuum to afford the titled compound (1.50 g, 82.6% yield) as a brown oil. LC-MS (ESI): m/z 296.0 $[M+H]^+$ Step 3. tert-butyl4-(3-(2-(1H-imidazol-1-yl)-6-(trifluoromethyl) pyrimidine-4-carboxamido)-5-fluorophenyl) piperazine-1-carboxylate To a solution of 2-(1H-imidazol-1-yl)-6-(trifluoromethyl) pyrimidine-4-carboxylic acid (200 mg, 0.78 mmol) in DCM (20 mL) at 0° C. were added DMF (0.02 mL, 0.23 mmol) and oxalyl chloride (0.10 mL, 1.16 mmol) dropwise under $N_2$ atmosphere. The resulting reaction mixture was stirred at room temperature for 0.5 hour. The solvent was removed in vacuum and the residue was dissolved in dry DCM (3 mL). The resulting solution was added into a solution of tert-butyl 4-(3-amino-5-fluorophenyl) piperazine-1-carboxylate (458 mg, 0.93 mmol, 60% purity) and triethyl amine (0.54 mL, 3.87 mmol) in DCM (20 mL) at 0° C. under $N_2$ atmosphere. The resulting mixture was stirred at room temperature for 1.5 hours. The mixture was mixed with water (100 mL) and the resulting mixture was extracted with EA (80 mL×2). The organic layers were combined, washed with brine (80 mL), dried over anhydrous $Na_2SO_4$, filtered and concentrated in vacuum. The residue was purified by silica gel column chromatography (PE/EA=100/1 to 3/2) to afford the titled compound (100 mg, 24.1% yield) as a yellow solid. LC-MS (ESI): m/z 536.2 $[M+H]^+$.

Step 4. N-(3-fluoro-5-(piperazin-1-yl) phenyl)-2-(1H-imidazol-1-yl)-6-(trifluoromethyl) pyramidine-4-carboxamide A mixture of tert-butyl4-(3-(2-(1H-imidazol-1-yl)-6-(trifluoromethyl) pyrimidine-4-carbox amido)-5-fluorophenyl) piperazine-1-carboxylate (100 mg, 0.19 mmol) and HCl/dioxane (4 mL, 4.0 M) was stirred at room temperature for 2 hr. The resulting mixture was evaporated under vacuum and the residue was slurried with EA (6 mL) to afford a crude material of the titled compound crude (60 mg), which was further purified by prep-HPLC (Waters 2767/2545/2489, Waters sunfire C18 10 μm OBD 19*250 mm, Mobile Phase A: 0.1% $NH_4OH$ in $H_2O$, Mobile Phase B: $CH_3CN$, Flow: 20 mL/min, Column temp: RT) to afford the titled compound (6.0 mg, 6.8% yield) as a yellow solid. LC-MS (ESI): m/z 436.1 $[M+H]^+$. 1H NMR (400 MHZ, DMSO-$d_6$) δ 10.70 (s, 1H), 9.08 (s, 1H), 8.32 (s, 1H), 8.29 (s, 1H), 7.30-7.26 (m, 2H), 7.26-7.24 (m, 1H), 6.66-6.60 (m, 1H), 3.15-3.11 (m, 4H), 2.89-2.82 (m, 4H).

The compounds below were synthesized following the procedures described for compound 175

| No. | Structure | Name | MS ESI $[M + H]^+$ | $^1H$ NMR (400 MHz, DMSO-$d_6$) δ |
|---|---|---|---|---|
| 176 | 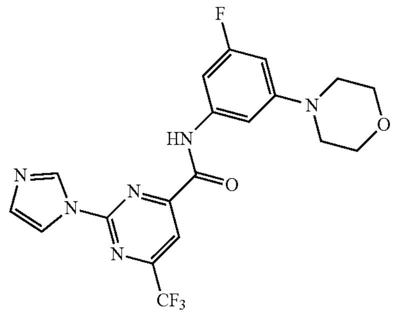 [SMILES: O=C(Nc1cc(F)cc(N2CCOCC2)c1)c1cc(C(F)(F)F)nc(-n2ccnc2)n1] | N-(3-fluoro-5-morpholinophenyl)-2-(1H-imidazol-1-yl)-6-(trifluoromethyl) pyrimidine-4-carboxamide | 437.2 | 10.74 (s, 1H), 9.08 (s, 1H), 8.32 (s, 1H), 8.29 (s, 1H), 7.34-7.24 (m, 3H), 6.68 (d, J = 12.6 Hz, 1H), 3.78-3.73 (m, 4H), 3.21-3.15 (m, 4H). |
| 177 | 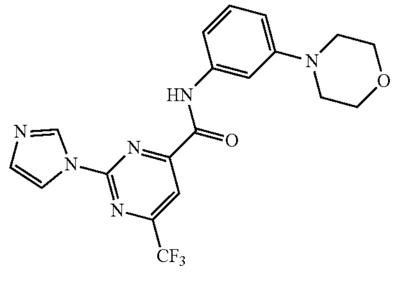 [SMILES: O=C(Nc1cccc(N2CCOCC2)c1)c1cc(C(F)(F)F)nc(-n2ccnc2)n1] | 2-(1H-imidazol-1-yl)-N-(3-morpholinophenyl)-6-(trifluoromethyl) pyrimidine-4-carboxamide | 419.1 | 10.68 (s, 1H), 9.10 (s, 1H), 8.32 (s, 1H), 8.30 (t, J = 1.4 Hz, 1H), 7.45 (s, 1H), 7.41 (d, J = 7.8 Hz, 1H), 7.30 (t, J = 8.1 Hz, 1H), 7.25 (s, 1H), 6.84 (dd, J = 8.0, 2.0 Hz, 1H), 3.80-3.75 (m, 4H), 3.17-3.12 (m, 4H). |

-continued

| No. | Structure | Name | MS ESI [M + H]+ | $^1$H NMR (400 MHz, DMSO-$d_6$) δ |
|---|---|---|---|---|
| 178 | 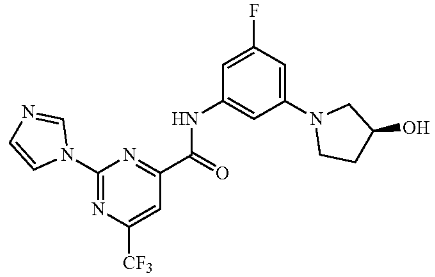 [SMILES: O=C(Nc1cc(F)cc(N2CC[C@H](O)C2)c1)c1cc(C(F)(F)F)nc(-n2ccnc2)n1] | (S)-N-(3-fluoro-5-(3-hydroxypyrrolidin-1-yl)phenyl)-2-(1H-imidazol-1-yl)-6-(trifluoromethyl) pyrimidine-4-carboxamide | 437.0 | 10.69 (s, 1H), 9.09 (s, 1H), 8.32 (s, 1H), 8.29 (s, 1H), 7.25 (s, 1H), 7.09-7.05 (m, 1H), 6.94 (s, 1H), 6.22-6.17 (m, 1H), 5.01 (d, J = 3.6 Hz, 1H), 4.42 (s, 1H), 3.43 (dd, J = 10.0, 4.6 Hz, 1H), 3.37 (d, J = 7.1 Hz, 1H), 3.30 (s, 1H), 3.11 (d, J = 10.9 Hz, 1H), 2.07-2.03 (m, 1H), 1.96-1.88 (m, 1H). |

Example 24

N-(3-fluoro-5-(2-methoxypropan-2-yl) phenyl)-2-(1H-imidazol-1-yl)-6-(trifluoromethyl) pyrimidine-4-carboxamide

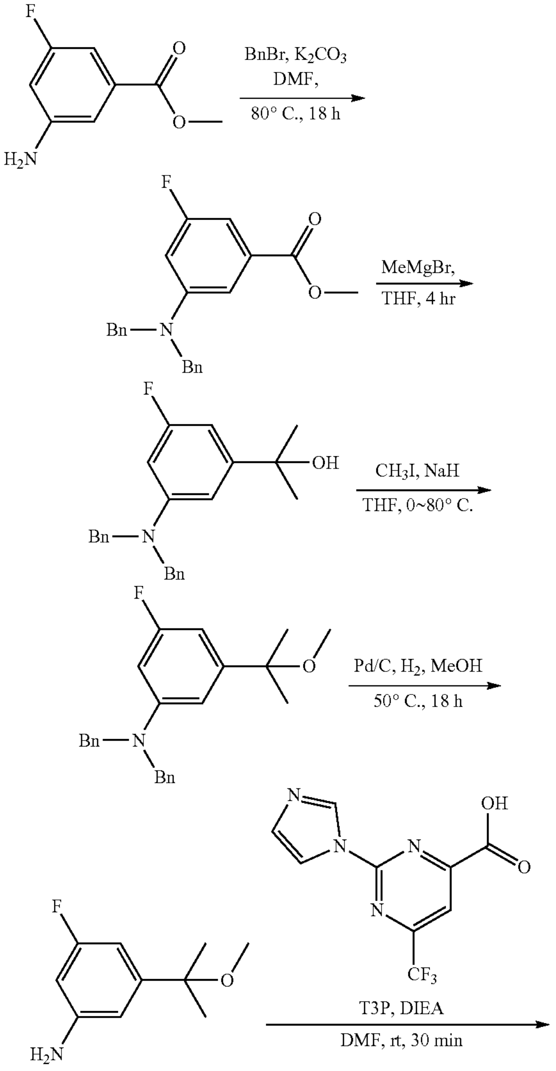

-continued

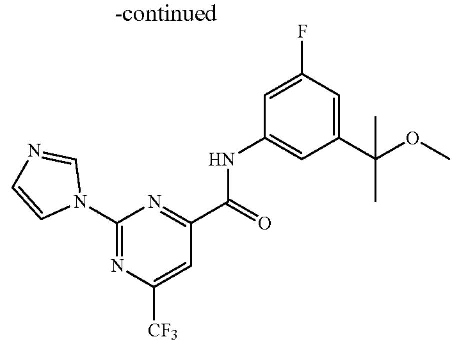

179

Step 1. Methyl 3-(dibenzylamino)-5-fluorobenzoate. To a solution of methyl 3-amino-5-fluoro benzoate (1.10 g, 6.50 mmol) in DMF (10 mL) were added BnBr (3.09 mL, 26.0 mmol) and $K_2CO_3$ (2.70 g, 19.5 mmol). The reaction was stirred at 80° C. for 18 hours. The reaction mixture was diluted with EA (100 mL) and brine (100 mL). The organic layer was separated, washed with further brine (100 mL×3) and concentrated in vacuum. The residue was purified by silica gel column chromatography eluting (PE/EA=1/0 ~10/1) to afford the title compound (2.2 g, 96.8% yield) as a white solid. LC-MS (ESI): m/z 350.1 $[M+H]^+$.

Step 2. 2-(3-(dibenzylamino)-5-fluorophenyl)propan-2-ol

To a solution of methyl 3-(dibenzylamino)-5-fluorobenzoate (2.00 g, 5.72 mmol) in THF (50 mL) was added MeMgBr (17.2 mL, 17.2 mmol, 1.0 M in THF) drop wise at 0° C. under $N_2$ atmosphere. The resulting reaction mixture was stirred at this temperature for 0.5 h, then stirred at 70° C. for 3 hours. The reaction mixture was cooled to room temperature, diluted with EA (100 mL) and brine (100 mL). The organic layer was separated and concentrated in vacuum. The residue was purified by silica gel column chromatography eluting (PE/EA=1/0 ~ 5/1) to afford the title compound (1.00 g, 50.0% yield) as a yellow solid. LC-MS (ESI): m/z 350.2 $[M+H]^+$.

Step 3. N,N-dibenzyl-3-fluoro-5-(2-methoxypropan-2-yl) aniline.

To a solution of 2-(3-(dibenzylamino)-5-fluorophenyl) propan-2-ol (400 mg, 1.14 mmol) in THF (50 mL) was added NaH (137 mg, 3.43 mmol, 60% in oil) portionwise at 0° C. under $N_2$ atmosphere. The resulting mixture was stirred at this temperature for 0.5 hour before iodomethane (0.21 mL, 3.43 mmol) was added. The reaction mixture was stirred at 70° C. for 3 hours, then cooled to room temperature and diluted with EA (30 mL) and brine (30 mL). The organic layer was separated and concentrated in vacuum. The residue was purified by silica gel column chromatography eluting (PE/EA=1/0~ 5/1) to afford the title compound (400 mg, 96.1% yield) as a yellow solid. LC-MS (ESI): m/z 364.2 $[M+H]^+$.

Step 4. 3-fluoro-5-(2-methoxypropan-2-yl) aniline.

To a solution of N,N-dibenzyl-3-fluoro-5-(2-methoxypropan-2-yl) aniline (500 mg, 1.37 mmol) in MeOH (20 mL) were added Pd/C (100 mg, 10%) and the reaction was stirred at 50° C. under $H_2$ atmosphere for 18 hours. The reaction mixture was filtered. The filtrate was concentrated in vacuum to afford the title compound (200 mg, 79.3% yield) as a yellow solid. LC-MS (ESI): m/z 184.1 $[M+H]^+$.

Step 5. N-(3-fluoro-5-(2-methoxypropan-2-yl) phenyl)-2-(1H-imidazol-1-yl)-6-(trifluoromethyl) pyrimidine-4-carboxamide.

To a solution of 3-fluoro-5-(2-methoxypropan-2-yl) aniline (30 mg, 0.16 mmol) in DMF (4 mL) were added DIEA (0.10 mL, 0.49 mmol), 2-(1H-imidazol-1-yl)-6-(trifluoromethyl) pyrimidine-4-carboxylic acid (42.3 mg, 0.16 mmol) and T3P (159 mg, 0.25 mmol, 50% in EA). The reaction was stirred at room temperature for 1 hour. The reaction mixture was purified by Prep-HPLC (Waters 2767/2545/2489, Waters Xbridge C18 10 μm OBD 19*250 mm, Mobile Phase A: 0.1% $NH_4OH$ in water, Mobile Phase B: $CH_3CN$, Flow: 20 mL/min, Column temp: RT) to afford the title compound (2.43 mg, 3.5% yield) as a white solid. LC-MS (ESI): m/z 424.1 $[M+H]^+$. $^1H$ NMR (400 MHZ, DMSO-$d_6$) δ 10.93 (s, 1H), 9.10 (s, 1H), 8.34 (s, 1H), 8.30 (s, 1H), 7.82-7.77 (m, 1H), 7.77-7.74 (m, 1H), 7.26 (s, 1H), 7.10-7.03 (m, 1H), 3.29 (s, 1H), 3.05 (s, 3H), 1.49 (s, 6H).

The compounds below were synthesized following the procedures described for compound 179.

Example 25

N-(3-(2-(dimethylamino) ethoxy)-5-fluorophenyl)-2-(1H-imidazol-1-yl)-6-(trifluoromethyl) pyrimidine-4-carboxamide

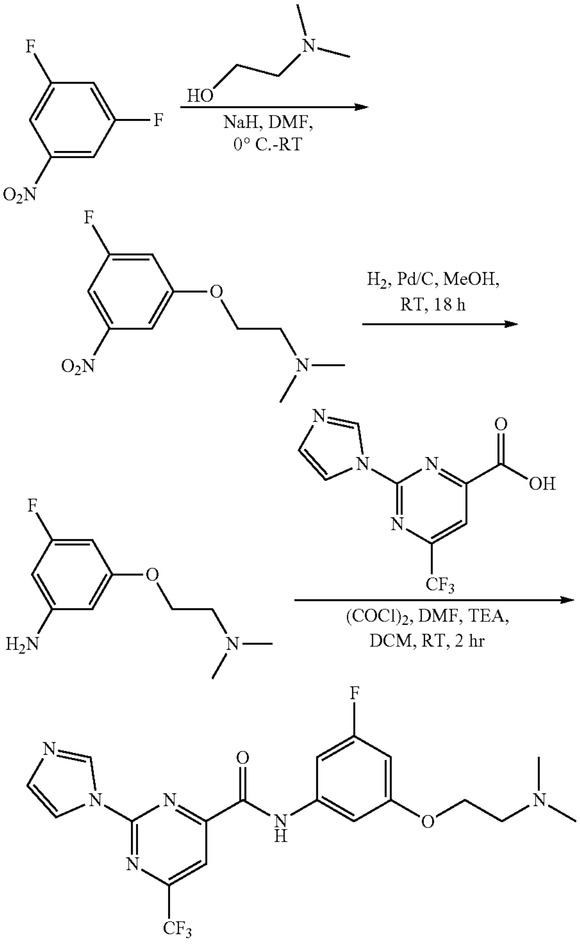

181

| No. | Structure | Name | MS ESI $[M + H]^+$ | $^1H$ NMR (400 MHz, DMSO-$d_6$) δ |
|---|---|---|---|---|
| 180 | 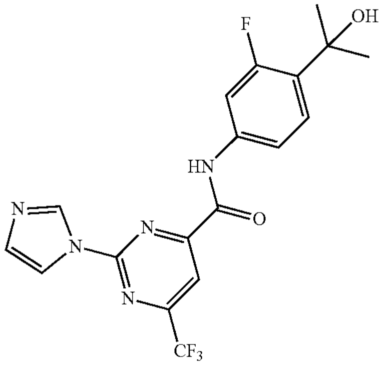 [SMILES: CC(C)(O)c1ccc(NC(=O)c2cc(C(F)(F)F)nc(-n3ccnc3)n2)cc1F] | N-(3-fluoro-4-(2-hydroxypropan-2-yl)phenyl)-2-(1H-imidazol-1-yl)-6-(trifluoromethyl) pyrimidine-4-carboxamide | 410.2 | 10.90 (s, 1H), 9.35 (s, 1H), 8.39 (d, J = 8.0 Hz, 2H), 7.77-7.65 (m, 3H), 7.40 (s, 1H), 1.50 (s, 6H). |

Step 1. 2-(3-fluoro-5-nitrophenoxy)-N,N-dimethylethanamine

To a solution of 2-(dimethylamino) ethanol (1.12 g, 12.6 mmol) in DMF (10 mL) was added NaH (360 mg, 15.09 mmol, 60% dispersion in mineral oil) portion wise at 0° C. under $N_2$ atmosphere. 1,3-Difluoro-5-nitrobenzene (2.00 g, 12.6 mmol) was added. The resulting suspension was stirred at room temperature for 2 hours. The reaction mixture was partitioned between EtOAc (20 mL) and water (80 mL). The organic layer was separated and the aqueous layer was extracted with EtOAc (20 mL×2). The organic layers were combined, washed with brine (80 mL), dried over anhydrous $Na_2SO_4$, filtered and concentrated to dryness to afford the titled compound (3.54 g, 80% purity, 100% yield) as a brown oil. LC-MS (ESI): m/z 229.0 $[M+H]^+$;

Step 2. 3-(2-(dimethylamino) ethoxy)-5-fluoroaniline

A solution of 2-(3-fluoro-5-nitrophenoxy)-N,N-dimethylethanamine (1.00 4.38 g, mmol) in MeOH (10 mL) was hydrogenated in the presence of 10% Pd/C (200 mg) at room temperature for 18 h under a balloon pressure of hydrogen gas. Insoluble solid was filtered through celite and the filtrate was concentrated to afford the titled compound (660 mg, 3.33 mmol, 76.0% yield) as dark oil. LC-MS (ESI): m/z 199.0 $[M+H]^+$;

Step 3. N-(3-(2-(dimethylamino) ethoxy)-5-fluorophenyl)-2-(1H-imidazol-1-yl)-6-(trifluoromethyl) pyrimidine-4-carboxamide To a solution of 2-(1H-imidazol-1-yl)-6-(trifluoromethyl) pyrimidine-4-carboxylic acid (150 mg, 0.58 mmol) in DCM (5 mL) at 0° C. were added DMF (1 drop) and $(COCl)_2$ (111 mg, 0.87 mmol) drop wise under $N_2$ atmosphere. The resulting reaction mixture was stirred at room temperature for 0.5 hour, then added into a solution of 3-(2-(dimethylamino)ethoxy)-5-fluoroaniline (138 mg, 0.70 mmol) and triethyl amine (0.38 mL, 2.91 mmol) in DCM (5 mL) at 0° C. under $N_2$ atmosphere. The resulting mixture was stirred at room temperature for 1 hr. The volatile was removed in vacuum and the residue was purified by silica gel chromatography (DCM/MeOH=100/1-10/1) to afford a crude product (110 mg), which was slurried in a mixture of PE and EA (3 mL, PE/EA=1/1). Filtration and dryness gave the titled compound (55 mg, 22.0% yield) as a light-yellow solid. LC-MS (ESI): m/z 439.1 $[M+H]^+$; $^1H$ NMR (400 MHZ, DMSO-$d_6$) δ 10.82 (s, 1H), 9.09 (s, 1H), 8.32 (s, 1H), 8.28 (t, J=1.2 Hz, 1H), 7.50-7.40 (m, 2H), 7.25 (s, 1H), 6.75 (d, J=10.8 Hz, 1H), 4.16 (t, J=5.6 Hz, 2H), 2.83 (s, 2H), 2.36 (s, 6H).

The compounds below were synthesized following the procedures described for compound 181.

Example 26 2-(1H-imidazol-1-yl)-N-((1r,4r)-4-methoxycyclohexyl)-6-(pyridin-4-yl) pyrimidine-4-carboxamide

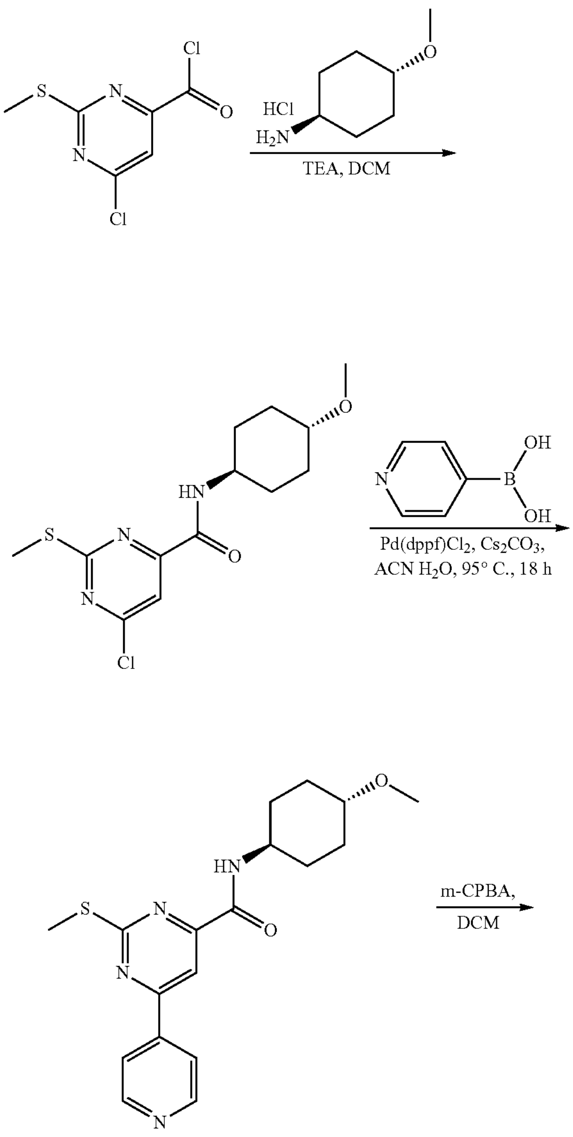

| No. | Structure | Name | MS ESI $[M + H]^+$ | $^1H$ NMR (400 MHz, DMSO-$d_6$) δ |
| --- | --- | --- | --- | --- |
| 182 | 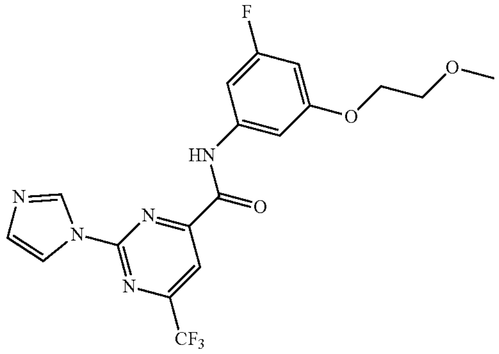 [SMILES: COCCOc1cc(F)cc(NC(=O)c2cc(C(F)(F)F)nc(-n3ccnc3)n2)c1] | N-(3-fluoro-5-(2-methoxyethoxy) phenyl)-2-(1H-imidazol-1-yl)-6-(trifluoromethyl) pyrimidine-4-carboxamide | 426.1 | 10.81 (s, 1H), 9.09 (s, 1H), 8.32 (s, 1H), 8.28 (s, 1H), 7.46 (d, J = 10.7 Hz, 1H), 7.41 (s, 1H), 7.25 (s, 1H), 6.75 (d, J = 11.0 Hz, 1H), 4.18-4.13 (m, 2H), 3.71-3.66 (m, 2H). |

-continued

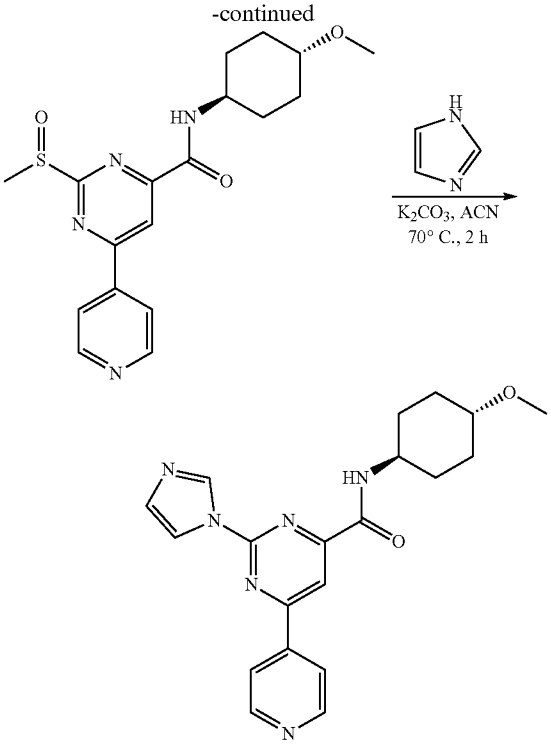

183

Step 1. 6-chloro-N-((1r,4r)-4-methoxycyclohexyl)-2-(methylthio)pyrimidine-4-carboxamide A mixture of 6-chloro-2-(methylthio) pyrimidine-4-carbonyl chloride (1.00 g, 4.48 mmol), (1r,4r)-4-methoxycyclohexanamine hydrochloride (0.89 g, 5.38 mmol), triethyl amine (1.86 mL, 13.45 mmol), in $CH_2Cl_2$ (20 mL) was stirred at room temperature for 2 hours. The mixture was diluted with water (60 mL), then extracted with EA (30 mL×2). The organic layers were combined, washed with brine (50 mL), dried over anhydrous $Na_2SO_4$, filtered and concentrated. The residue was purified by silica gel column chromatography (PE/EA=100/1-3/1) to afford the titled compound (1.60 g, 80% purity, 100% yield) as a white solid. LC-MS (ESI): m/z 316.1 $[M+H]^+$;

Step 2. N-((1r,4r)-4-methoxycyclohexyl)-2-(methylthio)-6-(pyridin-4-yl) pyrimidine-4-carboxamide A mixture of 6-chloro-N-((1r,4r)-4-methoxycyclohexyl)-2-(methylthio) pyrimidine-4-carbox amide (200 mg, 0.63 mmol), pyridin-4-ylboronic acid (156 mg, 1.27 mmol) and $Cs_2CO_3$ (411 mg, 1.26 mmol) in acetonitrile (6 mL) and $H_2O$ (2 mL) was heated at 95° C. in the presence of $Pd(dppf)Cl_2$ (46.7 mg, 0.063 mmol) for 18 hours under $N_2$ atmosphere. The solvent was removed in vacuum and the residue was purified on silica gel chromatography (PE/EA=20/1-1/3) to afford the titled compound (200 mg, 88.1% yield) as a yellow solid.LC-MS (ESI): m/z 359.1 $[M+H]^+$;

Step 3 N-((1r,4r)-4-methoxycyclohexyl)-2-(methylsulfinyl)-6-(pyridin-4-yl) pyrimidine-4-carboxamide A solution of N-((1r,4r)-4-methoxycyclohexyl)-2-(methylthio)-6-(pyridin-4-yl) pyrimidine-4-carboxamide (200 mg, 0.56 mmol) in DCM (6 mL) was treated with m-CPBA (125 mg, 0.61 mmol). The resulting reaction mixture was stirred at room temperature for 1 hour. The reaction mixture was washed with brine (10 mL), dried over anhydrous $Na_2SO_4$, filtered and concentrated to afford the titled compound (114 mg, 54.6% yield,) as an off-white solid. LC-MS (ESI): m/z 415.1 $[M+CH_3CN]^+$;

Step 4. 2-(1H-imidazol-1-yl)-N-((1r,4r)-4-methoxycyclohexyl)-6-(pyridin-4-yl) pyrimidine-4-carboxamide A mixture of N-((1r,4r)-4-methoxycyclohexyl)-2-(methylsulfinyl)-6-(pyridin-4-yl) pyrimidine-4-carboxamide (114 mg, 0.30 mmol), imidazole (31 mg, 0.46 mmol) and $K_2CO_3$ (84.15 mg, 0.61 mmol) in ACN (5 mL) was heated at 70° C. for 1 hour. The solvent was removed in vacuum and the residue was partitioned between $CH_2Cl_2$ (30 mL) and water (30 mL). The organic layer was separated and the aqueous layer was extracted with $CH_2Cl_2$ (30 mL×2). The organic layers were combined, washed with brine (30 mL), dried over anhydrous $Na_2SO_4$, filtered and concentrated to dryness. The residue was purified by silica gel chromatography (DCM/MeOH=100/1-20/1) to afford the titled product (35.0 mg, 29.2% yield) LC-MS (ESI): m/z 379.2 $[M+H]^+$; $^1H$ NMR (400 MHZ, DMSO-$d_6$) δ 9.12 (s, 1H), 8.90 (d, J=7.6 Hz, 1H), 8.84 (d, J=3.6 Hz, 2H), 8.50 (s, 1H), 8.43-8.30 (m, 3H), 7.22 (s, 1H), 3.98-3.80 (m, 1H), 3.27 (s, 3H), 3.20-3.05 (m, 1H), 2.08 (d, J=10.4 Hz, 2H), 1.88 (d, J=10.4 Hz, 2H), 1.68-1.50 (m, 2H), 1.35-1.20 (m, 2H).

The compounds below were synthesized following the procedures described for compound 183.

| No. | Structure | Name | MS ESI $[M + H]^+$ | $^1H$ NMR (400 MHz, DMSO-$d_6$) δ |
|---|---|---|---|---|
| 184 | 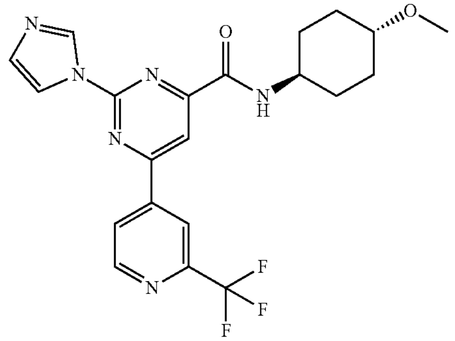 [SMILES: CO[C@H]1CC[C@H](NC(=O)c2cc(-c3ccnc(C(F)(F)F)c3)nc(-n3ccnc3)n2)CC1] | 2-(1H-imidazol-1-yl)-N-((1r,4r)-4-methoxycyclohexyl)-6-(2-(trifluoromethyl)pyridin-4-yl)pyrimidine-4-carboxamide | 447.1 | 9.16 (s, 1H), 9.02 (d, J = 5.0 Hz, 1H), 8.92 (d, J = 8.4 Hz, 1H), 8.81 (s, 1H), 8.72 (d, J = 4.5 Hz, 1H), 8.68 (s, 1H), 8.44 (s, 1H), 7.22 (s, 1H), 3.91 (s, 1H), 3.27 (s, 3H), 3.15 (s, 1H), 2.08 (d, J = 10.3 Hz, 2H), 1.89 (d, J = 11.6 Hz, 2H), 1.64-1.55 (m, 2H), 1.32-1.21 (m, 2H). |

Example 26

6-cyano-N-(3-fluorophenyl)-2-(1H-imidazol-1-yl)pyrimidine-4-carboxamide

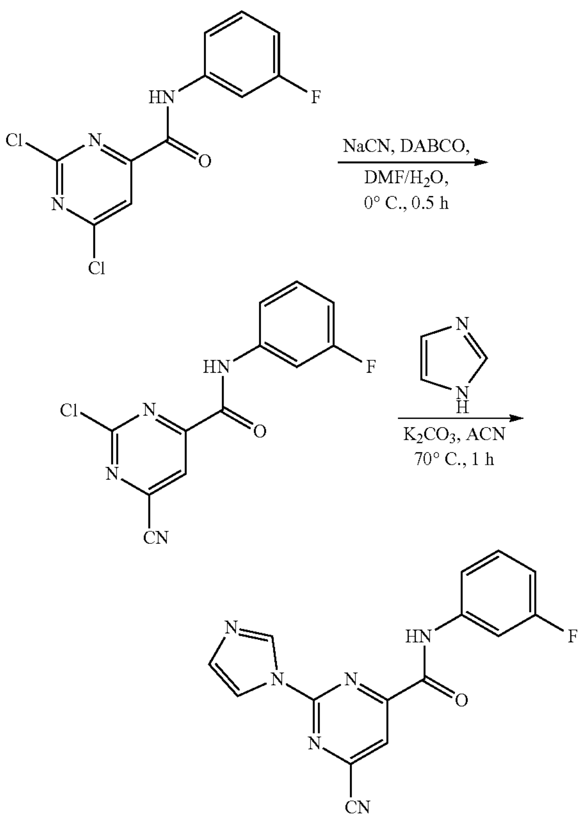

185

Step 1. 2-chloro-6-cyano-N-(3-fluorophenyl)pyrimidine-4-carboxamide

To a solution of 2,6-dichloro-N-(3-fluorophenyl)pyrimidine-4-carboxamide (100 mg, 0.350 mmol) in DMF (2 mL) and $H_2O$ (0.4 mL) were added DABCO (3.92 mg, 0.035 mmol) and NaCN (20.6 mg, 0.419 mmol) in one portion at 0° C. The reaction mixture was stirred at this temperature for 1h. The resulting mixture was partitioned between EtOAc (30 mL) and water (30 mL). The organic layer was separated and the aqueous layer was extracted with EtOAc (30 mL×2). The organic layers were combined, washed with brine (30 mL), dried over anhydrous $Na_2SO_4$, filtered and concentrated to dryness. The residue was purified by silica gel chromatography (PE/EA=20/1-4/1) to afford the titled compound (26 mg, 26.0% yield) as a light-yellow solid.

Step 2. 6-cyano-N-(3-fluorophenyl)-2-(1H-imidazol-1-yl)pyrimidine-4-carboxamide

A mixture of 2-chloro-6-cyano-N-(3-fluorophenyl)pyrimidine-4-carboxamide (26 mg, 0.094 mmol), imidazole (9.60 mg, 0.14 mmol) and $K_2CO_3$ (25.98 mg, 0.19 mmol) in acetonitrile (14 mL) was heated at 70° C. for 1 h. The solvent was removed in vacuum and the residue was partitioned between DCM (30 mL) and water (30 mL). The organic layer was separated and the aqueous layer was extracted with DCM (30 mL×2). The organic layers were combined, washed with brine (30 mL), dried over anhydrous $Na_2SO_4$, filtered and concentrated to dryness. The residue was purified on silica gel chromatography (DCM/MeOH=100/1-40/1) to afford crude product (17 mg), which was further purified by prep-HPLC (Waters 2767/2545/2489/Qda, Waters sunfire C18 10 μm OBD 19*250 mm, Mobile Phase A: 0.1% HCl in water, Mobile Phase B: $CH_3CN$, Flow: 20 mL/min, Column temp: RT) to afford the titled compound (20.0% yield) as a yellow solid. LC-MS (ESI): m/z 349.0 $[M+H]^+$; $^1H$ NMR (400 MHZ, DMSO-$d_6$) δ 11.01 (s, 1H), 9.62 (s, 1H), 8.70 (s, 1H), 8.49 (s, 1H), 7.83 (d, J=11.4 Hz, 1H), 7.75 (d, J=8.3 Hz, 1H), 7.54-7.47 (m, 2H), 7.09 (td, J=8.4, 2.1 Hz, 1H).

The compounds below were synthesized following the procedures described for compound 185.

| No. | Structure | Name | MS ESI $[M + H]^+$ | $^1H$ NMR (400 MHz, DMSO-$d_6$) δ |
|---|---|---|---|---|
| 186 | 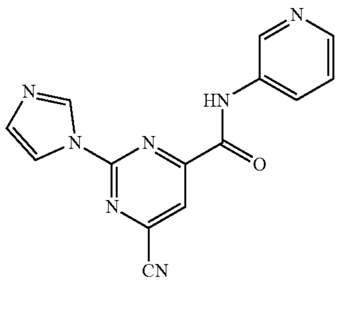 [SMILES: N#Cc1cc(C(=O)Nc2cccnc2)nc(-n2ccnc2)n1] | 6-cyano-2-(1H-imidazol-1-yl)-N-(pyridin-3-yl)pyrimidine-4-carboxamide | 292.1 | 10.98 (s, 1H), 9.08 (s, 1H), 9.02 (d, J = 2.3 Hz, 1H), 8.60 (s, 1H), 8.47-8.42 (m, 1H), 8.30 (s, 1H), 8.28-8.23 (m, 1H), 7.51 (dd, J = 8.4, 4.8 Hz, 1H), 7.25 (s, 1H). |
| 187 | 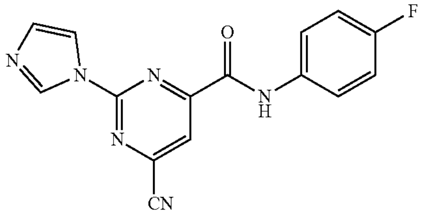 [SMILES: N#Cc1cc(C(=O)Nc2ccc(F)cc2)nc(-n2ccnc2)n1] | 6-cyano-N-(4-fluorophenyl)-2-(1H-imidazol-1-yl)pyrimidine-4-carboxamide | 309.1 | 10.85 (s, 1H), 9.07 (s, 1H), 8.57 (s, 1H), 8.30 (d, J = 1.3 Hz, 1H), 7.92-7.83 (m, 2H), 7.31 (t, J = 8.9 Hz, 2H), 7.24 (s, 1H). |

-continued

| No. | Structure | Name | MS ESI $[M + H]^+$ | $^1H$ NMR (400 MHz, DMSO-$d_6$) δ |
|---|---|---|---|---|
| 189 | 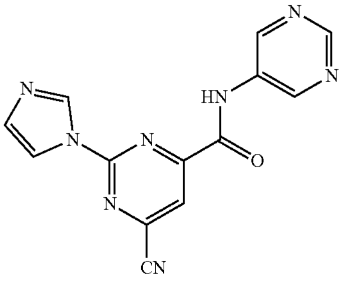 [SMILES: N#Cc1cc(C(=O)Nc2cncnc2)nc(-n2ccnc2)n1] | 6-cyano-2-(1H-imidazol-1-yl)-N-(pyrimidin-5-yl)pyrimidine-4-carboxamide | 293.0 | 11.13 (s, 1H), 9.25 (s, 2H), 9.06 (s, 2H), 8.63 (s, 1H), 8.29 (s, 1H), 7.26 (s, 1H). |

Example 27

2-(1H-imidazol-1-yl)-N-(2-(2-methoxyethoxy)pyrimidin-5-yl)-6-(trifluoromethyl)pyrimidine-4-carboxamide (Compound 188)

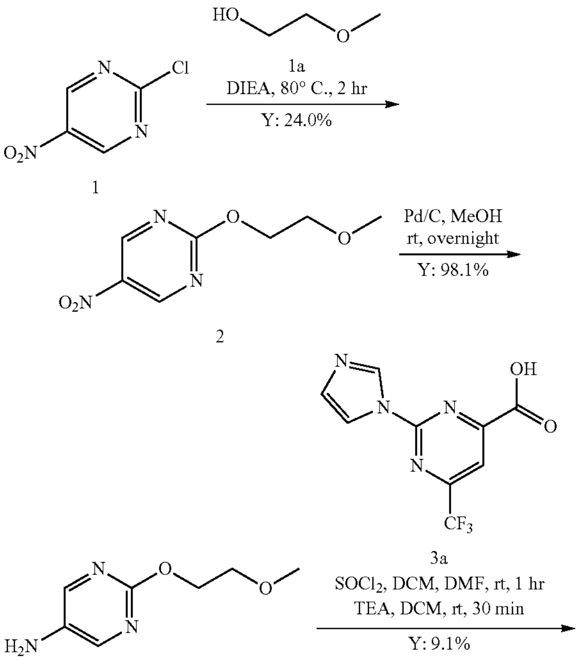

1

2

3

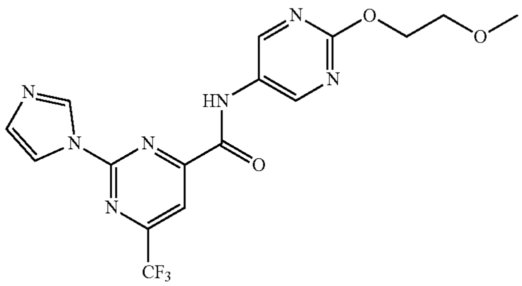

188

Step 1. 2-(2-methoxyethoxy)-5-nitropyrimidine

To a solution of Compound 1 (1 g, 6.27 mmol) in Compound 1a (6 mL, 75.70 mmol) were added DIEA (3.12 mL, 18.8 mmol), and the reaction was stirred at 80° C. for 2 hr. The reaction was diluted with EA (100 mL) and brine (100 mL). The organic layer was separated, concentrated in vacuum. The residue was purified using silica gel column chromatography eluting (PE/EA=10/1 to 3/1) to afford the title compound 2 (300 mg, 1.51 mmol, 24.0%) as a yellow solid. LC-MS (ESI): m/z N/A Step 2. 2-(2-methoxyethoxy) pyrimidin-5-amine To a solution of Compound 2 (300 mg, 1.50 mmol) in MeOH (10 mL) were added Pd/C 10% (100 mg, 0.94 mmol), and the reaction under H2 atmosphere was stirred at 50° C. overnight. The reaction mixture was filtered through Buchner funnel. The filtrate was collected, concentrated in vacuo, and dried to afford the title compound 3 (250 mg, 1.48 mmol, 98.1% yield, Lot #: $N_{200918}$-250-R1) as a gray solid. LC-MS (ESI): m/z 170.0 $[M+H]^+$ Step 3. 2-(1H-imidazol-1-yl)-N-(2-(2-methoxyethoxy) pyrimidin-5-yl)-6-(trifluoromethyl) pyrimidine-4-carboxamide To a solution of Compound 3a (200 mg, 0.78 mmol) in DCM (5 mL) were added oxalic dichloride (0.10 mL, 1.16 mmol) and DMF (0.01 mL, 0.08 mmol), and the reaction was stirred at room temperature for 2 hr. Then the mixture was dropped into the mixture of Compound 3 (144 mg, 0.85 mmol), DCM (5 mL) and TEA (0.43 mL, 3.01 mmol), then the mixture was stirred at RT for 1 hr and concentrated in vacuum. The residue was purified by Prep-HPLC (Waters 2767/2545/2489, Waters Xbridge C18 10 μm OBD 19*250 mm, Mobile Phase A: 0.1% $NH_4HCO_3$ in water, Mobile Phase B: $CH_3CN$, Flow: 20 mL/min, Column temp: RT) to afford the titled compound (28.71 mg, 0.07 mmol, 9.1% yield, Lot #: $N_{200918}$-252-P1) as a yellow solid. LC-MS (ESI): m/z 410.1 $[M+H]^+$. $^1H$ NMR (400 MHZ, DMSO-$d_6$) δ 11.07 (s, 1H), 9.06 (t, 1.2 Hz, 1H), 8.99 (s, 2H), 8.32 (s, 1H), 8.28 (t, 1.2 Hz, 1H), 7.26 (dd, J=1.4, 0.8 Hz, 1H), 4.49-4.43 (m, 2H), 3.73-3.67 (m, 2H), 3.32 (s, 3H).

The compounds below were synthesized following the procedures described for compound 185.

| No. | Structure | Name | MS ESI [M + H]+ | $^1$H NMR (400 MHz, DMSO-$d_6$) δ |
|---|---|---|---|---|
| 193 | 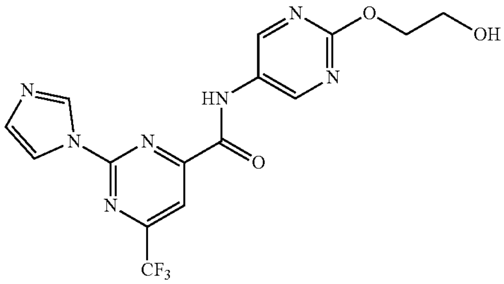 [SMILES: O=C(Nc1cnc(OCCO)nc1)c1cc(C(F)(F)F)nc(-n2ccnc2)n1] | N-(2-(2-hydroxyethoxy) pyrimidin-5-yl)-2-(1H-imidazol-1-yl)-6-(trifluoromethyl) pyrimidine-4-carboxamide | 396.4 | δ 11.06 (s, 1H), 9.06 (s, 1H), 8.98 (s, 2H), 8.32 (s, 1H), 8.28 (s, 1H), 7.26 (s, 1H), 4.91 (t, 4.0 Hz, 1H), 4.37-4.34 (m, 2H), 3.77-3.33 (s, 2H). |
| 194 | 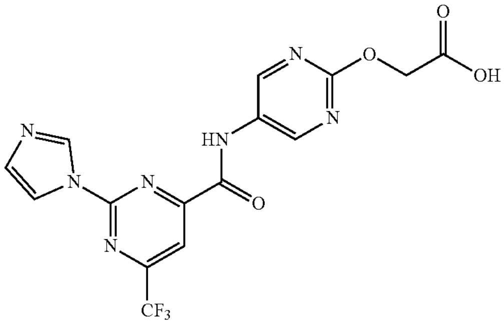 [SMILES: O=C(O)COc1ncc(NC(=O)c2cc(C(F)(F)F)nc(-n3ccnc3)n2)cn1] | 2-((5-(2-(1H-imidazol-1-yl)-6-(trifluoromethyl) pyrimidine-4-carboxamido) pyrimidin-2-yl)oxy) acetic acid | 410.4 | δ 13.01 (s, 1H), 11.06 (s, 1H), 9.06 (s, 1H), 8.98 (s, 2H), 8.34 (s, 1H), 8.27 (s, 1H), 7.24 (s, 1H), 4.48 (s, 2H) |
| 195 | 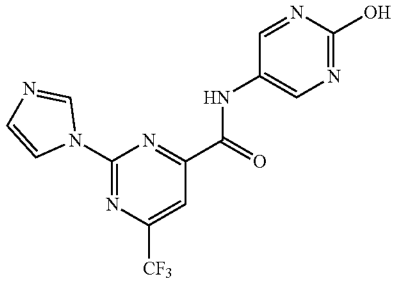 | N-(2-hydroxypyrimidin-5-yl)-2-(1H-imidazol-1-yl)-6-(trifluoromethyl) pyrimidine-4-carboxamide | | |

Example 28

6-(1H-imidazol-1-yl)-N-(pyridin-4-yl)-4-(trifluoromethyl) picolinamide

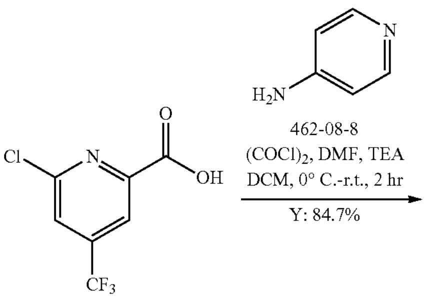

1

-continued

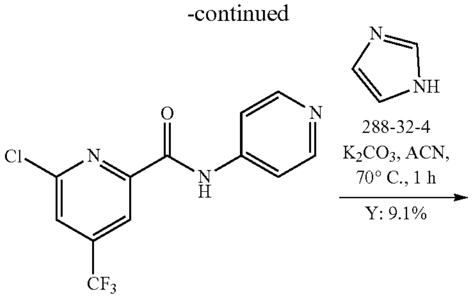

2

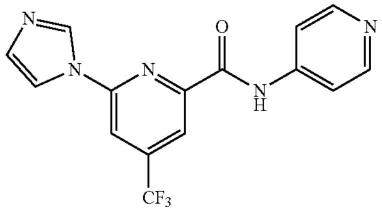

Step 1. 6-chloro-N-(pyridin-4-yl)-4-(trifluoromethyl) picolinamide

To a solution of Compound 1 (150 mg, 0.67 mmol) in DCM (5 mL) at 0° C. were added catalytic amount of DMF (0.01 mL, 0.07 mmol) and $(COCl)_2$ (126 mg, 1.0 mmol) drop wise under $N_2$ atmosphere. The resulting reaction mixture was stirred at room temperature for 0.5 h. After the acid chloride was formed as indicated by TLC, the resulting reaction mixture was added into a solution of pyridin-4-amine (75.1 mg, 0.80 mmol) and TEA (0.28 mL, 1.99 mmol) in DCM (5 mL) at 0° C. under $N_2$ atmosphere. The resulting mixture was stirred at room temperature for 1 hr. The reaction mixture was concentrated and the residue was purified by silica gel chromatography (PE/EA=20/1-1/2) to afford Compound 2 (170 mg, 0.56 mmol, 84.7% yield) as a white solid. LC-MS (ESI): m/z 302.0 $[M+H]^+$;

Step 2. 6-(1H-imidazol-1-yl)-N-(pyridin-4-yl)-4-(trifluoromethyl) picolinamide

To a solution of 1H-imidazole (57.5 mg, 0.85 mmol) in THF (5 mL) was added NaH (45.1 mg, 1.13 mmol, 60% in oil) at RT, then the mixture was stirred at RT for 0.5 hr before Compound 2 (170 mg, 0.564mmol) was added. The mixture was stirred at 80° C. for 2 hr. The reaction mixture was quenched with $H_2O$. The resulting reaction mixture was extracted with EtOAc (20 mL×2). The organic layers were combined, washed with brine, dried over anhydrous $Na_2SO_4$, filtered and concentrated to dryness. The residue was purified by silica gel chromatography (DCM/MeOH=100/1-20/1) to afford the titled compound (17 mg, 0.05 mmol, 9.1% yield, Lot #: $N_{200907}$-302-P1) as a white solid. LC-MS (ESI): m/z 334.0 $[M+H]^+$; $^1$H NMR (400 MHZ, DMSO-$d_6$) δ 10.88 (s, 1H), 9.14 (s, 1H), 8.62-8.58 (m, 2H), 8.56 (s, 1H), 8.49 (s, 1H), 8.27 (s, 1H), 8.01-7.96 (m, 2H), 7.24 (s, 1H).

The compounds below were synthesized following the procedures described for compound 185.

Biological Assay and Data

As stated above, the compounds of Formula I are CD38 inhibitors, and are useful in the treatment of diseases mediated by CD38. The biological activities of the compounds of Formula I can be determined by using any suitable assay for determining the activity of a candidate compound as a CD38 inhibitor.

CD38 Hydrolase Enzymatic Assay

A dilution of the test compounds 4× of the desired final concentration in sucrose buffer (0.25 M sucrose, 40 mM tris base, pH 7.4) was prepared. Also, a blank sample was prepared with 50 μl of sucrose buffer and no test compounds. A CD38 inhibitor 78c (as disclosed in J. Med. Chem. 2015, 58, 3548-3571) was used as a control for the CD38 activity.

rhCD38 enzyme powder (10818-H08H, Sino Biological Inc) were dissolved with rhCD38 enzyme buffer (MES, 25 mM; NaCl, 150 mM) to 50 ng/μl and stored at −80° C. 2.5X rhCD38 enzyme working fluid (0.125 ng/μl; BSA, 500 ng/μl) in sucrose buffer (0.25 M sucrose, 40 mM tris base, pH 7.4) was prepared. 2.5× substrate working fluid (ε-NAD, $N_{2630}$-25 MG, Sigma-Aldrich, 125 μM) in sucrose buffer (0.25 M sucrose, 40 mM tris base, pH 7.4) was also prepared.

The dynamic reading was performed at 25° C. with excitation light of 300 nm and emission light of 410 nm on the enzyme marker by contacting the above-prepared rhCD38 enzyme working fluid and the above-prepared solutions of the test compounds disclosed herein or the solution of the control. The readings were recorded for a total of 1 hour, and the data were analyzed with the point reading time of 20 mins.

Fluorescence was recorded by a microplate reader. Individual excel files containing fluorescence data were exported and the results were plotted against various drug concentrations and analyzed in GraphPad Prism 7.0 for concentration curve generation.

The $IC_{50}$ data from hCD38 enzyme inhibition for measuring the inhibitory effect on hCD38 are listed in table 1 below.

| No. | Structure | Name | MS ESI $[M + H]^+$ | $^1$H NMR (400 MHz, DMSO-$d_6$) δ |
|---|---|---|---|---|
| 191 | 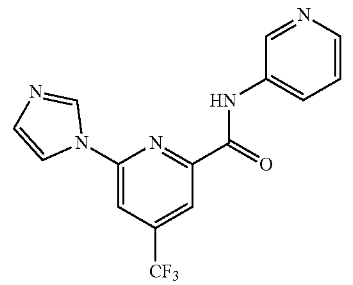 | 6-(1H-imidazol-1-yl)-N-(pyridin-3-yl)-4-(trifluoromethyl) picolinamide | 334.0 | 10.77 (s, 1H), 9.15 (s, 1H), 9.02 (d, J = 2.4 Hz, 1H), 8.54 (s, 1H), 8.50 (s, 1H), 8.41 (dd, J = 4.7, 1.3 Hz, 1H), 8.29-8.23 (m, 2H), 7.48 (dd, J = 8.2, 4.7 Hz, 1H), 7.23 (s, 1H). |
| 192 | 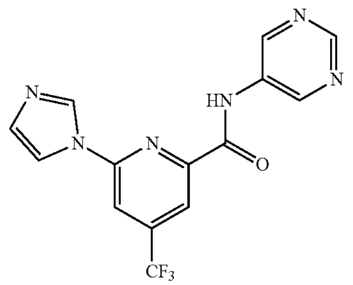 | 6-(1H-imidazol-1-yl)-N-(pyrimidin-5-yl)-4-(trifluoromethyl) picolinamide | 335.0 | 10.93 (s, 1H), 9.26 (s, 2H), 9.15 (s, 1H), 9.03 (s, 1H), 8.58 (s, 1H), 8.50 (s, 1H), 8.27 (s, 1H), 7.24 (s, 1H). |

TABLE 1

| Compound | hCD38 Enzyme inhibition $IC_{50}$ (nM) |
|---|---|
| Inhibition of human CD38 Enzyme in vitr | |
| 1 | 29 |
| 2 | 2706 |
| 3 | >10000 |
| 4 | 40 |
| 5 | 895 |
| 6 | >10000 |
| 7 | >10000 |
| 8 | >10000 |
| 9 | >10000 |
| 10 | 725 |
| 11 | 32 |
| 12 | >10000 |
| 13 | >10000 |
| 14 | 202 |
| 15 | 8051 |
| 16 | >10000 |
| 17 | >10000 |
| 18 | >10000 |
| 19 | >10000 |
| 20 | >10000 |
| 21 | 8 |
| 22 | 2755 |
| 23 | 45 |
| 24 | 30 |
| 26 | 46 |
| 27 | 842 |
| 28 | 22470 |
| 29 | 25 |
| 30 | 42 |
| 31 | 394 |
| 32 | 84 |
| 33 | 4079 |
| 34 | 3912 |
| 35 | 4 |
| 36 | 9754 |
| 37 | 348 |
| 38 | 456 |
| 39 | 225 |
| 40 | 96 |
| 41 | 13 |
| 42 | 11 |
| 43 | 106 |
| 44 | 87 |
| 45 | >10000 |
| 46 | 536 |
| 47 | 38 |
| 48 | 51 |
| 49 | 70 |
| 50 | >10000 |
| 51 | 9 |
| 52 | 55 |
| 53 | 36 |
| 54 | 6848 |
| 55 | >10000 |
| 56 | 765 |
| 57 | 114 |
| 58 | 3558 |
| 59 | >10000 |
| 60 | 17 |
| 61 | 15 |
| 62 | 4976 |
| 63 | 5428 |
| 64 | >10000 |
| 65 | 17 |
| 66 | 1.7 |
| 67 | >10000 |
| 68 | 190 |
| 69 | 111 |
| 70 | >10000 |
| 71 | 73 |
| 72 | 16 |
| 73 | 218 |
| 74 | 4044 |
| 75 | 389 |
| 76 | >10000 |

TABLE 1-continued

| Compound | hCD38 Enzyme inhibition $IC_{50}$ (nM) |
|---|---|
| Inhibition of human CD38 Enzyme in vitr | |
| 77 | 2451 |
| 78 | >10000 |
| 79 | 2194 |
| 80 | >10000 |
| 81 | 15 |
| 82 | 3 |
| 83 | 132 |
| 84 | 13 |
| 85 | 29 |
| 86 | 696 |
| 87 | 2 |
| 88 | 2 |
| 89 | 2 |
| 90 | 1 |
| 91 | 2 |
| 92 | 2 |
| 93 | 0.3 |
| 94 | 1 |
| 95 | 11 |
| 96 | 30 |
| 97 | 10 |
| 98 | 18 |
| 99 | 9 |
| 100 | 3429 |
| 101 | 17 |
| 102 | >10000 |
| 103 | 28 |
| 104 | 26 |
| 105 | 20 |
| 106 | 18 |
| 107 | 21 |
| 108 | 24 |
| 109 | 12 |
| 110 | 12 |
| 111 | 2 |
| 112 | 20 |
| 113 | 49 |
| 114 | 5 |
| 115 | 43 |
| 116 | >10000 |
| 117 | >10000 |
| 121 | 8 |
| 123 | 5 |
| 124 | 3 |
| 125 | 2 |
| 127 | 2 |
| 130 | 149 |
| 135 | 36 |
| 137 | >10000 |
| 138 | 76 |
| 141 | 1029 |
| 144 | 46 |
| 146 | 18 |
| 147 | 70 |
| 150 | 16 |
| 151 | 1555 |
| 152 | >10000 |
| 153 | >10000 |
| 154 | >10000 |
| 157 | 49 |
| 158 | 37 |
| 159 | 34 |
| 160 | 317 |
| 161 | 831 |
| 162 | >10000 |
| 163 | 92 |
| 164 | 4 |
| 165 | 3 |
| 166 | 5 |
| 167 | 4 |
| 168 | 4 |
| 169 | 20 |
| 170 | 13 |
| 171 | 9.8 |
| 172 | 8.2 |

TABLE 1-continued

| Inhibition of human CD38 Enzyme in vitr | |
|---|---|
| Compound | hCD38 Enzyme inhibition $IC_{50}$ (nM) |
| 173 | 6.8 |
| 174 | 5.4 |
| 175 | 68 |
| 176 | 20 |
| 177 | 38 |
| 178 | 17.3 |
| 179 | 585.7 |
| 180 | 11 |
| 181 | 25.4 |
| 182 | 9.6 |
| 183 | 28 |
| 184 | 28 |
| 185 | 2 |
| 186 | 2 |
| 187 | 2 |
| 188 | 10.7 |
| 189 | 12 |
| 190 | 2.8 |
| 191 | 3.8 |
| 192 | 6.1 |
| 193 | 11 |
| 194 | 30 |
| 195 | / |

Pharmacokinetics Study

Compounds disclosed herein were further studied with respect to CYP inhibition to investigate the drug-drug interaction.

0.1M K-Buffer with 5 mM $MgCl_2$ (K/Mg-buffer), pH 7.4 was preheated. A serial dilution of the test compounds disclosed herein and reference inhibitors (2C19:0.99 μM) in a 96-well plate. 8 μL of 10 mM test compounds were transferred to 12 μL of acetonitrile (ACN). The individual inhibitor spiking solutions for CYP 1A2, 2B6, 2C8, 2C19, 2C9, 2D6 and $3A_4$ were prepared with 8 μL of DMSO stock to 12 μL of ACN. 1:2 serial dilutions in DMSO: ACN mixture (v/v: 40:60) was prepared.

NADPH cofactor (66.7 mg NADPH in 10 mL 0.1 M K/Mg-buffer, pH7.4) was prepared. A substrate (2 mL for each isoform) was prepared (add HLM where required on ice). 0.2 mg/mL HLM solution (10 μL of 20 mg/mL to 990 μL of 0.1 M K/Mg-buffer) was prepared. 400 μL of 0.2 mg/mL HLM was added to the assay wells and then 2 μL of the test compound set (serially diluted as above) was added to the designated wells. 200 μL of 0.2 mg/mL HLM was added to the assay wells and then 1 μL of serially diluted reference inhibitor solution prepared above was added to the designated wells.

30 μL of test compound and reference compound in 0.2 mg/mL HLM solution as prepared above and 15 μL of substrate solution as prepared above were added to a 96-well assay plate on ice (in duplicate). The 96-well assay plate was pre-incubated with NADPH solution at 37° C. for 5 minutes. Then, 15 μL of pre-warmed 8 mM NADPH solution was added to the assay plates to initiate the reaction, and the assay plate was incubated at 37° C.: 5 min for 3A4; 10 min for 1A2, 2B6 and 2C9; 20 min for 2D6 and 2C8, and 45 min for 2C19. The reaction was stopped by adding 180 μL of ACN containing IS. After quenched, the plates were shaken for 10 min (600 rpm/min) and then centrifuged at 6000rpm for 15 min. Finally, 80 μL of the supernatant from each well was transferred into a 96-well sample plate containing 120 μL of ultra pure water for further analysis.

The CYP inhibition study showed that the compounds disclosed herein wherein $A_3$ is a substituted phenyl group having one or two carbon atoms replaced with N (e.g., pyridinyl or pyrimidinyl) showed no or very weak CYP inhibition, suggesting little or no drug-drug interaction.

It is to be understood that, if any prior art publication is referred to herein; such reference does not constitute an admission that the publication forms a part of the common general knowledge in the art in any country.

The disclosures of all publications, patents, patent applications, and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of formula I:

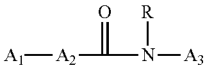

(I)

or a pharmaceutically acceptable salt thereof, wherein:

$A_1$ is

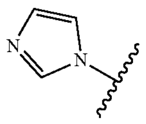

wherein $A_1$ is optionally substituted with 0, 1 or 2 substituents independently selected from methyl and trifluoromethyl;

$A_2$ is

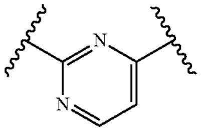

wherein $A_2$ is optionally substituted with 0 or 1 substituent selected from —CN, methyl, isopropyl, trifluoromethyl, methoxy, cyclobutoxy, oxetan-3-yloxy, $—NH_2$, $—NHCH_3$, and $—N(CH_3)_2$;

$A_3$ is

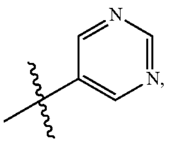

or

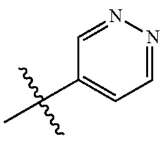

, wherein $A_3$ is optionally substituted with 0, 1 or 2 substituents independently selected from —CN, $—OCH_2CH_2OCH_3$, $—COCH_3$, —F, —Cl, methyl, trifluoromethyl, hydroxyethoxy, carboxymethoxy, hydroxy, and methoxy; and R is H or $C_{1-6}$ alkyl.

2. The compound of claim 1, wherein $A_1$ is unsubstituted.

3. The compound of claim 1, wherein $A_2$ is substituted with trifluoromethyl.

4. The compound of claim 1, wherein $A_3$ is

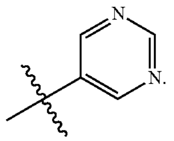 [SMILES: *c1cncnc1]

5. The compound of claim 1, wherein $A_3$ is

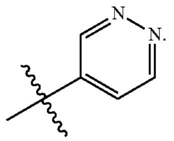

6. The compound of claim 1, wherein R is H.

7. The compound of claim 1, wherein R is $C_{1-6}$ alkyl.

8. The compound of claim 2, wherein $A_2$ is substituted with trifluoromethyl.

9. The compound of claim 8, wherein R is H.

10. The compound of claim 8, wherein R is methyl.

11. The compound of claim 9, wherein $A_3$ is

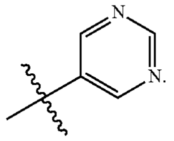

12. The compound of claim 11, wherein $A_3$ is substituted with a substituent selected from —CN, —$OCH_2CH_2OCH_3$, —$COCH_3$, —F, —Cl, methyl, trifluoromethyl, hydroxyethoxy, carboxymethoxy, hydroxy, and methoxy.

13. The compound of claim 9, wherein $A_3$ is

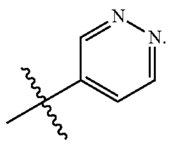

14. The compound of claim 13, wherein $A_3$ is unsubstituted with a substituent selected from —CN, —$OCH_2CH_2OCH_3$, —$COCH_3$, —F, —Cl, methyl, trifluoromethyl, hydroxyethoxy, carboxymethoxy, hydroxy, and methoxy.

15. The compound of claim 1, wherein the compound is

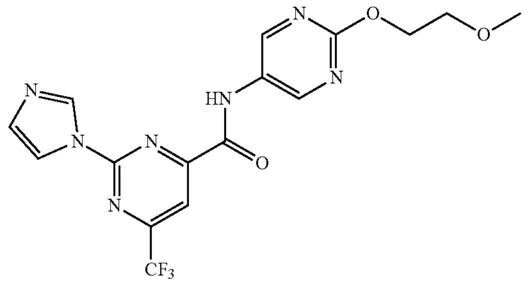 [SMILES: COCCOc1ncc(NC(=O)c2cc(C(F)(F)F)nc(-n3ccnc3)n2)cn1]

or a pharmaceutically acceptable salt thereof.

16. The compound of claim 1, wherein the compound is

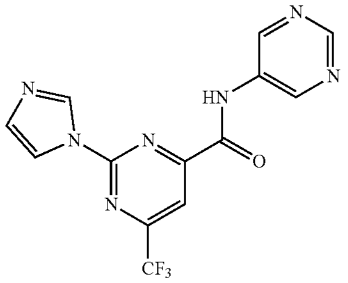 [SMILES: O=C(Nc1cncnc1)c1cc(C(F)(F)F)nc(-n2ccnc2)n1]

or a pharmaceutically acceptable salt thereof.

17. The compound of claim 1, wherein the compound is

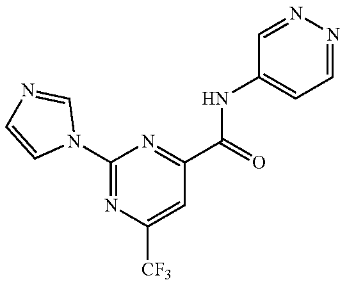 [SMILES: O=C(Nc1ccnnc1)c1cc(C(F)(F)F)nc(-n2ccnc2)n1]

or a pharmaceutically acceptable salt thereof.

18. The compound of claim 1, wherein the compound is

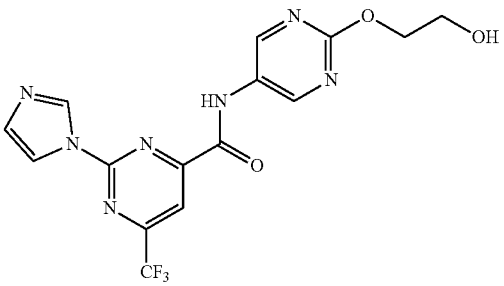 [SMILES: O=C(Nc1cnc(OCCO)nc1)c1cc(C(F)(F)F)nc(-n2ccnc2)n1]

or a pharmaceutically acceptable salt thereof.

19. The compound of claim 1, wherein the compound is

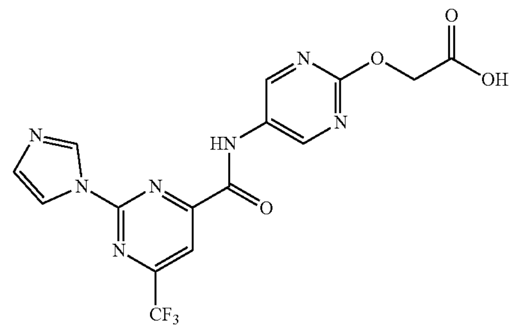 [SMILES: O=C(O)COc1ncc(NC(=O)c2cc(C(F)(F)F)nc(-n3ccnc3)n2)cn1]

or a pharmaceutically acceptable salt thereof.

20. The compound of claim 1, wherein the compound is

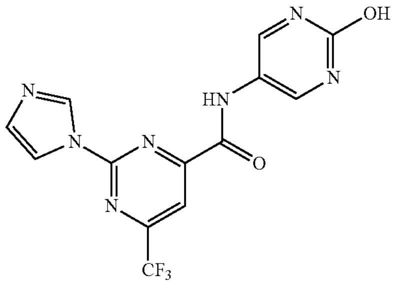

or a pharmaceutically acceptable salt thereof.

21. A pharmaceutical composition comprising:

a compound of claim 1 or a pharmaceutically acceptable salt thereof; and a pharmaceutically acceptable or excipient.

22. The pharmaceutical composition of claim 21, wherein the compound is

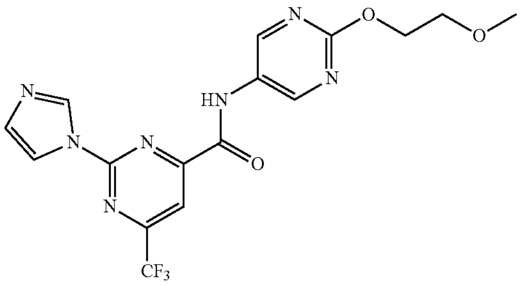 [SMILES: COCCOc1ncc(NC(=O)c2cc(C(F)(F)F)nc(-n3ccnc3)n2)cn1]

or a pharmaceutically acceptable salt thereof.

23. The pharmaceutical composition of claim 21, wherein the compound is

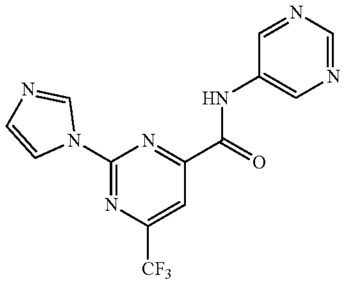

or a pharmaceutically acceptable salt thereof.

24. The pharmaceutical composition of claim 21, wherein the compound is

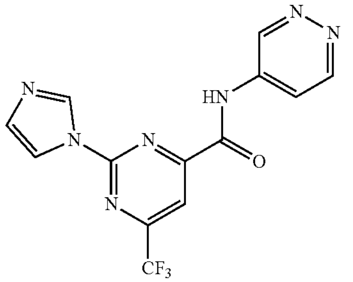 [SMILES: O=C(Nc1ccnnc1)c1cc(C(F)(F)F)nc(-n2ccnc2)n1]

or a pharmaceutically acceptable salt thereof.

25. The pharmaceutical composition of claim 21, wherein the compound is

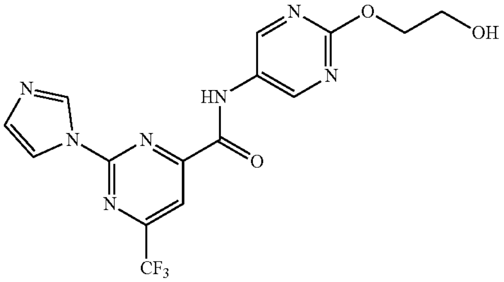 [SMILES: O=C(Nc1cnc(OCCO)nc1)c1cc(C(F)(F)F)nc(-n2ccnc2)n1]

or a pharmaceutically acceptable salt thereof.

26. The pharmaceutical composition of claim 21, wherein the compound is

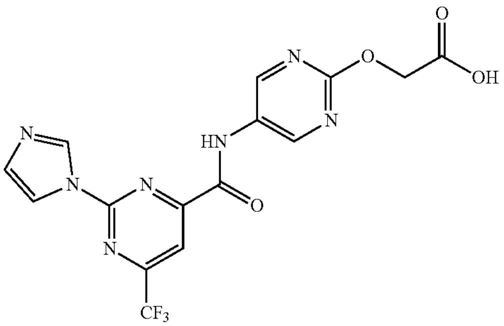 [SMILES: O=C(O)COc1ncc(NC(=O)c2cc(C(F)(F)F)nc(-n3ccnc3)n2)cn1]

or a pharmaceutically acceptable salt thereof.

27. The pharmaceutical composition of claim 21, wherein the compound is
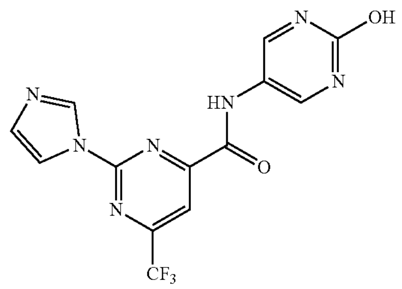 [SMILES: O=C(Nc1cnc(O)nc1)c1cc(C(F)(F)F)nc(-n2ccnc2)n1]
or a pharmaceutically acceptable salt thereof.
28. A method of inhibiting CD38 function in a cell, comprising contacting a compound of claim 1 or a pharmaceutically acceptable salt thereof with the cell.
* * * * *